US010759869B2

(12) United States Patent
Spriggs et al.

(10) Patent No.: US 10,759,869 B2
(45) Date of Patent: Sep. 1, 2020

(54) ANTIBODIES TO MUC16 AND METHODS OF USE THEREOF

(71) Applicant: Memorial Sloan Kettering Cancer Center, New York, NY (US)

(72) Inventors: David Spriggs, New York, NY (US); Dharmarao Thapi, Bayside Hills, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/695,311

(22) Filed: Sep. 5, 2017

(65) Prior Publication Data

US 2018/0230231 A1 Aug. 16, 2018

Related U.S. Application Data

(62) Division of application No. 14/850,675, filed on Sep. 10, 2015, now Pat. No. 9,790,283, which is a division of application No. 13/635,090, filed as application No. PCT/US2011/030025 on Mar. 25, 2011, now Pat. No. 9,169,328.

(60) Provisional application No. 61/317,964, filed on Mar. 26, 2010.

(51) Int. Cl.
*A61K 39/395* (2006.01)
*C07K 16/30* (2006.01)
*G01N 33/574* (2006.01)
*A61K 39/00* (2006.01)

(52) U.S. Cl.
CPC ... *C07K 16/3092* (2013.01); *G01N 33/57488* (2013.01); *A61K 2039/505* (2013.01); *A61K 2039/5156* (2013.01); *C07K 2317/24* (2013.01); *C07K 2317/33* (2013.01); *C07K 2317/34* (2013.01); *C07K 2317/622* (2013.01); *C07K 2317/77* (2013.01); *C07K 2317/92* (2013.01); *C07K 2319/02* (2013.01); *C07K 2319/03* (2013.01); *C07K 2319/33* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 4,975,369 | A | 12/1990 | Beavers et al. |
| 4,978,745 | A | 12/1990 | Schoemaker et al. |
| 5,057,313 | A | 10/1991 | Shih et al. |
| 5,225,539 | A | 7/1993 | Winter |
| 5,475,092 | A | 12/1995 | Chari et al. |
| 5,545,806 | A | 8/1996 | Lonberg et al. |
| 5,569,825 | A | 10/1996 | Lonberg et al. |
| 5,585,499 | A | 12/1996 | Chari et al. |
| 5,625,126 | A | 4/1997 | Lonberg et al. |
| 5,736,137 | A | 4/1998 | Anderson et al. |
| 5,846,545 | A | 12/1998 | Chari et al. |
| 5,976,818 | A | 11/1999 | O'Brien |
| 6,333,410 | B1 | 12/2001 | Chari et al. |
| 6,340,701 | B1 | 1/2002 | Chari et al. |
| 6,372,738 | B2 | 4/2002 | Chari et al. |
| 6,429,295 | B1 | 8/2002 | Carr Perez et al. |
| 7,202,346 | B2 | 4/2007 | Payne et al. |
| 7,227,002 | B1 | 6/2007 | Kufer et al. |
| 7,501,123 | B2 | 3/2009 | Roschke et al. |
| 7,585,952 | B2 | 9/2009 | D'Alessio et al. |
| 7,632,925 | B2 | 12/2009 | Kufer et al. |
| 7,662,387 | B2 | 2/2010 | Law et al. |
| 7,666,425 | B1 | 2/2010 | Bander |
| 7,959,923 | B2 | 6/2011 | You et al. |
| 9,169,328 | B2 | 10/2015 | Spriggs et al. |
| 9,790,283 | B2 | 10/2017 | Spriggs et al. |
| 2004/0057952 | A1 | 3/2004 | Payne et al. |
| 2004/0162413 | A1 | 8/2004 | Watkins et al. |
| 2006/0094069 | A1 | 5/2006 | Robertson et al. |

FOREIGN PATENT DOCUMENTS

| | | | |
|---|---|---|---|
| JP | 2006/502110 | | 1/2006 |
| RU | 2412947 | C2 | 2/2011 |
| WO | WO 1990/013678 | A1 | 11/1990 |
| WO | WO 1992/022653 | A1 | 12/1992 |
| WO | WO 2004/005470 | A2 | 1/2004 |
| WO | WO 2006/034488 | A2 | 3/2006 |
| WO | WO 2008/141044 | A2 | 11/2008 |
| WO | WO 2015/006043 | A1 | 1/2015 |

(Continued)

OTHER PUBLICATIONS

Badgwell et al., "Early detection of ovarian cancer," *Dis Markers*, 23(5-6):397-410 (2007).
Bafna et al., "MUC4, a multifunctional transmembrane glycoprotein, induces oncogenic transformation of NIH3T3 mouse fibroblast cells," *Cancer Res.*, 68(22):9231-9238 (2008).
Barber et al., "Chimeric NKG2D receptor-bearing T cells as immunotherapy for ovarian cancer," *Cancer Res.*, 67(10):5003-5008 (2007).

(Continued)

*Primary Examiner* — Sheela J. Huff
(74) *Attorney, Agent, or Firm* — Jones Day

(57) ABSTRACT

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

57 Claims, 69 Drawing Sheets

Specification includes a Sequence Listing.

(56) References Cited

FOREIGN PATENT DOCUMENTS

WO WO 2016/149368 A1 9/2016

OTHER PUBLICATIONS

Barber et al., "Immunotherapy with chimeric NKG2D receptors leads to long-term tumor-free survival and development of host antitumor immunity in murine ovarian cancer," *J Immunol.*, 180(1):72-78 (2008).
Bast et al., "A radioimmunoassay using a monoclonal antibody to monitor the course of epithelial ovarian cancer," *N Eng J Med.*, 309(15):883-887 (1983).
Bast et al., "New tumor markers: CA125 and beyond," *Int J Gynecol Cancer*, 15 Suppl 3:274-281 (2005).
Bast et al., "Reactivity of a monoclonal antibody with human ovarian carcinoma," *J Clin Invest.*, 68(5):1331-1337 (1981).
Bellone et al., "Generation of CA125-specific cytotoxic 1' lymphocytes in human leukocyte antigen-A2.1-positive healthy donors and patients with advanced ovarian cancer," *Am J Obstet Gynecol.*, 200(1):75e71-10 (2009).
Berek, "Immunotherapy of ovarian cancer with antibodies: a focus on oregovomab," *Expert Opinion on Biological Therapy*, 4(7):1159-1165 (2004).
Berek, "Immunotherapy of ovarian cancer with antibodies: a focus on oregovomab," *Expert Opin Biol Ther.*, 4(7):1159-1165 (2004).
Bernsel et al., "Improved membrane protein topology prediction by domain assignments," *Protein. Sci.*, 14(7):1723-1728 (2005).
Blalock et al., "Functions of MUC16 in Corneal Epithelial Cells," *Investigative Ophthalmology Visual Science*, vol. 48, No. 10, pp. 4509-4518 (2007).
Blalock et al., "Release of Membrane-Associated Mucins from Ocular Surface Epithelia," *Investigative Ophthalmology & Visual Science*, vol. 49, No. 5, pp. 1564-1871 (2008).
Borghouts et al., "Current strategies for the development of peptide-based anti-cancer therapeutics," *J Pept Sci.*,11(11):713-726 (2005).
Brand et al., "Prospect for anti-HER2 receptor therapy in breast cancer," *Anticancer Research*, 26:463-70 (2006).
Brentjens et al., "Eradication of systemic B-cell tumors by genetically targeted human T lymphocytes co-stimulated by CD80 and interleukin-15," *Nat Med.*, 9(3):279-286 (2003).
Brentjens et al., "Genetically targeted T cells eradicate systemic acute lymphoblastic leukemia xenografts," *Clin Cancer Res.*, 13(18 Pt 1):5426-5435 (2007).
Brentjens et al., "Somatic cell engineering and the immunotherapy of leukemias and lymphomas," *Adv Pharmacol*, 51:347-370 (2004).
Brentjens, "A Phase I trial for the treatment of chemo-refractory chronic lymphocytic leukemia with CD19-targeted autologous T cells," *Molecular Therapy* 16:S15 (2008).
Carpenito et al., "Control of large, established tumor xenografts with genetically retargeted human T cells containing CD28 and CD137 domains," *Proc Natl Acad Sci., USA*, 106(9):3360-3365 (2009).
Chang et al., "A novel peptide enhances therapeutic efficacy of liposomal anti-cancer drugs in mice models of human lung cancer," *PLoS One*, 4(1):e4171 (2009).
Cole et al., "The EBV-hybridoma technique and its application to human lung cancer," in *Monoclonal Antibodies and Cancer Therapy* (Sell, Ed.), pp. 77-96, Alan R. Liss, Inc. (1985).
Cote et al., "Generation of human monoclonal antibodies reactive with cellular antigens," *Proc Natl Acad Sci., USA*, 80(7):2026-2030 (1983).
Curiel et al., "Specific recruitment of regulatory T cells in ovarian carcinoma fosters immune privilege and predicts reduced survival," *Nat Med.*, 10(9):942-949 (2004).
Daly et al., "Recognition of human colon cancer by T cells transduced with a chimeric receptor gene," *Cancer Gene Ther.*, 7(2):284-291 (2000).
David et al., "Protein iodination with solid state lactoperoxidase," *Biochemistry*, 13(5):1014-1021 (1974).
Davies et al., "MUC16 is produced in tracheal surface epithelium and submucosal glands and is present in secretions from normal human airway and cultured bronchial epithelial cells," *Int j Biochem Cell Biol.*, 39(10):1943-1954 (2007).
Debat et al., "Overpassing an aberrant Vkappa gene to sequence an anti-idiotypic abzyme with beta-lactamase-like activity that could have a linkage with autoimmune diseases," *FASEB*, 15:815-822 (2001).
Doenecke et al., "Rapid amplification of cDNA ends (RACE) improves the PCR-based isolation of immunoglohulin variable region genes from murine and human lymphoma cells and cell lines," *Leukemia*, 11(10):1787-1792 (1997).
Elofsson et al., "Membrane protein structure: prediction versus reality," *Annu Rev BioChem.*, 76:125-140 (2007).
Faisal et al., "Leptasome-entrapped leptospiral antigens conferred significant higher levels of protection than those entrapped with PC-liposomes in a hamster model," *Vaccine*, 27(47):6537-6545 (2009).
Fendrick et al., "CA125 phosphorylation is associated with its secretion from the WISH human amnion cell line," *Tumour Biol.*, 18(5):278-289 (1997).
Fendrick et al., "Characterization of CA 125 synthesized by the human epithelial amnion WISH cell line," *Tumour Biol.*, 14(5):310-318 (1993).
Finney et al., "Activation of resting human primary T cells with chimeric receptors: costimulation from CD28, inducible costimulator, CD134, and CD137 in series with signals from the TCR zeta chain," *J Immunol.*, 172(1):104-113 (2004).
Fritsche et al., "CA 125 in ovarian cancer: advances and controversy," *Clin Chem.*, 44(7):1379-1380 (1998).
GenBank Accession No. AJ277812.1, "Mus musculus partial mRNA for immunoglobulin kappa light chain variable region (IGKV gene)" URL: http://www.ncbi.nlm.nih.gov/nuccore/7711058 (2001).
Giannakouros et al., "Transformation of NIH3T3 mouse fibroblast cells by MUC16 mucin (CA125) is driven by its cytoplasmic tail," *International Journal of Oncology*, 46(1):91-98 (2014).
Gong et al., "Cancer patient T cells genetically targeted to prostate-specific membrane antigen specifically lyse prostate cancer cells and release cytokines in response to prostate-specific membrane antigen," *Neoplasia*, 1(2):123-127 (1999).
Greenwood et al., "Preparation of iodine-131 labelled human growth hormone of high specific activity," *Nature*, 194:495-496 (1962).
Gubbels et al., "Mesothelin-MUC16 binding is a high affinity, N-glycan dependent interaction that facilitates peritoneal metastasis of ovarian tumors," *Molecular Cancer*, 5(1):50 (2006).
Habib-Agahi et al., "4-1BBL costimulation retrieves CD28 expression in activated T cells," *Cell Immunol.*, 256(1-2):39-46 (2009).
Habib-Agahi et al., "Co-stimulation with 4-1BB ligand allows extended T-cell proliferation, synergizes with CD80/CD86 and can reactivate anergic T cells," *Int Immunol.*, 19(12):1383-1394 (2007).
Habib-Agahi et al., "Co-stimulation with 4-1BB ligand allows extended T-cell proliferation, synergizes with CD80/CD86 and can reactivate anergic T cells," *Int Immunol.*, 19(12):1383-1394, Sup. List (2007).
Habib-Agahi et al., "Co-stimulation with 4-1BB ligand allows extended T-cell proliferation, synergizes with CD80/CD86 and can reactivate anergic T cells," *Int Immunol.*, 19(12):1383-1394, Sup. Fig. 1 (2007).
Habib-Agahi et al., "Co-stimulation with 4-1BB ligand allows extended T-cell proliferation, synergizes with CD80/CD86 and can reactivate anergic T cells," *Int Immunol* 19(12):1383-1394, Sup. Fig. 2 (2007).
Hamanishi et al., "Programmed cell death 1 ligand 1 and tumor-infiltrating CD8+ T lymphocytes arc prognostic factors of human ovarian cancer," *Proc Natl Acad Sci., USA*, 104(9):3360-3365 (2007).
Harris et al., "A comparison of the metastatic pattern of infiltrating lobular carcinoma and infiltrating duct carcinoma of the breast," *Br J Cancer*, 50(1):23-30 (1984).

(56) References Cited

OTHER PUBLICATIONS

Hedvat et al., "Application of tissue microarray technology to the study of non-Hodgkin's and Hodgkin's lymphoma," *Hum Pathol.*, 33(10):968-974 (2002).
High et al., "Sec61p is adjacent to nascent type I and type II signal-anchor proteins during their membrane insertion," *J Cell Biol.*, 121(4):743-750 (1993).
Hollingsworth, "Mucins in cancer: protection and control of the cell surface," *Nat Rev Cancer*, 4(1):45-60 (2004).
Hollyman et al., "Manufacturing validation of biologically functional T cells targeted to CD19 antigen for autologous adoptive cell therapy," *J Immuno Ther.*, 32(2):169-180 (2009).
Huang et al., "MUC1 cytoplasmic domain coactivates Wnt target gene transcription and confers transformation," *Cancer Biol. Ther.*, 2(6):702-706 (2003).
Hung et al., "Antigen-specific immunotherapy of cervical and ovarian cancer," *Immunol Rev.*, 222:43-69 (2008).
Huse et al., "Generation of a large combinatorial library of the immunoglobulin repertoire in phage lambda," *Science*, 246(4935):1275-1281 (1989).
Huwyler et al., "Tumor targeting using liposomal antineoplastic drugs," *Int J Nanomedicine*, 3(1):21-29 (2008).
Hwu et al., "In vivo antitumor activity of T cells redirected with chimeric antibody/T-cell receptor genes," *Cancer Res.*, 55(15):3369-3373 (1995).
Imai et al., "Chimeric receptors with 4-1BB signaling capacity provoke potent cytotoxicity against acute lymphoblastic leukemia," *Leukemia*, 18(4):676-684 (2004).
International Search Report for International Application No. PCT/US2016/022643, dated Sep. 5, 2016.
Invitation to Pay Additional Fees, and, Where Applicable, Protest Fee, with Communication Relating to the Results of the Partial International Search for PCT/US2016/022643, dated Jun. 30, 2016.
ISR PCT/US2011/030025 (2011).
Jensen et al., "Engineered CD20-specific primary human cytotoxic T lymphocytes for targeting B-cell malignancy," *Cytotherapy*, 5(2):131-138 (2003).
Kaneko et al., "A binding domain on mesothelin for CA125/MUC16," *J Biol Chem*, 284(6):3739-3749 (2009).
Kershaw et al., "A phase I study on adoptive immunotherapy using gene-modified T cells for ovarian cancer," *Clin Cancer Res.*, 12(20 Pt 1):6106-6115 (2006).
Kershaw et al., "Dual-specific T cells combine proliferation and antitumor activity," *Nat Biotechnol.*, 20(12):1221-1227 (2002).
Kochenderfer et al., "Construction and preclinical evaluation of an anti-CD19 chimeric antigen receptor," *J ImmunoTher.*, 32(7):689-702 (2009).
Kohler et al., "Continuous cultures of fused cells secreting antibody of predefined specificity," *Nature*, 256(5517):495-497 (1975).
Kononen et al., "Tissue microarrays for high-throughput molecular profiling of tumor specimens," *Nat Med.*, 4(7):844-847 (1998).
Kozbor et al., "Comparison of the specific IgM and IgG antibody response in humans induced by antigen (tetanus toxoid) or a polyclonal activator (EBV) in vitro," *Int Arch Allergy Appl Immunol.*, 72(3):260-266 (1983).
Krivak et al., "A Gynecologic Oncology Group Study of serum CA-125 levels in patients with stage III optimally debulked ovarian cancer treated with intraperitoneal compared to intravenous chemotherapy: an analysis of patients enrolled in GOG 172," *Gynecol Oncol.*, 115(1):81-85 (2009).
Lamers et al., "Gene-modified T cells for adoptive immunotherapy of renal cell cancer maintain transgene-specific immune functions in vivo," *Cancer Immunol ImmunoTher.*, 56(12):1875-1883 (2007).
Lamers et al., "Treatment of metastatic renal cell carcinoma with autologous T-lymphocytes genetically retargeted against carbonic anhydrase IX: first clinical experience," *J Clin Oncol.*, 24(13):e20-22 (2006).
Latouche et al., "Induction of human cytotoxic T lymphocytes by artificial antigen-presenting cells," *Nat Biotechnol.*, 18(4):405-409 (2000).
Leffers et al., "Prognostic significance of tumor-infiltrating T-lymphocytes in primary and metastatic lesions of advanced stage ovarian cancer," *Cancer Immunol ImmunoTher.*, 58(3):449-459 (2009).
Leffers et al., "Survival of ovarian cancer patients overexpressing the tumour antigen p53 is diminished in case of MHC class I down-regulation," *Gynecol Oncol.*, 110(3):365-373 (2008).
Li et al., "4-1BB (CD137) ligand enhanced anti-tumor immune response against mouse forestomach carcinoma in vivo," *Cell Mol Immunol.*, 5(5):379-384 (2008).
Li et al., "Interaction of human MUC1 and beta-catenin is regulated by Lck and ZAP-70 in activated Jurkat T cells," *Biochem Biophys Res Commun.*, 315(2):471-476 (2004).
Lolli et al., "The glycopeptides CSF114(Glc) detects serum antibodies in multiple sclerosis," *Journal of Neuroimmunology*, 167(1-2):131-137 (2005).
Loskog et al., "Addition of the CD28 signaling domain to chimeric T-cell receptors enhances chimeric T-cell resistance to T regulatory cells," *Leukemia*, 20(10):1819-1828 (2006).
Maher et al., "Human T-lymphocyte cytotoxicity and proliferation directed by a single chimeric TCRzeta /CD28 receptor," *Nat Biotechnol.*, 20(1):70-75 (2002).
Marcos-Silva et al., "A novel monoclonal antibody to a defined peptide epitope in MUC16," *Glycobiology*, 25(11):1172-1182 (2015).
Marcos-Silva et al., "Characterization of Binding Epitopes of CA125 Monoclonal Antibodies," *Journal of Proteome Research*, 13(7):3349-3359 (2014).
Markwell et al., "Surface-specific iodination of membrane proteins of viruses and eucaryotic cells using 1,3,4,6-tetrachloro-3alpha,6alpha-diphenylglycoluril," *Biochemistry*, 17(22):4807-4817 (1978).
Moeller et al., "A functional role for CD28 costimulation in tumor recognition by single-chain receptor-modified T cells," *Cancer Gene Ther.*, 11(5):371-379 (2004).
Moore et al., "Current stale of biomarker development for clinical application in epithelial ovarian cancer," *Gynecol Oncol.*, 116(2):240-245 (2010).
Nap et al., "Immunohistochemical characterization of 22 monoclonal antibodies against the CA125 antigen: 2nd report from the ISOBM TD-1 Workshop," *Tumour Biol.*, 17(6):325-331 (1996).
Nelson, "The impact of T-cell immunity on ovarian cancer outcomes," *Immunol Rev.*, 222:101-116, (2008).
Nustad et al., "Epitopes on CA 125 from cervical mucus and ascites fluid and characterization of six new antibodies. Third report from the ISOBM TD-1 workshop," *Tumour Biol.*, 23(5):303-314 (2002).
Nygren, "Conjugation of horseradish peroxidase to $F_{ab}$ fragments with different homobifunctional and heterobifunctional cross-linking reagents. A comparative study," *Journal of Histochemistry & Cytochemistry*, 30(5):407-412 (1982).
O'Brien et al., "More than 15 years of CA 125: what is known about the antigen, its structure and its function," *Int J Biol Markers*, 13(4):188-195 (1998).
O'Brien et al., "The CA 125 gene: a newly discovered extension of the glycosylated N-terminal domain doubles the size of this extracellular superstructure," *Tumour Biol.*, 23(3):154-169 (2002).
O'Brien et al., "The CA 125 gene: an extracellular superstructure dominated by repeat sequences," *Tumour Biol.*, 22(6):348-366 (2001).
Orlandi et al., "Cloning immunoglobulin variable domains for expression by the polymerase chain reaction," *Proc Natl Acad Sci., USA*, 86(10):3833-3837 (1989).
Pain et al., "Preparation of protein A-peroxidase monoconjugate using a heterobifunctional reagent, and its use in enzyme immunoassays," *J Immunol Methods*, 40(2):219-230 (1981).
Park, "The extracellular portion of the MUC16 cytoplasmic domain is detectable in ovarian carcinoma using a novel monoclonal antibody, 4H11," *Modern pathology*, 0893-3952 (21 (suppl. 1)):217A-218A (Jan. 1, 2008).
Parker et al., "Expansion and characterization of T cells transduced with a chimeric receptor against ovarian cancer," *Hum Gene Ther.*, 11(17):2377-2387 (2000).
Ponnusamy et al., "MUC4 activates HER2 signalling and enhances the motility of human ovarian cancer cells," *Br J Cancer*, 99(3):520-526 (2008).

(56) References Cited

OTHER PUBLICATIONS

Pule et al., "Virus-specific T cells engineered to coexpress tumor-specific receptors: persistence and antitumor activity in individuals with neuroblastoma," *Nat Med.*, 14(11):1264-1270 (2008).
Quintas-Cardama et al., "Multifactorial optimization of gammaretroviral gene transfer into human T lymphocytes for clinical application," *Hum Gene Ther.*, 18(12):1253-1260 (2007).
Ramsauer et al., "MUC4-ErbB2 complex formation and signaling in polarized CACO-2 epithelial cells indicate that Muc4 acts as an unorthodox ligand for ErbB2," *Mol Biol Cell* 17(7):2931-2941 (2006).
Rao et al., "Expression of the Carboxy-Terminal Portion of MUC16/CA125 Induces Transformation and Tumor Invasion," *PLoS One*, 10(5):e0126633 (2015).
Rao et al., "Novel Monoclonal Antibodies Against the Proximal (Carboxy-Terminal) Portions of MUC16," *Applied Immunohistochemistry & Molecular Morphology*, 18(5):462-472 (2010).
Raspollini et al., "Tumour-infiltrating gamma/delta T-lymphocytes are correlated with a brief disease-free interval in advanced ovarian serous carcinoma," *Ann Oncol.*, 16(4):590-596 (2005).
Ren et al., "Human MUC1 carcinoma-associated protein confers resistance to genotoxic anticancer agents," *Cancer Cell*, 5(2):163-175 (2004).
Ren et al., "MUC1 oncoprotein is targeted to mitochondria by heregulin-induced activation of c-Src and the molecular chaperone HSP90," *Oncogene*, 25(1):20-31 (2006).
Riviere et al., "Effects of retroviral vector design on expression of human adenosine deaminase in murine hone marrow transplant recipients engrafted with genetically modified cells," *Proc Natl Acad Sci., USA*, 92(15):6733-6737 (1995).
Rosen et al., "Potential markers that complement expression of CA125 in epithelial ovarian cancer," *Gynecol Oncol.*, 99(2):267-277 (2005).
Rustin et al., "Use of CA-125 in clinical trial evaluation of new therapeutic drugs for ovarian cancer," *Clin Cancer Res.*, 10(11):3919-3926 (2004).
Sadelain et al., "Targeting tumours with genetically enhanced T lymphocytes," *Nat Rev Cancer*, 3(1):35-45 (2003).
Sadelain et al., "The promise and potential pitfalls of chimeric antigen receptors," *Curr Opin Immunol.*, 21(2):215-223 (2009).
Salih et al., "Constitutive expression of functional 4-1BB (CD137) ligand on carcinoma cells," *J Immunol.*, 165(5):2903-2910 (2000).
Santos et al., "Sensitive in vivo imaging of T cells using a membrane-bound *Gaussia princeps* luciferase," *Nat Med.*, 15(3):338-344 (2009).
Sato et al., "Intraepithelial CD8+ tumor-infiltrating lymphocytes and a high CD8+/regulatory T cell ratio are associated with favorable prognosis in ovarian cancer," *Proc Natl Acad Sci., USA*, 102(51):18538-18543 (2005).
Savoldo et al., "Epstein Barr virus specific cytotoxic T lymphocytes expressing the anti-CD3Ozeta artificial chimeric T-cell receptor for immunotherapy of Hodgkin disease," *Blood*, 110(7):2620-2630 (2007).
Singer, "The structure and insertion of integral proteins in membranes," *Annu Rev Cell Biol.*, 6:247-296, A: pp. 247-268 (1990).
Singer, "The structure and insertion of integral proteins in membranes," *Annu Rev Cell Biol.*, 6:247-296, B: pp. 269:296 (1990).
Singh et al., "Clinical potential of mucins in diagnosis, prognosis, and therapy of ovarian cancer," *Lancet Oncol.*, 9(11):1076-1085 (2008).
Song et al., "Peptide ligand-mediated liposome distribution and targeting to EGFR expressing tumor in vivo," *Int J Pharm.*, 363(1-2):155-161 (2008).
Sorensen et al., "Chemoenzymatically synthesized multimeric Tn/STn MUC1 glycopeptides elicit cancer-specific anti-MUC1 antibody responses and override tolerance," *Glycobiology*, 16(2):96-107 (2006).
Soslow, "Histologic subtypes of ovarian carcinoma: an overview," *Int J Gynecol Pathol.*, 27(2):161-174 (2008).
Stephan et al., "T cell-encoded CD8O and 4-1BBL induce auto- and transcostimulation, resulting in tumor rejection," *Nat Med.*, 13(12):1440-1449 (2007).
Strome et al.,"A mechanistic perspective of monoclonal antibodies in cancer therapy beyond target-related effects," *The Oncologist*, 12:1084-95 (2007).
Sun et al., "Quality of life for patients with epithelial ovarian cancer," *Nat Clin Pract Oncol*, 4(1):18-29 (2007).
Till et al., "Adoptive immunotherapy for indolent non-Hodgkin lymphoma and mantle cell lymphoma using genetically modified autologous CD20-specific T cells," *Blood*, 112(6):2261-2271 (2008).
Tomsova et al., "Prognostic significance of CD3+ tumor-infiltrating lymphocytes in ovarian carcinoma," *Gynecol Oncol.*, 108(2):415-420 (2008).
Voinea et al., "Designing of 'intelligent' liposomes for efficient delivery of drugs," *J Cell Mol Med.*, 6(4):465-474 (2002).
Wan et al., "Expression of co-stimulator 4-1BB molecule in hepatocellular carcinoma and adjacent non-tumor liver tissue, and its possible role in tumor immunity," *World J Gastroenterol.*, 10(2):195-199 (2004).
Wang et al., "A T cell-independent antitumor response in mice with bone marrow cells retrovirally transduced with an antibody/Fc-gamma chain chimeric receptor gene recognizing a human ovarian cancer antigen," *Nat Med.*, 4(2):168-172 (1998).
Wang et al., "Universal PCR amplification of mouse immunoglobulin gene variable regions: the design of degenerate primers and an assessment of the effect of DNA polymerase 3' to 5' exonuclease activity," *J Immunol Methods*, 233(1-2):167-177 (2000).
Westwood et al., "Adoptive transfer of T cells modified with a humanized chimeric receptor gene inhibits growth of Lewis-Y-expressing tumors in mice," *Proc Natl Acad Sci., USA*, 102(52):19051-19056 (2005).
Wilkie et al., "Retargeting of human T cells to tumor-associated MUC1: the evolution of a chimeric antigen receptor," *J Immunol.*, 180(7):4901-4909 (2008).
Wolf et al., "The expression of the regulatory T cell-specific forkhead box transcription factor FoxP3 is associated with poor prognosis in ovarian cancer," *Clin Cancer Res.*, 11(23):8326-8331 (2005).
Woo et al., "Regulatory CD4(+)CD25(+) T cells in tumors from patients with early-stage non-small cell lung cancer and late-stage ovarian cancer," *Cancer Res.*, 61(12):4766-4772 (2001).
Written Opinion of the International Searching Authority for International Application No. PCT/US2016/022643, dated Sep. 5, 2016.
Written Opinion of the International Searching Authority for International Application No. PCT/US2011/030025, dated Feb. 8, 2012.
Yin et al., "Molecular cloning of the CA125 ovarian cancer antigen: identification as a new mucin, MUC16," *J. Biol Chem.*, 276(29):27371-27375 (2001).
Yin et al., "Ovarian cancer antigen CA125 is encoded by the MUC16 mucin gene," *Int J Cancer*, 98(5):737-740 (2002).
Zhang et al., "Intratumoral T cells, recurrence, and survival in epithelial ovarian cancer," *N Engl J Med.*, 348(3):203-213 (2003).
Sun et al., "Metabolic and Functional Profiling of the Normal Rat Retina," *J Comp Neurol*, 505:92-113 (2007).
Ahmad et al., 2004, "Galectin-3 precipitates as a pentamer with synthetic multivalent carbohydrates and forms heterogeneous cross-linked complexes," J. Biol. Chem. 279, 10841-10847.
Alper et al., 2001, "Epidermal growth factor receptor signaling and the invasive phenotype of ovarian carcinoma cells," J. Natl. Cancer Inst. 93, 1375-1384.
Bast et al., 1998, "CA125: the past and the future," Int. J. Biol. Markers 13, 179-187.
Burton et al., 2015, "Antibody responses to envelope glycoproteins in HIV-1 infection," Nat Immunol 16, 571-576.
Cheon et al., 2009, "CA125/MUC16 is dispensable for mouse development and reproduction," PLoS One 4: e4675.
Cohen-Anisfeld et al., 1993, "A practical, convergent method for glycopeptide synthesis," J. Am. Chem. Soc., 115:10531-10537.
Corrales et al., 2009, "Conjunctival mucin mRNA expression in contact lens wear," Optom. Vis. Sci. 86: 1051-1058.

(56) References Cited

OTHER PUBLICATIONS

Duraisamy et al., 2006, "Distinct evolution of the human carcinoma-associated transmembrane mucins, MUC1, MUC4 and MUC16," Gene 373: 28-34.
Fernandez-Tejada et al., 2014, "Chemical synthesis of the β-subunit of human luteinizing (hLH) and chorionic gonadotropin (hCG) glycoprotein hormones," J. Am. Chem. Soc. 136, 8450-8458.
Govindarajan et al., 2010, "Membrane-tethered mucins have multiple functions on the ocular surface," Exp. Eye Res. 90: 655-663.
Granovsky et al., 2000, "Suppression of tumor growth and metastasis in Mgat5-deficient mice," Nat. Med. 6, 306-312.
Heller et al., 1996, "Resampling procedures to compare two survival distributions in the presence of right censored data," Biometrics 52: 1204-1213.
Hirabayashi et al., 2002, "Oligosaccharide specificity of galectins: a search by frontal affinity chromatography," Biochim. Biophys. Acta 1572, 232-254.
Huang et al., 2005, "MUC1 oncoprotein blocks glycogen synthase kinase 3beta-mediated phosphorylation and degradation of beta-catenin," Cancer Res. 65: 10413-10422.
Kabawat et al., 1983, "Tissue distribution of a coelomic-epithelium-related antigen recognized by the monoclonal antibody OC125," Int. J. Gynecol. Pathol. 2: 275-285.
Lajoie et al., 2007, "Plasma membrane domain organization regulates EGFR signaling in tumor cells," J. Cell Biol. 179, 341-356.
Lau et al., 2007, "Complex N-glycan number and degree of branching cooperate to regulate cell proliferation and differentiation," Cell 129, 123-134.
Li et al., 2003, "Human DF3/MUC1 carcinoma-associated protein functions as an oncogene," Oncogene 22: 6107-6110.
Likhosherstov et al., 1986, "A new simple synthesis of amino sugar β-d-glycosylamines," Carbohydr. Res. 146, C1-C5.
Liu et al., 2004, "A genetically defined model for human ovarian cancer," Cancer Res. 64: 1655-1663.
Lloyd et al., 2001, "Synthesis and secretion of the ovarian cancer antigen CA 125 by the human cancer cell line NIH:OVCAR-3," Tumour Biol. 22: 77-82.
Mascola et al., 2013, "HIV-1 neutralizing antibodies: understanding nature's pathways," Immunol. Rev. 254, 225-244.
Mazal et al., 2013, "Monoclonal antibodies toward different Tn-amino acid backbones display distinct recognition patterns on human cancer cells. Implications for effective immuno-targeting of cancer," Cancer Immunol. Immunother. 62, 1107-1122.
Mazzoletti et al., 2010, "PI3K/AKT/mTOR Inhibitors in Ovarian Cancer," Curr. Med. Chem. 17: 4433-4447.
Nakada et al., 1993, "Epitopic structure of Tn glycophorin A for an anti-Tn antibody (MLS 128)," Proc. Natl. Acad. Sci. USA 90, 2495-2499.
Ohno et al., 1985, "Antigen-binding specificities of antibodies are primarily determined by seven residues of VH," Proc. Natl. Acad. Sci. U.S.A., 82(9):2945-2949.
Osinaga et al., 2000, "Analysis of the fine specificity of Tn-binding proteins using synthetic glycopeptide epitopes and a biosensor based on surface plasmon resonance spectroscopy," FEBS Lett. 469, 24-28.
Partridge et al., 2004, "Regulation of cytokine receptors by Golgi N-glycan processing and endocytosis," Science 306, 120-124.
Ramsauer et al., 2003, "Muc4/sialomucin complex, the intramembrane ErbB2 ligand, translocates ErbB2 to the apical surface in polarized epithelial cells," J. Biol. Chem. 278: 30142-30147.
Rao et al., 2017, "Antibodies Against Specific MUC16 Glycosylation Sites Inhibit Ovarian Cancer Growth," ACS Chem. Biol. 12(8):2085-2096.
Rao et al., 2011, "Dual-fluorescence isogenic high-content screening for MUC16/CA125 selective agents," Mol. Cancer Ther. 10: 1939-1948.
Scholler et al., 2007, "CA125 in ovarian cancer," Biomark Med. 1, 513-523.
Seelenmeyer et al., 2003, "The cancer antigen CA125 represents a novel counter receptor for galectin-1," J. Cell Sci. 116(Pt 7): 1305-1318.
Shinoda et al., 2008, "Kruppel-like factor 5 causes cartilage degradation through transactivation of matrix metalloproteinase 9," J. Biol. Chem. 283: 24682-24689.
Strausberg et al., 2002, "Generation and initial analysis of more than 15,000 full-length human and mouse cDNA sequences," Proc. Natl. Acad. Sci. USA 99: 16899-16903.
Taylor et al., 2010, "Integrative genomic profiling of human prostate cancer," Cancer Cell 18: 11-22.
The Cancer Genome Atlas Research Network, 2008, "Comprehensive genomic characterization defines human glioblastoma genes and core pathways," Nature 455:1061-1068.
Thapi et al., Published Apr. 2013, "Abstract 3045: Glycosylation dependence in MUC16/CA125 expression in ovarian cancer," Proceedings: AACR 104th Annual Meeting 2013; Apr. 6-10, 2013; Washington, DC; DOI: 10.1158/1538-7445.AM2013-3045.
Ventura et al., 2010, "Activation of the MEK-S6 pathway in high-grade ovarian cancers," (2010) Appl. Immunohistochem. Mol. Morphol. 18: 499-508.
Wang et al., Published Aug. 2015, "Abstract 141: MUC16/CA125 and Epithelial Growth Factor Receptor functionality in ovarian cancer," Proceedings: AACR 106th Annual Meeting 2015; Apr. 18-22, 2015; Philadelphia, PA; DOI: 10.1158/1538-7445.AM2015-141.
Wang et al., 2012, "An advance in the chemical synthesis of homogeneous N-linked glycopolypeptides by convergent aspartylation," Angew. Chem. Int. Ed. 51, 11571-11575.
Xing et al., 2006, "A mouse model for the molecular characterization of brcal-associated ovarian carcinoma," Cancer Res. 66: 8949-8953.
Zorn et al., 2009, "The prognostic value of pretreatment CA 125 in patients with advanced ovarian carcinoma: a Gynecologic Oncology Group study," Cancer 115: 1028-1035.
Pule et al., "Artifical T-cell receptors," *Cytotherapy*, 5(3):211-226 (2003).
Dondelinger et al., "Understanding the Significance and Implications of Antibody Numbering and Antigen-Binding Surface/Residue Definition," *Front. Immunol.*, 9:1-15 (2008).
Finkelstein et al. eds., *Protein Physics: A Course of Lectures*, 4th Edition, Academic Press, Cambridge, MA, p. 23 (2012).
Yarilin, "Immunology Basics," Education material for students of medical universities, *Moscow, Medicine*, pp. 172-174 (1999) (English translation only).
Almagro et al., "Humanization of antibodies," *Front. Biosci.*, 13:1619-1633 (2008).
De Genst et al., "Antibody repertoire development in camelids," *Develop. Comp. Immunol.*, 30(1-2):187-198 (2006).
Diamond et al., "Somatic mutation of the T15 heavy chain gives rise to an antibody with autoantibody specificity," *Proc. Natl. Acad. Sci.* USA, 81:5841-5844 (1984).
Kang et al., "Antibody redesign by chain shuffling from random combinatorial immunoglobulin libraries," *Proc. Natl. Acad. Sci.* USA, 88:11120-11123 (1991).
Rudikoff et al., "Single amino acid substitution altering antigen-binding specificity," *Proc. Natl. Acad. Sci.* USA, 79:1979-1983 (1982).
Sadelain et al., "The basic principles of chimeric antigen receptor design," *Cancer Discovery*, 3:388-398 (2013).
Sikkink et al., "Biochemical and aggregation analysis of Bence Jones proteins from different light chain diseases," *Amyloid*, 15(1):29-39 (2008).
Yoshinaga et al., "Ig L-chain Shuffling for Affinity Maturation of Phage Library-derived Human Anti-human MCP-1 Antibody Blocking its Chemotactic Activity," *J. Biochem.*, 143(5):593-601 (2008).

Peptide 1 near Cleavage Site:
NFSPLARRVDRVAIYEE (SEQ ID NO:01)

Peptide 2 before Transmembrane:
TLDRSSVLVDGYSPNRNE (SEQ ID NO:02)

Peptide 3 inside Transmembrane:
CGVLVTTRRRKKEGEYNVQQQ (SEQ ID NO:03)

FIGURE 1

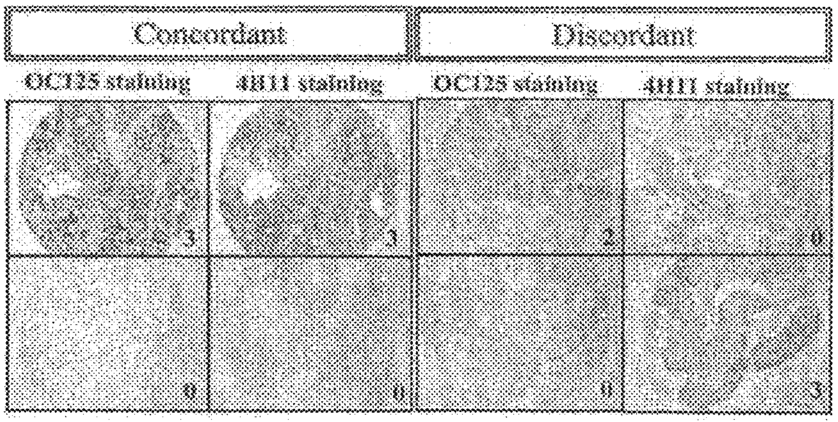

Tissue microarrays were scored from 0 to 3 in one-half (+) increments for cytoplasmic and/or membranous staining
0 – no staining
1 – strong or weak <5%
1+ – strong or weak 5-50%
2 – strong 51-75% or weak 51-100%
2+ – strong (76-99%)
3 – strong (100%)

| | Stain score | | |
|---|---|---|---|
| n=518 | 0 | 1-1+ | 2-3 |
| OC125 | 60 (11%) | 122 (24%) | 336 (65%) |
| 4H11 | 128 (25%) | 116 (22%) | 273 (53%) |

Concordance between OC125 and 4H11 staining was based on the amount of difference between the scores
Concordant = 0 – ½ difference
Partially concordant = 1-1 ½ difference
Discordant = 2-3 difference

| OC125/4H11 (n=518) | |
|---|---|
| Concordant | 286 (55%) |
| Partially concordant | 193 (37%) |
| Discordant | 39 (8%) |

Of the 39 discordant cases,
OC125 > 4H11 in 59%
4H11 > OC125 in 41%

| | |
|---|---|
| OC125>4H11 | 23 (59%) |
| 4H11>OC125 | 16 (41%) |

Overall 3-4% of all ovarian serous carcinomas expressed 4H11 but not OC125

4A5 VH (SEQ ID NO:04)

gtgaagctggaggagtcagggggaggcttcgtgaagcctggagggtccctcaaaatctcctgtgcagcctctggattcac
tttcagaaactatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctccacttg
caaatgggcagtctgaggtctggggacacggccatgtattactgtgcaaggcagggatttggtaactacggtgattacta
tgctatggactactggggccaagggaccacggtcaccgtctcctca

FIG. 8B

4A5 VL (SEQ ID NO:05)

gacattgagctcacccagtctccatcctccctggctgtgtcagcaggagagaaggtcactatgagctgcaaatccagtca
gagtctgctcaacagtagaacccgaaagaaccagttggcttggtaccagcaaaaaacaggacagtctcctgaactgctga
tctactgggcatccactcggcaatctggggtccctgatcgcttcacaggcagtggatctgggacagatttcactctcacc
atcagcagtgtgcaggctgaagacctggcagtttattactgccagcaatcttataatctactcacgttcggtcctgggac
caagctggagatcaaacgg

FIG. 8C

4H11 VH (SEQ ID NO:06)

gtgaagctgcaggagtcagggggaggcttcgtgaagcctggagggtccctcaaagtctcctgtgcagcctctggattcac
tttcagtagctatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctgcacctg
caaatgggcagtctgaggtctggggacacggccatgtattactgtgcaaggcagggatttggtaactacggtgattacta
tgctatggactactggggccaagggaccacggtcaccgtctcctca

FIG. 8D

4H11 VL (SEQ ID NO:07)

gacattgagctcacccagtctccatcctccctggctgtgtcagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgccagcaatcttataatctactcacgttcggtcctgggac
caagctggaggtcaaacgg

FIG. 8E

9B11 VH (SEQ ID NO:08)

gtgaagctggaggagtcagggggagacttggtgaagcctggagggtccctgaaactctcctgtgcagtctctggattcac
tttcagtagccattccatgtcttggattcgtcagactccagagaagaggctagagtgggtcgcatccgtgagtagtggtg
gtaggatctactattcggacagtgtgaagggccgattcaccgtcaccagagaaaatgacaggaacaccctgtatttgtta
atgagtagtctgaggtctgaggacacggccatgtattattgtggaagaggacaggtattttatgctttggacaattgggg
ccaagggaccacggtcaccgtctcctca

FIG. 8F

9B11 VL.A (SEQ ID NO:09)

gacattgagctcacccagtctccatcctccctggctgtgccagcaggagagaaggtcactatgagctgcaaatccagtca
gagtctgctcaacagtagaacccgaaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagtttattactgccagcaatcctataatctactcacgttcggtcctgggac
caagctggaggtcaaacgg

FIG. 8G

9B11 VL.B (SEQ ID NO:10)

gacattgagctcacccagtctccaaagctcctgatctacaaggtttccaaccgattttctggggtcccagacaggttcag
tggcagtggatcagggacagatttcacactcaagatcagcagagtggaggctgaggatctgggagtttattactgctttc
aaggttcacatgttccgtggacgttcggtggagggaccaagctggagatcaaacgg

FIG. 8H

24B3-VH (SEQ ID NO:11)

GAGGTGAAGCTGGAGGAGTCAGGACCTGAACTGGTGAAGCCTGGGGCTTCAGTGAAGATATCCTGCAAGGCTTCTGGTTA
CTCATTTACTGGCTACTTTATGAACTGGGTGAAGCAGACCCATGGAAAGAGCCTTGAGTGGATTGGACGTATTAATCCTT
ACAATGGTGCTACTTTCTACAATCAGAAGTTCACGGGCAAGGCCACAATGACTGTAGACAAATCCTCTACCACAGCCCAC
ATGGAGCTCCTGAGCCTGACATCTGAGGACTCTGCAGTCTATTATTGTGGAAAGGGGAATTACTACGGCCCCTTTGATTA
CTGGGGCCAAGGGACCACGGTCACCGTCTCCTCA

FIG. 8I

24B3-VL (SEQ ID NO:12)

GACATTGAGCTCACCCAGTCTCCATCTTATCTTGCTGCATCTCCTGAAGAAACCATTACTATTAATTGCAGGGCAAGTAA
GAGCATTAGCAAATATTTAGCCTGGTATCAAAAGAAACCTGGCAAAACTAATAAGCTTCTTATCTACTCTGGATCCACTT
TGCAATCTGGAATTCCATCAAGGTTCAGTGGCAGTGGATCTGGTACAGATTTCACTCTCACCATCAGTAGCCTGGAGCCT
GAAGATTTTGCAATGTATTACTGTCAACAGCATAATGAATACCCGTGGACGTTCGGTGGAGGGACCAAGCTGGAGATCAA
ACGGGCGGCCGCA

FIG. 9A

Homo sapiens MUCIN-16 (GenBank NP_078966) (SEQ ID NO:13)

```
   1 mlkpsglpgs ssptrslmtg srstkatpem dsgltgatls pktstgaivv tehtlpftsp
  61 dktlasptss vvgrttqslg vmssalpest srgmthseqr tspslspqvn gtpsrnypat
 121 smvsglsspr trtsstegnf tkeastytlt vettsgpvte kytvptetst tegdstetpw
 181 dtryipvkit spmktfadst askenapvsm tpaettvtds htpgrtnpsf gtlyssfldl
 241 spkgtpnsrg etslelilst tgypfsspep gsaghsrist saplsssasv ldnkisetsi
 301 fsgqsltspl spgvpearas tmpnsaipfs mtlsnaetsa ervrstissl gtpsistkqt
 361 aetiltfhaf aetmdipsth iaktlasewl gspgtlggts tsaltttsps ttlvseetnt
 421 hhstsgkete gtlntsmtpl etsapgeese mtatlvptlg fttldskirs psqvsshpt
 481 relrttgsts grqssstash gssdilratt astskasswt sestaqgfse pqhtqwvets
 541 psmkterppa stsvaapitt svpsvvsgft tlktsstkgi wleetsadtl igestagptt
 601 hqfavptgis mtggsstrgs qgtthlltra tassetsadl tlstngvpvs vspavsktaa
 661 gssppggtkp sytmvssvip etsslqssaf regtslgltp lntrhpfssp epdsaghtki
 721 stsipllssa svledkvsat stfshhkats sittgtpeis tktkpssavl ssmtlsnaat
 781 spervrnats plthpspsge etagsvltls tsaettdspn ihptgtltse ssespstlsl
 841 psvsgvkttf sstpsthlf tsgeetests npsvsqpets vsrvrttlas tsvptpvfpt
 901 mdtwptrsaq fsshlvssl ratsstsvtn stgsalpkis hltgtatmsq tnrdtfndsa
 961 apqsttwpet sprfktglps atttvstsat slsatvmvsk ftspatssme atsirepstt
1021 ilttettngp gsmavastni pigkgyiteg rldtshlpig ttassetsmd ftmakesvsm
1081 svspsqsmda agsstpgrts qfvdtfsddv yhltsreiti prdgtssalr pqmtathpps
1141 pdpgsarstw lgilssspss ptpkvtmsst fstqrvttsm imdtvetsrw nmpnlpstts
1201 ltpsniptsg aigkstlvpl dtpspatsle asegglptls typestntps ihlgahasse
1261 spstikltma svvkpgsytp ltfpsiethi hvstarmays sgsspemtap getntgstwd
1321 pttyitttdp kdtssaqvst phsvrtlrtt enhpktesat paaysgspki ssspnltspa
1381 tkawtitdtt ehstqlhytk laekssgfet qsapgpvsvv iptsptigss tleltsdvpg
1441 eplvlapseq ttitlpmatw lstsltesma stdldissps spmstfaifp pmstpshels
1501 kseadtsair ntdsttldqh lgirslgrtg dlttvpitpl tttwtsvieh stqaqdtlsa
1561 tmsptnvtqs lkdqtsipas aspshltevy pelgtqgrss seattfwkps tdtlsreiet
1621 gptniqstpp mdntttgsss sgvtlgiahl pigtsspaet stnmalerrs statvsmagt
1681 mgllvtsapg rsisqslgrv ssvlsestte gvtdsskgss prlntqgnta lsssiepsya
1741 egsqmstsip ltssptrpdv efiggstfwt kevttvmtsd iskssartes ssatlmstal
1801 gstentgkek lrtasmdlps ptpsmevtpw isltlsnapn ttdsldlshg vhtssagtla
1861 tdrslntgvt rasrlengsd tssksismgn sthtsmtyte ksevsssihp rpetsapgae
1921 ttltstpgnr aisltlpfss ipveevistg itsgpdinsa pmthspitpp tivwtstgti
1981 eqstqplhav ssekvsvqtq stpyvnsvav aaspthensv sagsstsspy ssasleslds
2041 tisrrnaits wlwdlttslp tttwpstsls ealssghsgv snpsstttef plfsaastsa
2101 akqrnpetet hgpqntaast lntdassvtg lsetpvgasi ssevplpmai tsrsdvsglt
2161 sestanpslg tassagtklt rtislptses lvsfrmnkdp wtvsiplgsh pttntetsip
2221 vnsagppgls tvasdvidtp sdgaesiptv sfspspdtev ttishfpekt thsfrtissl
2281 theltsrvtp ipgdwmssam stkptgasps itlgerrtit saapttspiv ltasftetst
2341 vsldnettvk tsdildarkt nelpsdssss sdlintsias stmdvtktas isptsisgmt
2401 assspslfss drpqvptstt etntatspsv ssntysldgg snvggtpstl ppftithpve
2461 tssallawsr pvrtfstmvs tdtasgenpt ssnsvvtsvp apgtwtsvgs ttdlpamgfl
2521 ktspageahs llastiepat aftphlsaav vtgssatsea sllttseska ihsspqtptt
```

FIG. 9B

```
2581 ptsganwets atpesllvvt etsdttltsk ilvtdtilfs tvstppskfp stgtlsgasf
2641 ptllpdtpai pltateptss latsfdstpl vtiasdslgt vpettltmse tsngdalvlk
2701 tvsnpdrsip gitiqgvtes plhpsstsps kivaprntty egsitvalst lpagttgslv
2761 fsqssenset talvdssagl erasvmpltt gsqgmassgg irsgsthstg tktfsslplt
2821 mnpgevtams eittnrltat qstapkgipv kptsaesgll tpvsassspe kafasltta p
2881 ptwgipqstl tfefsevpsl dtksaslptp gqslntipds dastasssls kspeknprar
2941 mmtstkaisa ssfqstgfte tpegsaspsm aghep rvpts gtgdpryase smsypdpska
3001 ssamtstsla skltrlfstg qaarsgssss pislstsket sflsptasts rktslflgps
3061 marqpnilvh lqtsaltlsp tstlnmsqee ppeltssqti aeeegttaet qtltftpset
3121 ptsllpvssp teptarrkss petwassisv paktslvett dgtlvttikm ssqaaqgnst
3181 wpapaeetgs spagtspgsp emsttlkims skepsispei rstvrnspwk tpettvpmet
3241 tvepvtlqst algsgstsis hlptgttspt ksptenmlat ervslspspp eawtnlysgt
3301 pggtrqslat mssvslespt arsitgtggq sspelvsktt gmefsmwhgs tggttgdthv
3361 slstssnile dpvtspnsvs sltdkskhkt etwvsttaip stvlnnkima aeqgtsrsvd
3421 eaysstsswe dqtsgsditl gaspdvtntl yitstaqtts lvslpsgdqg itsltnpsgg
3481 ktssassvts psiglelra nvsavksdia ptsghlsqts spaevsildv ttaptpgist
3541 titt mgtnsi stttpnpevg mstmdstpat erttstehp stwsstaasd swtvtdmtsn
3601 lkvarspgti stmhttsfla sstelds mst phgritvigt slvtpssdas avktetstse
3661 rtlspsdtta stpistfsrv grmsisvpdi lstswtpsst esedvpvsmv stdhastktd
3721 pntplstflf dslstldwdt grslssatat tsapqgattp qeltletmis patsqlpfsi
3781 ghitsavtpa amarssgvtf srpdptskka eqtstqlptt tsahpgqvpr saattldvip
3841 htaktpdatf qrqgqtaltt earatsdswn ekekstpsap witemmnsvs edtikevtss
3901 ssvlrtlntl dinlesgtts spswksspye riapsesttd keaihpstnt vetrgwvtss
3961 ehashstips hsasskltsp vvttstreqa ivsmatttwp estrartepn sfltielrdv
4021 spymdtsstt qtsiisspgs taitkgprte itsskrisss flaqsmrssd spseaitrls
4081 nfpamtesgg milamqtspp gatslsaptl dtsatsswtg tplattqrft ysekttlfsk
4141 gpedtsqpsp psveetssss slvpihatts psnilltsqg hspsstppvt svflsetsgl
4201 gkttdmsris lepgtslppn lsstageals tyeasrdtka ihhsadtavt nmeatsseys
4261 pipghtkpsk atsplvtshi mgditsstsv fgssettsie tvssvnqglq erstsqvass
4321 atetstvith vssgdatthv tktqatfssg tsissphqfi tstntftdvs tnpstslimt
4381 essgvtittq tgptgaatqg pylldtstmp yltetplavt pdfmqsektt liskgpkdvs
4441 wtsppsvaet sypssltpfl vttippatst lqghtsspv satsvltsgl vkttdmlnts
4501 mepvtnspqn lnnpsneila tlaattdiet ihpsinkavt nmgtassahv lhstlpvsse
4561 pstatspmvp assmgdalas isipgsettd iegeptsslt agrkenstlq emnsttesni
4621 ilsnvsvgai teatkmevps fdatfiptpa qstkfpdifs vassrlsnsp pmtisthmtt
4681 tqtgssgats kiplaldtst letsagtpsv vtegfahski ttamnndvkd vsqtnppfqd
4741 eassps sqap vlvttlpssv aftpqwhsts spvsmssvlt sslvktagkv dtsletvtss
4801 pqsmsntldd isvtsaattd ietthpsint vvtnvgttgs afeshstvsa ypepskvtsp
4861 nvttstmedt tisrsipkss ktrtetett ssltpklret sisqeitsst etstvpykel
4921 tgattevsrt dvtssssts f pgpdqstvsl distetntrl stspimtesa eitittqtgp
4981 hgatsqdtft mdpsnttpqa gihsamthgf sqldvttlms ripqdvswts ppsvdktssp
5041 ssflsspamt tpslisstlp edklsspmts lltsglvkit dilrtrlepv tsslpnfsst
5101 sdkilatskd skdtkeifps inteetnvka nnsghesh sp aladsetpka ttqmvitttv
5161 gdpapstsmp vhgsssttni kreptyfltp rlretstsqe ssfptdtsfl lskvptgtit
```

FIG. 9C

```
5221 svsstgvnss skistpdhdk stvppdtftg eiprvftssi ktksaemtit tqasppesas
5281 hstlpldtst tlsqggthst vtggfpysev ttlmgmgpgn vswmttppve etssvsslms
5341 spamtspspv sstspqsips splpvtalpt svlvtttdvl gttspasvts sppnlssith
5401 erpatykdta hteaasmhst ntavtnvgts gsghksqssv ladsetskat plmsttstlg
5461 dtsvststpn isqtnqiqte ptaslsprlr esstsektss ttetntafsy vptgaitqas
5521 rtsisssrts isdldrptia pdistgmitr lftspimtks aemtvttqtt tpgatsqgil
5581 pwdtsttlfq ggthstvsqg fphseittlr srtpgdvswm ttppveetss gfslmspsmt
5641 spspvsstsp esipssplpv talltsvlvt ttnvlgttsp epvtssppnl ssptqerltt
5701 ykdtahteam hasmhtntav anvgtsisgh esqssvpads htskatspmg itfamgdtsv
5761 ststpaffet riqtestssl ipglrdtrts eeintvtets tvlsevpttt ttevsrtevi
5821 tssrttisgp dhskmspyis tetitrlstf pfvtgstema itnqtgpigt isqatltldt
5881 sstaswegth spvtqrfphs eetttmsrst kgvswqspps veetsspssp vplpaitshs
5941 slysavsgss ptsalpvtsl ltsgrrktid mldthselvt sslpsassfs geiltseast
6001 ntetihfsen taetnmgttn smhklhssvs ihsqpsghtp pkvtgsmmed aivststpgs
6061 petknvdrds tspltpelke dstalvmnst tesntvfssv sldaatevsr aevtyydptf
6121 mpasaqstks pdispeasss hsnsppltis thktiatqtg psgvtslgql tldtstiats
6181 agtpsartqd fvdsettsvm nndlndvlkt spfsaeeans lssqapllvt tspspvtstl
6241 qehstsslvs vtsvptptla kitdmdtnle pvtrspqnlr ntlatseatt dthtmhpsin
6301 tavanvgtts spnefyftvs pdsdpykats avvitstsgd sivstsmprs samkkiesat
6361 tfslifrlre tstsqkigss sdtstvfdka ftaattevsr teltsssrts iqgtekptms
6421 pdtstrsvtm lstfagltks eertiatqtg phratsqgtl twdtsittsq agthsamthg
6481 fsqldlstlt srvpeyisgt sppsvektss sssllslpai tspspvpttl pesrpsspvh
6541 ltslptsglv kttdmlasva slppnlgsts hkipttsedi kdtekmypst niavtnvgtt
6601 tsekesyssv payseppkvt spmvtsfnir dtivstsmpg sseitrieme stfslahglk
6661 gtstsqdpiv steksavlhk lttgatetsr tevassrrts ipgpdhstes pdistevips
6721 lpislgites snmtiitrtg pplgstsqgt ftldtpttss ragthsmatq efphsemttv
6781 mnkdpeilsw tippsiekts fssslmpspa mtsppvsstl pktihttpsp mtslltpslv
6841 mttdtlgtsp epttssppnl sstsheiltt dedttaieam hpststaatn vettssghgs
6901 qssvladsek tkatapmdtt stmghttvst smsvssettk ikrestyslt pglretsisq
6961 nasfstdtsi vlsevptgtt aevsrtevts sgrtsipgps qstvlpeist rtmtrlfasp
7021 tmtesaemti ptqtgpsgst sqdtltldts ttksqakths tltqrfphse mttlmsrgpg
7081 dmswqsspsl enpsslpsll slpattsppp isstlpvtis ssplpvtsll tsspvtttdm
7141 lhtspelvts sppklshtsd erlttgkdtt nteavhpstn taasnveips sghespssal
7201 adsetskats pmfitstqed ttvaistphf letsriqkes isslspklre tgssvetssa
7261 ietsavlsev sigatteisr tevtssarts isgsaestml peisttrkii kfptspilae
7321 ssemtiktqt sppgstsest ftldtsttps lvithstmtq rlphseittl vsrgagdvpr
7381 psslpveets ppssqlslsa mispspvsst lpasshsssa svtslltpgq vkttevldas
7441 aepetsspps lsstsveila tsevttdtek ihpfsntavt kvgtsssghe spssvlpdse
7501 ttkatsamgt isimgdtsvs tltpalsntr kiqsepassl ttrlretsts eetslatean
7561 tvlskvstga ttevsrteai sfsrtsmsgp eqstmsqdis igtiprisas svltesakmt
7621 ittqtgpsss tlestlnlnt attpswveth sivlggfphp emttsmgrgp ggvswpsppf
7681 vketsppssp lslpavtsph pvsttflahi ppsplpvtsl ltsgpatttd ilgtstepgt
7741 ssssslstts herlttykdt ahteavhpst ntggtnvatt ssgyksqssv ladsspmctt
7801 stmgdtsvlt stpafletrr iqtelasslt pglressgse gtssgtkmst vlskvptgat
```

FIG. 9D

| | | | | | | |
|---|---|---|---|---|---|---|
| 7861 | teiskedvts | ipgpaqstis | pdistrtvsw | fstspvmtes | aeitmnthts | plgattqgts |
| 7921 | tldtssttsl | tmthstisqg | fshsqmstlm | rrgpedvswm | sppllektrp | sfslmsspat |
| 7981 | tspspvsstl | pesissspl p | vtslltsgla | kttdmlhkss | epvtnspanl | sstsveilat |
| 8041 | sevttdtekt | hpssnrtvtd | vgtsssghes | tsfvladsqt | skvtspmvit | stmedtsvst |
| 8101 | stpgffetsr | iqteptsslt | lglrktssse | gtslatemst | vlsgvptgat | aevsrtevts |
| 8161 | ssrtsisgfa | qltvspetst | etitrlptss | imtesaemmi | ktqtdppgst | pesthtvdis |
| 8221 | ttpnwvetha | tvtqrfshse | mttlvsrspg | dmlwpsqssv | eetssassll | slpattspsp |
| 8281 | vsstlvedfp | saslpvtsll | npglvittdr | mgisrepgts | stsnlsstsh | erlttledtv |
| 8341 | dtedmqpsth | tavtnvrtsi | sghesqssvl | sdsetpkats | pmgttytmge | tsvsistsdf |
| 8401 | fetsriqiep | tssltsglre | tsssersssa | tegstvlsev | psgattevsr | tevissrgts |
| 8461 | msgpdqftis | pdisteaitr | lstspimtes | aesaitietg | spgatsegtl | tldtstttfw |
| 8521 | sgthstaspg | fshsemttlm | srtpgdvpwp | slpsveeass | vsssisspam | tstsffstlp |
| 8581 | esissphpv | talltlgpvk | ttdmlrtsse | petssppnls | stsaeilats | evtkdrekih |
| 8641 | psspntpvvnv | gtviykhlsp | ssvladlvtt | kptspmatts | tlgntsvsts | tpafpetmmt |
| 8701 | qptssltsgl | reistsqets | satersasls | gmptgattkv | srtealslgr | tstpgpaqst |
| 8761 | ispeistetl | tristplttt | gsaemtitpk | tghsgassqg | tftldtssra | swpgthsaat |
| 8821 | hrsphsgmtt | pmsrgpedvs | wpsrpsvekt | sppsslvsls | avtspsplys | tpsesshssp |
| 8881 | lrvtslftpv | mmkttdmldt | slepvttspp | smnitsdesl | atskatmete | aiqlsentav |
| 8941 | tqmgtisarq | efyssypglp | epskvtspvv | tsstikdivs | ttipassеit | riemestatl |
| 9001 | tptpretsts | qeihsatkps | tvpykaltsa | tiedsmtqvm | sssrgpspdq | stmsqdiste |
| 9061 | vitrlstspi | ktestemtit | tqtgspgats | rgtltldtst | tfmsgthsta | sqgfshsgmt |
| 9121 | almsrtpgdv | pwlshpsvee | assasfslss | pvmtsssp vs | stlpdsihss | slpvtsllts |
| 9181 | glvkttellg | tssepatssp | pnlsstsaei | laitevttdt | eklemtnvvt | sgythespss |
| 9241 | vladsvttka | tssmgitypt | gdtnvltstp | afsdtsriqt | ksklsltpgl | metsiseets |
| 9301 | satekstvls | svptgattev | srteaissr | tsipgpaqst | mssdtsmeti | tristpltrk |
| 9361 | estdmaitpk | tgpsgatsqg | tftldssstа | swpgthsatt | qrfpqsvvtt | pmsrgpedvs |
| 9421 | wpsplsvekn | sppsslvsss | svtspsplys | tpsgsshssp | vpvtslftsi | mmkatdmlda |
| 9481 | slepettsap | nmnitsdesl | aaskattete | aihvfentaa | shvettsate | elysssppgfs |
| 9541 | eptkvispvv | tsssirdnmv | sttmpgssgi | trieiesmss | ltpglretrt | sqditsstet |
| 9601 | stvlykmpsg | atpevsrtev | mpssrtsipg | paqstmsldi | sdevvtrlst | spimtesaei |
| 9661 | tittqtgysl | atsqvtlplg | tsmtflsgth | stmsqglshs | emtnlmsrgp | eslswtsprf |
| 9721 | vettrsssl | tslplttsls | pvsstlldss | psspl pvtsl | ilpglvktte | vldtssepkt |
| 9781 | ssspnlssts | veipatseim | tdtekihpss | ntavakvrts | ssvheshssv | ladsettiti |
| 9841 | psmgitsavd | dttvftsnpa | fsetrripte | ptfsltpgfr | etstseetts | itetsavlyg |
| 9901 | vptsattevs | mteimssnri | hipdsdqstm | spdiitevit | rlsssmmse | stqmtittqk |
| 9961 | sspgataqst | ltlatttapl | arthstvppr | flhsemttlm | srspenpswk | sslfvektss |
| 10021 | sssllslpvt | tspsvsstlp | qsipsssfsv | tslltpgmvk | ttdtstepgt | slspnlsgts |
| 10081 | veilaasevt | tdtekihpss | smavtnvgtt | ssghelyssv | sihsepskat | ypvgtpssma |
| 10141 | etsistsmpa | nfettgfeae | pfshltsgfr | ktnmsldtss | vtptntpssp | gsthllqssk |
| 10201 | tdftssakts | spdwppasqy | teipvdiitp | fnaspsites | tgitsfpesr | ftmsvtesth |
| 10261 | hlstdllpsa | etistgtvmp | slseamtsfa | ttgvpraisg | sgspfsrtes | gpgdatlsti |
| 10321 | aeslpsstpv | pfsssstfttt | dsstipalhe | itsssatpyr | vdtslgtess | ttegrlvmvs |
| 10381 | tldtssqpgr | tsssspildtr | mtesvelgtv | tsayqvpsls | trltrtdgim | ehitkipnea |
| 10441 | ahrgtirpvk | gpqtstspas | pkglhtggtk | rmettttalk | ttttalktts | ratlttsvyt |

FIG. 9E 10501 ptlgtltpln asmgmastip temmittpyv fpdvpettss latslgaets talprttpsv
10561 fnresettas lvsrsgaers pviqtldvss sepdttaswv ihpaetiptv skttpnffhs
10621 eldtvsstat shgadvssai ptnispseld altplvtisg tdtsttfptl tksphetetr
10681 ttwlthpaet sstiprtipn fshhesdatp siatspgaet ssaipimtvs pgaedlvtsq
10741 vtssgtdrnm tiptltlspg epktiaslvt hpeaqtssai ptstispavs rlvtsmvtsl
10801 aaktsttnra ltnspgepat tvslvthpaq tsptvpwtts iffhsksdtt psmttshgae
10861 sssavptptv stevpgvvtp lvtssravis ttipiltlsp gepettpsma tshgeeassa
10921 iptptvspgv pgvvtslvts sravtsttip iltfslgepe ttpsmatshg teagsavptv
10981 lpevpgmvts lvassravts ttlptltlsp gepettpsma tshgaeasst vptvspevpg
11041 vvtslvtsss gvnstsiptl ilspgelett psmatshgae assavptptv spgvsgvvtp
11101 lvtssravts ttipiltlss sepettpsma tshgveassa vltvspevpg mvtslvtssr
11161 avtsttiptl tissdepett tslvthseak misaiptlav sptvqglvts lvtssgsets
11221 afsnltvass qpetidswva hpgteassvv ptltvstgep ftnislvthp aessstlprt
11281 tsrfshseld tmpstvtspe aesssaistt ispgipgvlt slvtssgrdi satfptvpes
11341 pheseatasw vthpavtstt vprttpnysh sepdttpsia tspgaeatsd fptitvspdv
11401 pdmvtsqvts sgtdtsitip tltlssgepe tttsfityse thtssaiptl pvspgaskml
11461 tslvissgtd stttfptltе tpyepettai qlihpaetnt mvprttpkfs hsksdttlpv
11521 aitspgpeas savstttisp dmsdlvtslv pssgtdtstt fptlsetpye pettatwlth
11581 paetsttvsg tipnfshrgs dtapsmvtsp gvdtrsgvpt ttippsipgv vtsqvtssat
11641 dtstaiptlt pspgepetta ssathpgtqt gftvpirtvp ssepdtmasw vthppqtstp
11701 vsrttssfsh sspdatpvma tsprteassa vlttispgap emvtsqitss gaatsttvpt
11761 lthspgmpet tallsthprt etsktfpast vfpqvsetta sltirpgaet stalptqtts
11821 slftllvtgt srvdlsptas pgvsaktapl sthpgtetst miptstlslg llettgllat
11881 sssaetstst ltltvspavs glssasittd kpqtvtswnt etspsvtsvg ppefsrtvtg
11941 ttmtlipsem ptppktshge gvspttilrt tmveatnlat tgssptvakt tttfntlags
12001 lftplttpgm stlasesvts rtsynhrswi sttssynrry wtpatstpvt stfspgists
12061 sipsstaatv pfmvpftlnf titnlqyeed mrhpgsrkfn ateralqgll kplfrnssle
12121 ylysgcrlas lrpekdssat avdaicthrp dpedlgldre rlywelsnlt ngiqelgpyt
12181 ldrnslyvng fthrssmptt stpgtstvdv gtsgtpsssp spttagpllm pftlnftitn
12241 lqyeedmrrt gsrkfntmes vlqgllkplf kntsvgplys gcrltllrpe kdgaatgvda
12301 icthrldpks pglnreqlyw elskltndie elgpytldrn slyvngfthq ssvsttstpg
12361 tstvdlrtsg tpsslsspti maagpllvpf tlnftitnlq ygedmghpgs rkfnttervl
12421 qgllgpifkn tsvgplysgc rltslrsekd gaatgvdaic ihhldpkspg lnrerlywel
12481 sqltngikel gpytldrnsl yvngfthrts vptsstpgts tvdlgtsgtp fslpspatag
12541 pllvlftlnf titnlkyeed mhrpgsrkfn ttervlqtll gpmfkntsvg llysgcrltl
12601 lrsekdgaat gvdaicthrl dpkspgvdre qlywelsqlt ngikelgpyt ldrnslyvng
12661 fthwipvpts stpgtstvdl gsgtpsslps pttagpllvp ftlnftitnl kyeedmhcpg
12721 srkfntterv lqsllgpmfk ntsvgplysg crltllrsek dgaatgvdai cthrldpksp
12781 gvdreqlywe lsqltngike lgpytldrns lyvngfthqt sapntstpgt stvdlgtsgt
12841 psslpsptsa gpllvpftln ftitnlqyee dmhhpgsrkf ntterv1qgl lgpmfkntsv
12901 gllysgcrlt llrpekngaa tgmdaicshr ldpkspglnr eqlywelsql thgikelgpy
12961 tldrnslyvn gfthrssvap tstpgtstvd lgtsgtpssl psptsavpll vpftlnftit
13021 nlqygedmrh pgsrkfntte rvlqgllgpl fknssvgply sgcrlislrs ekdgaatgvd
13081 aicthhlnpq spgldreqly wqlsqmtngi kelgpytldr nslyvngfth rssgltstp

FIG. 9F 13141 wtstvdlgts gtpspvpspt ttgpllvpft lnftitnlqy eenmghpgsr kfnitesvlq
13201 gllkplfkst svgplysgcr ltllrpekdg vatrvdaict hrpdpkipgl drqqlywels
13261 qlthsitelg pytldrdsly vngftqrssv pttstpgtft vqpetsetps slpgptatgp
13321 vllpftlnft itnlqyeedm rrpgsrkfnt tervlqgllm plfkntsvss lysgcrltll
13381 rpekdgaatr vdavcthrpd pkspgldrer lywklsqlth gitelgpytl drhslyvngf
13441 thqssmtttr tpdtstmhla tsrtpaslsg pmtaspllvl ftinftitnl ryeenmhhpg
13501 srkfntterv lqgllrpvfk ntsvgplysg crltllrpkk dgaatkvdai ctyrpdpksp
13561 gldreqlywe lsqlthsite lgpytldrds lyvngftqrs svpttsipgt ptvdlgtsgt
13621 pvskpgpsaa spllvlftln ftitnlryee nmqhpgsrkf nttervlqgl lrslfkstsv
13681 gplysgcrlt llrpekdgta tgvdaicthh pdpksprldr eqlywelsql thnitelgpy
13741 aldndslfvn gfthrssvst tstpgtptvy lgasktpasi fgpsasshll ilftlnftit
13801 nlryeenmwp gsrkfntter vlqgllrplf kntsvgplys gcrltllrpe kdgeatgvda
13861 icthrpdptg pgldreqlyl elsqlthsit elgpytldrd slyvngfthr ssvpttstgv
13921 vseepftlnf tinnlrymad mgqpgslkfn itdnvmqhll splfqrsslg arytgcrvia
13981 lrsvkngaet rvdllctylq plsgpglpik qvfhelsqqt hgitrlgpys ldkdslylng
14041 ynepgpdepp ttpkpattfl pplseattam gyhlktltln ftisnlqysp dmgkgsatfn
14101 stegvlqhll rplfqkssmg pfylgcqlis lrpekdgaat gvdttctyhp dpvgpgldiq
14161 qlywelsqlt hgvtqlgfyv ldrdslfing yapqnlsirg eyqinfhivn wnlsnpdpts
14221 seyitllrdi qdkvttlykg sqlhdtfrfc lvtnltmdsv lvtvkalfss nldpslveqv
14281 fldktlnasf hwlgstyqlv dihvtemess vyqptsssst qhfylnftit nlpysqdkaq
14341 pgttnyqrnk rniedalnql frnssiksyf sdcqvstfrs vpnrhhtgvd slcnfsplar
14401 rvdrvaiyee flrmtrngtq lqnftldrss vlvdgyspnr nepltgnsdl pfwaviligl
14461 agllgvitcl icgvlvttrr rkkegeynvq qqcpgyyqsh ldledlq

FIG. 9G

Peptide 1

14394 14410 nfsplar rvdrvaiyee (SEQ ID NO:01)

FIG. 9H

Peptide 2

14425 14442 tldrss vlvdgyspnr ne (SEQ ID NO:02)

FIG. 9I

Peptide 3

14472 14492 cgvlvttrr rkkegeynvq qq (SEQ ID NO:03)

FIG. 9J

Transmembrane Region:

14452 14475 fwaviligl agllgvitcl icgvl (SEQ ID NO:14)

FIG. 9K

Peptide containing the cysteine loop peptide:

14367 14398 ksyf sdcqvstfrs vpnrhhtgvd slcnfspl (SEQ ID NO:15)

Figure 17:
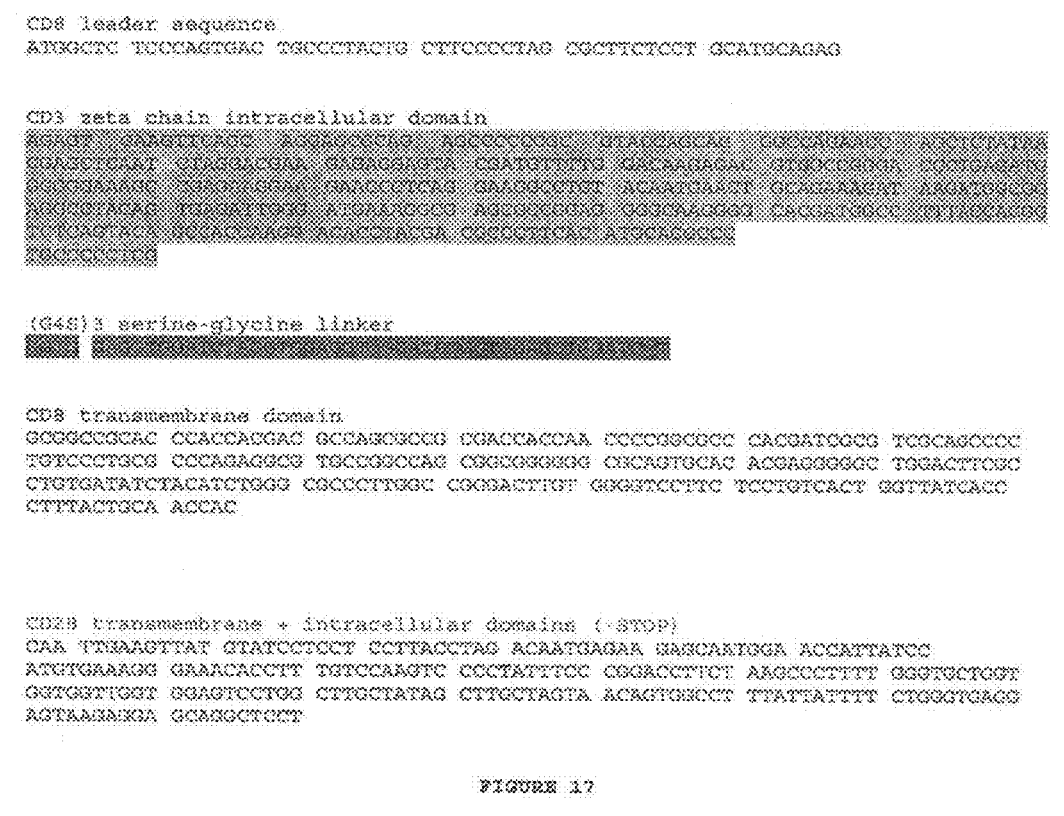

CD8 leader sequence
ATGGCTC TCCCAGTGAC TGCCCTACTG CTTCCCCTAG CGCTTCTCCT GCATGCAGAG CD3 zeta chain intracellular domain
[illegible]

(G4S)3 serine-glycine linker
[illegible]

CD8 transmembrane domain
GCGGCCGCAC CCACCACGAC GCCAGCGCCG CGACCACCAA CCCCGGCGCC CACGATCGCG TCGCAGCCCC
TGTCCCTGCG CCCAGAGGCG TGCCGGCCAG CGGCGGGGGG CGCAGTGCAC ACGAGGGGGC TGGACTTCGC
CTGTGATATCTACATCTGGG CGCCCTTGGC CGGGACTTGT GGGGTCCTTC TCCTGTCACT GGTTATCACC
CTTTACTGCA ACCAC CD28 transmembrane + intracellular domains (-STOP)
CAA TTGAAGTTAT GTATCCTCCT CCTTACCTAG ACAATGAGAA GAGCAATGGA ACCATTATCC
ATGTGAAAGG GAAACACCTT TGTCCAAGTC CCCTATTTCC CGGACCTTCT AAGCCCTTTT GGGTGCTGGT
GGTGGTTGGT GGAGTCCTGG CTTGCTATAG CTTGCTAGTA ACAGTGGCCT TTATTATTTT CTGGGTGAGG
AGTAAGAGGA GCAGGCTCCT

```
        BamHI
        ~~~~~~
1       GGATCCGGAT TAGTCCAATT TGTTAAAGAC AGGATATCAG TGGTCCAGGC TCTAGTTTTG ACTCAACAAT ATCACCAGCT GAAGCCTATA GAGTACGAGC
        CCTAGGCCTA ATCAGGTTAA ACAATTTCTG TCCTATAGTC ACCAGGTCCG AGATCAAAAC TGAGTTGTTA TAGTGGTCGA CTTCGGATAT CTCATGCTCG
101     CATAGATAAA ATAAAAGATT TTATTTAGTC TCCAGAAAAA GGGGGGAATG AAAGACCCCA CCTGTAGGTT TGGCAAGCTA GCTTAAGTAA CGCCATTTTG
        GTATCTATTT TATTTTCTAA AATAAATCAG AGGTCTTTTT CCCCCCTTAC TTTCTGGGGT GGACATCCAA ACCGTTCGAT CGAATTCATT GCGGTAAAAC
201     CAAGGCATGG AAAAATACAT AACTGAGAAT AGAGAAGTTC AGATCAAGGT CAGGAACAGA TGGAACAGCT GAATATGGGC CAAACAGGAT ATCTGTGGTA
        GTTCCGTACC TTTTTATGTA TTGACTCTTA TCTCTTCAAG TCTAGTTCCA GTCCTTGTCT ACCTTGTCGA CTTATACCCG GTTTGTCCTA TAGACACCAT
301     AGCAGTTCCT GCCCCGGCTC AGGGCCAAGA ACAGATGGAA CAGCTGAATA TGGGCCAAAC AGGATATCTG TGGTAAGCAG TTCCTGCCCC GGCTCAGGGC
        TCGTCAAGGA CGGGGCCGAG TCCCGGTTCT TGTCTACCTT GTCGACTTAT ACCCGGTTTG TCCTATAGAC ACCATTCGTC AAGGACGGGG CCGAGTCCCG
401     CAAGAACAGA TGGTCCCCAG ATGCGGTCCA GCCCTCAGCA GTTTCTAGAG AACCATCAGA TGTTTCCAGG GTGCCCCAAG GACCTGAAAT GACCCTGTGC
        GTTCTTGTCT ACCAGGGGTC TACGCCAGGT CGGGAGTCGT CAAAGATCTC TTGGTAGTCT ACAAAGGTCC CACGGGGTTC CTGGACTTTA CTGGGACACG
501     CTTATTTGAA CTAACCAATC AGTTCGCTTC TCGCTTCTGT TCGCGCGCTT CTGCTCCCCG AGCTCAATAA AAGAGCCCAC AACCCCTCAC TCGGGGCGCC
        GAATAAACTT GATTGGTTAG TCAAGCGAAG AGCGAAGACA AGCGCGCGAA GACGAGGGGC TCGAGTTATT TTCTCGGGTG TTGGGGAGTG AGCCCCGCGG
601     AGTCCTCCGA TTGACTGAGT CGCCCGGGTA CCCGTGTATC CAATAAACCC TCTTGCAGTT GCATCCGACT TGTGGTCTCG CTGTTCCTTG GGAGGGTCTC
        TCAGGAGGCT AACTGACTCA GCGGGCCCAT GGGCACATAG GTTATTTGGG AGAACGTCAA CGTAGGCTGA ACACCAGAGC GACAAGGAAC CCTCCCAGAG
701     CTCTGAGTGA TTGACTACCC GTCAGCGGGG GTCTTTCACA CATGCAGCAT GTATCAAAAT TAATTTGGTT TTTTTTCTTA AGTATTTACA TTAAATGGCC
        GAGACTCACT AACTGATGGG CAGTCGCCCC CAGAAAGTGT GTACGTCGTA CATAGTTTTA ATTAAACCAA AAAAAAGAAT TCATAAATGT AATTTACCGG
801     ATAGTACTTA AAGTTACATT GGCTTCCTTG AAATAAACAT GGAGTATTCA GAATGTGTCA TAAATATTTC TAATTTTAAG ATAGTATCTC CATTGGCTTT
        TATCATGAAT TTCAATGTAA CCGAAGGAAC TTTATTTGTA CCTCATAAGT CTTACACAGT ATTTATAAAG ATTAAAATTC TATCATAGAG GTAACCGAAA
901     CTACTTTTTC TTTTATTTTT TTTTGTCCTC TGTCTTCCAT TTGTTGTTGT TGTTGTTTGT TTGTTTGTTT GTTGGTTGGT TGGTTAATTT TTTTTTAAAG
        GATGAAAAAG AAAATAAAAA AAAACAGGAG ACAGAAGGTA AACAACAACA ACAACAAACA AACAAACAAA CAACCAACCA ACCAATTAAA AAAAAATTTC
1001    ATCCTACACT ATAGTTCAAG CTAGACTATT AGCTACTCTG TAACCCAGGG TGAACTTGAA GTCATGGGTA GCCTGCTGTT TTAGCCTTCC CACATCTAAG
        TAGGATGTGA TATCAAGTTC GATCTGATAA TCGATGAGAC ATTGGGTCCC ACTTGAACTT CAGTACCCAT CGGACGACAA AATCGGAAGG GTGTAGATTC
1101    ATTACAGGTA TGAGCTATCA TTTTTGGTAT ATTGATTGAT TGATTGATTG ATGTGTGTGT GTGTGATTGT GTTTGTGTGT GTGACTGTGA AAATGTGTGT
        TAATGTCCAT ACTCGATAGT AAAAACCATA TAACTAACTA ACTAACTAAC TACACACACA CACACTAACA CAAACACACA CACTGACACT TTTACACACA
1201    ATGGGTGTGT GTGAATGTGT GTATGTATGT GTGTGTGTGA GTGTGTGTGT GTGTGTGTGC ATGTGTGTGT GTGTGACTGT GTCTATGTGT ATGACTGTGT
        TACCCACACA CACTTACACA CATACATACA CACACACACT CACACACACA CACACACACG TACACACACA CACACTGACA CAGATACACA TACTGACACA
1301    GTGTGTGTGT GTGTGTGTGT GTGTGTGTGT GTGTGTGTGT GTTGTGAAAA AATATTCTAT GGTAGTGAGA GCCAACGCTC CGGCTCAGGT GTCAGGTTGG
        CACACACACA CACACACACA CACACACACA CACACACACA CAACACTTTT TTATAAGATA CCATCACTCT CGGTTGCGAG GCCGAGTCCA CAGTCCAACC
                                             EcoRI
                                             ~~~~~~
1401    TTTTTGAGAC AGAGTCTTTC ACTTAGCTTG GAATTCACTG GCCGTCGTTT TACAACGTCG TGACTGGGAA AACCCTGGCG TTACCCAACT TAATCGCCTT
        AAAAACTCTG TCTCAGAAAG TGAATCGAAC CTTAAGTGAC CGGCAGCAAA ATGTTGCAGC ACTGACCCTT TTGGGACCGC AATGGGTTGA ATTAGCGGAA
1501    GCAGCACATC CCCCTTTCGC CAGCTGGCGT AATAGCGAAG AGGCCCGCAC CGATCGCCCT TCCCAACAGT TGCGCAGCCT GAATGGCGAA TGGCGCCTGA
        CGTCGTGTAG GGGGAAAGCG GTCGACCGCA TTATCGCTTC TCCGGGCGTG GCTAGCGGGA AGGGTTGTCA ACGCGTCGGA CTTACCGCTT ACCGCGGACT
1601    TGCGGTATTT TCTCCTTACG CATCTGTGCG GTATTTCACA CCGCATATGG TGCACTCTCA GTACAATCTG CTCTGATGCC GCATAGTTAA GCCAGCCCCG
        ACGCCATAAA AGAGGAATGC GTAGACACGC CATAAAGTGT GGCGTATACC ACGTGAGAGT CATGTTAGAC GAGACTACGG CGTATCAATT CGGTCGGGGC
1701    ACACCCGCCA ACACCCGCTG ACGCGCCCTG ACGGGCTTGT CTGCTCCCGG CATCCGCTTA CAGACAAGCT GTGACCGTCT CCGGGAGCTG CATGTGTCAG
        TGTGGGCGGT TGTGGGCGAC TGCGCGGGAC TGCCCGAACA GACGAGGGCC GTAGGCGAAT GTCTGTTCGA CACTGGCAGA GGCCCTCGAC GTACACAGTC
1801    AGGTTTTCAC CGTCATCACC GAAACGCGCG ATGACGAAAG GGCCTCGTGA TACGCCTATT TTTATAGGTT AATGTCATGA TAATAATGGT TTCTTAGACG
        TCCAAAAGTG GCAGTAGTGG CTTTGCGCGC TACTGCTTTC CCGGAGCACT ATGCGGATAA AAATATCCAA TTACAGTACT ATTATTACCA AAGAATCTGC
1901    TCAGGTGGCA CTTTTCGGGG AAATGTGCGC GGAACCCCTA TTTGTTTATT TTTCTAAATA CATTCAAATA TGTATCCGCT CATGAGACAA TAACCCTGAT
        AGTCCACCGT GAAAAGCCCC TTTACACGCG CCTTGGGGAT AAACAAATAA AAAGATTTAT GTAAGTTTAT ACATAGGCGA GTACTCTGTT ATTGGGACTA
2001    AAATGCTTCA ATAATATTGA AAAAGGAAGA GTATGAGTAT TCAACATTTC CGTGTCGCCC TTATTCCCTT TTTTGCGGCA TTTTGCCTTC CTGTTTTTGC
        TTTACGAAGT TATTATAACT TTTTCCTTCT CATACTCATA AGTTGTAAAG GCACAGCGGG AATAAGGGAA AAAACGCCGT AAAACGGAAG GACAAAAACG
```

FIG. 18B

2101 TCACCCAGAA ACGCTGGTGA AAGTAAAAGA TGCTGAAGAT CAGTTGGGTG CACGAGTGGG TTACATCGAA CTGGATCTCA ACAGCGGTAA GATCCTTGAG
AGTGGGTCTT TGCGACCACT TTCATTTTCT ACGACTTCTA GTCAACCCAC GTGCTCACCC AATGTAGCTT GACCTAGAGT TGTCGCCATT CTAGGAACTC
2201 AGTTTTCGCC CCGAAGAACG TTTTCCAATG ATGAGCACTT TTAAAGTTCT GCTATGTGGC GCGGTATTAT CCCGTATTGA CGCCGGGCAA GAGCAACTCG
TCAAAAGCGG GGCTTCTTGC AAAAGGTTAC TACTCGTGAA AATTTCAAGA CGATACACCG CGCCATAATA GGGCATAACT GCGGCCCGTT CTCGTTGAGC
2301 GTCGCCGCAT ACACTATTCT CAGAATGACT TGGTTGAGTA CTCACCAGTC ACAGAAAAGC ATCTTACGGA TGGCATGACA GTAAGAGAAT TATGCAGTGC
CAGCGGCGTA TGTGATAAGA GTCTTACTGA ACCAACTCAT GAGTGGTCAG TGTCTTTTCG TAGAATGCCT ACCGTACTGT CATTCTCTTA ATACGTCACG
2401 TGCCATAACC ATGAGTGATA ACACTGCGGC CAACTTACTT CTGACAACGA TCGGAGGACC GAAGGAGCTA ACCGCTTTTT TGCACAACAT GGGGGATCAT
ACGGTATTGG TACTCACTAT TGTGACGCCG GTTGAATGAA GACTGTTGCT AGCCTCCTGG CTTCCTCGAT TGGCGAAAAA ACGTGTTGTA CCCCCTAGTA
2501 GTAACTCGCC TTGATCGTTG GGAACCGGAG CTGAATGAAG CCATACCAAA CGACGAGCGT GACACCACGA TGCCTGTAGC AATGGCAACA ACGTTGCGCA
CATTGAGCGG AACTAGCAAC CCTTGGCCTC GACTTACTTC GGTATGGTTT GCTGCTCGCA CTGTGGTGCT ACGGACATCG TTACCGTTGT TGCAACGCGT
2601 AACTATTAAC TGGCGAACTA CTTACTCTAG CTTCCCGGCA ACAATTAATA GACTGGATGG AGGCGGATAA AGTTGCAGGA CCACTTCTGC GCTCGGCCCT
TTGATAATTG ACCGCTTGAT GAATGAGATC GAAGGGCCGT TGTTAATTAT CTGACCTACC TCCGCCTATT TCAACGTCCT GGTGAAGACG CGAGCCGGGA
2701 TCCGGCTGGC TGGTTTATTG CTGATAAATC TGGAGCCGGT GAGCGTGGGT CTCGCGGTAT CATTGCAGCA CTGGGGCCAG ATGGTAAGCC CTCCCGTATC
AGGCCGACCG ACCAAATAAC GACTATTTAG ACCTCGGCCA CTCGCACCCA GAGCGCCATA GTAACGTCGT GACCCCGGTC TACCATTCGG GAGGGCATAG
2801 GTAGTTATCT ACACGACGGG GAGTCAGGCA ACTATGGATG AACGAAATAG ACAGATCGCT GAGATAGGTG CCTCACTGAT TAAGCATTGG TAACTGTCAG
CATCAATAGA TGTGCTGCCC CTCAGTCCGT TGATACCTAC TTGCTTTATC TGTCTAGCGA CTCTATCCAC GGAGTGACTA ATTCGTAACC ATTGACAGTC
2901 ACCAAGTTTA CTCATATATA CTTTAGATTG ATTTAAAACT TCATTTTTAA TTTAAAAGGA TCTAGGTGAA GATCCTTTTT GATAATCTCA TGACCAAAAT
TGGTTCAAAT GAGTATATAT GAAATCTAAC TAAATTTTGA AGTAAAAATT AAATTTTCCT AGATCCACTT CTAGGAAAAA CTATTAGAGT ACTGGTTTTA
3001 CCCTTAACGT GAGTTTTCGT TCCACTGAGC GTCAGACCCC GTAGAAAAGA TCAAAGGATC TTCTTGAGAT CCTTTTTTTC TGCGCGTAAT CTGCTGCTTG
GGGAATTGCA CTCAAAAGCA AGGTGACTCG CAGTCTGGGG CATCTTTTCT AGTTTCCTAG AAGAACTCTA GGAAAAAAAG ACGCGCATTA GACGACGAAC
3101 CAAACAAAAA AACCACCGCT ACCAGCGGTG GTTTGTTTGC CGGATCAAGA GCTACCAACT CTTTTTCCGA AGGTAACTGG CTTCAGCAGA GCGCAGATAC
GTTTGTTTTT TTGGTGGCGA TGGTCGCCAC CAAACAAACG GCCTAGTTCT CGATGGTTGA GAAAAAGGCT TCCATTGACC GAAGTCGTCT CGCGTCTATG
3201 CAAATACTGT CCTTCTAGTG TAGCCGTAGT TAGGCCACCA CTTCAAGAAC TCTGTAGCAC CGCCTACATA CCTCGCTCTG CTAATCCTGT TACCAGTGGC
GTTTATGACA GGAAGATCAC ATCGGCATCA ATCCGGTGGT GAAGTTCTTG AGACATCGTG GCGGATGTAT GGAGCGAGAC GATTAGGACA ATGGTCACCG
3301 TGCTGCCAGT GGCGATAAGT CGTGTCTTAC CGGGTTGGAC TCAAGACGAT AGTTACCGGA TAAGGCGCAG CGGTCGGGCT GAACGGGGGG TTCGTGCACA
ACGACGGTCA CCGCTATTCA GCACAGAATG GCCCAACCTG AGTTCTGCTA TCAATGGCCT ATTCCGCGTC GCCAGCCCGA CTTGCCCCCC AAGCACGTGT
3401 CAGCCCAGCT TGGAGCGAAC GACCTACACC GAACTGAGAT ACCTACAGCG TGAGCATTGA GAAAGCGCCA CGCTTCCCGA AGGGAGAAAG GCGGACAGGT
GTCGGGTCGA ACCTCGCTTG CTGGATGTGG CTTGACTCTA TGGATGTCGC ACTCGTAACT CTTTCGCGGT GCGAAGGGCT TCCCTCTTTC CGCCTGTCCA
3501 ATCCGGTAAG CGGCAGGGTC GGAACAGGAG AGCGCACGAG GGAGCTTCCA GGGGGAAACG CCTGGTATCT TTATAGTCCT GTCGGGTTTC GCCACCTCTG
TAGGCCATTC GCCGTCCCAG CCTTGTCCTC TCGCGTGCTC CCTCGAAGGT CCCCCTTTGC GGACCATAGA AATATCAGGA CAGCCCAAAG CGGTGGAGAC
3601 ACTTGAGCGT CGATTTTTGT GATGCTCGTC AGGGGGGCGG AGCCTATGGA AAAACGCCAG CAACGCGGCC TTTTTACGGT TCCTGGCCTT TTGCTGGCCT
TGAACTCGCA GCTAAAAACA CTACGAGCAG TCCCCCCGCC TCGGATACCT TTTTGCGGTC GTTGCGCCGG AAAAATGCCA AGGACCGGAA AACGACCGGA
3701 TTTGCTCACA TGTTCTTTCC TGCGTTATCC CCTGATTCTG TGGATAACCG TATTACCGCC TTTGAGTGAG CTGATACCGC TCGCCGCAGC CGAACGACCG
AAACGAGTGT ACAAGAAAGG ACGCAATAGG GGACTAAGAC ACCTATTGGC ATAATGGCGG AAACTCACTC GACTATGGCG AGCGGCGTCG GCTTGCTGGC
3801 AGCGCAGCGA GTCAGTGAGC GAGGAAGCGG AAGAGCGCCC AATACGCAAA CCGCCTCTCC CCGCGCGTTG GCCGATTCAT TAATGCAGCT GGCACGACAG
TCGCGTCGCT CAGTCACTCG CTCCTTCGCC TTCTCGCGGG TTATGCGTTT GGCGGAGAGG GGCGCGCAAC CGGCTAAGTA ATTACGTCGA CCGTGCTGTC
3901 GTTTCCCGAC TGGAAAGCGG GCAGTGAGCG CAACGCAATT AATGTGAGTT AGCTCACTCA TTAGGCACCC CAGGCTTTAC ACTTTATGCT TCCGGCTCGT
CAAAGGGCTG ACCTTTCGCC CGTCACTCGC GTTGCGTTAA TTACACTCAA TCGAGTGAGT AATCCGTGGG GTCCGAAATG TGAAATACGA AGGCCGAGCA
4001 ATGTTGTGTG GAATTGTGAG CGGATAACAA TTTCACACAG GAAACAGCTA TGACCATGAT TACGCCAAGC TTTGCTCTTA GGAGTTTCCT AATACATCCC
TACAACACAC CTTAACACTC GCCTATTGTT AAAGTGTGTC CTTTGTCGAT ACTGGTACTA ATGCGGTTCG AAACGAGAAT CCTCAAAGGA TTATGTAGGG
4101 AAACTCAAAT ATATAAAGCA TTTGACTTGT TCTATGCCCT AGGGGGCGGG GGGAAGCTAA GCCAGCTTTT TTTAACATTT AAAATGTTAA TTCCATTTTA
TTTGAGTTTA TATATTTCGT AAACTGAACA AGATACGGGA TCCCCCGCCC CCCTTCGATT CGGTCGAAAA AAATTGTAAA TTTTACAATT AAGGTAAAAT
4201 AATGCACAGA TGTTTTTATT TCATAAGGGT TTCAATGTGC ATGAATGCTG CAATATTCCT GTTACCAAAG CTAGTATAAA TAAAAATAGA TAAACGTGGA
TTACGTGTCT ACAAAAATAA AGTATTCCCA AAGTTACACG TACTTACGAC GTTATAAGGA CAATGGTTTC GATCATATTT ATTTTTATCT ATTTGCACCT
4301 AATTACTTAG AGTTTCTGTC ATTAACGTTT CCTTCCTCAG TTGACAACAT AAATGCGCTG CTGAGCAAGC CAGTTTGCAT CTGTCAGGAT CAATTTCCCA

FIG. 18C

```
     TTAATGAATC TCAAAGACAG TAATTGCAAA GGAAGGAGTC AACTGTTGTA TTTACGCGAC GACTCGTTCG GTCAAACGTA GACAGTCCTA GTTAAAGGGT
4401 TTATGCCAGT CATATTAATT ACTAGTCAAT TAGTTGATTT TTATTTTTGA CATATACATG TGAATGAAAG ACCCCACCTG TAGGTTTGGC AAGCTAGCTT
     AATACGGTCA GTATAATTAA TGATCAGTTA ATCAACTAAA AATAAAAACT GTATATGTAC ACTTACTTTC TGGGGTGGAC ATCCAAACCG TTCGATCGAA
4501 AAGTAACGCC ATTTTGCAAG GCATGGAAAA ATACATAACT GAGAATAGAA AAGTTCAGAT CAAGGTCAGG AACAGATGGA ACAGCTGAAT ATGGGCCAAA
     TTCATTGCGG TAAAACGTTC CGTACCTTTT TATGTATTGA CTCTTATCTT TTCAAGTCTA GTTCCAGTCC TTGTCTACCT TGTCGACTTA TACCCGGTTT
4601 CAGGATATCT GTGGTAAGCA GTTCCTGCCC CGGCTCAGGG CCAAGAACAG ATGGAACAGC TGAATATGGG CCAAACAGGA TATCTGTGGT AAGCAGTTCC
     GTCCTATAGA CACCATTCGT CAAGGACGGG GCCGAGTCCC GGTTCTTGTC TACCTTGTCG ACTTATACCC GGTTTGTCCT ATAGACACCA TTCGTCAAGG
4701 TGCCCCGGCT CAGGGCCAAG AACAGATGGT CCCCAGATGC GGTCCAGCCC TCAGCAGTTT CTAGAGAACC ATCAGATGTT TCCAGGGTGC CCCAAGGACC
     ACGGGGCCGA GTCCCGGTTC TTGTCTACCA GGGGTCTACG CCAGGTCGGG AGTCGTCAAA GATCTCTTGG TAGTCTACAA AGGTCCCACG GGGTTCCTGG
4801 TGAAATGACC CTGTGCCTTA TTTGAACTAA CCAATCAGTT CGCTTCTCGC TTCTGTTCGC GCGCTTATGC TCCCCGAGCT CAATAAAAGA GCCCACAACC
     ACTTTACTGG GACACGGAAT AAACTTGATT GGTTAGTCAA GCGAAGAGCG AAGACAAGCG CGCGAATACG AGGGGCTCGA GTTATTTTCT CGGGTGTTGG
4901 CCTCACTCGG GGCGCCAGTC CTCCGATTGA CTGAGTCGCC CGGGTACCCG TGTATCCAAT AAACCCTCTT GCAGTTGCAT CCGACTTGTG GTCTCGCTGT
     GGAGTGAGCC CCGCGGTCAG GAGGCTAACT GACTCAGCGG GCCCATGGGC ACATAGGTTA TTTGGGAGAA CGTCAACGTA GGCTGAACAC CAGAGCGACA
5001 TCCTTGGGAG GGTCTCCTCT GAGTGATTGA CTACCCGTCA GCGGGGGTCT TTCATTTGGG GGCTCGTCCG GGATCGGGAG ACCCCTGCCC AGGGACCACC
     AGGAACCCTC CCAGAGGAGA CTCACTAACT GATGGGCAGT CGCCCCCAGA AAGTAAACCC CCGAGCAGGC CCTAGCCCTC TGGGGACGGG TCCCTGGTGG
5101 GACCCACCAC CGGGAGGTAA GCTGGCCAGC AACTTATCTG TGTCTGTCCG ATTGTCTAGT GTCTATGACT GATTTTATGC GCCTGCGTCG GTACTAGTTA
     CTGGGTGGTG GCCCTCCATT CGACCGGTCG TTGAATAGAC ACAGACAGGC TAACAGATCA CAGATACTGA CTAAAATACG CGGACGCAGC CATGATCAAT
5201 GCTAACTAGC TCTGTATCTG GCGGACCCGT GGTGGAACTG ACGAGTTCGG AACACCCGGC CGCAACCCTG GGAGACGTCC CAGGGACTTC GGGGGCCGTT
     CGATTGATCG AGACATAGAC CGCCTGGGCA CCACCTTGAC TGCTCAAGCC TTGTGGGCCG GCGTTGGGAC CCTCTGCAGG GTCCCTGAAG CCCCCGGCAA
5301 TTTGTGGCCC GACCTGAGTC CTAAAATCCC GATCGTTTAG GACTCTTTGG TGCACCCCCC TTAGAGGAGG GATATGTGGT TCTGGTAGGA GACGAGAACC
     AAACACCGGG CTGGACTCAG GATTTTAGGG CTAGCAAATC CTGAGAAACC ACGTGGGGGG AATCTCCTCC CTATACACCA AGACCATCCT CTGCTCTTGG
5401 TAAAACAGTT CCCGCCTCCG TCTGAATTTT TGCTTTCGGT TTGGGACCGA AGCCGCGCCG CGCGTCTTGT CTGCTGCAGC ATCGTTCTGT GTTGTCTCTG
     ATTTTGTCAA GGGCGGAGGC AGACTTAAAA ACGAAAGCCA AACCCTGGCT TCGGCGCGGC GCGCAGAACA GACGACGTCG TAGCAAGACA CAACAGAGAC
5501 TCTGACTGTG TTTCTGTATT TGTCTGAAAA TATGGGCCCG GGCTAGACTG TTACCACTCC CTTAAGTTTG ACCTTAGGTC ACTGGAAAGA TGTCGAGCGG
     AGACTGACAC AAAGACATAA ACAGACTTTT ATACCCGGGC CCGATCTGAC AATGGTGAGG GAATTCAAAC TGGAATCCAG TGACCTTTCT ACAGCTCGCC
5601 ATCGCTCACA ACCAGTCGGT AGATGTCAAG AAGAGACGTT GGGTTACCTT CTGCTCTGCA GAATGGCCAA CCTTTAACGT CGGATGGCCG CGAGACGGCA
     TAGCGAGTGT TGGTCAGCCA TCTACAGTTC TTCTCTGCAA CCCAATGGAA GACGAGACGT CTTACCGGTT GGAAATTGCA GCCTACCGGC GCTCTGCCGT
5701 CCTTTAACCG AGACCTCATC ACCCAGGTTA AGATCAAGGT CTTTTCACCT GGCCCGCATG GACACCCAGA CCAGGTCCCC TACATCGTGA CCTGGGAAGC
     GGAAATTGGC TCTGGAGTAG TGGGTCCAAT TCTAGTTCCA GAAAAGTGGA CCGGGCGTAC CTGTGGGTCT GGTCCAGGGG ATGTAGCACT GGACCCTTCG
5801 CTTGGCTTTT GACCCCCCTC CCTGGGTCAA GCCCTTTGTA CACCCTAAGC CTCCGCCTCC TCTTCCTCCA TCCGCCCCGT CTCTCCCCCT TGAACCTCCT
     GAACCGAAAA CTGGGGGGAG GGACCCAGTT CGGGAAACAT GTGGGATTCG GAGGCGGAGG AGAAGGAGGT AGGCGGGGCA GAGAGGGGGA ACTTGGAGGA
5901 CGTTCGACCC CGCCTCGATC CTCCCTTTAT CCAGCCCTCA CTCCTTCTCT AGGCGCCCCC ATATGGCCAT ATGAGATCTT ATATGGGGCA CCCCCGCCCC
     GCAAGCTGGG GCGGAGCTAG GAGGGAAATA GGTCGGGAGT GAGGAAGAGA TCCGCGGGGG TATACCGGTA TACTCTAGAA TATACCCCGT GGGGGCGGGG
```

```
6001  TTGTAAACTT CCCTGACCCT GACATGACAA GAGTTACTAA CAGCCCCTCT CTCCAAGCTC ACTTACAGGC TCTCTACTTA GTCCAGCACG AAGTCTGGAG
      AACATTTGAA GGGACTGGGA CTGTACTGTT CTCAATGATT GTCGGGGAGA GAGGTTCGAG TGAATGTCCG AGAGATGAAT CAGGTCGTGC TTCAGACCTC
6101  ACCTCTGGCG GCAGCCTACC AAGAACAACT GGACCGACCG GTGGTACCTC ACCCTTACCG AGTCGGCGAC ACAGTGTGGG TCCGCCGACA CCAGACTAAG
      TGGAGACCGC CGTCGGATGG TTCTTGTTGA CCTGGCTGGC CACCATGGAG TGGGAATGGC TCAGCCGCTG TGTCACACCC AGGCGGCTGT GGTCTGATTC
                                                                                                          PmlI
                                                                                                          ~~~~
6201  AACCTAGAAC CTCGCTGGAA AGGACCTTAC ACAGTCCTGC TGACCACCCC CACCGCCCTC AAAGTAGACG GCATCGCAGC TTGGATACAC GCCGCCCACG
      TTGGATCTTG GAGCGACCTT TCCTGGAATG TGTCAGGACG ACTGGTGGGG GTGGCGGGAG TTTCATCTGC CGTAGCGTCG AACCTATGTG CGGCGGGTGC
                                                                                  CD8-Leader
                                                    ~~~~~~~~~~~~~~~~~~~~~~~~~~~~~~~~~~~~~~~~~~~~~~~~~~~~~~~~~~~~~~~
      PmlI                                         NcoI
      ~~                                          ~~~~~~
6301  TGAAGGCTGC CGACCCCGGG GGTGGACCAT CCTCTAGACT GCCATGGCTC TCCCAGTGAC TGCCCTACTG CTTCCCCTAG CGCTTCTCCT GCATGCAGAG
      ACTTCCGACG GCTGGGGCCC CCACCTGGTA GGAGATCTGA CGGTACCGAG AGGGTCACTG ACGGGATGAC GAAGGGGATC GCGAAGAGGA CGTACGTCTC
                                                              VH
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6401  GTGAAGCTGC AGGAGTCAGG GGGAGGCTTC GTGAAGCCTG GAGGGTCCCT CAAAGTCTCC TGTGCAGCCT CTGGATTCAC TTTCAGTAGC TATGCCATGT
      CACTTCGACG TCCTCAGTCC CCCTCCGAAG CACTTCGGAC CTCCCAGGGA GTTTCAGAGG ACACGTCGGA GACCTAAGTG AAAGTCATCG ATACGGTACA
                                                              VH
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6501  CCTGGGTTCG CCTGAGTCCG GAGATGAGGC TGGAGTGGGT CGCAACCATT AGCAGTGCTG GTGGTTACAT CTTCTATTCT GACAGTGTGC AGGGACGATT
      GGACCCAAGC GGACTCAGGC CTCTACTCCG ACCTCACCCA GCGTTGGTAA TCGTCACGAC CACCAATGTA GAAGATAAGA CTGTCACACG TCCCTGCTAA
                                                              VH
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6601  CACCATTTCC AGAGACAATG CCAAGAACAC CCTGCACCTG CAAATGGGCA GTCTGAGGTC TGGGGACACG GCCATGTATT ACTGTGCAAG GCAGGGATTT
      GTGGTAAAGG TCTCTGTTAC GGTTCTTGTG GGACGTGGAC GTTTACCCGT CAGACTCCAG ACCCCTGTGC CGGTACATAA TGACACGTTC CGTCCCTAAA
                                                                                 (G4S)3 Serine-glycine linker
                                                                                 ~~~~~~~~~~~~~~~~~~~~~~~~~~~~~~
                                      VH
      ~~~~~~~~~~~~~~~~~~~~~~~~~~~~~~~~~~~~~~~~~~~~~~~~~~~~~~~~~~~~~~~~~~~~~~~~~~~~~~~
6701  GGTAACTACG GTGATTACTA TGCTATGGAC TACTGGGGCC AAGGGACCAC GGTCACCGTC TCCTCAGGTG GAGGTGGATC AGGTGGAGGT GGATCTGGTG
      CCATTGATGC CACTAATGAT ACGATACCTG ATGACCCCGG TTCCCTGGTG CCAGTGGCAG AGGAGTCCAC CTCCACCTAG TCCACCTCCA CCTAGACCAC
                                                              VL
                 ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
(G4S)3 Serine-glycine linker
      ~~~~~~~~~~~~
6801  GAGGTGGATC TGACATTGAG CTCACCCAGT CTCCATCCTC CCTGGCTGTG TCAGCAGGAG AGAAGGTCAC TATGAGCTGC AAATCCAGTC AGAGTCTGCT
      CTCCACCTAG ACTGTAACTC GAGTGGGTCA GAGGTAGGAG GGACCGACAC AGTCGTCCTC TCTTCCAGTG ATACTCGACG TTTAGGTCAG TCTCAGACGA
                                                              VL
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6901  CAACAGTAGA ACCCGAAAGA ACCAGTTGGC TTGGTACCAG CAAAAACCAG GACAGTCTCC TGAACTGCTG ATCTACTGGG CATCCACTAG GCAATCTGGA
      GTTGTCATCT TGGGCTTTCT TGGTCAACCG AACCATGGTC GTTTTTGGTC CTGTCAGAGG ACTTGACGAC TAGATGACCC GTAGGTGATC CGTTAGACCT
                                                              VL
```

FIG. 18D

```
7001   GTCCCTGATC GCTTCACAGG CAGTGGATCT GGGACAGATT TCACTCTCAC CATCAGCAGT GTGCAGGCTG AAGACCTGGC AGTTTATTAC TGCCAGCAAT
       CAGGGACTAG CGAAGTGTCC GTCACCTAGA CCCTGTCTAA AGTGAGAGTG GTAGTCGTCA CACGTCCGAC TTCTGGACCG TCAAATAATG ACGGTCGTTA
                                 VL                                                        CD8 transmembrane domain

                                                             NotI
7101   CTTATAATCT ACTCACGTTC GGTCCTGGGA CCAAGCTGGA GATCAAACGG GCGGCCGCAC CCACCACGAC GCCAGCGCCG CGACCACCAA CCCCGGCGCC
       GAATATTAGA TGAGTGCAAG CCAGGACCCT GGTTCGACCT CTAGTTTGCC CGCCGGCGTG GGTGGTGCTG CGGTCGCGGC GCTGGTGGTT GGGGCCGCGG
                                                  Cd8 transmembrane domain

7201   CACGATCGCG TCGCAGCCCC TGTCCCTGCG CCCAGAGGCG TGCCGGCCAG CGGCGGGGGG CGCAGTGCAC ACGAGGGGGC TGGACTTCGC CTGTGATATC
       GTGCTAGCGC AGCGTCGGGG ACAGGGACGC GGGTCTCCGC ACGGCCGGTC GCCGCCCCCC GCGTCACGTG TGCTCCCCCG ACCTGAAGCG GACACTATAG
                         Cd8 transmembrane domain

                                                                                       CD3 zeta chain intracellular domain
7301   TACATCTGGG CGCCCTTGGC CGGGACTTGT GGGGTCCTTC TCCTGTCACT GGTTATCACC CTTTACTGCA ACCACAGAGT GAAGTTCAGC AGGAGCGCAG
       ATGTAGACCC GCGGGAACCG GCCCTGAACA CCCCAGGAAG AGGACAGTGA CCAATAGTGG GAAATGACGT TGGTGTCTCA CTTCAAGTCG TCCTCGCGTC
                                              CD3 zeta chain intracellular domain

7401   AGCCCCCCGC GTACCAGCAG GGCCAGAACC AGCTCTATAA CGAGCTCAAT CTAGGACGAA GAGAGGAGTA CGATGTTTTG GACAAGAGAC GTGGCCGGGA
       TCGGGGGGCG CATGGTCGTC CCGGTCTTGG TCGAGATATT GCTCGAGTTA GATCCTGCTT CTCTCCTCAT GCTACAAAAC CTGTTCTCTG CACCGGCCCT
                                              CD3 zeta chain intracellular domain

7501   CCCTGAGATG GGGGGAAAGC CGAGAAGGAA GAACCCTCAG GAAGGCCTGT ACAATGAACT GCAGAAAGAT AAGATGGCGG AGGCCTACAG TGAGATTGGG
       GGGACTCTAC CCCCCTTTCG GCTCTTCCTT CTTGGGAGTC CTTCCGGACA TGTTACTTGA CGTCTTTCTA TTCTACCGCC TCCGGATGTC ACTCTAACCC
                                              CD3 zeta chain intracellular domain

7601   ATGAAAGGCG AGCGCCGGAG GGGCAAGGGG CACGATGGCC TTTACCAGGG TCTCAGTACA GCCACCAAGG ACACCTACGA CGCCCTTCAC ATGCAGGCCC
       TACTTTCCGC TCGCGGCCTC CCCGTTCCCC GTGCTACCGG AAATGGTCCC AGAGTCATGT CGGTGGTTCC TGTGGATGCT GCGGGAAGTG TACGTCCGGG
       CD3 zeta chain intracellular domain
                             XhoI
7701   TGCCCCCTCG CTAACAGCCA CTCGAG
       ACGGGGGAGC GATTGTCGGT GAGCTC
```

FIG. 18E

Figure 18 top strand: SEQ ID NO:37
Figure 18 bottom strand: SEQ ID NO:38

FIG. 19A

```
          BamHI
          ~~~~~~
   1      GGATCCGGAT TAGTCCAATT TGTTAAAGAC AGGATATCAG TGGTCCAGGC TCTAGTTTTG ACTCAACAAT ATCACCAGCT GAAGCCTATA GAGTACGAGC
          CCTAGGCCTA ATCAGGTTAA ACAATTTCTG TCCTATAGTC ACCAGGTCCG AGATCAAAAC TGAGTTGTTA TAGTGGTCGA CTTCGGATAT CTCATGCTCG
 101      CATAGATAAA ATAAAAGATT TTATTTAGTC TCCAGAAAAA GGGGGGAATG AAAGACCCCA CCTGTAGATT TGGCAAGCTA GCTTAAGTAA CGCCATTTTG
          GTATCTATTT TATTTTCTAA AATAAATCAG AGGTCTTTTT CCCCCCTTAC TTTCTGGGGT GGACATCTAA ACCGTTCGAT CGAATTCATT GCGGTAAAAC
 201      CAAGGCATGG AAAAATACAT AACTGAGAAT AGAGAAGTTC AGATCAAGGT CAGGAACAGA TGGAACAGCT GAATATGGGC CAAACAGGAT ATCTGTGGTA
          GTTCCGTACC TTTTTATGTA TTGACTCTTA TCTCTTCAAG TCTAGTTCCA GTCCTTGTCT ACCTTGTCGA CTTATACCCG GTTTGTCCTA TAGACACCAT
 301      AGCAGTTCCT GCCCCGGCTC AGGGCCAAGA ACAGATGGAA CAGCTGAATA TGGGCCAAAC AGGATATCTG TGGTAAGCAG TTCCTGCCCC GGCTCAGGGC
          TCGTCAAGGA CGGGGCCGAG TCCCGGTTCT TGTCTACCTT GTCGACTTAT ACCCGGTTTG TCCTATAGAC ACCATTCGTC AAGGACGGGG CCGAGTCCCG
 401      CAAGAACAGA TGGTCCCCAG ATGCGGTCCA GCCCTCAGCA GTTTCTAGAG AACCATCAGA TGTTTCCAGG GTGCCCCAAG GACCTGAAAT GACCCTGTGC
          GTTCTTGTCT ACCAGGGGTC TACGCCAGGT CGGGAGTCGT CAAAGATCTC TTGGTAGTCT ACAAAGGTCC CACGGGGTTC CTGGACTTTA CTGGGACACG
 501      CTTATTTGAA CTAACCAATC AGTTCGCTTC TCGCTTCTGT TCGCGCGCTT CTGCTCCCCG AGCTCAATAA AAGAGCCCAC AACCCCTCAC TCGGGGCGCC
          GAATAAACTT GATTGGTTAG TCAAGCGAAG AGCGAAGACA AGCGCGCGAA GACGAGGGGC TCGAGTTATT TTCTCGGGTG TTGGGGAGTG AGCCCCGCGG
 601      AGTCCTCCGA TTGACTGAGT CGCCCGGGTA CCCGTGTATC CAATAAACCC TCTTGCAGTT GCATCCGACT TGTGGTCTCG CTGTTCCTTG GGAGGGTCTC
          TCAGGAGGCT AACTGACTCA GCGGGCCCAT GGGCACATAG GTTATTTGGG AGAACGTCAA CGTAGGCTGA ACACCAGAGC GACAAGGAAC CCTCCCAGAG
 701      CTCTGAGTGA TTGACTACCC GTCAGCGGGG GTCTTTCACA CATGCAGCAT GTATCAAAAT TAATTTGGTT TTTTTTCTTA AGTATTTACA TTAAATGGCC
          GAGACTCACT AACTGATGGG CAGTCGCCCC CAGAAAGTGT GTACGTCGTA CATAGTTTTA ATTAAACCAA AAAAAAGAAT TCATAAATGT AATTTACCGG
 801      ATAGTACTTA AAGTTACATT GGCTTCCTTG AAATAAACAT GGAGTATTCA GAATGTGTCA TAAATATTTC TAATTTTAAG ATAGTATCTC CATTGGCTTT
          TATCATGAAT TTCAATGTAA CCGAAGGAAC TTTATTTGTA CCTCATAAGT CTTACACAGT ATTTATAAAG ATTAAAATTC TATCATAGAG GTAACCGAAA
 901      CTACTTTTTC TTTTATTTTT TTTTGTCCTC TGTCTTCCAT TTGTTGTTGT TGTTGTTTGT TTGTTTGTTT GTTGGTTGGT TGGTTAATTT TTTTTTAAAG
          GATGAAAAAG AAAATAAAAA AAAACAGGAG ACAGAAGGTA AACAACAACA ACAACAAACA AACAAACAAA CAACCAACCA ACCAATTAAA AAAAAATTTC
1001      ATCCTACACT ATAGTTCAAG CTAGACTATT AGCTACTCTG TAACCCAGGG TGACCTTGAA GTCATGGGTA GCCTGCTGTT TTAGCCTTCC CACATCTAAG
          TAGGATGTGA TATCAAGTTC GATCTGATAA TCGATGAGAC ATTGGGTCCC ACTGGAACTT CAGTACCCAT CGGACGACAA AATCGGAAGG GTGTAGATTC
1101      ATTACAGGTA TGAGCTATCA TTTTTGGTAT ATTGATTGAT TGATTGATTG ATGTGTGTGT GTGTGATTGT GTTTGTGTGT GTGACTGTGA AAATGTGTGT
          TAATGTCCAT ACTCGATAGT AAAAACCATA TAACTAACTA ACTAACTAAC TACACACACA CACACTAACA CAAACACACA CACTGACACT TTTACACACA
1201      ATGGGTGTGT GTGAATGTGT GTATGTATGT GTGTGTGTGA GTGTGTGTGT GTGTGTGTGC ATGTGTGTGT GTGTGACTGT GTCTATGTGT ATGACTGTGT
          TACCCACACA CACTTACACA CATACATACA CACACACACT CACACACACA CACACACACG TACACACACA CACACTGACA CAGATACACA TACTGACACA
1301      GTGTGTGTGT GTGTGTGTGT GTGTGTGTGT GTGTGTGTGT GTTGTGAAAA AATATTCTAT GGTAGTGAGA GCCAACGCTC CGGCTCAGGT GTCAGGTTGG
          CACACACACA CACACACACA CACACACACA CACACACACA CAACACTTTT TTATAAGATA CCATCACTCT CGGTTGCGAG GCCGAGTCCA CAGTCCAACC
                                          EcoRI
                                          ~~~~~~
1401      TTTTTGAGAC AGAGTCTTTC ACTTAGCTTG GAATTCACTG GCCGTCGTTT TACAACGTCG TGACTGGGAA AACCCTGGCG TTACCCAACT TAATCGCCTT
          AAAAACTCTG TCTCAGAAAG TGAATCGAAC CTTAAGTGAC CGGCAGCAAA ATGTTGCAGC ACTGACCCTT TTGGGACCGC AATGGGTTGA ATTAGCGGAA
1501      GCAGCACATC CCCCTTTCGC CAGCTGGCGT AATAGCGAAG AGGCCCGCAC CGATCGCCCT TCCCAACAGT TGCGCAGCCT GAATGGCGAA TGGCGCCTGA
          CGTCGTGTAG GGGGAAAGCG GTCGACCGCA TTATCGCTTC TCCGGGCGTG GCTAGCGGGA AGGGTTGTCA ACGCGTCGGA CTTACCGCTT ACCGCGGACT
1601      TGCGGTATTT TCTCCTTACG CATCTGTGCG GTATTTCACA CCGCATATGG TGCACTCTCA GTACAATCTG CTCTGATGCC GCATAGTTAA GCCAGCCCCG
          ACGCCATAAA AGAGGAATGC GTAGACACGC CATAAAGTGT GGCGTATACC ACGTGAGAGT CATGTTAGAC GAGACTACGG CGTATCAATT CGGTCGGGGC
1701      ACACCCGCCA ACACCCGCTG ACGCGCCCTG ACGGGCTTGT CTGCTCCCGG CATCCGCTTA CAGACAAGCT GTGACCGTCT CCGGGAGCTG CATGTGTCAG
          TGTGGGCGGT TGTGGGCGAC TGCGCGGGAC TGCCCGAACA GACGAGGGCC GTAGGCGAAT GTCTGTTCGA CACTGGCAGA GGCCCTCGAC GTACACAGTC
1801      AGGTTTTCAC CGTCATCACC GAAACGCGCG ATGACGAAAG GGCCTCGTGA TACGCCTATT TTTATAGGTT AATGTCATGA TAATAATGGT TTCTTAGACG
          TCCAAAAGTG GCAGTAGTGG CTTTGCGCGC TACTGCTTTC CCGGAGCACT ATGCGGATAA AAATATCCAA TTACAGTACT ATTATTACCA AAGAATCTGC
1901      TCAGGTGGCA CTTTTCGGGG AAATGTGCGC GGAACCCCTA TTTGTTTATT TTTCTAAATA CATTCAAATA TGTATCCGCT CATGAGACAA TAACCCTGAT
          AGTCCACCGT GAAAAGCCCC TTTACACGCG CCTTGGGGAT AAACAAATAA AAAGATTTAT GTAAGTTTAT ACATAGGCGA GTACTCTGTT ATTGGGACTA
2001      AAATGCTTCA ATAATATTGA AAAAGGAAGA GTATGAGTAT TCAACATTTC CGTGTCGCCC TTATTCCCTT TTTTGCGGCA TTTTGCCTTC CTGTTTTTGC
          TTTACGAAGT TATTATAACT TTTTCCTTCT CATACTCATA AGTTGTAAAG GCACAGCGGG AATAAGGGAA AAAACGCCGT AAAACGGAAG GACAAAAACG
```

FIG. 19B

```
2101  TCACCCAGAA ACGCTGGTGA AAGTAAAAGA TGCTGAAGAT CAGTTGGGTG CACGAGTGGG TTACATCGAA CTGGATCTCA ACAGCGGTAA GATCCTTGAG
      AGTGGGTCTT TGCGACCACT TTCATTTTCT ACGACTTCTA GTCAACCCAC GTGCTCACCC AATGTAGCTT GACCTAGAGT TGTCGCCATT CTAGGAACTC
2201  AGTTTTCGCC CCGAAGAACG TTTTCCAATG ATGAGCACTT TTAAAGTTCT GCTATGTGGC GCGGTATTAT CCCGTATTGA CGCCGGGCAA GAGCAACTCG
      TCAAAAGCGG GGCTTCTTGC AAAAGGTTAC TACTCGTGAA AATTTCAAGA CGATACACCG CGCCATAATA GGGCATAACT GCGGCCCGTT CTCGTTGAGC
2301  GTCGCCGCAT ACACTATTCT CAGAATGACT TGGTTGAGTA CTCACCAGTC ACAGAAAAGC ATCTTACGGA TGGCATGACA GTAAGAGAAT TATGCAGTGC
      CAGCGGCGTA TGTGATAAGA GTCTTACTGA ACCAACTCAT GAGTGGTCAG TGTCTTTTCG TAGAATGCCT ACCGTACTGT CATTCTCTTA ATACGTCACG
2401  TGCCATAACC ATGAGTGATA ACACTGCGGC CAACTTACTT CTGACAACGA TCGGAGGACC GAAGGAGCTA ACCGCTTTTT TGCACAACAT GGGGGATCAT
      ACGGTATTGG TACTCACTAT TGTGACGCCG GTTGAATGAA GACTGTTGCT AGCCTCCTGG CTTCCTCGAT TGGCGAAAAA ACGTGTTGTA CCCCCTAGTA
2501  GTAACTCGCC TTGATCGTTG GGAACCGGAG CTGAATGAAG CCATACCAAA CGACGAGCGT GACACCACGA TGCCTGTAGC AATGGCAACA ACGTTGCGCA
      CATTGAGCGG AACTAGCAAC CCTTGGCCTC GACTTACTTC GGTATGGTTT GCTGCTCGCA CTGTGGTGCT ACGGACATCG TTACCGTTGT TGCAACGCGT
2601  AACTATTAAC TGGCGAACTA CTTACTCTAG CTTCCCGGCA ACAATTAATA GACTGGATGG AGGCGGATAA AGTTGCAGGA CCACTTCTGC GCTCGGCCCT
      TTGATAATTG ACCGCTTGAT GAATGAGATC GAAGGGCCGT TGTTAATTAT CTGACCTACC TCCGCCTATT TCAACGTCCT GGTGAAGACG CGAGCCGGGA
2701  TCCGGCTGGC TGGTTTATTG CTGATAAATC TGGAGCCGGT GAGCGTGGGT CTCGCGGTAT CATTGCAGCA CTGGGGCCAG ATGGTAAGCC CTCCCGTATC
      AGGCCGACCG ACCAAATAAC GACTATTTAG ACCTCGGCCA CTCGCACCCA GAGCGCCATA GTAACGTCGT GACCCCGGTC TACCATTCGG GAGGGCATAG
2801  GTAGTTATCT ACACGACGGG GAGTCAGGCA ACTATGGATG AACGAAATAG ACAGATCGCT GAGATAGGTG CCTCACTGAT TAAGCATTGG TAACTGTCAG
      CATCAATAGA TGTGCTGCCC CTCAGTCCGT TGATACCTAC TTGCTTTATC TGTCTAGCGA CTCTATCCAC GGAGTGACTA ATTCGTAACC ATTGACAGTC
2901  ACCAAGTTTA CTCATATATA CTTTAGATTG ATTTAAAACT TCATTTTTAA TTTAAAAGGA TCTAGGTGAA GATCCTTTTT GATAATCTCA TGACCAAAAT
      TGGTTCAAAT GAGTATATAT GAAATCTAAC TAAATTTTGA AGTAAAAATT AAATTTTCCT AGATCCACTT CTAGGAAAAA CTATTAGAGT ACTGGTTTTA
3001  CCCTTAACGT GAGTTTTCGT TCCACTGAGC GTCAGACCCC GTAGAAAAGA TCAAAGGATC TTCTTGAGAT CCTTTTTTTC TGCGCGTAAT CTGCTGCTTG
      GGGAATTGCA CTCAAAAGCA AGGTGACTCG CAGTCTGGGG CATCTTTTCT AGTTTCCTAG AAGAACTCTA GGAAAAAAAG ACGCGCATTA GACGACGAAC
3101  CAAACAAAAA AACCACCGCT ACCAGCGGTG GTTTGTTTGC CGGATCAAGA GCTACCAACT CTTTTTCCGA AGGTAACTGG CTTCAGCAGA GCGCAGATAC
      GTTTGTTTTT TTGGTGGCGA TGGTCGCCAC CAAACAAACG GCCTAGTTCT CGATGGTTGA GAAAAAGGCT TCCATTGACC GAAGTCGTCT CGCGTCTATG
3201  CAAATACTGT CCTTCTAGTG TAGCCGTAGT TAGGCCACCA CTTCAAGAAC TCTGTAGCAC CGCCTACATA CCTCGCTCTG CTAATCCTGT TACCAGTGGC
      GTTTATGACA GGAAGATCAC ATCGGCATCA ATCCGGTGGT GAAGTTCTTG AGACATCGTG GCGGATGTAT GGAGCGAGAC GATTAGGACA ATGGTCACCG
3301  TGCTGCCAGT GGCGATAAGT CGTGTCTTAC CGGGTTGGAC TCAAGACGAT AGTTACCGGA TAAGGCGCAG CGGTCGGGCT GAACGGGGGG TTCGTGCACA
      ACGACGGTCA CCGCTATTCA GCACAGAATG GCCCAACCTG AGTTCTGCTA TCAATGGCCT ATTCCGCGTC GCCAGCCCGA CTTGCCCCCC AAGCACGTGT
3401  CAGCCCAGCT TGGAGCGAAC GACCTACACC GAACTGAGAT ACCTACAGCG TGAGCTATGA GAAAGCGCCA CGCTTCCCGA AGGGAGAAAG GCGGACAGGT
      GTCGGGTCGA ACCTCGCTTG CTGGATGTGG CTTGACTCTA TGGATGTCGC ACTCGATACT CTTTCGCGGT GCGAAGGGCT TCCCTCTTTC CGCCTGTCCA
3501  ATCCGGTAAG CGGCAGGGTC GGAACAGGAG AGCGCACGAG GGAGCTTCCA GGGGGAAACG CCTGGTATCT TTATAGTCCT GTCGGGTTTC GCCACCTCTG
      TAGGCCATTC GCCGTCCCAG CCTTGTCCTC TCGCGTGCTC CCTCGAAGGT CCCCCTTTGC GGACCATAGA AATATCAGGA CAGCCCAAAG CGGTGGAGAC
3601  ACTTGAGCGT CGATTTTTGT GATGCTCGTC AGGGGGGCGG AGCCTATGGA AAAACGCCAG CAACGCGGCC TTTTTACGGT TCCTGGCCTT TTGCTGGCCT
      TGAACTCGCA GCTAAAAACA CTACGAGCAG TCCCCCCGCC TCGGATACCT TTTTGCGGTC GTTGCGCCGG AAAAATGCCA AGGACCGGAA AACGACCGGA
3701  TTTGCTCACA TGTTCTTTCC TGCGTTATCC CCTGATTCTG TGGATAACCG TATTACCGCC TTTGAGTGAG CTGATACCGC TCGCCGCAGC CGAACGACCG
      AAACGAGTGT ACAAGAAAGG ACGCAATAGG GGACTAAGAC ACCTATTGGC ATAATGGCGG AAACTCACTC GACTATGGCG AGCGGCGTCG GCTTGCTGGC
3801  AGCGCAGCGA GTCAGTGAGC GAGGAAGCGG AAGAGCGCCC AATACGCAAA CCGCCTCTCC CCGCGCGTTG GCCGATTCAT TAATGCAGCT GGCACGACAG
      TCGCGTCGCT CAGTCACTCG CTCCTTCGCC TTCTCGCGGG TTATGCGTTT GGCGGAGAGG GGCGCGCAAC CGGCTAAGTA ATTACGTCGA CCGTGCTGTC
3901  GTTTCCCGAC TGGAAAGCGG GCAGTGAGCG CAACGCAATT AATGTGAGTT AGCTCACTCA TTAGGCACCC CAGGCTTTAC ACTTTATGCT TCCGGCTCGT
      CAAAGGGCTG ACCTTTCGCC CGTCACTCGC GTTGCGTTAA TTACACTCAA TCGAGTGAGT AATCCGTGGG GTCCGAAATG TGAAATACGA AGGCCGAGCA
4001  ATGTTGTGTG GAATTGTGAG CGGATAACAA TTTCACACAG GAAACAGCTA TGACCATGAT TACGCCAAGC TTTGCTCTTA GGAGTTTCCT AATACATCCC
      TACAACACAC CTTAACACTC GCCTATTGTT AAAGTGTGTC CTTTGTCGAT ACTGGTACTA ATGCGGTTCG AAACGAGAAT CCTCAAAGGA TTATGTAGGG
4101  AAACTCAAAT ATATAAAGCA TTTGACTTGT TCTATGCCCT AGGGGGCGGG GGGAAGCTAA GCCAGCTTTT TTTAACATTT AAAATGTTAA TTCCATTTTA
      TTTGAGTTTA TATATTTCGT AAACTGAACA AGATACGGGA TCCCCCGCCC CCCTTCGATT CGGTCGAAAA AAATTGTAAA TTTTACAATT AAGGTAAAAT
4201  AATGCACAGA TGTTTTTATT TCATAAGGGT TTCAATGTGC ATGAATGCTG CAATATTCCT GTTACCAAAG CTAGTATAAA TAAAAATAGA TAAACGTGGA
      TTACGTGTCT ACAAAAATAA AGTATTCCCA AAGTTACACG TACTTACGAC GTTATAAGGA CAATGGTTTC GATCATATTT ATTTTTATCT ATTTGCACCT
```

FIG. 19C

```
4301  AATTACTTAG AGTTTCTGTC ATTAACGTTT CCTTCCTCAG TTGACAACAT AAATGCGCTG CTGAGCAAGC CAGTTTGCAT CTGTCAGGAT CAATTTCCCA
      TTAATGAATC TCAAAGACAG TAATTGCAAA GGAAGGAGTC AACTGTTGTA TTTACGCGAC GACTCGTTCG GTCAAACGTA GACAGTCCTA GTTAAAGGGT
4401  TTATGCCAGT CATATTAATT ACTAGTCAAT TAGTTGATTT TTATTTTTGA CATATACATG TGAATGAAAG ACCCCACCTG TAGGTTTGGC AAGCTAGCTT
      AATACGGTCA GTATAATTAA TGATCAGTTA ATCAACTAAA AATAAAAACT GTATATGTAC ACTTACTTTC TGGGGTGGAC ATCCAAACCG TTCGATCGAA
4501  AAGTAACGCC ATTTTGCAAG GCATGGAAAA ATACATAACT GAGAATAGAA AAGTTCAGAT CAAGGTCAGG AACAGATGGA ACAGCTGAAT ATGGGCCAAA
      TTCATTGCGG TAAAACGTTC CGTACCTTTT TATGTATTGA CTCTTATCTT TTCAAGTCTA GTTCCAGTCC TTGTCTACCT TGTCGACTTA TACCCGGTTT
4601  CAGGATATCT GTGGTAAGCA GTTCCTGCCC CGGCTCAGGG CCAAGAACAG ATGGAACAGC TGAATATGGG CCAAACAGGA TATCTGTGGT AAGCAGTTCC
      GTCCTATAGA CACCATTCGT CAAGGACGGG GCCGAGTCCC GGTTCTTGTC TACCTTGTCG ACTTATACCC GGTTTGTCCT ATAGACACCA TTCGTCAAGG
4701  TGCCCCGGCT CAGGGCCAAG AACAGATGGT CCCCAGATGC GGTCCAGCCC TCAGCAGTTT CTAGAGAACC ATCAGATGTT TCCAGGGTGC CCCAAGGACC
      ACGGGGCCGA GTCCCGGTTC TTGTCTACCA GGGGTCTACG CCAGGTCGGG AGTCGTCAAA GATCTCTTGG TAGTCTACAA AGGTCCCACG GGGTTCCTGG
4801  TGAAATGACC CTGTGCCTTA TTTGAACTAA CCAATCAGTT CGCTTCTCGC TTCTGTTCGC GCGCTTATGC TCCCCGAGCT CAATAAAAGA GCCCACAACC
      ACTTTACTGG GACACGGAAT AAACTTGATT GGTTAGTCAA GCGAAGAGCG AAGACAAGCG CGCGAATACG AGGGGCTCGA GTTATTTTCT CGGGTGTTGG
4901  CCTCACTCGG GGCGCCAGTC CTCCGATTGA CTGAGTCGCC CGGGTACCCG TGTATCCAAT AAACCCTCTT GCAGTTGCAT CCGACTTGTG GTCTCGCTGT
      GGAGTGAGCC CCGCGGTCAG GAGGCTAACT GACTCAGCGG GCCCATGGGC ACATAGGTTA TTTGGGAGAA CGTCAACGTA GGCTGAACAC CAGAGCGACA
5001  TCCTTGGGAG GGTCTCCTCT GAGTGATTGA CTACCCGTCA GCGGGGGTCT TTCATTTGGG GGCTCGTCCG GGATCGGGAG ACCCCTGCCC AGGGACCACC
      AGGAACCCTC CCAGAGGAGA CTCACTAACT GATGGGCAGT CGCCCCCAGA AAGTAAACCC CCGAGCAGGC CCTAGCCCTC TGGGGACGGG TCCCTGGTGG
5101  GACCCACCAC CGGGAGGTAA GCTGGCCAGC AACTTATCTG TGTCTGTCCG ATTGTCTAGT GTCTATGACT GATTTTATGC GCCTGCGTCG GTACTAGTTA
      CTGGGTGGTG GCCCTCCATT CGACCGGTCG TTGAATAGAC ACAGACAGGC TAACAGATCA CAGATACTGA CTAAAATACG CGGACGCAGC CATGATCAAT
5201  GCTAACTAGC TCTGTATCTG GCGGACCCGT GGTGGAACTG ACGAGTTCGG AACACCGGGC CGCAACCCTG GGAGACGTCC CAGGGACTTC GGGGGCCGTT
      CGATTGATCG AGACATAGAC CGCCTGGGCA CCACCTTGAC TGCTCAAGCC TTGTGGCCCG GCGTTGGGAC CCTCTGCAGG GTCCCTGAAG CCCCCGGCAA
5301  TTTGTGGCCC GACCTGAGTC CTAAAATCCC GATCGTTTAG GACTCTTTGG TGCACCCCCC TTAGAGGAGG GATATGTGGT TCTGGTAGGA GACGAGAACC
      AAACACCGGG CTGGACTCAG GATTTTAGGG CTAGCAAATC CTGAGAAACC ACGTGGGGGG AATCTCCTCC CTATACACCA AGACCATCCT CTGCTCTTGG
5401  TAAAACAGTT CCCGCCTCCG TCTGAATTTT TGCTTTCGGT TTGGGACCGA AGCCGCGCCG CGCGTCTTGT CTGCTGCAGC ATCGTTCTGT GTTGTCTCTG
      ATTTTGTCAA GGGCGGAGGC AGACTTAAAA ACGAAAGCCA AACCCTGGCT TCGGCGCGGC GCGCAGAACA GACGACGTCG TAGCAAGACA CAACAGAGAC
5501  TCTGACTGTG TTTCTGTATT TGTCTGAAAA TATGGGCCCG GGCTAGACTG TTACCACTCC CTTAAGTTTG ACCTTAGGTC ACTGGAAAGA TGTCGAGCGG
      AGACTGACAC AAAGACATAA ACAGACTTTT ATACCCGGGC CCGATCTGAC AATGGTGAGG GAATTCAAAC TGGAATCCAG TGACCTTTCT ACAGCTCGCC
5601  ATCGCTCACA ACCAGTCGGT AGATGTCAAG AAGAGACGTT GGGTTACCTT CTGCTCTGCA GAATGGCCAA CCTTTAACGT CGGATGGCCG CGAGACGGCA
      TAGCGAGTGT TGGTCAGCCA TCTACAGTTC TTCTCTGCAA CCCAATGGAA GACGAGACGT CTTACCGGTT GGAAATTGCA GCCTACCGGC GCTCTGCCGT
5701  CCTTTAACCG AGACCTCATC ACCCAGGTTA AGATCAAGGT CTTTTCACCT GGCCCGCATG GACACCCAGA CCAGGTCCCC TACATCGTGA CCTGGGAAGC
      GGAAATTGGC TCTGGAGTAG TGGGTCCAAT TCTAGTTCCA GAAAAGTGGA CCGGGCGTAC CTGTGGGTCT GGTCCAGGGG ATGTAGCACT GGACCCTTCG
5801  CTTGGCTTTT GACCCCCCTC CCTGGGTCAA GCCCTTTGTA CACCCTAAGC CTCCGCCTCC TCTTCCTCCA TCCGCCCCGT CTCTCCCCCT TGAACCTCCT
      GAACCGAAAA CTGGGGGGAG GGACCCAGTT CGGGAAACAT GTGGGATTCG GAGGCGGAGG AGAAGGAGGT AGGCGGGGCA GAGAGGGGGA ACTTGGAGGA
5901  CGTTCGACCC CGCCTCGATC CTCCCTTTAT CCAGCCCTCA CTCCTTCTCT AGGCGCCCCC ATATGGCCAT ATGAGATCTT ATATGGGGCA CCCCCGCCCC
      GCAAGCTGGG GCGGAGCTAG GAGGGAAATA GGTCGGGAGT GAGGAAGAGA TCCGCGGGGG TATACCGGTA TACTCTAGAA TATACCCCGT GGGGGCGGGG
6001  TTGTAAACTT CCCTGACCCT GACATGACAA GAGTTACTAA CAGCCCCTCT CTCCAAGCTC ACTTACAGGC TCTCTACTTA GTCCAGCACG AAGTCTGGAG
      AACATTTGAA GGGACTGGGA CTGTACTGTT CTCAATGATT GTCGGGGAGA GAGGTTCGAG TGAATGTCCG AGAGATGAAT CAGGTCGTGC TTCAGACCTC
```

```
6101   ACCTCTGGCG GCAGCCTACC AAGAACAACT GGACCGACCG GTGGTACCTC ACCCTTACCG AGTCGGCGAC ACAGTGTGGG TCCGCCGACA CCAGACTAAG
       TGGAGACCGC CGTCGGATGG TTCTTGTTGA CCTGGCTGGC CACCATGGAG TGGGAATGGC TCAGCCGCTG TGTCACACCC AGGCGGCTGT GGTCTGATTC
                                                                                                              PmlI
                                                                                                              ~~~~
6201   AACCTAGAAC CTCGCTGGAA AGGACCTTAC ACAGTCCTGC TGACCACCCC CACCGCCCTC AAAGTAGACG GCATCGCAGC TTGGATACAC GCCGCCCACG
       TTGGATCTTG GAGCGACCTT TCCTGGAATG TGTCAGGACG ACTGGTGGGG GTGGCGGGAG TTTCATCTGC CGTAGCGTCG AACCTATGTG CGGCGGGTGC
                                                                                                                VH
                                                                                                               ~~~
                                                                                     CD8-Leader
                                                                ~~~~~~~~~~~~~~~~~~~~~~~~~~~~~~~~~~~~~~~~~~~~~~~~~~~~~~~~~~
       PmlI                                        NcoI
       ~~                                         ~~~~~~
6301   TGAAGGCTGC CGACCCCGGG GGTGGACCAT CCTCTAGACT GCCATGGCTC TCCCAGTGAC TGCCCTACTG CTTCCCCTAG CGCTTCTCCT GCATGCAGAG
       ACTTCCGACG GCTGGGGCCC CCACCTGGTA GGAGATCTGA CGGTACCGAG AGGGTCACTG ACGGGATGAC GAAGGGGATC GCGAAGAGGA CGTACGTCTC
                                                                    VH
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6401   GTGAAGCTGC AGGAGTCAGG GGGAGGCTTC GTGAAGCCTG GAGGGTCCCT CAAAGTCTCC TGTGCAGCCT CTGGATTCAC TTTCAGTAGC TATGCCATGT
       CACTTCGACG TCCTCAGTCC CCCTCCGAAG CACTTCGGAC CTCCCAGGGA GTTTCAGAGG ACACGTCGGA GACCTAAGTG AAAGTCATCG ATACGGTACA
                                                                    VH
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6501   CCTGGGTTCG CCTGAGTCCG GAGATGAGGC TGGAGTGGGT CGCAACCATT AGCAGTGCTG GTGGTTACAT CTTCTATTCT GACAGTGTGC AGGGACGATT
       GGACCCAAGC GGACTCAGGC CTCTACTCCG ACCTCACCCA GCGTTGGTAA TCGTCACGAC CACCAATGTA GAAGATAAGA CTGTCACACG TCCCTGCTAA
                                                                    VH
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
6601   CACCATTTCC AGAGACAATG CCAAGAACAC CCTGCACCTG CAAATGGGCA GTCTGAGGTC TGGGGACACG GCCATGTATT ACTGTGCAAG GCAGGGATTT
       GTGGTAAAGG TCTCTGTTAC GGTTCTTGTG GGACGTGGAC GTTTACCCGT CAGACTCCAG ACCCCTGTGC CGGTACATAA TGACACGTTC CGTCCCTAAA
                                                                                    (G4S)3 Glycine-Serine Linker
                                                                                ~~~~~~~~~~~~~~~~~~~~~~~~~~~~~~~~~~~
                                     VH
       ~~~~~~~~~~~~~~~~~~~~~~~~~~~~~~~~~~~~~~~~~~~~~~~~~~~~~~~~~~~~~~~~~~~~~~~~~~~
6701   GGTAACTACG GTGATTACTA TGCTATGGAC TACTGGGGCC AAGGGACCAC GGTCACCGTC TCCTCAGGTG GAGGTGGATC AGGTGGAGGT GGATCTGGTG
       CCATTGATGC CACTAATGAT ACGATACCTG ATGACCCCGG TTCCCTGGTG CCAGTGGCAG AGGAGTCCAC CTCCACCTAG TCCACCTCCA CCTAGACCAC
                                                                    VL
```

FIG. 19D

```
                (G4S)3 Glycine-Serine linker
6801    GAGGTGGATC TGACATTGAG CTCACCCAGT CTCCATCCTC CCTGGCTGTG TCAGCAGGAG AGAAGGTCAC TATGAGCTGC AAATCCAGTC AGAGTCTGCT
        CTCCACCTAG ACTGTAACTC GAGTGGGTCA GAGGTAGGAG GGACCGACAC AGTCGTCCTC TCTTCCAGTG ATACTCGACG TTTAGGTCAG TCTCAGACGA
                                                          VL

6901    CAACAGTAGA ACCCGAAAGA ACCAGTTGGC TTGGTACCAG CAAAAACCAG GACAGTCTCC TGAACTGCTG ATCTACTGGG CATCCACTAG GCAATCTGGA
        GTTGTCATCT TGGGCTTTCT TGGTCAACCG AACCATGGTC GTTTTTGGTC CTGTCAGAGG ACTTGACGAC TAGATGACCC GTAGGTGATC CGTTAGACCT
                                                          VL

7001    GTCCCTGATC GCTTCACAGG CAGTGGATCT GGGACAGATT TCACTCTCAC CATCAGCAGT GTGCAGGCTG AAGACCTGGC AGTTTATTAC TGCCAGCAAT
        CAGGGACTAG CGAAGTGTCC GTCACCTAGA CCCTGTCTAA AGTGAGAGTG GTAGTCGTCA CACGTCCGAC TTCTGGACCG TCAAATAATG ACGGTCGTTA

                          VL                                     CD28 transmembrane + intracellular domains (~STOP)
                                                            NotI
7101    CTTATAATCT ACTCACGTTC GGTCCTGGGA CCAAGCTGGA GATCAAACGG GCGGCCGCAA TTGAAGTTAT GTATCCTCCT CCTTACCTAG ACAATGAGAA
        GAATATTAGA TGAGTGCAAG CCAGGACCCT GGTTCGACCT CTAGTTTGCC CGCCGGCGTT AACTTCAATA CATAGGAGGA GGAATGGATC TGTTACTCTT
                                CD28 transmembrane + intracellular domains (~STOP)

7201    GAGCAATGGA ACCATTATCC ATGTGAAAGG GAAACACCTT TGTCCAAGTC CCCTATTTCC CGGACCTTCT AAGCCCTTTT GGGTGCTGGT GGTGGTTGGT
        CTCGTTACCT TGGTAATAGG TACACTTTCC CTTTGTGGAA ACAGGTTCAG GGGATAAAGG GCCTGGAAGA TTCGGGAAAA CCCACGACCA CCACCAACCA
                                CD28 transmembrane + intracellular domains (~STOP)

7301    GGAGTCCTGG CTTGCTATAG CTTGCTAGTA ACAGTGGCCT TTATTATTTT CTGGGTGAGG AGTAAGAGGA GCAGGCTCCT GCACAGTGAC TACATGAACA
        CCTCAGGACC GAACGATATC GAACGATCAT TGTCACCGGA AATAATAAAA GACCCACTCC TCATTCTCCT CGTCCGAGGA CGTGTCACTG ATGTACTTGT
                CD28 transmembrane + intracellular domains (~STOP)

                                                                                   CD3 zeta chain intracellular domain
7401    TGACTCCCCG CCGCCCCGGG CCCACCCGCA AGCATTACCA GCCCTATGCC CCACCACGCG ACTTCGCAGC CTATCGCTCC AGAGTGAAGT TCAGCAGGAG
        ACTGAGGGGC GGCGGGGCCC GGGTGGGCGT TCGTAATGGT CGGGATACGG GGTGGTGCGC TGAAGCGTCG GATAGCGAGG TCTCACTTCA AGTCGTCCTC
                                          CD3 zeta chain intracellular domain

7501    CGCAGAGCCC CCCGCGTACC AGCAGGGCCA GAACCAGCTC TATAACGAGC TCAATCTAGG ACGAAGAGAG GAGTACGATG TTTTGGACAA GAGACGTGGC
        GCGTCTCGGG GGGCGCATGG TCGTCCCGGT CTTGGTCGAG ATATTGCTCG AGTTAGATCC TGCTTCTCTC CTCATGCTAC AAAACCTGTT CTCTGCACCG
                                          CD3 zeta chain intracellular domain

7601    CGGGACCCTG AGATGGGGGG AAAGCCGAGA AGGAAGAACC CTCAGGAAGG CCTGTACAAT GAACTGCAGA AAGATAAGAT GGCGGAGGCC TACAGTGAGA
        GCCCTGGGAC TCTACCCCCC TTTCGGCTCT TCCTTCTTGG GAGTCCTTCC GGACATGTTA CTTGACGTCT TTCTATTCTA CCGCCTCCGG ATGTCACTCT
                                          CD3 zeta chain intracellular domain
```

FIG. 19E

```
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
7701   TTGGGATGAA AGGCGAGCGC CGGAGGGGCA AGGGGCACGA TGGCCTTTAC CAGGGTCTCA GTACAGCCAC CAAGGACACC TACGACGCCC TTCACATGCA
       AACCCTACTT TCCGCTCGCG GCCTCCCCGT TCCCCGTGCT ACCGGAAATG GTCCCAGAGT CATGTCGGTG GTTCCTGTGG ATGCTGCGGG AAGTGTACGT
       CD3 zeta chain intracellular domain
       ~~~~~~~~~~~~~~~~~
                                  XhoI
                                ~~~~~~~
7801   GGCCCTGCCC CCTCGCTAAC AGCCACTCGA G
       CCGGGACGGG GGAGCGATTG TCGGTGAGCT C

       Figure 19 top strand: SEQ ID NO:39
       Figure 19 bottom strand: SEQ ID NO:40
```

1. Mouse MUC16-CD Peptide 1 (SEQ ID NO:21):

TLDRKSVFVDGYSQNRDD 19 AA

2. Mouse 1st Cysteine Loop peptide 2 (SEQ ID NO:22):

KSYFSDCQVLAFRSVSNNNNHTGVDSLCNFSPL 33 AA

3. Mouse 2nd Cysteine Loop peptide 3 (SEQ ID NO:23):

SLYSNCRLASLRPKKNGTATGVNAICSYHQN 32 AA

Alignment of mouse MUC16 (SEQ ID NO:24) and human MUC16 (SEQ ID NO:25) amino acid sequences

FIG. 24A Nucleotide sequence encoding 12B10.3G10-$V_H$ (SEQ ID NO:26)

GAGGTGAAGCTGGAGGAGTCAGGTGGAGGATTGGTGCAGCCTAAAGGATCATTGAAACTCTCATGTGCCGCCTCT
GGTTTCACCTTCAATACCTATGCCGTGCACTGGGTCCGCCAGGCTCCAGGAAAGGGTATGGAATGGGTTGCTCGC
ATAAGAAGTAAAAGTGGAAATTATGCAACATATTATGCCGATTCAGTGAAAGACAGATTCACCATCTCCAGAAAT
GATTCACAGAGCATGCTCTATCTGCAAATGAACAACCTGAAAACTGAGGACACAGCCATATATTACTGTGTGAGA
GCGGGTAACAACGGGGCCTTTCCTTACTGGGGCCAAGGGACCACGGTCACCGTCTCCTCA

FIG. 24B 12B10.3G10-$V_H$ Amino Acid sequence (SEQ ID NO:27)

EVKLEESGGGLVQPKGSLKLSCAASGFTFNTYAVHWVRQAPGKGMEWVARIRSKSGNYAT
YYADSVKDRFTISRNDSQSMLYLQMNNLKTEDTAIYYCVRAGNNGAFPYWGQGTTVTVSS

FIG. 24C Nucleotide sequence encoding 12B10.3G10-$V_L$ (SEQ ID NO:28)

Note the VL has an optional *NotI* site added by the primer for cloning.

GACATTGAGCTCACCCAGTCTCCATCCTCACTGTCTGCATCTCTGGGAGGCAGAGTCACCATCACTTGCAAGGCT
AGCCAAGATATTAAGAAGTATATAGCTTGGTACCAACACAAGCCTGGAAAAACTCCTCGACTACTCATACATTTC
ACATCTACATTACAGACAGGCATCCCATCAAGGTTCAGTGGACGTGGGTCTGGGAGAGACTATTCCTTCAGCATC
AGCAACCTGGAGTCTGAAGATATTGCAACTTATTATTGTCTACAGTATGATAGTCTGTACACGTTCGGAGGGGGG
ACCAAGCTGGAGATCAAACGGGCGGCCGCA

FIG. 24D 12B10.3G10-$V_L$ Amino Acid sequence (SEQ ID NO:29)

DIELTQSPSSLSASLGGRVTITCKASQDIKKYIAWYQHKPGKTPRLLIHFTSTLQTGIPS
RFSGRGSGRDYSFSISNLESEDIATYYCLQYDSLYTFGGGTKLEIKRAAA

SEQUENCE LISTING

<160> NUMBER OF SEQ ID NOS: 40

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

```
Asn Phe Ser Pro Leu Ala Arg Arg Val Asp Arg Val Ala Ile Tyr Glu
1               5                   10                  15

Glu
```

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

```
Thr Leu Asp Arg Ser Ser Val Leu Val Asp Gly Tyr Ser Pro Asn Arg
1               5                   10                  15

Asn Glu
```

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

```
Cys Gly Val Leu Val Thr Thr Arg Arg Arg Lys Lys Glu Gly Glu Tyr
1               5                   10                  15

Asn Val Gln Gln Gln
            20
```

<210> SEQ ID NO 4
<211> LENGTH: 366
<212> TYPE: DNA
<213> ORGANISM: Artificial Sequence
<220> FEATURE:
<223> OTHER INFORMATION: Synthetic

<400> SEQUENCE: 4

```
gtgaagctgg aggagtcagg gggaggcttc gtgaagcctg gagggtccct caaaatctcc      60

tgtgcagcct ctggattcac tttcagaaac tatgccatgt cctgggttcg cctgagtccg     120

gagatgaggc tggagtgggt cgcaaccatt agcagtgctg gtggttacat cttctattct     180

gacagtgtgc agggacgatt caccatttcc agagacaatg ccaagaacac cctccacttg     240

caaatgggca gtctgaggtc tggggacacg gccatgtatt actgtgcaag gcagggattt     300

ggtaactacg gtgattacta tgctatggac tactggggcc aagggaccac ggtcaccgtc     360

tcctca                                                                366
```

<210> SEQ ID NO 5
<211> LENGTH: 339
<212> TYPE: DNA
<213> ORGANISM: Artificial Sequence
<220> FEATURE:
<223> OTHER INFORMATION: Synthetic

<400> SEQUENCE: 5
gacattgagc tcacccagtc tccatcctcc ctggctgtgt cagcaggaga gaaggtcact 60
atgagctgca aatccagtca gagtctgctc aacagtagaa cccgaaagaa ccagttggct 120
tggtaccagc aaaaaacagg acagtctcct gaactgctga tctactgggc atccactcgg 180
caatctgggg tccctgatcg cttcacaggc agtggatctg ggacagattt cactctcacc 240
atcagcagtg tgcaggctga agacctggca gtttattact gccagcaatc ttataatcta 300
ctcacgttcg gtcctgggac caagctggag atcaaacgg 339

<210> SEQ ID NO 6
<211> LENGTH: 366
<212> TYPE: DNA
<213> ORGANISM: Artificial Sequence
<220> FEATURE:
<223> OTHER INFORMATION: Synthetic

<400> SEQUENCE: 6
gtgaagctgc aggagtcagg gggaggcttc gtgaagcctg gagggtccct caaagtctcc 60
tgtgcagcct ctggattcac tttcagtagc tatgccatgt cctgggttcg cctgagtccg 120
gagatgaggc tggagtgggt cgcaaccatt agcagtgctg gtggttacat cttctattct 180
gacagtgtgc agggacgatt caccatttcc agagacaatg ccaagaacac cctgcacctg 240
caaatgggca gtctgaggtc tggggacacg gccatgtatt actgtgcaag gcagggattt 300
ggtaactacg gtgattacta tgctatggac tactggggcc aagggaccac ggtcaccgtc 360
tcctca 366

<210> SEQ ID NO 7
<211> LENGTH: 339
<212> TYPE: DNA
<213> ORGANISM: Artificial Sequence
<220> FEATURE:
<223> OTHER INFORMATION: Synthetic

<400> SEQUENCE: 7
gacattgagc tcacccagtc tccatcctcc ctggctgtgt cagcaggaga gaaggtcact 60
atgagctgca aatccagtca gagtctgctc aacagtagaa cccgaaagaa ccagttggct 120
tggtaccagc aaaaaccagg acagtctcct gaactgctga tctactgggc atccactagg 180
caatctggag tccctgatcg cttcacaggc agtggatctg ggacagattt cactctcacc 240
atcagcagtg tgcaggctga agacctggca gtttattact gccagcaatc ttataatcta 300
ctcacgttcg gtcctgggac caagctggag gtcaaacgg 339

<210> SEQ ID NO 8
<211> LENGTH: 348
<212> TYPE: DNA
<213> ORGANISM: Artificial Sequence
<220> FEATURE:
<223> OTHER INFORMATION: Synthetic

<400> SEQUENCE: 8
gtgaagctgg aggagtcagg gggagacttg gtgaagcctg gagggtccct gaaactctcc 60
tgtgcagtct ctggattcac tttcagtagc cattccatgt cttggattcg tcagactcca 120
gagaagaggc tagagtgggt cgcatccgtg agtagtggtg gtaggatcta ctattcggac 180
agtgtgaagg gccgattcac cgtcaccaga gaaaatgaca ggaacaccct gtatttgtta 240

-continued atgagtagtc tgaggtctga ggacacggcc atgtattatt gtggaagagg acaggtattt 300
tatgctttgg acaattgggg ccaagggacc acggtcaccg tctcctca 348

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacattgagc tcacccagtc tccatcctcc ctggctgtgt cagcaggaga gaaggtcact 60
atgagctgca aatccagtca gagtctgctc aacagtagaa cccgaaagaa ccagttggct 120
tggtaccagc aaaaaccagg acagtctcct gaactgctga tctactgggc atccactagg 180
caatctggag tccctgatcg cttcacaggc agtggatctg ggacagattt cactctcacc 240
atcagcagtg tgcaggctga agacctggca gtttattact gccagcaatc ttataatcta 300
ctcacgttcg gtcctgggac caagctggag gtcaaacgg 339

<210> SEQ ID NO 10
<211> LENGTH: 216
<212> TYPE: DNA
<213> ORGANISM: Artificial Sequence
<220> FEATURE:
<223> OTHER INFORMATION: Synthetic

<400> SEQUENCE: 10
gacattgagc tcacccagtc tccaaagctc ctgatctaca aggtttccaa ccgattttct 60
ggggtcccag acaggttcag tggcagtgga tcagggacag atttcacact caagatcagc 120
agagtggagg ctgaggatct gggagtttat tactgctttc aaggttcaca tgttccgtgg 180
acgttcggtg gagggaccaa gctggagatc aaacgg 216

<210> SEQ ID NO 11
<211> LENGTH: 354
<212> TYPE: DNA
<213> ORGANISM: Artificial Sequence
<220> FEATURE:
<223> OTHER INFORMATION: Synthetic

<400> SEQUENCE: 11
gaggtgaagc tggaggagtc aggacctgaa ctggtgaagc ctggggcttc agtgaagata 60
tcctgcaagg cttctggtta ctcatttact ggctacttta tgaactgggt gaagcagacc 120
catggaaaga gccttgagtg gattggacgt attaatcctt acaatggtgc tactttctac 180
aatcagaagt tcacgggcaa ggccacaatg actgtagaca aatcctctac cacagcccac 240
atggagctcc tgagcctgac atctgaggac tctgcagtct attattgtgg aaaggggaat 300
tactacggcc cctttgatta ctggggccaa gggaccacgg tcaccgtctc ctca 354

<210> SEQ ID NO 12
<211> LENGTH: 333
<212> TYPE: DNA
<213> ORGANISM: Artificial Sequence
<220> FEATURE:
<223> OTHER INFORMATION: Synthetic

<400> SEQUENCE: 12
gacattgagc tcacccagtc tccatcttat cttgctgcat ctcctgaaga aaccattact 60
attaattgca gggcaagtaa gagcattagc aaatatttag cctggtatca aaagaaacct 120

```
gggaaaacta ataagcttct tatctactct ggatccactt tgcaatctgg aattccatca    180

aggttcagtg gcagtggatc tggtacagat ttcactctca ccatcagtag cctggagcct    240

gaagattttg caatgtatta ctgtcaacag cataatgaat acccgtggac gttcggtgga    300

gggaccaagc tggagatcaa acgggcggcc gca                                 333


<210> SEQ ID NO 13
<211> LENGTH: 14507
<212> TYPE: PRT
<213> ORGANISM: Homo sapiens

<400> SEQUENCE: 13

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
        195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
        275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335
```

-continued

```
Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
        355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
        435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
        515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
        595                 600                 605

Ile Ser Met Thr Gly Gly Ser Ser Thr Arg Gly Ser Gln Gly Thr Thr
    610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
        675                 680                 685

Ala Phe Arg Glu Gly Thr Ser Leu Gly Leu Thr Pro Leu Asn Thr Arg
    690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750
```

-continued

```
Thr Thr Gly Thr Pro Glu Ile Ser Thr Lys Thr Lys Pro Ser Ser Ala
        755                 760                 765

Val Leu Ser Ser Met Thr Leu Ser Asn Ala Ala Thr Ser Pro Glu Arg
    770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
        835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
        915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
        995                 1000                1005

Met Glu  Ala Thr Ser Ile Arg  Glu Pro Ser Thr Thr  Ile Leu Thr
    1010                 1015                 1020

Thr Glu  Thr Thr Asn Gly Pro  Gly Ser Met Ala Val  Ala Ser Thr
    1025                 1030                 1035

Asn Ile  Pro Ile Gly Lys Gly  Tyr Ile Thr Glu Gly  Arg Leu Asp
    1040                 1045                 1050

Thr Ser  His Leu Pro Ile Gly  Thr Thr Ala Ser Ser  Glu Thr Ser
    1055                 1060                 1065

Met Asp  Phe Thr Met Ala Lys  Glu Ser Val Ser Met  Ser Val Ser
    1070                 1075                 1080

Pro Ser  Gln Ser Met Asp Ala  Ala Gly Ser Ser Thr  Pro Gly Arg
    1085                 1090                 1095

Thr Ser  Gln Phe Val Asp Thr  Phe Ser Asp Asp Val  Tyr His Leu
    1100                 1105                 1110

Thr Ser  Arg Glu Ile Thr Ile  Pro Arg Asp Gly Thr  Ser Ser Ala
    1115                 1120                 1125

Leu Thr  Pro Gln Met Thr Ala  Thr His Pro Pro Ser  Pro Asp Pro
    1130                 1135                 1140

Gly Ser  Ala Arg Ser Thr Trp  Leu Gly Ile Leu Ser  Ser Ser Pro
    1145                 1150                 1155

Ser Ser  Pro Thr Pro Lys Val  Thr Met Ser Ser Thr  Phe Ser Thr
```

```
    1160                1165                1170

Gln Arg  Val Thr Thr Ser Met  Ile Met Asp Thr Val  Glu Thr Ser
    1175                1180                1185

Arg Trp  Asn Met Pro Asn Leu  Pro Ser Thr Thr Ser  Leu Thr Pro
    1190                1195                1200

Ser Asn  Ile Pro Thr Ser Gly  Ala Ile Gly Lys Ser  Thr Leu Val
    1205                1210                1215

Pro Leu  Asp Thr Pro Ser Pro  Ala Thr Ser Leu Glu  Ala Ser Glu
    1220                1225                1230

Gly Gly  Leu Pro Thr Leu Ser  Thr Tyr Pro Glu Ser  Thr Asn Thr
    1235                1240                1245

Pro Ser  Ile His Leu Gly Ala  His Ala Ser Ser Glu  Ser Pro Ser
    1250                1255                1260

Thr Ile  Lys Leu Thr Met Ala  Ser Val Val Lys Pro  Gly Ser Tyr
    1265                1270                1275

Thr Pro  Leu Thr Phe Pro Ser  Ile Glu Thr His Ile  His Val Ser
    1280                1285                1290

Thr Ala  Arg Met Ala Tyr Ser  Ser Gly Ser Ser Pro  Glu Met Thr
    1295                1300                1305

Ala Pro  Gly Glu Thr Asn Thr  Gly Ser Thr Trp Asp  Pro Thr Thr
    1310                1315                1320

Tyr Ile  Thr Thr Thr Asp Pro  Lys Asp Thr Ser Ser  Ala Gln Val
    1325                1330                1335

Ser Thr  Pro His Ser Val Arg  Thr Leu Arg Thr Thr  Glu Asn His
    1340                1345                1350

Pro Lys  Thr Glu Ser Ala Thr  Pro Ala Ala Tyr Ser  Gly Ser Pro
    1355                1360                1365

Lys Ile  Ser Ser Ser Pro Asn  Leu Thr Ser Pro Ala  Thr Lys Ala
    1370                1375                1380

Trp Thr  Ile Thr Asp Thr Thr  Glu His Ser Thr Gln  Leu His Tyr
    1385                1390                1395

Thr Lys  Leu Ala Glu Lys Ser  Ser Gly Phe Glu Thr  Gln Ser Ala
    1400                1405                1410

Pro Gly  Pro Val Ser Val Val  Ile Pro Thr Ser Pro  Thr Ile Gly
    1415                1420                1425

Ser Ser  Thr Leu Glu Leu Thr  Ser Asp Val Pro Gly  Glu Pro Leu
    1430                1435                1440

Val Leu  Ala Pro Ser Glu Gln  Thr Thr Ile Thr Leu  Pro Met Ala
    1445                1450                1455

Thr Trp  Leu Ser Thr Ser Leu  Thr Glu Glu Met Ala  Ser Thr Asp
    1460                1465                1470

Leu Asp  Ile Ser Ser Pro Ser  Ser Pro Met Ser Thr  Phe Ala Ile
    1475                1480                1485

Phe Pro  Pro Met Ser Thr Pro  Ser His Glu Leu Ser  Lys Ser Glu
    1490                1495                1500

Ala Asp  Thr Ser Ala Ile Arg  Asn Thr Asp Ser Thr  Thr Leu Asp
    1505                1510                1515

Gln His  Leu Gly Ile Arg Ser  Leu Gly Arg Thr Gly  Asp Leu Thr
    1520                1525                1530

Thr Val  Pro Ile Thr Pro Leu  Thr Thr Thr Trp Thr  Ser Val Ile
    1535                1540                1545

Glu His  Ser Thr Gln Ala Gln  Asp Thr Leu Ser Ala  Thr Met Ser
    1550                1555                1560
```

-continued

```
Pro Thr  His Val Thr Gln Ser  Leu Lys Asp Gln Thr  Ser Ile Pro
    1565                 1570                 1575

Ala Ser  Ala Ser Pro Ser His  Leu Thr Glu Val Tyr  Pro Glu Leu
    1580                 1585                 1590

Gly Thr  Gln Gly Arg Ser Ser  Ser Glu Ala Thr Thr  Phe Trp Lys
    1595                 1600                 1605

Pro Ser  Thr Asp Thr Leu Ser  Arg Glu Ile Glu Thr  Gly Pro Thr
    1610                 1615                 1620

Asn Ile  Gln Ser Thr Pro Pro  Met Asp Asn Thr Thr  Thr Gly Ser
    1625                 1630                 1635

Ser Ser  Ser Gly Val Thr Leu  Gly Ile Ala His Leu  Pro Ile Gly
    1640                 1645                 1650

Thr Ser  Ser Pro Ala Glu Thr  Ser Thr Asn Met Ala  Leu Glu Arg
    1655                 1660                 1665

Arg Ser  Ser Thr Ala Thr Val  Ser Met Ala Gly Thr  Met Gly Leu
    1670                 1675                 1680

Leu Val  Thr Ser Ala Pro Gly  Arg Ser Ile Ser Gln  Ser Leu Gly
    1685                 1690                 1695

Arg Val  Ser Ser Val Leu Ser  Glu Ser Thr Thr Glu  Gly Val Thr
    1700                 1705                 1710

Asp Ser  Ser Lys Gly Ser Ser  Pro Arg Leu Asn Thr  Gln Gly Asn
    1715                 1720                 1725

Thr Ala  Leu Ser Ser Ser Leu  Glu Pro Ser Tyr Ala  Glu Gly Ser
    1730                 1735                 1740

Gln Met  Ser Thr Ser Ile Pro  Leu Thr Ser Ser Pro  Thr Thr Pro
    1745                 1750                 1755

Asp Val  Glu Phe Ile Gly Gly  Ser Thr Phe Trp Thr  Lys Glu Val
    1760                 1765                 1770

Thr Thr  Val Met Thr Ser Asp  Ile Ser Lys Ser Ser  Ala Arg Thr
    1775                 1780                 1785

Glu Ser  Ser Ser Ala Thr Leu  Met Ser Thr Ala Leu  Gly Ser Thr
    1790                 1795                 1800

Glu Asn  Thr Gly Lys Glu Lys  Leu Arg Thr Ala Ser  Met Asp Leu
    1805                 1810                 1815

Pro Ser  Pro Thr Pro Ser Met  Glu Val Thr Pro Trp  Ile Ser Leu
    1820                 1825                 1830

Thr Leu  Ser Asn Ala Pro Asn  Thr Thr Asp Ser Leu  Asp Leu Ser
    1835                 1840                 1845

His Gly  Val His Thr Ser Ser  Ala Gly Thr Leu Ala  Thr Asp Arg
    1850                 1855                 1860

Ser Leu  Asn Thr Gly Val Thr  Arg Ala Ser Arg Leu  Glu Asn Gly
    1865                 1870                 1875

Ser Asp  Thr Ser Ser Lys Ser  Leu Ser Met Gly Asn  Ser Thr His
    1880                 1885                 1890

Thr Ser  Met Thr Tyr Thr Glu  Lys Ser Glu Val Ser  Ser Ser Ile
    1895                 1900                 1905

His Pro  Arg Pro Glu Thr Ser  Ala Pro Gly Ala Glu  Thr Thr Leu
    1910                 1915                 1920

Thr Ser  Thr Pro Gly Asn Arg  Ala Ile Ser Leu Thr  Leu Pro Phe
    1925                 1930                 1935

Ser Ser  Ile Pro Val Glu Glu  Val Ile Ser Thr Gly  Ile Thr Ser
    1940                 1945                 1950
```

```
Gly Pro  Asp Ile Asn Ser Ala  Pro Met Thr His Ser  Pro Ile Thr
    1955                 1960                 1965

Pro Pro  Thr Ile Val Trp Thr  Ser Thr Gly Thr Ile  Glu Gln Ser
    1970                 1975                 1980

Thr Gln  Pro Leu His Ala Val  Ser Ser Glu Lys Val  Ser Val Gln
    1985                 1990                 1995

Thr Gln  Ser Thr Pro Tyr Val  Asn Ser Val Ala Val  Ser Ala Ser
    2000                 2005                 2010

Pro Thr  His Glu Asn Ser Val  Ser Ser Gly Ser Ser  Thr Ser Ser
    2015                 2020                 2025

Pro Tyr  Ser Ser Ala Ser Leu  Glu Ser Leu Asp Ser  Thr Ile Ser
    2030                 2035                 2040

Arg Arg  Asn Ala Ile Thr Ser  Trp Leu Trp Asp Leu  Thr Thr Ser
    2045                 2050                 2055

Leu Pro  Thr Thr Thr Trp Pro  Ser Thr Ser Leu Ser  Glu Ala Leu
    2060                 2065                 2070

Ser Ser  Gly His Ser Gly Val  Ser Asn Pro Ser Ser  Thr Thr Thr
    2075                 2080                 2085

Glu Phe  Pro Leu Phe Ser Ala  Ala Ser Thr Ser Ala  Ala Lys Gln
    2090                 2095                 2100

Arg Asn  Pro Glu Thr Glu Thr  His Gly Pro Gln Asn  Thr Ala Ala
    2105                 2110                 2115

Ser Thr  Leu Asn Thr Asp Ala  Ser Ser Val Thr Gly  Leu Ser Glu
    2120                 2125                 2130

Thr Pro  Val Gly Ala Ser Ile  Ser Ser Glu Val Pro  Leu Pro Met
    2135                 2140                 2145

Ala Ile  Thr Ser Arg Ser Asp  Val Ser Gly Leu Thr  Ser Glu Ser
    2150                 2155                 2160

Thr Ala  Asn Pro Ser Leu Gly  Thr Ala Ser Ser Ala  Gly Thr Lys
    2165                 2170                 2175

Leu Thr  Arg Thr Ile Ser Leu  Pro Thr Ser Glu Ser  Leu Val Ser
    2180                 2185                 2190

Phe Arg  Met Asn Lys Asp Pro  Trp Thr Val Ser Ile  Pro Leu Gly
    2195                 2200                 2205

Ser His  Pro Thr Thr Asn Thr  Glu Thr Ser Ile Pro  Val Asn Ser
    2210                 2215                 2220

Ala Gly  Pro Pro Gly Leu Ser  Thr Val Ala Ser Asp  Val Ile Asp
    2225                 2230                 2235

Thr Pro  Ser Asp Gly Ala Glu  Ser Ile Pro Thr Val  Ser Phe Ser
    2240                 2245                 2250

Pro Ser  Pro Asp Thr Glu Val  Thr Thr Ile Ser His  Phe Pro Glu
    2255                 2260                 2265

Lys Thr  Thr His Ser Phe Arg  Thr Ile Ser Ser Leu  Thr His Glu
    2270                 2275                 2280

Leu Thr  Ser Arg Val Thr Pro  Ile Pro Gly Asp Trp  Met Ser Ser
    2285                 2290                 2295

Ala Met  Ser Thr Lys Pro Thr  Gly Ala Ser Pro Ser  Ile Thr Leu
    2300                 2305                 2310

Gly Glu  Arg Arg Thr Ile Thr  Ser Ala Ala Pro Thr  Thr Ser Pro
    2315                 2320                 2325

Ile Val  Leu Thr Ala Ser Phe  Thr Glu Thr Ser Thr  Val Ser Leu
    2330                 2335                 2340

Asp Asn  Glu Thr Thr Val Lys  Thr Ser Asp Ile Leu  Asp Ala Arg
```

-continued

```
    2345                2350                2355

Lys Thr  Asn Glu Leu Pro Ser  Asp Ser Ser Ser Ser  Ser Asp Leu
    2360                2365                2370

Ile Asn  Thr Ser Ile Ala Ser  Ser Thr Met Asp Val  Thr Lys Thr
    2375                2380                2385

Ala Ser  Ile Ser Pro Thr Ser  Ile Ser Gly Met Thr  Ala Ser Ser
    2390                2395                2400

Ser Pro  Ser Leu Phe Ser Ser  Asp Arg Pro Gln Val  Pro Thr Ser
    2405                2410                2415

Thr Thr  Glu Thr Asn Thr Ala  Thr Ser Pro Ser Val  Ser Ser Asn
    2420                2425                2430

Thr Tyr  Ser Leu Asp Gly Gly  Ser Asn Val Gly Gly  Thr Pro Ser
    2435                2440                2445

Thr Leu  Pro Pro Phe Thr Ile  Thr His Pro Val Glu  Thr Ser Ser
    2450                2455                2460

Ala Leu  Leu Ala Trp Ser Arg  Pro Val Arg Thr Phe  Ser Thr Met
    2465                2470                2475

Val Ser  Thr Asp Thr Ala Ser  Gly Glu Asn Pro Thr  Ser Ser Asn
    2480                2485                2490

Ser Val  Val Thr Ser Val Pro  Ala Pro Gly Thr Trp  Thr Ser Val
    2495                2500                2505

Gly Ser  Thr Thr Asp Leu Pro  Ala Met Gly Phe Leu  Lys Thr Ser
    2510                2515                2520

Pro Ala  Gly Glu Ala His Ser  Leu Leu Ala Ser Thr  Ile Glu Pro
    2525                2530                2535

Ala Thr  Ala Phe Thr Pro His  Leu Ser Ala Ala Val  Val Thr Gly
    2540                2545                2550

Ser Ser  Ala Thr Ser Glu Ala  Ser Leu Leu Thr Thr  Ser Glu Ser
    2555                2560                2565

Lys Ala  Ile His Ser Ser Pro  Gln Thr Pro Thr Thr  Pro Thr Ser
    2570                2575                2580

Gly Ala  Asn Trp Glu Thr Ser  Ala Thr Pro Glu Ser  Leu Leu Val
    2585                2590                2595

Val Thr  Glu Thr Ser Asp Thr  Thr Leu Thr Ser Lys  Ile Leu Val
    2600                2605                2610

Thr Asp  Thr Ile Leu Phe Ser  Thr Val Ser Thr Pro  Pro Ser Lys
    2615                2620                2625

Phe Pro  Ser Thr Gly Thr Leu  Ser Gly Ala Ser Phe  Pro Thr Leu
    2630                2635                2640

Leu Pro  Asp Thr Pro Ala Ile  Pro Leu Thr Ala Thr  Glu Pro Thr
    2645                2650                2655

Ser Ser  Leu Ala Thr Ser Phe  Asp Ser Thr Pro Leu  Val Thr Ile
    2660                2665                2670

Ala Ser  Asp Ser Leu Gly Thr  Val Pro Glu Thr Thr  Leu Thr Met
    2675                2680                2685

Ser Glu  Thr Ser Asn Gly Asp  Ala Leu Val Leu Lys  Thr Val Ser
    2690                2695                2700

Asn Pro  Asp Arg Ser Ile Pro  Gly Ile Thr Ile Gln  Gly Val Thr
    2705                2710                2715

Glu Ser  Pro Leu His Pro Ser  Ser Thr Ser Pro Ser  Lys Ile Val
    2720                2725                2730

Ala Pro  Arg Asn Thr Thr Tyr  Glu Gly Ser Ile Thr  Val Ala Leu
    2735                2740                2745
```

-continued

```
Ser Thr Leu Pro Ala Gly Thr Thr Gly Ser Leu Val Phe Ser Gln
    2750                2755                2760

Ser Ser Glu Asn Ser Glu Thr Thr Ala Leu Val Asp Ser Ser Ala
    2765                2770                2775

Gly Leu Glu Arg Ala Ser Val Met Pro Leu Thr Thr Gly Ser Gln
    2780                2785                2790

Gly Met Ala Ser Ser Gly Gly Ile Arg Ser Gly Ser Thr His Ser
    2795                2800                2805

Thr Gly Thr Lys Thr Phe Ser Ser Leu Pro Leu Thr Met Asn Pro
    2810                2815                2820

Gly Glu Val Thr Ala Met Ser Glu Ile Thr Thr Asn Arg Leu Thr
    2825                2830                2835

Ala Thr Gln Ser Thr Ala Pro Lys Gly Ile Pro Val Lys Pro Thr
    2840                2845                2850

Ser Ala Glu Ser Gly Leu Leu Thr Pro Val Ser Ala Ser Ser Ser
    2855                2860                2865

Pro Ser Lys Ala Phe Ala Ser Leu Thr Thr Ala Pro Pro Thr Trp
    2870                2875                2880

Gly Ile Pro Gln Ser Thr Leu Thr Phe Glu Phe Ser Glu Val Pro
    2885                2890                2895

Ser Leu Asp Thr Lys Ser Ala Ser Leu Pro Thr Pro Gly Gln Ser
    2900                2905                2910

Leu Asn Thr Ile Pro Asp Ser Asp Ala Ser Thr Ala Ser Ser Ser
    2915                2920                2925

Leu Ser Lys Ser Pro Glu Lys Asn Pro Arg Ala Arg Met Met Thr
    2930                2935                2940

Ser Thr Lys Ala Ile Ser Ala Ser Ser Phe Gln Ser Thr Gly Phe
    2945                2950                2955

Thr Glu Thr Pro Glu Gly Ser Ala Ser Pro Ser Met Ala Gly His
    2960                2965                2970

Glu Pro Arg Val Pro Thr Ser Gly Thr Gly Asp Pro Arg Tyr Ala
    2975                2980                2985

Ser Glu Ser Met Ser Tyr Pro Asp Pro Ser Lys Ala Ser Ser Ala
    2990                2995                3000

Met Thr Ser Thr Ser Leu Ala Ser Lys Leu Thr Thr Leu Phe Ser
    3005                3010                3015

Thr Gly Gln Ala Ala Arg Ser Gly Ser Ser Ser Ser Pro Ile Ser
    3020                3025                3030

Leu Ser Thr Glu Lys Glu Thr Ser Phe Leu Ser Pro Thr Ala Ser
    3035                3040                3045

Thr Ser Arg Lys Thr Ser Leu Phe Leu Gly Pro Ser Met Ala Arg
    3050                3055                3060

Gln Pro Asn Ile Leu Val His Leu Gln Thr Ser Ala Leu Thr Leu
    3065                3070                3075

Ser Pro Thr Ser Thr Leu Asn Met Ser Gln Glu Glu Pro Pro Glu
    3080                3085                3090

Leu Thr Ser Ser Gln Thr Ile Ala Glu Glu Glu Gly Thr Thr Ala
    3095                3100                3105

Glu Thr Gln Thr Leu Thr Phe Thr Pro Ser Glu Thr Pro Thr Ser
    3110                3115                3120

Leu Leu Pro Val Ser Ser Pro Thr Glu Pro Thr Ala Arg Arg Lys
    3125                3130                3135
```

-continued

```
Ser Ser  Pro Glu Thr Trp Ala  Ser Ser Ile Ser Val  Pro Ala Lys
    3140                 3145                 3150

Thr Ser  Leu Val Glu Thr Thr  Asp Gly Thr Leu Val  Thr Thr Ile
    3155                 3160                 3165

Lys Met  Ser Ser Gln Ala Ala  Gln Gly Asn Ser Thr  Trp Pro Ala
    3170                 3175                 3180

Pro Ala  Glu Glu Thr Gly Ser  Ser Pro Ala Gly Thr  Ser Pro Gly
    3185                 3190                 3195

Ser Pro  Glu Met Ser Thr Thr  Leu Lys Ile Met Ser  Ser Lys Glu
    3200                 3205                 3210

Pro Ser  Ile Ser Pro Glu Ile  Arg Ser Thr Val Arg  Asn Ser Pro
    3215                 3220                 3225

Trp Lys  Thr Pro Glu Thr Thr  Val Pro Met Glu Thr  Thr Val Glu
    3230                 3235                 3240

Pro Val  Thr Leu Gln Ser Thr  Ala Leu Gly Ser Gly  Ser Thr Ser
    3245                 3250                 3255

Ile Ser  His Leu Pro Thr Gly  Thr Thr Ser Pro Thr  Lys Ser Pro
    3260                 3265                 3270

Thr Glu  Asn Met Leu Ala Thr  Glu Arg Val Ser Leu  Ser Pro Ser
    3275                 3280                 3285

Pro Pro  Glu Ala Trp Thr Asn  Leu Tyr Ser Gly Thr  Pro Gly Gly
    3290                 3295                 3300

Thr Arg  Gln Ser Leu Ala Thr  Met Ser Ser Val Ser  Leu Glu Ser
    3305                 3310                 3315

Pro Thr  Ala Arg Ser Ile Thr  Gly Thr Gly Gln Gln  Ser Ser Pro
    3320                 3325                 3330

Glu Leu  Val Ser Lys Thr Thr  Gly Met Glu Phe Ser  Met Trp His
    3335                 3340                 3345

Gly Ser  Thr Gly Gly Thr Thr  Gly Asp Thr His Val  Ser Leu Ser
    3350                 3355                 3360

Thr Ser  Ser Asn Ile Leu Glu  Asp Pro Val Thr Ser  Pro Asn Ser
    3365                 3370                 3375

Val Ser  Ser Leu Thr Asp Lys  Ser Lys His Lys Thr  Glu Thr Trp
    3380                 3385                 3390

Val Ser  Thr Thr Ala Ile Pro  Ser Thr Val Leu Asn  Asn Lys Ile
    3395                 3400                 3405

Met Ala  Ala Glu Gln Gln Thr  Ser Arg Ser Val Asp  Glu Ala Tyr
    3410                 3415                 3420

Ser Ser  Thr Ser Ser Trp Ser  Asp Gln Thr Ser Gly  Ser Asp Ile
    3425                 3430                 3435

Thr Leu  Gly Ala Ser Pro Asp  Val Thr Asn Thr Leu  Tyr Ile Thr
    3440                 3445                 3450

Ser Thr  Ala Gln Thr Thr Ser  Leu Val Ser Leu Pro  Ser Gly Asp
    3455                 3460                 3465

Gln Gly  Ile Thr Ser Leu Thr  Asn Pro Ser Gly Gly  Lys Thr Ser
    3470                 3475                 3480

Ser Ala  Ser Ser Val Thr Ser  Pro Ser Ile Gly Leu  Glu Thr Leu
    3485                 3490                 3495

Arg Ala  Asn Val Ser Ala Val  Lys Ser Asp Ile Ala  Pro Thr Ala
    3500                 3505                 3510

Gly His  Leu Ser Gln Thr Ser  Ser Pro Ala Glu Val  Ser Ile Leu
    3515                 3520                 3525

Asp Val  Thr Thr Ala Pro Thr  Pro Gly Ile Ser Thr  Thr Ile Thr
```

-continued

```
    3530                3535                3540

Thr Met  Gly Thr Asn Ser Ile  Ser Thr Thr Thr Pro  Asn Pro Glu
    3545                3550                3555

Val Gly  Met Ser Thr Met Asp  Ser Thr Pro Ala Thr  Glu Arg Arg
    3560                3565                3570

Thr Thr  Ser Thr Glu His Pro  Ser Thr Trp Ser Ser  Thr Ala Ala
    3575                3580                3585

Ser Asp  Ser Trp Thr Val Thr  Asp Met Thr Ser Asn  Leu Lys Val
    3590                3595                3600

Ala Arg  Ser Pro Gly Thr Ile  Ser Thr Met His Thr  Thr Ser Phe
    3605                3610                3615

Leu Ala  Ser Ser Thr Glu Leu  Asp Ser Met Ser Thr  Pro His Gly
    3620                3625                3630

Arg Ile  Thr Val Ile Gly Thr  Ser Leu Val Thr Pro  Ser Ser Asp
    3635                3640                3645

Ala Ser  Ala Val Lys Thr Glu  Thr Ser Thr Ser Glu  Arg Thr Leu
    3650                3655                3660

Ser Pro  Ser Asp Thr Thr Ala  Ser Thr Pro Ile Ser  Thr Phe Ser
    3665                3670                3675

Arg Val  Gln Arg Met Ser Ile  Ser Val Pro Asp Ile  Leu Ser Thr
    3680                3685                3690

Ser Trp  Thr Pro Ser Ser Thr  Glu Ala Glu Asp Val  Pro Val Ser
    3695                3700                3705

Met Val  Ser Thr Asp His Ala  Ser Thr Lys Thr Asp  Pro Asn Thr
    3710                3715                3720

Pro Leu  Ser Thr Phe Leu Phe  Asp Ser Leu Ser Thr  Leu Asp Trp
    3725                3730                3735

Asp Thr  Gly Arg Ser Leu Ser  Ser Ala Thr Ala Thr  Thr Ser Ala
    3740                3745                3750

Pro Gln  Gly Ala Thr Thr Pro  Gln Glu Leu Thr Leu  Glu Thr Met
    3755                3760                3765

Ile Ser  Pro Ala Thr Ser Gln  Leu Pro Phe Ser Ile  Gly His Ile
    3770                3775                3780

Thr Ser  Ala Val Thr Pro Ala  Ala Met Ala Arg Ser  Ser Gly Val
    3785                3790                3795

Thr Phe  Ser Arg Pro Asp Pro  Thr Ser Lys Lys Ala  Glu Gln Thr
    3800                3805                3810

Ser Thr  Gln Leu Pro Thr Thr  Thr Ser Ala His Pro  Gly Gln Val
    3815                3820                3825

Pro Arg  Ser Ala Ala Thr Thr  Leu Asp Val Ile Pro  His Thr Ala
    3830                3835                3840

Lys Thr  Pro Asp Ala Thr Phe  Gln Arg Gln Gly Gln  Thr Ala Leu
    3845                3850                3855

Thr Thr  Glu Ala Arg Ala Thr  Ser Asp Ser Trp Asn  Glu Lys Glu
    3860                3865                3870

Lys Ser  Thr Pro Ser Ala Pro  Trp Ile Thr Glu Met  Met Asn Ser
    3875                3880                3885

Val Ser  Glu Asp Thr Ile Lys  Glu Val Thr Ser Ser  Ser Ser Val
    3890                3895                3900

Leu Arg  Thr Leu Asn Thr Leu  Asp Ile Asn Leu Glu  Ser Gly Thr
    3905                3910                3915

Thr Ser  Ser Pro Ser Trp Lys  Ser Ser Pro Tyr Glu  Arg Ile Ala
    3920                3925                3930
```

```
Pro Ser Glu Ser Thr Thr Asp Lys Glu Ala Ile His Pro Ser Thr
    3935                3940                3945

Asn Thr Val Glu Thr Thr Gly Trp Val Thr Ser Ser Glu His Ala
    3950                3955                3960

Ser His Ser Thr Ile Pro Ala His Ser Ala Ser Ser Lys Leu Thr
    3965                3970                3975

Ser Pro Val Val Thr Thr Ser Thr Arg Glu Gln Ala Ile Val Ser
    3980                3985                3990

Met Ser Thr Thr Thr Trp Pro Glu Ser Thr Arg Ala Arg Thr Glu
    3995                4000                4005

Pro Asn Ser Phe Leu Thr Ile Glu Leu Arg Asp Val Ser Pro Tyr
    4010                4015                4020

Met Asp Thr Ser Ser Thr Thr Gln Thr Ser Ile Ile Ser Ser Pro
    4025                4030                4035

Gly Ser Thr Ala Ile Thr Lys Gly Pro Arg Thr Glu Ile Thr Ser
    4040                4045                4050

Ser Lys Arg Ile Ser Ser Ser Phe Leu Ala Gln Ser Met Arg Ser
    4055                4060                4065

Ser Asp Ser Pro Ser Glu Ala Ile Thr Arg Leu Ser Asn Phe Pro
    4070                4075                4080

Ala Met Thr Glu Ser Gly Gly Met Ile Leu Ala Met Gln Thr Ser
    4085                4090                4095

Pro Pro Gly Ala Thr Ser Leu Ser Ala Pro Thr Leu Asp Thr Ser
    4100                4105                4110

Ala Thr Ala Ser Trp Thr Gly Thr Pro Leu Ala Thr Thr Gln Arg
    4115                4120                4125

Phe Thr Tyr Ser Glu Lys Thr Thr Leu Phe Ser Lys Gly Pro Glu
    4130                4135                4140

Asp Thr Ser Gln Pro Ser Pro Pro Ser Val Glu Glu Thr Ser Ser
    4145                4150                4155

Ser Ser Ser Leu Val Pro Ile His Ala Thr Thr Ser Pro Ser Asn
    4160                4165                4170

Ile Leu Leu Thr Ser Gln Gly His Ser Pro Ser Ser Thr Pro Pro
    4175                4180                4185

Val Thr Ser Val Phe Leu Ser Glu Thr Ser Gly Leu Gly Lys Thr
    4190                4195                4200

Thr Asp Met Ser Arg Ile Ser Leu Glu Pro Gly Thr Ser Leu Pro
    4205                4210                4215

Pro Asn Leu Ser Ser Thr Ala Gly Glu Ala Leu Ser Thr Tyr Glu
    4220                4225                4230

Ala Ser Arg Asp Thr Lys Ala Ile His His Ser Ala Asp Thr Ala
    4235                4240                4245

Val Thr Asn Met Glu Ala Thr Ser Ser Glu Tyr Ser Pro Ile Pro
    4250                4255                4260

Gly His Thr Lys Pro Ser Lys Ala Thr Ser Pro Leu Val Thr Ser
    4265                4270                4275

His Ile Met Gly Asp Ile Thr Ser Ser Thr Ser Val Phe Gly Ser
    4280                4285                4290

Ser Glu Thr Thr Glu Ile Glu Thr Val Ser Ser Val Asn Gln Gly
    4295                4300                4305

Leu Gln Glu Arg Ser Thr Ser Gln Val Ala Ser Ser Ala Thr Glu
    4310                4315                4320
```

-continued

```
Thr Ser  Thr Val Ile Thr His  Val Ser Ser Gly Asp  Ala Thr Thr
    4325                 4330                 4335

His Val  Thr Lys Thr Gln Ala  Thr Phe Ser Ser Gly  Thr Ser Ile
    4340                 4345                 4350

Ser Ser  Pro His Gln Phe Ile  Thr Ser Thr Asn Thr  Phe Thr Asp
    4355                 4360                 4365

Val Ser  Thr Asn Pro Ser Thr  Ser Leu Ile Met Thr  Glu Ser Ser
    4370                 4375                 4380

Gly Val  Thr Ile Thr Thr Gln  Thr Gly Pro Thr Gly  Ala Ala Thr
    4385                 4390                 4395

Gln Gly  Pro Tyr Leu Leu Asp  Thr Ser Thr Met Pro  Tyr Leu Thr
    4400                 4405                 4410

Glu Thr  Pro Leu Ala Val Thr  Pro Asp Phe Met Gln  Ser Glu Lys
    4415                 4420                 4425

Thr Thr  Leu Ile Ser Lys Gly  Pro Lys Asp Val Ser  Trp Thr Ser
    4430                 4435                 4440

Pro Pro  Ser Val Ala Glu Thr  Ser Tyr Pro Ser Ser  Leu Thr Pro
    4445                 4450                 4455

Phe Leu  Val Thr Thr Ile Pro  Pro Ala Thr Ser Thr  Leu Gln Gly
    4460                 4465                 4470

Gln His  Thr Ser Ser Pro Val  Ser Ala Thr Ser Val  Leu Thr Ser
    4475                 4480                 4485

Gly Leu  Val Lys Thr Thr Asp  Met Leu Asn Thr Ser  Met Glu Pro
    4490                 4495                 4500

Val Thr  Asn Ser Pro Gln Asn  Leu Asn Asn Pro Ser  Asn Glu Ile
    4505                 4510                 4515

Leu Ala  Thr Leu Ala Ala Thr  Thr Asp Ile Glu Thr  Ile His Pro
    4520                 4525                 4530

Ser Ile  Asn Lys Ala Val Thr  Asn Met Gly Thr Ala  Ser Ser Ala
    4535                 4540                 4545

His Val  Leu His Ser Thr Leu  Pro Val Ser Ser Glu  Pro Ser Thr
    4550                 4555                 4560

Ala Thr  Ser Pro Met Val Pro  Ala Ser Ser Met Gly  Asp Ala Leu
    4565                 4570                 4575

Ala Ser  Ile Ser Ile Pro Gly  Ser Glu Thr Thr Asp  Ile Glu Gly
    4580                 4585                 4590

Glu Pro  Thr Ser Ser Leu Thr  Ala Gly Arg Lys Glu  Asn Ser Thr
    4595                 4600                 4605

Leu Gln  Glu Met Asn Ser Thr  Thr Glu Ser Asn Ile  Ile Leu Ser
    4610                 4615                 4620

Asn Val  Ser Val Gly Ala Ile  Thr Glu Ala Thr Lys  Met Glu Val
    4625                 4630                 4635

Pro Ser  Phe Asp Ala Thr Phe  Ile Pro Thr Pro Ala  Gln Ser Thr
    4640                 4645                 4650

Lys Phe  Pro Asp Ile Phe Ser  Val Ala Ser Ser Arg  Leu Ser Asn
    4655                 4660                 4665

Ser Pro  Pro Met Thr Ile Ser  Thr His Met Thr Thr  Thr Gln Thr
    4670                 4675                 4680

Gly Ser  Ser Gly Ala Thr Ser  Lys Ile Pro Leu Ala  Leu Asp Thr
    4685                 4690                 4695

Ser Thr  Leu Glu Thr Ser Ala  Gly Thr Pro Ser Val  Val Thr Glu
    4700                 4705                 4710

Gly Phe  Ala His Ser Lys Ile  Thr Thr Ala Met Asn  Asn Asp Val
```

```
    4715                4720                4725

Lys Asp Val Ser Gln Thr Asn Pro Pro Phe Gln Asp Glu Ala Ser
    4730                4735                4740

Ser Pro Ser Ser Gln Ala Pro Val Leu Val Thr Thr Leu Pro Ser
    4745                4750                4755

Ser Val Ala Phe Thr Pro Gln Trp His Ser Thr Ser Ser Pro Val
    4760                4765                4770

Ser Met Ser Ser Val Leu Thr Ser Ser Leu Val Lys Thr Ala Gly
    4775                4780                4785

Lys Val Asp Thr Ser Leu Glu Thr Val Thr Ser Ser Pro Gln Ser
    4790                4795                4800

Met Ser Asn Thr Leu Asp Asp Ile Ser Val Thr Ser Ala Ala Thr
    4805                4810                4815

Thr Asp Ile Glu Thr Thr His Pro Ser Ile Asn Thr Val Val Thr
    4820                4825                4830

Asn Val Gly Thr Thr Gly Ser Ala Phe Glu Ser His Ser Thr Val
    4835                4840                4845

Ser Ala Tyr Pro Glu Pro Ser Lys Val Thr Ser Pro Asn Val Thr
    4850                4855                4860

Thr Ser Thr Met Glu Asp Thr Thr Ile Ser Arg Ser Ile Pro Lys
    4865                4870                4875

Ser Ser Lys Thr Thr Arg Thr Glu Thr Glu Thr Thr Ser Ser Leu
    4880                4885                4890

Thr Pro Lys Leu Arg Glu Thr Ser Ile Ser Gln Glu Ile Thr Ser
    4895                4900                4905

Ser Thr Glu Thr Ser Thr Val Pro Tyr Lys Glu Leu Thr Gly Ala
    4910                4915                4920

Thr Thr Glu Val Ser Arg Thr Asp Val Thr Ser Ser Ser Ser Thr
    4925                4930                4935

Ser Phe Pro Gly Pro Asp Gln Ser Thr Val Ser Leu Asp Ile Ser
    4940                4945                4950

Thr Glu Thr Asn Thr Arg Leu Ser Thr Ser Pro Ile Met Thr Glu
    4955                4960                4965

Ser Ala Glu Ile Thr Ile Thr Thr Gln Thr Gly Pro His Gly Ala
    4970                4975                4980

Thr Ser Gln Asp Thr Phe Thr Met Asp Pro Ser Asn Thr Thr Pro
    4985                4990                4995

Gln Ala Gly Ile His Ser Ala Met Thr His Gly Phe Ser Gln Leu
    5000                5005                5010

Asp Val Thr Thr Leu Met Ser Arg Ile Pro Gln Asp Val Ser Trp
    5015                5020                5025

Thr Ser Pro Pro Ser Val Asp Lys Thr Ser Ser Pro Ser Ser Phe
    5030                5035                5040

Leu Ser Ser Pro Ala Met Thr Thr Pro Ser Leu Ile Ser Ser Thr
    5045                5050                5055

Leu Pro Glu Asp Lys Leu Ser Ser Pro Met Thr Ser Leu Leu Thr
    5060                5065                5070

Ser Gly Leu Val Lys Ile Thr Asp Ile Leu Arg Thr Arg Leu Glu
    5075                5080                5085

Pro Val Thr Ser Ser Leu Pro Asn Phe Ser Ser Thr Ser Asp Lys
    5090                5095                5100

Ile Leu Ala Thr Ser Lys Asp Ser Lys Asp Thr Lys Glu Ile Phe
    5105                5110                5115
```

```
Pro Ser Ile Asn Thr Glu Glu Thr Asn Val Lys Ala Asn Asn Ser
    5120                5125                5130

Gly His Glu Ser His Ser Pro Ala Leu Ala Asp Ser Glu Thr Pro
    5135                5140                5145

Lys Ala Thr Thr Gln Met Val Ile Thr Thr Thr Val Gly Asp Pro
    5150                5155                5160

Ala Pro Ser Thr Ser Met Pro Val His Gly Ser Ser Glu Thr Thr
    5165                5170                5175

Asn Ile Lys Arg Glu Pro Thr Tyr Phe Leu Thr Pro Arg Leu Arg
    5180                5185                5190

Glu Thr Ser Thr Ser Gln Glu Ser Ser Phe Pro Thr Asp Thr Ser
    5195                5200                5205

Phe Leu Leu Ser Lys Val Pro Thr Gly Thr Ile Thr Glu Val Ser
    5210                5215                5220

Ser Thr Gly Val Asn Ser Ser Ser Lys Ile Ser Thr Pro Asp His
    5225                5230                5235

Asp Lys Ser Thr Val Pro Pro Asp Thr Phe Thr Gly Glu Ile Pro
    5240                5245                5250

Arg Val Phe Thr Ser Ser Ile Lys Thr Lys Ser Ala Glu Met Thr
    5255                5260                5265

Ile Thr Thr Gln Ala Ser Pro Pro Glu Ser Ala Ser His Ser Thr
    5270                5275                5280

Leu Pro Leu Asp Thr Ser Thr Thr Leu Ser Gln Gly Gly Thr His
    5285                5290                5295

Ser Thr Val Thr Gln Gly Phe Pro Tyr Ser Glu Val Thr Thr Leu
    5300                5305                5310

Met Gly Met Gly Pro Gly Asn Val Ser Trp Met Thr Thr Pro Pro
    5315                5320                5325

Val Glu Glu Thr Ser Ser Val Ser Ser Leu Met Ser Ser Pro Ala
    5330                5335                5340

Met Thr Ser Pro Ser Pro Val Ser Ser Thr Ser Pro Gln Ser Ile
    5345                5350                5355

Pro Ser Ser Pro Leu Pro Val Thr Ala Leu Pro Thr Ser Val Leu
    5360                5365                5370

Val Thr Thr Thr Asp Val Leu Gly Thr Thr Ser Pro Glu Ser Val
    5375                5380                5385

Thr Ser Ser Pro Pro Asn Leu Ser Ser Ile Thr His Glu Arg Pro
    5390                5395                5400

Ala Thr Tyr Lys Asp Thr Ala His Thr Glu Ala Ala Met His His
    5405                5410                5415

Ser Thr Asn Thr Ala Val Thr Asn Val Gly Thr Ser Gly Ser Gly
    5420                5425                5430

His Lys Ser Gln Ser Ser Val Leu Ala Asp Ser Glu Thr Ser Lys
    5435                5440                5445

Ala Thr Pro Leu Met Ser Thr Thr Ser Thr Leu Gly Asp Thr Ser
    5450                5455                5460

Val Ser Thr Ser Thr Pro Asn Ile Ser Gln Thr Asn Gln Ile Gln
    5465                5470                5475

Thr Glu Pro Thr Ala Ser Leu Ser Pro Arg Leu Arg Glu Ser Ser
    5480                5485                5490

Thr Ser Glu Lys Thr Ser Ser Thr Thr Glu Thr Asn Thr Ala Phe
    5495                5500                5505
```

```
Ser Tyr  Val Pro Thr Gly Ala  Ile Thr Gln Ala Ser  Arg Thr Glu
    5510                 5515                 5520

Ile Ser  Ser Ser Arg Thr Ser  Ile Ser Asp Leu Asp  Arg Pro Thr
    5525                 5530                 5535

Ile Ala  Pro Asp Ile Ser Thr  Gly Met Ile Thr Arg  Leu Phe Thr
    5540                 5545                 5550

Ser Pro  Ile Met Thr Lys Ser  Ala Glu Met Thr Val  Thr Thr Gln
    5555                 5560                 5565

Thr Thr  Thr Pro Gly Ala Thr  Ser Gln Gly Ile Leu  Pro Trp Asp
    5570                 5575                 5580

Thr Ser  Thr Thr Leu Phe Gln  Gly Gly Thr His Ser  Thr Val Ser
    5585                 5590                 5595

Gln Gly  Phe Pro His Ser Glu  Ile Thr Thr Leu Arg  Ser Arg Thr
    5600                 5605                 5610

Pro Gly  Asp Val Ser Trp Met  Thr Thr Pro Pro Val  Glu Glu Thr
    5615                 5620                 5625

Ser Ser  Gly Phe Ser Leu Met  Ser Pro Ser Met Thr  Ser Pro Ser
    5630                 5635                 5640

Pro Val  Ser Ser Thr Ser Pro  Glu Ser Ile Pro Ser  Ser Pro Leu
    5645                 5650                 5655

Pro Val  Thr Ala Leu Leu Thr  Ser Val Leu Val Thr  Thr Thr Asn
    5660                 5665                 5670

Val Leu  Gly Thr Thr Ser Pro  Glu Pro Val Thr Ser  Ser Pro Pro
    5675                 5680                 5685

Asn Leu  Ser Ser Pro Thr Gln  Glu Arg Leu Thr Thr  Tyr Lys Asp
    5690                 5695                 5700

Thr Ala  His Thr Glu Ala Met  His Ala Ser Met His  Thr Asn Thr
    5705                 5710                 5715

Ala Val  Ala Asn Val Gly Thr  Ser Ile Ser Gly His  Glu Ser Gln
    5720                 5725                 5730

Ser Ser  Val Pro Ala Asp Ser  His Thr Ser Lys Ala  Thr Ser Pro
    5735                 5740                 5745

Met Gly  Ile Thr Phe Ala Met  Gly Asp Thr Ser Val  Ser Thr Ser
    5750                 5755                 5760

Thr Pro  Ala Phe Phe Glu Thr  Arg Ile Gln Thr Glu  Ser Thr Ser
    5765                 5770                 5775

Ser Leu  Ile Pro Gly Leu Arg  Asp Thr Arg Thr Ser  Glu Glu Ile
    5780                 5785                 5790

Asn Thr  Val Thr Glu Thr Ser  Thr Val Leu Ser Glu  Val Pro Thr
    5795                 5800                 5805

Thr Thr  Thr Thr Glu Val Ser  Arg Thr Glu Val Ile  Thr Ser Ser
    5810                 5815                 5820

Arg Thr  Thr Ile Ser Gly Pro  Asp His Ser Lys Met  Ser Pro Tyr
    5825                 5830                 5835

Ile Ser  Thr Glu Thr Ile Thr  Arg Leu Ser Thr Phe  Pro Phe Val
    5840                 5845                 5850

Thr Gly  Ser Thr Glu Met Ala  Ile Thr Asn Gln Thr  Gly Pro Ile
    5855                 5860                 5865

Gly Thr  Ile Ser Gln Ala Thr  Leu Thr Leu Asp Thr  Ser Ser Thr
    5870                 5875                 5880

Ala Ser  Trp Glu Gly Thr His  Ser Pro Val Thr Gln  Arg Phe Pro
    5885                 5890                 5895

His Ser  Glu Glu Thr Thr Thr  Met Ser Arg Ser Thr  Lys Gly Val
```

-continued

```
    5900                5905                5910

Ser Trp  Gln Ser Pro Pro Ser  Val Glu Glu Thr Ser  Ser Pro Ser
    5915                5920                5925

Ser Pro  Val Pro Leu Pro Ala  Ile Thr Ser His Ser  Ser Leu Tyr
    5930                5935                5940

Ser Ala  Val Ser Gly Ser Ser  Pro Thr Ser Ala Leu  Pro Val Thr
    5945                5950                5955

Ser Leu  Leu Thr Ser Gly Arg  Arg Lys Thr Ile Asp  Met Leu Asp
    5960                5965                5970

Thr His  Ser Glu Leu Val Thr  Ser Ser Leu Pro Ser  Ala Ser Ser
    5975                5980                5985

Phe Ser  Gly Glu Ile Leu Thr  Ser Glu Ala Ser Thr  Asn Thr Glu
    5990                5995                6000

Thr Ile  His Phe Ser Glu Asn  Thr Ala Glu Thr Asn  Met Gly Thr
    6005                6010                6015

Thr Asn  Ser Met His Lys Leu  His Ser Ser Val Ser  Ile His Ser
    6020                6025                6030

Gln Pro  Ser Gly His Thr Pro  Pro Lys Val Thr Gly  Ser Met Met
    6035                6040                6045

Glu Asp  Ala Ile Val Ser Thr  Ser Thr Pro Gly Ser  Pro Glu Thr
    6050                6055                6060

Lys Asn  Val Asp Arg Asp Ser  Thr Ser Pro Leu Thr  Pro Glu Leu
    6065                6070                6075

Lys Glu  Asp Ser Thr Ala Leu  Val Met Asn Ser Thr  Thr Glu Ser
    6080                6085                6090

Asn Thr  Val Phe Ser Ser Val  Ser Leu Asp Ala Ala  Thr Glu Val
    6095                6100                6105

Ser Arg  Ala Glu Val Thr Tyr  Tyr Asp Pro Thr Phe  Met Pro Ala
    6110                6115                6120

Ser Ala  Gln Ser Thr Lys Ser  Pro Asp Ile Ser Pro  Glu Ala Ser
    6125                6130                6135

Ser Ser  His Ser Asn Ser Pro  Pro Leu Thr Ile Ser  Thr His Lys
    6140                6145                6150

Thr Ile  Ala Thr Gln Thr Gly  Pro Ser Gly Val Thr  Ser Leu Gly
    6155                6160                6165

Gln Leu  Thr Leu Asp Thr Ser  Thr Ile Ala Thr Ser  Ala Gly Thr
    6170                6175                6180

Pro Ser  Ala Arg Thr Gln Asp  Phe Val Asp Ser Glu  Thr Thr Ser
    6185                6190                6195

Val Met  Asn Asn Asp Leu Asn  Asp Val Leu Lys Thr  Ser Pro Phe
    6200                6205                6210

Ser Ala  Glu Glu Ala Asn Ser  Leu Ser Ser Gln Ala  Pro Leu Leu
    6215                6220                6225

Val Thr  Thr Ser Pro Ser Pro  Val Thr Ser Thr Leu  Gln Glu His
    6230                6235                6240

Ser Thr  Ser Ser Leu Val Ser  Val Thr Ser Val Pro  Thr Pro Thr
    6245                6250                6255

Leu Ala  Lys Ile Thr Asp Met  Asp Thr Asn Leu Glu  Pro Val Thr
    6260                6265                6270

Arg Ser  Pro Gln Asn Leu Arg  Asn Thr Leu Ala Thr  Ser Glu Ala
    6275                6280                6285

Thr Thr  Asp Thr His Thr Met  His Pro Ser Ile Asn  Thr Ala Val
    6290                6295                6300
```

```
Ala Asn Val Gly Thr Thr Ser Ser Pro Asn Glu Phe Tyr Phe Thr
    6305                6310                6315

Val Ser Pro Asp Ser Asp Pro Tyr Lys Ala Thr Ser Ala Val Val
    6320                6325                6330

Ile Thr Ser Thr Ser Gly Asp Ser Ile Val Ser Thr Ser Met Pro
    6335                6340                6345

Arg Ser Ser Ala Met Lys Lys Ile Glu Ser Glu Thr Thr Phe Ser
    6350                6355                6360

Leu Ile Phe Arg Leu Arg Glu Thr Ser Thr Ser Gln Lys Ile Gly
    6365                6370                6375

Ser Ser Ser Asp Thr Ser Thr Val Phe Asp Lys Ala Phe Thr Ala
    6380                6385                6390

Ala Thr Thr Glu Val Ser Arg Thr Glu Leu Thr Ser Ser Ser Arg
    6395                6400                6405

Thr Ser Ile Gln Gly Thr Glu Lys Pro Thr Met Ser Pro Asp Thr
    6410                6415                6420

Ser Thr Arg Ser Val Thr Met Leu Ser Thr Phe Ala Gly Leu Thr
    6425                6430                6435

Lys Ser Glu Glu Arg Thr Ile Ala Thr Gln Thr Gly Pro His Arg
    6440                6445                6450

Ala Thr Ser Gln Gly Thr Leu Thr Trp Asp Thr Ser Ile Thr Thr
    6455                6460                6465

Ser Gln Ala Gly Thr His Ser Ala Met Thr His Gly Phe Ser Gln
    6470                6475                6480

Leu Asp Leu Ser Thr Leu Thr Ser Arg Val Pro Glu Tyr Ile Ser
    6485                6490                6495

Gly Thr Ser Pro Pro Ser Val Glu Lys Thr Ser Ser Ser Ser Ser
    6500                6505                6510

Leu Leu Ser Leu Pro Ala Ile Thr Ser Pro Ser Pro Val Pro Thr
    6515                6520                6525

Thr Leu Pro Glu Ser Arg Pro Ser Ser Pro Val His Leu Thr Ser
    6530                6535                6540

Leu Pro Thr Ser Gly Leu Val Lys Thr Thr Asp Met Leu Ala Ser
    6545                6550                6555

Val Ala Ser Leu Pro Pro Asn Leu Gly Ser Thr Ser His Lys Ile
    6560                6565                6570

Pro Thr Thr Ser Glu Asp Ile Lys Asp Thr Glu Lys Met Tyr Pro
    6575                6580                6585

Ser Thr Asn Ile Ala Val Thr Asn Val Gly Thr Thr Thr Ser Glu
    6590                6595                6600

Lys Glu Ser Tyr Ser Ser Val Pro Ala Tyr Ser Glu Pro Pro Lys
    6605                6610                6615

Val Thr Ser Pro Met Val Thr Ser Phe Asn Ile Arg Asp Thr Ile
    6620                6625                6630

Val Ser Thr Ser Met Pro Gly Ser Ser Glu Ile Thr Arg Ile Glu
    6635                6640                6645

Met Glu Ser Thr Phe Ser Leu Ala His Gly Leu Lys Gly Thr Ser
    6650                6655                6660

Thr Ser Gln Asp Pro Ile Val Ser Thr Glu Lys Ser Ala Val Leu
    6665                6670                6675

His Lys Leu Thr Thr Gly Ala Thr Glu Thr Ser Arg Thr Glu Val
    6680                6685                6690
```

```
Ala Ser Ser Arg Arg Thr Ser Ile Pro Gly Pro Asp His Ser Thr
    6695                6700                6705

Glu Ser Pro Asp Ile Ser Thr Glu Val Ile Pro Ser Leu Pro Ile
    6710                6715                6720

Ser Leu Gly Ile Thr Glu Ser Ser Asn Met Thr Ile Ile Thr Arg
    6725                6730                6735

Thr Gly Pro Pro Leu Gly Ser Thr Ser Gln Gly Thr Phe Thr Leu
    6740                6745                6750

Asp Thr Pro Thr Thr Ser Ser Arg Ala Gly Thr His Ser Met Ala
    6755                6760                6765

Thr Gln Glu Phe Pro His Ser Glu Met Thr Thr Val Met Asn Lys
    6770                6775                6780

Asp Pro Glu Ile Leu Ser Trp Thr Ile Pro Pro Ser Ile Glu Lys
    6785                6790                6795

Thr Ser Phe Ser Ser Ser Leu Met Pro Ser Pro Ala Met Thr Ser
    6800                6805                6810

Pro Pro Val Ser Ser Thr Leu Pro Lys Thr Ile His Thr Thr Pro
    6815                6820                6825

Ser Pro Met Thr Ser Leu Leu Thr Pro Ser Leu Val Met Thr Thr
    6830                6835                6840

Asp Thr Leu Gly Thr Ser Pro Glu Pro Thr Thr Ser Ser Pro Pro
    6845                6850                6855

Asn Leu Ser Ser Thr Ser His Glu Ile Leu Thr Thr Asp Glu Asp
    6860                6865                6870

Thr Thr Ala Ile Glu Ala Met His Pro Ser Thr Ser Thr Ala Ala
    6875                6880                6885

Thr Asn Val Glu Thr Thr Ser Ser Gly His Gly Ser Gln Ser Ser
    6890                6895                6900

Val Leu Ala Asp Ser Glu Lys Thr Lys Ala Thr Ala Pro Met Asp
    6905                6910                6915

Thr Thr Ser Thr Met Gly His Thr Thr Val Ser Thr Ser Met Ser
    6920                6925                6930

Val Ser Ser Glu Thr Thr Lys Ile Lys Arg Glu Ser Thr Tyr Ser
    6935                6940                6945

Leu Thr Pro Gly Leu Arg Glu Thr Ser Ile Ser Gln Asn Ala Ser
    6950                6955                6960

Phe Ser Thr Asp Thr Ser Ile Val Leu Ser Glu Val Pro Thr Gly
    6965                6970                6975

Thr Thr Ala Glu Val Ser Arg Thr Glu Val Thr Ser Ser Gly Arg
    6980                6985                6990

Thr Ser Ile Pro Gly Pro Ser Gln Ser Thr Val Leu Pro Glu Ile
    6995                7000                7005

Ser Thr Arg Thr Met Thr Arg Leu Phe Ala Ser Pro Thr Met Thr
    7010                7015                7020

Glu Ser Ala Glu Met Thr Ile Pro Thr Gln Thr Gly Pro Ser Gly
    7025                7030                7035

Ser Thr Ser Gln Asp Thr Leu Thr Leu Asp Thr Ser Thr Thr Lys
    7040                7045                7050

Ser Gln Ala Lys Thr His Ser Thr Leu Thr Gln Arg Phe Pro His
    7055                7060                7065

Ser Glu Met Thr Thr Leu Met Ser Arg Gly Pro Gly Asp Met Ser
    7070                7075                7080

Trp Gln Ser Ser Pro Ser Leu Glu Asn Pro Ser Ser Leu Pro Ser
```

```
    7085                7090                7095

Leu Leu  Ser Leu Pro Ala Thr  Thr Ser Pro Pro Pro  Ile Ser Ser
    7100                7105                7110

Thr Leu  Pro Val Thr Ile Ser  Ser Ser Pro Leu Pro  Val Thr Ser
    7115                7120                7125

Leu Leu  Thr Ser Ser Pro Val  Thr Thr Thr Asp Met  Leu His Thr
    7130                7135                7140

Ser Pro  Glu Leu Val Thr Ser  Ser Pro Pro Lys Leu  Ser His Thr
    7145                7150                7155

Ser Asp  Glu Arg Leu Thr Thr  Gly Lys Asp Thr Thr  Asn Thr Glu
    7160                7165                7170

Ala Val  His Pro Ser Thr Asn  Thr Ala Ala Ser Asn  Val Glu Ile
    7175                7180                7185

Pro Ser  Ser Gly His Glu Ser  Pro Ser Ser Ala Leu  Ala Asp Ser
    7190                7195                7200

Glu Thr  Ser Lys Ala Thr Ser  Pro Met Phe Ile Thr  Ser Thr Gln
    7205                7210                7215

Glu Asp  Thr Thr Val Ala Ile  Ser Thr Pro His Phe  Leu Glu Thr
    7220                7225                7230

Ser Arg  Ile Gln Lys Glu Ser  Ile Ser Ser Leu Ser  Pro Lys Leu
    7235                7240                7245

Arg Glu  Thr Gly Ser Ser Val  Glu Thr Ser Ser Ala  Ile Glu Thr
    7250                7255                7260

Ser Ala  Val Leu Ser Glu Val  Ser Ile Gly Ala Thr  Thr Glu Ile
    7265                7270                7275

Ser Arg  Thr Glu Val Thr Ser  Ser Ser Arg Thr Ser  Ile Ser Gly
    7280                7285                7290

Ser Ala  Glu Ser Thr Met Leu  Pro Glu Ile Ser Thr  Thr Arg Lys
    7295                7300                7305

Ile Ile  Lys Phe Pro Thr Ser  Pro Ile Leu Ala Glu  Ser Ser Glu
    7310                7315                7320

Met Thr  Ile Lys Thr Gln Thr  Ser Pro Pro Gly Ser  Thr Ser Glu
    7325                7330                7335

Ser Thr  Phe Thr Leu Asp Thr  Ser Thr Thr Pro Ser  Leu Val Ile
    7340                7345                7350

Thr His  Ser Thr Met Thr Gln  Arg Leu Pro His Ser  Glu Ile Thr
    7355                7360                7365

Thr Leu  Val Ser Arg Gly Ala  Gly Asp Val Pro Arg  Pro Ser Ser
    7370                7375                7380

Leu Pro  Val Glu Glu Thr Ser  Pro Pro Ser Ser Gln  Leu Ser Leu
    7385                7390                7395

Ser Ala  Met Ile Ser Pro Ser  Pro Val Ser Ser Thr  Leu Pro Ala
    7400                7405                7410

Ser Ser  His Ser Ser Ser Ala  Ser Val Thr Ser Leu  Leu Thr Pro
    7415                7420                7425

Gly Gln  Val Lys Thr Thr Glu  Val Leu Asp Ala Ser  Ala Glu Pro
    7430                7435                7440

Glu Thr  Ser Ser Pro Pro Ser  Leu Ser Ser Thr Ser  Val Glu Ile
    7445                7450                7455

Leu Ala  Thr Ser Glu Val Thr  Thr Asp Thr Glu Lys  Ile His Pro
    7460                7465                7470

Phe Ser  Asn Thr Ala Val Thr  Lys Val Gly Thr Ser  Ser Ser Gly
    7475                7480                7485
```

```
His Glu Ser Pro Ser Ser Val Leu Pro Asp Ser Glu Thr Thr Lys
    7490                7495                7500

Ala Thr Ser Ala Met Gly Thr Ile Ser Ile Met Gly Asp Thr Ser
    7505                7510                7515

Val Ser Thr Leu Thr Pro Ala Leu Ser Asn Thr Arg Lys Ile Gln
    7520                7525                7530

Ser Glu Pro Ala Ser Ser Leu Thr Thr Arg Leu Arg Glu Thr Ser
    7535                7540                7545

Thr Ser Glu Glu Thr Ser Leu Ala Thr Glu Ala Asn Thr Val Leu
    7550                7555                7560

Ser Lys Val Ser Thr Gly Ala Thr Thr Glu Val Ser Arg Thr Glu
    7565                7570                7575

Ala Ile Ser Phe Ser Arg Thr Ser Met Ser Gly Pro Glu Gln Ser
    7580                7585                7590

Thr Met Ser Gln Asp Ile Ser Ile Gly Thr Ile Pro Arg Ile Ser
    7595                7600                7605

Ala Ser Ser Val Leu Thr Glu Ser Ala Lys Met Thr Ile Thr Thr
    7610                7615                7620

Gln Thr Gly Pro Ser Glu Ser Thr Leu Glu Ser Thr Leu Asn Leu
    7625                7630                7635

Asn Thr Ala Thr Thr Pro Ser Trp Val Glu Thr His Ser Ile Val
    7640                7645                7650

Ile Gln Gly Phe Pro His Pro Glu Met Thr Thr Ser Met Gly Arg
    7655                7660                7665

Gly Pro Gly Gly Val Ser Trp Pro Ser Pro Pro Phe Val Lys Glu
    7670                7675                7680

Thr Ser Pro Pro Ser Ser Pro Leu Ser Leu Pro Ala Val Thr Ser
    7685                7690                7695

Pro His Pro Val Ser Thr Thr Phe Leu Ala His Ile Pro Pro Ser
    7700                7705                7710

Pro Leu Pro Val Thr Ser Leu Leu Thr Ser Gly Pro Ala Thr Thr
    7715                7720                7725

Thr Asp Ile Leu Gly Thr Ser Thr Glu Pro Gly Thr Ser Ser Ser
    7730                7735                7740

Ser Ser Leu Ser Thr Thr Ser His Glu Arg Leu Thr Thr Tyr Lys
    7745                7750                7755

Asp Thr Ala His Thr Glu Ala Val His Pro Ser Thr Asn Thr Gly
    7760                7765                7770

Gly Thr Asn Val Ala Thr Thr Ser Ser Gly Tyr Lys Ser Gln Ser
    7775                7780                7785

Ser Val Leu Ala Asp Ser Ser Pro Met Cys Thr Thr Ser Thr Met
    7790                7795                7800

Gly Asp Thr Ser Val Leu Thr Ser Thr Pro Ala Phe Leu Glu Thr
    7805                7810                7815

Arg Arg Ile Gln Thr Glu Leu Ala Ser Ser Leu Thr Pro Gly Leu
    7820                7825                7830

Arg Glu Ser Ser Gly Ser Glu Gly Thr Ser Ser Gly Thr Lys Met
    7835                7840                7845

Ser Thr Val Leu Ser Lys Val Pro Thr Gly Ala Thr Thr Glu Ile
    7850                7855                7860

Ser Lys Glu Asp Val Thr Ser Ile Pro Gly Pro Ala Gln Ser Thr
    7865                7870                7875
```

```
Ile Ser Pro Asp Ile Ser Thr Arg Thr Val Ser Trp Phe Ser Thr
    7880                7885                7890

Ser Pro Val Met Thr Glu Ser Ala Glu Ile Thr Met Asn Thr His
    7895                7900                7905

Thr Ser Pro Leu Gly Ala Thr Thr Gln Gly Thr Ser Thr Leu Asp
    7910                7915                7920

Thr Ser Ser Thr Thr Ser Leu Thr Met Thr His Ser Thr Ile Ser
    7925                7930                7935

Gln Gly Phe Ser His Ser Gln Met Ser Thr Leu Met Arg Arg Gly
    7940                7945                7950

Pro Glu Asp Val Ser Trp Met Ser Pro Pro Leu Leu Glu Lys Thr
    7955                7960                7965

Arg Pro Ser Phe Ser Leu Met Ser Ser Pro Ala Thr Thr Ser Pro
    7970                7975                7980

Ser Pro Val Ser Ser Thr Leu Pro Glu Ser Ile Ser Ser Ser Pro
    7985                7990                7995

Leu Pro Val Thr Ser Leu Leu Thr Ser Gly Leu Ala Lys Thr Thr
    8000                8005                8010

Asp Met Leu His Lys Ser Ser Glu Pro Val Thr Asn Ser Pro Ala
    8015                8020                8025

Asn Leu Ser Ser Thr Ser Val Glu Ile Leu Ala Thr Ser Glu Val
    8030                8035                8040

Thr Thr Asp Thr Glu Lys Thr His Pro Ser Ser Asn Arg Thr Val
    8045                8050                8055

Thr Asp Val Gly Thr Ser Ser Ser Gly His Glu Ser Thr Ser Phe
    8060                8065                8070

Val Leu Ala Asp Ser Gln Thr Ser Lys Val Thr Ser Pro Met Val
    8075                8080                8085

Ile Thr Ser Thr Met Glu Asp Thr Ser Val Ser Thr Ser Thr Pro
    8090                8095                8100

Gly Phe Phe Glu Thr Ser Arg Ile Gln Thr Glu Pro Thr Ser Ser
    8105                8110                8115

Leu Thr Leu Gly Leu Arg Lys Thr Ser Ser Ser Glu Gly Thr Ser
    8120                8125                8130

Leu Ala Thr Glu Met Ser Thr Val Leu Ser Gly Val Pro Thr Gly
    8135                8140                8145

Ala Thr Ala Glu Val Ser Arg Thr Glu Val Thr Ser Ser Ser Arg
    8150                8155                8160

Thr Ser Ile Ser Gly Phe Ala Gln Leu Thr Val Ser Pro Glu Thr
    8165                8170                8175

Ser Thr Glu Thr Ile Thr Arg Leu Pro Thr Ser Ser Ile Met Thr
    8180                8185                8190

Glu Ser Ala Glu Met Met Ile Lys Thr Gln Thr Asp Pro Pro Gly
    8195                8200                8205

Ser Thr Pro Glu Ser Thr His Thr Val Asp Ile Ser Thr Thr Pro
    8210                8215                8220

Asn Trp Val Glu Thr His Ser Thr Val Thr Gln Arg Phe Ser His
    8225                8230                8235

Ser Glu Met Thr Thr Leu Val Ser Arg Ser Pro Gly Asp Met Leu
    8240                8245                8250

Trp Pro Ser Gln Ser Ser Val Glu Glu Thr Ser Ser Ala Ser Ser
    8255                8260                8265

Leu Leu Ser Leu Pro Ala Thr Thr Ser Pro Ser Pro Val Ser Ser
```

```
    8270                8275                8280

Thr Leu  Val Glu Asp Phe Pro  Ser Ala Ser Leu Pro  Val Thr Ser
    8285                8290                8295

Leu Leu  Asn Pro Gly Leu Val  Ile Thr Thr Asp Arg  Met Gly Ile
    8300                8305                8310

Ser Arg  Glu Pro Gly Thr Ser  Ser Thr Ser Asn Leu  Ser Ser Thr
    8315                8320                8325

Ser His  Glu Arg Leu Thr Thr  Leu Glu Asp Thr Val  Asp Thr Glu
    8330                8335                8340

Asp Met  Gln Pro Ser Thr His  Thr Ala Val Thr Asn  Val Arg Thr
    8345                8350                8355

Ser Ile  Ser Gly His Glu Ser  Gln Ser Ser Val Leu  Ser Asp Ser
    8360                8365                8370

Glu Thr  Pro Lys Ala Thr Ser  Pro Met Gly Thr Thr  Tyr Thr Met
    8375                8380                8385

Gly Glu  Thr Ser Val Ser Ile  Ser Thr Ser Asp Phe  Phe Glu Thr
    8390                8395                8400

Ser Arg  Ile Gln Ile Glu Pro  Thr Ser Ser Leu Thr  Ser Gly Leu
    8405                8410                8415

Arg Glu  Thr Ser Ser Ser Glu  Arg Ile Ser Ser Ala  Thr Glu Gly
    8420                8425                8430

Ser Thr  Val Leu Ser Glu Val  Pro Ser Gly Ala Thr  Thr Glu Val
    8435                8440                8445

Ser Arg  Thr Glu Val Ile Ser  Ser Arg Gly Thr Ser  Met Ser Gly
    8450                8455                8460

Pro Asp  Gln Phe Thr Ile Ser  Pro Asp Ile Ser Thr  Glu Ala Ile
    8465                8470                8475

Thr Arg  Leu Ser Thr Ser Pro  Ile Met Thr Glu Ser  Ala Glu Ser
    8480                8485                8490

Ala Ile  Thr Ile Glu Thr Gly  Ser Pro Gly Ala Thr  Ser Glu Gly
    8495                8500                8505

Thr Leu  Thr Leu Asp Thr Ser  Thr Thr Thr Phe Trp  Ser Gly Thr
    8510                8515                8520

His Ser  Thr Ala Ser Pro Gly  Phe Ser His Ser Glu  Met Thr Thr
    8525                8530                8535

Leu Met  Ser Arg Thr Pro Gly  Asp Val Pro Trp Pro  Ser Leu Pro
    8540                8545                8550

Ser Val  Glu Glu Ala Ser Ser  Val Ser Ser Ser Leu  Ser Ser Pro
    8555                8560                8565

Ala Met  Thr Ser Thr Ser Phe  Phe Ser Thr Leu Pro  Glu Ser Ile
    8570                8575                8580

Ser Ser  Ser Pro His Pro Val  Thr Ala Leu Leu Thr  Leu Gly Pro
    8585                8590                8595

Val Lys  Thr Thr Asp Met Leu  Arg Thr Ser Ser Glu  Pro Glu Thr
    8600                8605                8610

Ser Ser  Pro Pro Asn Leu Ser  Ser Thr Ser Ala Glu  Ile Leu Ala
    8615                8620                8625

Thr Ser  Glu Val Thr Lys Asp  Arg Glu Lys Ile His  Pro Ser Ser
    8630                8635                8640

Asn Thr  Pro Val Val Asn Val  Gly Thr Val Ile Tyr  Lys His Leu
    8645                8650                8655

Ser Pro  Ser Ser Val Leu Ala  Asp Leu Val Thr Thr  Lys Pro Thr
    8660                8665                8670
```

Ser Pro Met Ala Thr Thr Ser Thr Leu Gly Asn Thr Ser Val Ser
8675 8680 8685

Thr Ser Thr Pro Ala Phe Pro Glu Thr Met Met Thr Gln Pro Thr
8690 8695 8700

Ser Ser Leu Thr Ser Gly Leu Arg Glu Ile Ser Thr Ser Gln Glu
8705 8710 8715

Thr Ser Ser Ala Thr Glu Arg Ser Ala Ser Leu Ser Gly Met Pro
8720 8725 8730

Thr Gly Ala Thr Thr Lys Val Ser Arg Thr Glu Ala Leu Ser Leu
8735 8740 8745

Gly Arg Thr Ser Thr Pro Gly Pro Ala Gln Ser Thr Ile Ser Pro
8750 8755 8760

Glu Ile Ser Thr Glu Thr Ile Thr Arg Ile Ser Thr Pro Leu Thr
8765 8770 8775

Thr Thr Gly Ser Ala Glu Met Thr Ile Thr Pro Lys Thr Gly His
8780 8785 8790

Ser Gly Ala Ser Ser Gln Gly Thr Phe Thr Leu Asp Thr Ser Ser
8795 8800 8805

Arg Ala Ser Trp Pro Gly Thr His Ser Ala Ala Thr His Arg Ser
8810 8815 8820

Pro His Ser Gly Met Thr Thr Pro Met Ser Arg Gly Pro Glu Asp
8825 8830 8835

Val Ser Trp Pro Ser Arg Pro Ser Val Glu Lys Thr Ser Pro Pro
8840 8845 8850

Ser Ser Leu Val Ser Leu Ser Ala Val Thr Ser Pro Ser Pro Leu
8855 8860 8865

Tyr Ser Thr Pro Ser Glu Ser Ser His Ser Ser Pro Leu Arg Val
8870 8875 8880

Thr Ser Leu Phe Thr Pro Val Met Met Lys Thr Thr Asp Met Leu
8885 8890 8895

Asp Thr Ser Leu Glu Pro Val Thr Thr Ser Pro Pro Ser Met Asn
8900 8905 8910

Ile Thr Ser Asp Glu Ser Leu Ala Thr Ser Lys Ala Thr Met Glu
8915 8920 8925

Thr Glu Ala Ile Gln Leu Ser Glu Asn Thr Ala Val Thr Gln Met
8930 8935 8940

Gly Thr Ile Ser Ala Arg Gln Glu Phe Tyr Ser Ser Tyr Pro Gly
8945 8950 8955

Leu Pro Glu Pro Ser Lys Val Thr Ser Pro Val Val Thr Ser Ser
8960 8965 8970

Thr Ile Lys Asp Ile Val Ser Thr Thr Ile Pro Ala Ser Ser Glu
8975 8980 8985

Ile Thr Arg Ile Glu Met Glu Ser Thr Ser Thr Leu Thr Pro Thr
8990 8995 9000

Pro Arg Glu Thr Ser Thr Ser Gln Glu Ile His Ser Ala Thr Lys
9005 9010 9015

Pro Ser Thr Val Pro Tyr Lys Ala Leu Thr Ser Ala Thr Ile Glu
9020 9025 9030

Asp Ser Met Thr Gln Val Met Ser Ser Ser Arg Gly Pro Ser Pro
9035 9040 9045

Asp Gln Ser Thr Met Ser Gln Asp Ile Ser Thr Glu Val Ile Thr
9050 9055 9060

```
Arg Leu Ser Thr Ser Pro Ile Lys Thr Glu Ser Thr Glu Met Thr
    9065                9070                9075

Ile Thr Thr Gln Thr Gly Ser Pro Gly Ala Thr Ser Arg Gly Thr
    9080                9085                9090

Leu Thr Leu Asp Thr Ser Thr Thr Phe Met Ser Gly Thr His Ser
    9095                9100                9105

Thr Ala Ser Gln Gly Phe Ser His Ser Gln Met Thr Ala Leu Met
    9110                9115                9120

Ser Arg Thr Pro Gly Asp Val Pro Trp Leu Ser His Pro Ser Val
    9125                9130                9135

Glu Glu Ala Ser Ser Ala Ser Phe Ser Leu Ser Ser Pro Val Met
    9140                9145                9150

Thr Ser Ser Ser Pro Val Ser Ser Thr Leu Pro Asp Ser Ile His
    9155                9160                9165

Ser Ser Ser Leu Pro Val Thr Ser Leu Leu Thr Ser Gly Leu Val
    9170                9175                9180

Lys Thr Thr Glu Leu Leu Gly Thr Ser Ser Glu Pro Glu Thr Ser
    9185                9190                9195

Ser Pro Pro Asn Leu Ser Ser Thr Ser Ala Glu Ile Leu Ala Ile
    9200                9205                9210

Thr Glu Val Thr Thr Asp Thr Glu Lys Leu Glu Met Thr Asn Val
    9215                9220                9225

Val Thr Ser Gly Tyr Thr His Glu Ser Pro Ser Ser Val Leu Ala
    9230                9235                9240

Asp Ser Val Thr Thr Lys Ala Thr Ser Ser Met Gly Ile Thr Tyr
    9245                9250                9255

Pro Thr Gly Asp Thr Asn Val Leu Thr Ser Thr Pro Ala Phe Ser
    9260                9265                9270

Asp Thr Ser Arg Ile Gln Thr Lys Ser Lys Leu Ser Leu Thr Pro
    9275                9280                9285

Gly Leu Met Glu Thr Ser Ile Ser Glu Glu Thr Ser Ser Ala Thr
    9290                9295                9300

Glu Lys Ser Thr Val Leu Ser Ser Val Pro Thr Gly Ala Thr Thr
    9305                9310                9315

Glu Val Ser Arg Thr Glu Ala Ile Ser Ser Ser Arg Thr Ser Ile
    9320                9325                9330

Pro Gly Pro Ala Gln Ser Thr Met Ser Ser Asp Thr Ser Met Glu
    9335                9340                9345

Thr Ile Thr Arg Ile Ser Thr Pro Leu Thr Arg Lys Glu Ser Thr
    9350                9355                9360

Asp Met Ala Ile Thr Pro Lys Thr Gly Pro Ser Gly Ala Thr Ser
    9365                9370                9375

Gln Gly Thr Phe Thr Leu Asp Ser Ser Ser Thr Ala Ser Trp Pro
    9380                9385                9390

Gly Thr His Ser Ala Thr Thr Gln Arg Phe Pro Gln Ser Val Val
    9395                9400                9405

Thr Thr Pro Met Ser Arg Gly Pro Glu Asp Val Ser Trp Pro Ser
    9410                9415                9420

Pro Leu Ser Val Glu Lys Asn Ser Pro Pro Ser Ser Leu Val Ser
    9425                9430                9435

Ser Ser Ser Val Thr Ser Pro Ser Pro Leu Tyr Ser Thr Pro Ser
    9440                9445                9450

Gly Ser Ser His Ser Ser Pro Val Pro Val Thr Ser Leu Phe Thr
```

-continued

```
    9455                9460                9465

Ser Ile  Met Met Lys Ala Thr  Asp Met Leu Asp Ala  Ser Leu Glu
    9470                9475                9480

Pro Glu  Thr Thr Ser Ala Pro  Asn Met Asn Ile Thr  Ser Asp Glu
    9485                9490                9495

Ser Leu  Ala Ala Ser Lys Ala  Thr Thr Glu Thr Glu  Ala Ile His
    9500                9505                9510

Val Phe  Glu Asn Thr Ala Ala  Ser His Val Glu Thr  Thr Ser Ala
    9515                9520                9525

Thr Glu  Glu Leu Tyr Ser Ser  Ser Pro Gly Phe Ser  Glu Pro Thr
    9530                9535                9540

Lys Val  Ile Ser Pro Val Val  Thr Ser Ser Ser Ile  Arg Asp Asn
    9545                9550                9555

Met Val  Ser Thr Thr Met Pro  Gly Ser Ser Gly Ile  Thr Arg Ile
    9560                9565                9570

Glu Ile  Glu Ser Met Ser Ser  Leu Thr Pro Gly Leu  Arg Glu Thr
    9575                9580                9585

Arg Thr  Ser Gln Asp Ile Thr  Ser Ser Thr Glu Thr  Ser Thr Val
    9590                9595                9600

Leu Tyr  Lys Met Pro Ser Gly  Ala Thr Pro Glu Val  Ser Arg Thr
    9605                9610                9615

Glu Val  Met Pro Ser Ser Arg  Thr Ser Ile Pro Gly  Pro Ala Gln
    9620                9625                9630

Ser Thr  Met Ser Leu Asp Ile  Ser Asp Glu Val Val  Thr Arg Leu
    9635                9640                9645

Ser Thr  Ser Pro Ile Met Thr  Glu Ser Ala Glu Ile  Thr Ile Thr
    9650                9655                9660

Thr Gln  Thr Gly Tyr Ser Leu  Ala Thr Ser Gln Val  Thr Leu Pro
    9665                9670                9675

Leu Gly  Thr Ser Met Thr Phe  Leu Ser Gly Thr His  Ser Thr Met
    9680                9685                9690

Ser Gln  Gly Leu Ser His Ser  Glu Met Thr Asn Leu  Met Ser Arg
    9695                9700                9705

Gly Pro  Glu Ser Leu Ser Trp  Thr Ser Pro Arg Phe  Val Glu Thr
    9710                9715                9720

Thr Arg  Ser Ser Ser Ser Leu  Thr Ser Leu Pro Leu  Thr Thr Ser
    9725                9730                9735

Leu Ser  Pro Val Ser Ser Thr  Leu Leu Asp Ser Ser  Pro Ser Ser
    9740                9745                9750

Pro Leu  Pro Val Thr Ser Leu  Ile Leu Pro Gly Leu  Val Lys Thr
    9755                9760                9765

Thr Glu  Val Leu Asp Thr Ser  Ser Glu Pro Lys Thr  Ser Ser Ser
    9770                9775                9780

Pro Asn  Leu Ser Ser Thr Ser  Val Glu Ile Pro Ala  Thr Ser Glu
    9785                9790                9795

Ile Met  Thr Asp Thr Glu Lys  Ile His Pro Ser Ser  Asn Thr Ala
    9800                9805                9810

Val Ala  Lys Val Arg Thr Ser  Ser Ser Val His Glu  Ser His Ser
    9815                9820                9825

Ser Val  Leu Ala Asp Ser Glu  Thr Thr Ile Thr Ile  Pro Ser Met
    9830                9835                9840

Gly Ile  Thr Ser Ala Val Asp  Asp Thr Thr Val Phe  Thr Ser Asn
    9845                9850                9855
```

```
Pro Ala  Phe Ser Glu Thr Arg  Arg Ile Pro Thr Glu  Pro Thr Phe
    9860                9865                9870

Ser Leu  Thr Pro Gly Phe Arg  Glu Thr Ser Thr Ser  Glu Glu Thr
    9875                9880                9885

Thr Ser  Ile Thr Glu Thr Ser  Ala Val Leu Tyr Gly  Val Pro Thr
    9890                9895                9900

Ser Ala  Thr Thr Glu Val Ser  Met Thr Glu Ile Met  Ser Ser Asn
    9905                9910                9915

Arg Ile  His Ile Pro Asp Ser  Asp Gln Ser Thr Met  Ser Pro Asp
    9920                9925                9930

Ile Ile  Thr Glu Val Ile Thr  Arg Leu Ser Ser Ser  Ser Met Met
    9935                9940                9945

Ser Glu  Ser Thr Gln Met Thr  Ile Thr Thr Gln Lys  Ser Ser Pro
    9950                9955                9960

Gly Ala  Thr Ala Gln Ser Thr  Leu Thr Leu Ala Thr  Thr Thr Ala
    9965                9970                9975

Pro Leu  Ala Arg Thr His Ser  Thr Val Pro Pro Arg  Phe Leu His
    9980                9985                9990

Ser Glu  Met Thr Thr Leu Met   Ser Arg Ser Pro Glu   Asn Pro Ser
    9995                10000                10005

Trp Lys   Ser Ser Leu Phe Val   Glu Lys Thr Ser Ser   Ser Ser Ser
    10010                10015                10020

Leu Leu   Ser Leu Pro Val Thr   Thr Ser Pro Ser Val   Ser Ser Thr
    10025                10030                10035

Leu Pro   Gln Ser Ile Pro Ser   Ser Ser Phe Ser Val   Thr Ser Leu
    10040                10045                10050

Leu Thr   Pro Gly Met Val Lys   Thr Thr Asp Thr Ser   Thr Glu Pro
    10055                10060                10065

Gly Thr   Ser Leu Ser Pro Asn   Leu Ser Gly Thr Ser   Val Glu Ile
    10070                10075                10080

Leu Ala   Ala Ser Glu Val Thr   Thr Asp Thr Glu Lys   Ile His Pro
    10085                10090                10095

Ser Ser   Ser Met Ala Val Thr   Asn Val Gly Thr Thr   Ser Ser Gly
    10100                10105                10110

His Glu   Leu Tyr Ser Ser Val   Ser Ile His Ser Glu   Pro Ser Lys
    10115                10120                10125

Ala Thr   Tyr Pro Val Gly Thr   Pro Ser Ser Met Ala   Glu Thr Ser
    10130                10135                10140

Ile Ser   Thr Ser Met Pro Ala   Asn Phe Glu Thr Thr   Gly Phe Glu
    10145                10150                10155

Ala Glu   Pro Phe Ser His Leu   Thr Ser Gly Phe Arg   Lys Thr Asn
    10160                10165                10170

Met Ser   Leu Asp Thr Ser Ser   Val Thr Pro Thr Asn   Thr Pro Ser
    10175                10180                10185

Ser Pro   Gly Ser Thr His Leu   Leu Gln Ser Ser Lys   Thr Asp Phe
    10190                10195                10200

Thr Ser   Ser Ala Lys Thr Ser   Ser Pro Asp Trp Pro   Pro Ala Ser
    10205                10210                10215

Gln Tyr   Thr Glu Ile Pro Val   Asp Ile Ile Thr Pro   Phe Asn Ala
    10220                10225                10230

Ser Pro   Ser Ile Thr Glu Ser   Thr Gly Ile Thr Ser   Phe Pro Glu
    10235                10240                10245
```

```
Ser Arg   Phe Thr Met Ser Val   Thr Glu Ser Thr His   His Leu Ser
    10250                 10255                 10260

Thr Asp   Leu Leu Pro Ser Ala   Glu Thr Ile Ser Thr   Gly Thr Val
    10265                 10270                 10275

Met Pro   Ser Leu Ser Glu Ala   Met Thr Ser Phe Ala   Thr Thr Gly
    10280                 10285                 10290

Val Pro   Arg Ala Ile Ser Gly   Ser Gly Ser Pro Phe   Ser Arg Thr
    10295                 10300                 10305

Glu Ser   Gly Pro Gly Asp Ala   Thr Leu Ser Thr Ile   Ala Glu Ser
    10310                 10315                 10320

Leu Pro   Ser Ser Thr Pro Val   Pro Phe Ser Ser Ser   Thr Phe Thr
    10325                 10330                 10335

Thr Thr   Asp Ser Ser Thr Ile   Pro Ala Leu His Glu   Ile Thr Ser
    10340                 10345                 10350

Ser Ser   Ala Thr Pro Tyr Arg   Val Asp Thr Ser Leu   Gly Thr Glu
    10355                 10360                 10365

Ser Ser   Thr Thr Glu Gly Arg   Leu Val Met Val Ser   Thr Leu Asp
    10370                 10375                 10380

Thr Ser   Ser Gln Pro Gly Arg   Thr Ser Ser Ser Pro   Ile Leu Asp
    10385                 10390                 10395

Thr Arg   Met Thr Glu Ser Val   Glu Leu Gly Thr Val   Thr Ser Ala
    10400                 10405                 10410

Tyr Gln   Val Pro Ser Leu Ser   Thr Arg Leu Thr Arg   Thr Asp Gly
    10415                 10420                 10425

Ile Met   Glu His Ile Thr Lys   Ile Pro Asn Glu Ala   Ala His Arg
    10430                 10435                 10440

Gly Thr   Ile Arg Pro Val Lys   Gly Pro Gln Thr Ser   Thr Ser Pro
    10445                 10450                 10455

Ala Ser   Pro Lys Gly Leu His   Thr Gly Gly Thr Lys   Arg Met Glu
    10460                 10465                 10470

Thr Thr   Thr Thr Ala Leu Lys   Thr Thr Thr Thr Ala   Leu Lys Thr
    10475                 10480                 10485

Thr Ser   Arg Ala Thr Leu Thr   Thr Ser Val Tyr Thr   Pro Thr Leu
    10490                 10495                 10500

Gly Thr   Leu Thr Pro Leu Asn   Ala Ser Met Gln Met   Ala Ser Thr
    10505                 10510                 10515

Ile Pro   Thr Glu Met Met Ile   Thr Thr Pro Tyr Val   Phe Pro Asp
    10520                 10525                 10530

Val Pro   Glu Thr Thr Ser Ser   Leu Ala Thr Ser Leu   Gly Ala Glu
    10535                 10540                 10545

Thr Ser   Thr Ala Leu Pro Arg   Thr Thr Pro Ser Val   Phe Asn Arg
    10550                 10555                 10560

Glu Ser   Glu Thr Thr Ala Ser   Leu Val Ser Arg Ser   Gly Ala Glu
    10565                 10570                 10575

Arg Ser   Pro Val Ile Gln Thr   Leu Asp Val Ser Ser   Ser Glu Pro
    10580                 10585                 10590

Asp Thr   Thr Ala Ser Trp Val   Ile His Pro Ala Glu   Thr Ile Pro
    10595                 10600                 10605

Thr Val   Ser Lys Thr Thr Pro   Asn Phe Phe His Ser   Glu Leu Asp
    10610                 10615                 10620

Thr Val   Ser Ser Thr Ala Thr   Ser His Gly Ala Asp   Val Ser Ser
    10625                 10630                 10635

Ala Ile   Pro Thr Asn Ile Ser   Pro Ser Glu Leu Asp   Ala Leu Thr
```

-continued

```
    10640               10645               10650

Pro Leu Val Thr Ile Ser Gly Thr Asp Thr Ser Thr Thr Phe Pro
    10655               10660               10665

Thr Leu Thr Lys Ser Pro His Glu Thr Glu Thr Arg Thr Thr Trp
    10670               10675               10680

Leu Thr His Pro Ala Glu Thr Ser Ser Thr Ile Pro Arg Thr Ile
    10685               10690               10695

Pro Asn Phe Ser His His Glu Ser Asp Ala Thr Pro Ser Ile Ala
    10700               10705               10710

Thr Ser Pro Gly Ala Glu Thr Ser Ser Ala Ile Pro Ile Met Thr
    10715               10720               10725

Val Ser Pro Gly Ala Glu Asp Leu Val Thr Ser Gln Val Thr Ser
    10730               10735               10740

Ser Gly Thr Asp Arg Asn Met Thr Ile Pro Thr Leu Thr Leu Ser
    10745               10750               10755

Pro Gly Glu Pro Lys Thr Ile Ala Ser Leu Val Thr His Pro Glu
    10760               10765               10770

Ala Gln Thr Ser Ser Ala Ile Pro Thr Ser Thr Ile Ser Pro Ala
    10775               10780               10785

Val Ser Arg Leu Val Thr Ser Met Val Thr Ser Leu Ala Ala Lys
    10790               10795               10800

Thr Ser Thr Thr Asn Arg Ala Leu Thr Asn Ser Pro Gly Glu Pro
    10805               10810               10815

Ala Thr Thr Val Ser Leu Val Thr His Pro Ala Gln Thr Ser Pro
    10820               10825               10830

Thr Val Pro Trp Thr Thr Ser Ile Phe Phe His Ser Lys Ser Asp
    10835               10840               10845

Thr Thr Pro Ser Met Thr Thr Ser His Gly Ala Glu Ser Ser Ser
    10850               10855               10860

Ala Val Pro Thr Pro Thr Val Ser Thr Glu Val Pro Gly Val Val
    10865               10870               10875

Thr Pro Leu Val Thr Ser Ser Arg Ala Val Ile Ser Thr Thr Ile
    10880               10885               10890

Pro Ile Leu Thr Leu Ser Pro Gly Glu Pro Glu Thr Thr Pro Ser
    10895               10900               10905

Met Ala Thr Ser His Gly Glu Glu Ala Ser Ser Ala Ile Pro Thr
    10910               10915               10920

Pro Thr Val Ser Pro Gly Val Pro Gly Val Val Thr Ser Leu Val
    10925               10930               10935

Thr Ser Ser Arg Ala Val Thr Ser Thr Thr Ile Pro Ile Leu Thr
    10940               10945               10950

Phe Ser Leu Gly Glu Pro Glu Thr Thr Pro Ser Met Ala Thr Ser
    10955               10960               10965

His Gly Thr Glu Ala Gly Ser Ala Val Pro Thr Val Leu Pro Glu
    10970               10975               10980

Val Pro Gly Met Val Thr Ser Leu Val Ala Ser Ser Arg Ala Val
    10985               10990               10995

Thr Ser Thr Thr Leu Pro Thr Leu Thr Leu Ser Pro Gly Glu Pro
    11000               11005               11010

Glu Thr Thr Pro Ser Met Ala Thr Ser His Gly Ala Glu Ala Ser
    11015               11020               11025

Ser Thr Val Pro Thr Val Ser Pro Glu Val Pro Gly Val Val Thr
    11030               11035               11040
```

-continued

```
Ser Leu Val Thr Ser Ser Ser Gly Val Asn Ser Thr Ser Ile Pro
    11045               11050               11055

Thr Leu Ile Leu Ser Pro Gly Glu Leu Glu Thr Thr Pro Ser Met
    11060               11065               11070

Ala Thr Ser His Gly Ala Glu Ala Ser Ser Ala Val Pro Thr Pro
    11075               11080               11085

Thr Val Ser Pro Gly Val Ser Gly Val Val Thr Pro Leu Val Thr
    11090               11095               11100

Ser Ser Arg Ala Val Thr Ser Thr Thr Ile Pro Ile Leu Thr Leu
    11105               11110               11115

Ser Ser Ser Glu Pro Glu Thr Thr Pro Ser Met Ala Thr Ser His
    11120               11125               11130

Gly Val Glu Ala Ser Ser Ala Val Leu Thr Val Ser Pro Glu Val
    11135               11140               11145

Pro Gly Met Val Thr Ser Leu Val Thr Ser Ser Arg Ala Val Thr
    11150               11155               11160

Ser Thr Thr Ile Pro Thr Leu Thr Ile Ser Ser Asp Glu Pro Glu
    11165               11170               11175

Thr Thr Thr Ser Leu Val Thr His Ser Glu Ala Lys Met Ile Ser
    11180               11185               11190

Ala Ile Pro Thr Leu Ala Val Ser Pro Thr Val Gln Gly Leu Val
    11195               11200               11205

Thr Ser Leu Val Thr Ser Ser Gly Ser Glu Thr Ser Ala Phe Ser
    11210               11215               11220

Asn Leu Thr Val Ala Ser Ser Gln Pro Glu Thr Ile Asp Ser Trp
    11225               11230               11235

Val Ala His Pro Gly Thr Glu Ala Ser Ser Val Val Pro Thr Leu
    11240               11245               11250

Thr Val Ser Thr Gly Glu Pro Phe Thr Asn Ile Ser Leu Val Thr
    11255               11260               11265

His Pro Ala Glu Ser Ser Ser Thr Leu Pro Arg Thr Thr Ser Arg
    11270               11275               11280

Phe Ser His Ser Glu Leu Asp Thr Met Pro Ser Thr Val Thr Ser
    11285               11290               11295

Pro Glu Ala Glu Ser Ser Ser Ala Ile Ser Thr Thr Ile Ser Pro
    11300               11305               11310

Gly Ile Pro Gly Val Leu Thr Ser Leu Val Thr Ser Ser Gly Arg
    11315               11320               11325

Asp Ile Ser Ala Thr Phe Pro Thr Val Pro Glu Ser Pro His Glu
    11330               11335               11340

Ser Glu Ala Thr Ala Ser Trp Val Thr His Pro Ala Val Thr Ser
    11345               11350               11355

Thr Thr Val Pro Arg Thr Thr Pro Asn Tyr Ser His Ser Glu Pro
    11360               11365               11370

Asp Thr Thr Pro Ser Ile Ala Thr Ser Pro Gly Ala Glu Ala Thr
    11375               11380               11385

Ser Asp Phe Pro Thr Ile Thr Val Ser Pro Asp Val Pro Asp Met
    11390               11395               11400

Val Thr Ser Gln Val Thr Ser Ser Gly Thr Asp Thr Ser Ile Thr
    11405               11410               11415

Ile Pro Thr Leu Thr Leu Ser Ser Gly Glu Pro Glu Thr Thr Thr
    11420               11425               11430
```

-continued

```
Ser Phe Ile Thr Tyr Ser Glu Thr His Thr Ser Ser Ala Ile Pro
    11435               11440               11445

Thr Leu Pro Val Ser Pro Gly Ala Ser Lys Met Leu Thr Ser Leu
    11450               11455               11460

Val Ile Ser Ser Gly Thr Asp Ser Thr Thr Thr Phe Pro Thr Leu
    11465               11470               11475

Thr Glu Thr Pro Tyr Glu Pro Glu Thr Thr Ala Ile Gln Leu Ile
    11480               11485               11490

His Pro Ala Glu Thr Asn Thr Met Val Pro Arg Thr Thr Pro Lys
    11495               11500               11505

Phe Ser His Ser Lys Ser Asp Thr Thr Leu Pro Val Ala Ile Thr
    11510               11515               11520

Ser Pro Gly Pro Glu Ala Ser Ser Ala Val Ser Thr Thr Thr Ile
    11525               11530               11535

Ser Pro Asp Met Ser Asp Leu Val Thr Ser Leu Val Pro Ser Ser
    11540               11545               11550

Gly Thr Asp Thr Ser Thr Thr Phe Pro Thr Leu Ser Glu Thr Pro
    11555               11560               11565

Tyr Glu Pro Glu Thr Thr Ala Thr Trp Leu Thr His Pro Ala Glu
    11570               11575               11580

Thr Ser Thr Thr Val Ser Gly Thr Ile Pro Asn Phe Ser His Arg
    11585               11590               11595

Gly Ser Asp Thr Ala Pro Ser Met Val Thr Ser Pro Gly Val Asp
    11600               11605               11610

Thr Arg Ser Gly Val Pro Thr Thr Thr Ile Pro Pro Ser Ile Pro
    11615               11620               11625

Gly Val Val Thr Ser Gln Val Thr Ser Ser Ala Thr Asp Thr Ser
    11630               11635               11640

Thr Ala Ile Pro Thr Leu Thr Pro Ser Pro Gly Glu Pro Glu Thr
    11645               11650               11655

Thr Ala Ser Ser Ala Thr His Pro Gly Thr Gln Thr Gly Phe Thr
    11660               11665               11670

Val Pro Ile Arg Thr Val Pro Ser Ser Glu Pro Asp Thr Met Ala
    11675               11680               11685

Ser Trp Val Thr His Pro Pro Gln Thr Ser Thr Pro Val Ser Arg
    11690               11695               11700

Thr Thr Ser Ser Phe Ser His Ser Ser Pro Asp Ala Thr Pro Val
    11705               11710               11715

Met Ala Thr Ser Pro Arg Thr Glu Ala Ser Ser Ala Val Leu Thr
    11720               11725               11730

Thr Ile Ser Pro Gly Ala Pro Glu Met Val Thr Ser Gln Ile Thr
    11735               11740               11745

Ser Ser Gly Ala Ala Thr Ser Thr Thr Val Pro Thr Leu Thr His
    11750               11755               11760

Ser Pro Gly Met Pro Glu Thr Thr Ala Leu Leu Ser Thr His Pro
    11765               11770               11775

Arg Thr Glu Thr Ser Lys Thr Phe Pro Ala Ser Thr Val Phe Pro
    11780               11785               11790

Gln Val Ser Glu Thr Thr Ala Ser Leu Thr Ile Arg Pro Gly Ala
    11795               11800               11805

Glu Thr Ser Thr Ala Leu Pro Thr Gln Thr Thr Ser Ser Leu Phe
    11810               11815               11820

Thr Leu Leu Val Thr Gly Thr Ser Arg Val Asp Leu Ser Pro Thr
```

```
    11825               11830               11835

Ala Ser Pro Gly Val Ser Ala Lys Thr Ala Pro Leu Ser Thr His
    11840               11845               11850

Pro Gly Thr Glu Thr Ser Thr Met Ile Pro Thr Ser Thr Leu Ser
    11855               11860               11865

Leu Gly Leu Leu Glu Thr Thr Gly Leu Leu Ala Thr Ser Ser Ser
    11870               11875               11880

Ala Glu Thr Ser Thr Ser Thr Leu Thr Leu Thr Val Ser Pro Ala
    11885               11890               11895

Val Ser Gly Leu Ser Ser Ala Ser Ile Thr Thr Asp Lys Pro Gln
    11900               11905               11910

Thr Val Thr Ser Trp Asn Thr Glu Thr Ser Pro Ser Val Thr Ser
    11915               11920               11925

Val Gly Pro Pro Glu Phe Ser Arg Thr Val Thr Gly Thr Thr Met
    11930               11935               11940

Thr Leu Ile Pro Ser Glu Met Pro Thr Pro Pro Lys Thr Ser His
    11945               11950               11955

Gly Glu Gly Val Ser Pro Thr Thr Ile Leu Arg Thr Thr Met Val
    11960               11965               11970

Glu Ala Thr Asn Leu Ala Thr Thr Gly Ser Ser Pro Thr Val Ala
    11975               11980               11985

Lys Thr Thr Thr Thr Phe Asn Thr Leu Ala Gly Ser Leu Phe Thr
    11990               11995               12000

Pro Leu Thr Thr Pro Gly Met Ser Thr Leu Ala Ser Glu Ser Val
    12005               12010               12015

Thr Ser Arg Thr Ser Tyr Asn His Arg Ser Trp Ile Ser Thr Thr
    12020               12025               12030

Ser Ser Tyr Asn Arg Arg Tyr Trp Thr Pro Ala Thr Ser Thr Pro
    12035               12040               12045

Val Thr Ser Thr Phe Ser Pro Gly Ile Ser Thr Ser Ser Ile Pro
    12050               12055               12060

Ser Ser Thr Ala Ala Thr Val Pro Phe Met Val Pro Phe Thr Leu
    12065               12070               12075

Asn Phe Thr Ile Thr Asn Leu Gln Tyr Glu Glu Asp Met Arg His
    12080               12085               12090

Pro Gly Ser Arg Lys Phe Asn Ala Thr Glu Arg Glu Leu Gln Gly
    12095               12100               12105

Leu Leu Lys Pro Leu Phe Arg Asn Ser Ser Leu Glu Tyr Leu Tyr
    12110               12115               12120

Ser Gly Cys Arg Leu Ala Ser Leu Arg Pro Glu Lys Asp Ser Ser
    12125               12130               12135

Ala Thr Ala Val Asp Ala Ile Cys Thr His Arg Pro Asp Pro Glu
    12140               12145               12150

Asp Leu Gly Leu Asp Arg Glu Arg Leu Tyr Trp Glu Leu Ser Asn
    12155               12160               12165

Leu Thr Asn Gly Ile Gln Glu Leu Gly Pro Tyr Thr Leu Asp Arg
    12170               12175               12180

Asn Ser Leu Tyr Val Asn Gly Phe Thr His Arg Ser Ser Met Pro
    12185               12190               12195

Thr Thr Ser Thr Pro Gly Thr Ser Thr Val Asp Val Gly Thr Ser
    12200               12205               12210

Gly Thr Pro Ser Ser Ser Pro Ser Pro Thr Thr Ala Gly Pro Leu
    12215               12220               12225
```

-continued

```
Leu Met   Pro Phe Thr Leu Asn   Phe Thr Ile Thr Asn   Leu Gln Tyr
    12230                12235                12240

Glu Glu   Asp Met Arg Arg Thr   Gly Ser Arg Lys Phe   Asn Thr Met
    12245                12250                12255

Glu Ser   Val Leu Gln Gly Leu   Leu Lys Pro Leu Phe   Lys Asn Thr
    12260                12265                12270

Ser Val   Gly Pro Leu Tyr Ser   Gly Cys Arg Leu Thr   Leu Leu Arg
    12275                12280                12285

Pro Glu   Lys Asp Gly Ala Ala   Thr Gly Val Asp Ala   Ile Cys Thr
    12290                12295                12300

His Arg   Leu Asp Pro Lys Ser   Pro Gly Leu Asn Arg   Glu Gln Leu
    12305                12310                12315

Tyr Trp   Glu Leu Ser Lys Leu   Thr Asn Asp Ile Glu   Glu Leu Gly
    12320                12325                12330

Pro Tyr   Thr Leu Asp Arg Asn   Ser Leu Tyr Val Asn   Gly Phe Thr
    12335                12340                12345

His Gln   Ser Ser Val Ser Thr   Thr Ser Thr Pro Gly   Thr Ser Thr
    12350                12355                12360

Val Asp   Leu Arg Thr Ser Gly   Thr Pro Ser Ser Leu   Ser Ser Pro
    12365                12370                12375

Thr Ile   Met Ala Ala Gly Pro   Leu Leu Val Pro Phe   Thr Leu Asn
    12380                12385                12390

Phe Thr   Ile Thr Asn Leu Gln   Tyr Gly Glu Asp Met   Gly His Pro
    12395                12400                12405

Gly Ser   Arg Lys Phe Asn Thr   Thr Glu Arg Val Leu   Gln Gly Leu
    12410                12415                12420

Leu Gly   Pro Ile Phe Lys Asn   Thr Ser Val Gly Pro   Leu Tyr Ser
    12425                12430                12435

Gly Cys   Arg Leu Thr Ser Leu   Arg Ser Glu Lys Asp   Gly Ala Ala
    12440                12445                12450

Thr Gly   Val Asp Ala Ile Cys   Ile His His Leu Asp   Pro Lys Ser
    12455                12460                12465

Pro Gly   Leu Asn Arg Glu Arg   Leu Tyr Trp Glu Leu   Ser Gln Leu
    12470                12475                12480

Thr Asn   Gly Ile Lys Glu Leu   Gly Pro Tyr Thr Leu   Asp Arg Asn
    12485                12490                12495

Ser Leu   Tyr Val Asn Gly Phe   Thr His Arg Thr Ser   Val Pro Thr
    12500                12505                12510

Ser Ser   Thr Pro Gly Thr Ser   Thr Val Asp Leu Gly   Thr Ser Gly
    12515                12520                12525

Thr Pro   Phe Ser Leu Pro Ser   Pro Ala Thr Ala Gly   Pro Leu Leu
    12530                12535                12540

Val Leu   Phe Thr Leu Asn Phe   Thr Ile Thr Asn Leu   Lys Tyr Glu
    12545                12550                12555

Glu Asp   Met His Arg Pro Gly   Ser Arg Lys Phe Asn   Thr Thr Glu
    12560                12565                12570

Arg Val   Leu Gln Thr Leu Leu   Gly Pro Met Phe Lys   Asn Thr Ser
    12575                12580                12585

Val Gly   Leu Leu Tyr Ser Gly   Cys Arg Leu Thr Leu   Leu Arg Ser
    12590                12595                12600

Glu Lys   Asp Gly Ala Ala Thr   Gly Val Asp Ala Ile   Cys Thr His
    12605                12610                12615
```

```
Arg Leu   Asp Pro Lys Ser Pro   Gly Val Asp Arg Glu   Gln Leu Tyr
    12620                 12625                 12630

Trp Glu   Leu Ser Gln Leu Thr   Asn Gly Ile Lys Glu   Leu Gly Pro
    12635                 12640                 12645

Tyr Thr   Leu Asp Arg Asn Ser   Leu Tyr Val Asn Gly   Phe Thr His
    12650                 12655                 12660

Trp Ile   Pro Val Pro Thr Ser   Ser Thr Pro Gly Thr   Ser Thr Val
    12665                 12670                 12675

Asp Leu   Gly Ser Gly Thr Pro   Ser Ser Leu Pro Ser   Pro Thr Thr
    12680                 12685                 12690

Ala Gly   Pro Leu Leu Val Pro   Phe Thr Leu Asn Phe   Thr Ile Thr
    12695                 12700                 12705

Asn Leu   Lys Tyr Glu Glu Asp   Met His Cys Pro Gly   Ser Arg Lys
    12710                 12715                 12720

Phe Asn   Thr Thr Glu Arg Val   Leu Gln Ser Leu Leu   Gly Pro Met
    12725                 12730                 12735

Phe Lys   Asn Thr Ser Val Gly   Pro Leu Tyr Ser Gly   Cys Arg Leu
    12740                 12745                 12750

Thr Leu   Leu Arg Ser Glu Lys   Asp Gly Ala Ala Thr   Gly Val Asp
    12755                 12760                 12765

Ala Ile   Cys Thr His Arg Leu   Asp Pro Lys Ser Pro   Gly Val Asp
    12770                 12775                 12780

Arg Glu   Gln Leu Tyr Trp Glu   Leu Ser Gln Leu Thr   Asn Gly Ile
    12785                 12790                 12795

Lys Glu   Leu Gly Pro Tyr Thr   Leu Asp Arg Asn Ser   Leu Tyr Val
    12800                 12805                 12810

Asn Gly   Phe Thr His Gln Thr   Ser Ala Pro Asn Thr   Ser Thr Pro
    12815                 12820                 12825

Gly Thr   Ser Thr Val Asp Leu   Gly Thr Ser Gly Thr   Pro Ser Ser
    12830                 12835                 12840

Leu Pro   Ser Pro Thr Ser Ala   Gly Pro Leu Leu Val   Pro Phe Thr
    12845                 12850                 12855

Leu Asn   Phe Thr Ile Thr Asn   Leu Gln Tyr Glu Glu   Asp Met His
    12860                 12865                 12870

His Pro   Gly Ser Arg Lys Phe   Asn Thr Thr Glu Arg   Val Leu Gln
    12875                 12880                 12885

Gly Leu   Leu Gly Pro Met Phe   Lys Asn Thr Ser Val   Gly Leu Leu
    12890                 12895                 12900

Tyr Ser   Gly Cys Arg Leu Thr   Leu Leu Arg Pro Glu   Lys Asn Gly
    12905                 12910                 12915

Ala Ala   Thr Gly Met Asp Ala   Ile Cys Ser His Arg   Leu Asp Pro
    12920                 12925                 12930

Lys Ser   Pro Gly Leu Asn Arg   Glu Gln Leu Tyr Trp   Glu Leu Ser
    12935                 12940                 12945

Gln Leu   Thr His Gly Ile Lys   Glu Leu Gly Pro Tyr   Thr Leu Asp
    12950                 12955                 12960

Arg Asn   Ser Leu Tyr Val Asn   Gly Phe Thr His Arg   Ser Ser Val
    12965                 12970                 12975

Ala Pro   Thr Ser Thr Pro Gly   Thr Ser Thr Val Asp   Leu Gly Thr
    12980                 12985                 12990

Ser Gly   Thr Pro Ser Ser Leu   Pro Ser Pro Thr Thr   Ala Val Pro
    12995                 13000                 13005

Leu Leu   Val Pro Phe Thr Leu   Asn Phe Thr Ile Thr   Asn Leu Gln
```

```
    13010               13015               13020

Tyr Gly  Glu Asp Met Arg His  Pro Gly Ser Arg Lys  Phe Asn Thr
    13025               13030               13035

Thr Glu  Arg Val Leu Gln Gly  Leu Leu Gly Pro Leu  Phe Lys Asn
    13040               13045               13050

Ser Ser  Val Gly Pro Leu Tyr  Ser Gly Cys Arg Leu  Ile Ser Leu
    13055               13060               13065

Arg Ser  Glu Lys Asp Gly Ala  Ala Thr Gly Val Asp  Ala Ile Cys
    13070               13075               13080

Thr His  His Leu Asn Pro Gln  Ser Pro Gly Leu Asp  Arg Glu Gln
    13085               13090               13095

Leu Tyr  Trp Gln Leu Ser Gln  Met Thr Asn Gly Ile  Lys Glu Leu
    13100               13105               13110

Gly Pro  Tyr Thr Leu Asp Arg  Asn Ser Leu Tyr Val  Asn Gly Phe
    13115               13120               13125

Thr His  Arg Ser Ser Gly Leu  Thr Thr Ser Thr Pro  Trp Thr Ser
    13130               13135               13140

Thr Val  Asp Leu Gly Thr Ser  Gly Thr Pro Ser Pro  Val Pro Ser
    13145               13150               13155

Pro Thr  Thr Thr Gly Pro Leu  Leu Val Pro Phe Thr  Leu Asn Phe
    13160               13165               13170

Thr Ile  Thr Asn Leu Gln Tyr  Glu Glu Asn Met Gly  His Pro Gly
    13175               13180               13185

Ser Arg  Lys Phe Asn Ile Thr  Glu Ser Val Leu Gln  Gly Leu Leu
    13190               13195               13200

Lys Pro  Leu Phe Lys Ser Thr  Ser Val Gly Pro Leu  Tyr Ser Gly
    13205               13210               13215

Cys Arg  Leu Thr Leu Leu Arg  Pro Glu Lys Asp Gly  Val Ala Thr
    13220               13225               13230

Arg Val  Asp Ala Ile Cys Thr  His Arg Pro Asp Pro  Lys Ile Pro
    13235               13240               13245

Gly Leu  Asp Arg Gln Gln Leu  Tyr Trp Glu Leu Ser  Gln Leu Thr
    13250               13255               13260

His Ser  Ile Thr Glu Leu Gly  Pro Tyr Thr Leu Asp  Arg Asp Ser
    13265               13270               13275

Leu Tyr  Val Asn Gly Phe Thr  Gln Arg Ser Ser Val  Pro Thr Thr
    13280               13285               13290

Ser Thr  Pro Gly Thr Phe Thr  Val Gln Pro Glu Thr  Ser Glu Thr
    13295               13300               13305

Pro Ser  Ser Leu Pro Gly Pro  Thr Ala Thr Gly Pro  Val Leu Leu
    13310               13315               13320

Pro Phe  Thr Leu Asn Phe Thr  Ile Thr Asn Leu Gln  Tyr Glu Glu
    13325               13330               13335

Asp Met  Arg Arg Pro Gly Ser  Arg Lys Phe Asn Thr  Thr Glu Arg
    13340               13345               13350

Val Leu  Gln Gly Leu Leu Met  Pro Leu Phe Lys Asn  Thr Ser Val
    13355               13360               13365

Ser Ser  Leu Tyr Ser Gly Cys  Arg Leu Thr Leu Leu  Arg Pro Glu
    13370               13375               13380

Lys Asp  Gly Ala Ala Thr Arg  Val Asp Ala Val Cys  Thr His Arg
    13385               13390               13395

Pro Asp  Pro Lys Ser Pro Gly  Leu Asp Arg Glu Arg  Leu Tyr Trp
    13400               13405               13410
```

```
Lys Leu Ser Gln Leu Thr His Gly Ile Thr Glu Leu Gly Pro Tyr
    13415               13420               13425

Thr Leu Asp Arg His Ser Leu Tyr Val Asn Gly Phe Thr His Gln
    13430               13435               13440

Ser Ser Met Thr Thr Thr Arg Thr Pro Asp Thr Ser Thr Met His
    13445               13450               13455

Leu Ala Thr Ser Arg Thr Pro Ala Ser Leu Ser Gly Pro Met Thr
    13460               13465               13470

Ala Ser Pro Leu Leu Val Leu Phe Thr Ile Asn Phe Thr Ile Thr
    13475               13480               13485

Asn Leu Arg Tyr Glu Glu Asn Met His His Pro Gly Ser Arg Lys
    13490               13495               13500

Phe Asn Thr Thr Glu Arg Val Leu Gln Gly Leu Leu Arg Pro Val
    13505               13510               13515

Phe Lys Asn Thr Ser Val Gly Pro Leu Tyr Ser Gly Cys Arg Leu
    13520               13525               13530

Thr Leu Leu Arg Pro Lys Lys Asp Gly Ala Ala Thr Lys Val Asp
    13535               13540               13545

Ala Ile Cys Thr Tyr Arg Pro Asp Pro Lys Ser Pro Gly Leu Asp
    13550               13555               13560

Arg Glu Gln Leu Tyr Trp Glu Leu Ser Gln Leu Thr His Ser Ile
    13565               13570               13575

Thr Glu Leu Gly Pro Tyr Thr Leu Asp Arg Asp Ser Leu Tyr Val
    13580               13585               13590

Asn Gly Phe Thr Gln Arg Ser Ser Val Pro Thr Thr Ser Ile Pro
    13595               13600               13605

Gly Thr Pro Thr Val Asp Leu Gly Thr Ser Gly Thr Pro Val Ser
    13610               13615               13620

Lys Pro Gly Pro Ser Ala Ala Ser Pro Leu Leu Val Leu Phe Thr
    13625               13630               13635

Leu Asn Phe Thr Ile Thr Asn Leu Arg Tyr Glu Glu Asn Met Gln
    13640               13645               13650

His Pro Gly Ser Arg Lys Phe Asn Thr Thr Glu Arg Val Leu Gln
    13655               13660               13665

Gly Leu Leu Arg Ser Leu Phe Lys Ser Thr Ser Val Gly Pro Leu
    13670               13675               13680

Tyr Ser Gly Cys Arg Leu Thr Leu Leu Arg Pro Glu Lys Asp Gly
    13685               13690               13695

Thr Ala Thr Gly Val Asp Ala Ile Cys Thr His His Pro Asp Pro
    13700               13705               13710

Lys Ser Pro Arg Leu Asp Arg Glu Gln Leu Tyr Trp Glu Leu Ser
    13715               13720               13725

Gln Leu Thr His Asn Ile Thr Glu Leu Gly Pro Tyr Ala Leu Asp
    13730               13735               13740

Asn Asp Ser Leu Phe Val Asn Gly Phe Thr His Arg Ser Ser Val
    13745               13750               13755

Ser Thr Thr Ser Thr Pro Gly Thr Pro Thr Val Tyr Leu Gly Ala
    13760               13765               13770

Ser Lys Thr Pro Ala Ser Ile Phe Gly Pro Ser Ala Ala Ser His
    13775               13780               13785

Leu Leu Ile Leu Phe Thr Leu Asn Phe Thr Ile Thr Asn Leu Arg
    13790               13795               13800
```

-continued

```
Tyr Glu   Glu Asn Met Trp Pro   Gly Ser Arg Lys Phe   Asn Thr Thr
    13805                 13810                 13815

Glu Arg   Val Leu Gln Gly Leu   Leu Arg Pro Leu Phe   Lys Asn Thr
    13820                 13825                 13830

Ser Val   Gly Pro Leu Tyr Ser   Gly Cys Arg Leu Thr   Leu Leu Arg
    13835                 13840                 13845

Pro Glu   Lys Asp Gly Glu Ala   Thr Gly Val Asp Ala   Ile Cys Thr
    13850                 13855                 13860

His Arg   Pro Asp Pro Thr Gly   Pro Gly Leu Asp Arg   Glu Gln Leu
    13865                 13870                 13875

Tyr Leu   Glu Leu Ser Gln Leu   Thr His Ser Ile Thr   Glu Leu Gly
    13880                 13885                 13890

Pro Tyr   Thr Leu Asp Arg Asp   Ser Leu Tyr Val Asn   Gly Phe Thr
    13895                 13900                 13905

His Arg   Ser Ser Val Pro Thr   Thr Ser Thr Gly Val   Val Ser Glu
    13910                 13915                 13920

Glu Pro   Phe Thr Leu Asn Phe   Thr Ile Asn Asn Leu   Arg Tyr Met
    13925                 13930                 13935

Ala Asp   Met Gly Gln Pro Gly   Ser Leu Lys Phe Asn   Ile Thr Asp
    13940                 13945                 13950

Asn Val   Met Gln His Leu Leu   Ser Pro Leu Phe Gln   Arg Ser Ser
    13955                 13960                 13965

Leu Gly   Ala Arg Tyr Thr Gly   Cys Arg Val Ile Ala   Leu Arg Ser
    13970                 13975                 13980

Val Lys   Asn Gly Ala Glu Thr   Arg Val Asp Leu Leu   Cys Thr Tyr
    13985                 13990                 13995

Leu Gln   Pro Leu Ser Gly Pro   Gly Leu Pro Ile Lys   Gln Val Phe
    14000                 14005                 14010

His Glu   Leu Ser Gln Gln Thr   His Gly Ile Thr Arg   Leu Gly Pro
    14015                 14020                 14025

Tyr Ser   Leu Asp Lys Asp Ser   Leu Tyr Leu Asn Gly   Tyr Asn Glu
    14030                 14035                 14040

Pro Gly   Pro Asp Glu Pro Pro   Thr Thr Pro Lys Pro   Ala Thr Thr
    14045                 14050                 14055

Phe Leu   Pro Pro Leu Ser Glu   Ala Thr Thr Ala Met   Gly Tyr His
    14060                 14065                 14070

Leu Lys   Thr Leu Thr Leu Asn   Phe Thr Ile Ser Asn   Leu Gln Tyr
    14075                 14080                 14085

Ser Pro   Asp Met Gly Lys Gly   Ser Ala Thr Phe Asn   Ser Thr Glu
    14090                 14095                 14100

Gly Val   Leu Gln His Leu Leu   Arg Pro Leu Phe Gln   Lys Ser Ser
    14105                 14110                 14115

Met Gly   Pro Phe Tyr Leu Gly   Cys Gln Leu Ile Ser   Leu Arg Pro
    14120                 14125                 14130

Glu Lys   Asp Gly Ala Ala Thr   Gly Val Asp Thr Thr   Cys Thr Tyr
    14135                 14140                 14145

His Pro   Asp Pro Val Gly Pro   Gly Leu Asp Ile Gln   Gln Leu Tyr
    14150                 14155                 14160

Trp Glu   Leu Ser Gln Leu Thr   His Gly Val Thr Gln   Leu Gly Phe
    14165                 14170                 14175

Tyr Val   Leu Asp Arg Asp Ser   Leu Phe Ile Asn Gly   Tyr Ala Pro
    14180                 14185                 14190

Gln Asn   Leu Ser Ile Arg Gly   Glu Tyr Gln Ile Asn   Phe His Ile
```

```
    14195                 14200                 14205

Val Asn   Trp Asn Leu Ser Asn   Pro Asp Pro Thr Ser   Ser Glu Tyr
    14210                 14215                 14220

Ile Thr   Leu Leu Arg Asp Ile   Gln Asp Lys Val Thr   Thr Leu Tyr
    14225                 14230                 14235

Lys Gly   Ser Gln Leu His Asp   Thr Phe Arg Phe Cys   Leu Val Thr
    14240                 14245                 14250

Asn Leu   Thr Met Asp Ser Val   Leu Val Thr Val Lys   Ala Leu Phe
    14255                 14260                 14265

Ser Ser   Asn Leu Asp Pro Ser   Leu Val Glu Gln Val   Phe Leu Asp
    14270                 14275                 14280

Lys Thr   Leu Asn Ala Ser Phe   His Trp Leu Gly Ser   Thr Tyr Gln
    14285                 14290                 14295

Leu Val   Asp Ile His Val Thr   Glu Met Glu Ser Ser   Val Tyr Gln
    14300                 14305                 14310

Pro Thr   Ser Ser Ser Ser Thr   Gln His Phe Tyr Leu   Asn Phe Thr
    14315                 14320                 14325

Ile Thr   Asn Leu Pro Tyr Ser   Gln Asp Lys Ala Gln   Pro Gly Thr
    14330                 14335                 14340

Thr Asn   Tyr Gln Arg Asn Lys   Arg Asn Ile Glu Asp   Ala Leu Asn
    14345                 14350                 14355

Gln Leu   Phe Arg Asn Ser Ser   Ile Lys Ser Tyr Phe   Ser Asp Cys
    14360                 14365                 14370

Gln Val   Ser Thr Phe Arg Ser   Val Pro Asn Arg His   His Thr Gly
    14375                 14380                 14385

Val Asp   Ser Leu Cys Asn Phe   Ser Pro Leu Ala Arg   Arg Val Asp
    14390                 14395                 14400

Arg Val   Ala Ile Tyr Glu Glu   Phe Leu Arg Met Thr   Arg Asn Gly
    14405                 14410                 14415

Thr Gln   Leu Gln Asn Phe Thr   Leu Asp Arg Ser Ser   Val Leu Val
    14420                 14425                 14430

Asp Gly   Tyr Ser Pro Asn Arg   Asn Glu Pro Leu Thr   Gly Asn Ser
    14435                 14440                 14445

Asp Leu   Pro Phe Trp Ala Val   Ile Leu Ile Gly Leu   Ala Gly Leu
    14450                 14455                 14460

Leu Gly   Val Ile Thr Cys Leu   Ile Cys Gly Val Leu   Val Thr Thr
    14465                 14470                 14475

Arg Arg   Arg Lys Lys Glu Gly   Glu Tyr Asn Val Gln   Gln Gln Cys
    14480                 14485                 14490

Pro Gly   Tyr Tyr Gln Ser His   Leu Asp Leu Glu Asp   Leu Gln
    14495                 14500                 14505


<210> SEQ ID NO 14
<211> LENGTH: 24
<212> TYPE: PRT
<213> ORGANISM: Artificial Sequence
<220> FEATURE:
<223> OTHER INFORMATION: Synthetic

<400> SEQUENCE: 14

Phe Trp Ala Val Ile Leu Ile Gly Leu Ala Gly Leu Leu Gly Leu Ile
1               5                   10                  15

Thr Cys Leu Ile Cys Gly Val Leu
            20
```

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

```
Lys Ser Tyr Phe Ser Asp Cys Gln Val Ser Thr Phe Arg Ser Val Pro
1               5                   10                  15

Asn Arg His His Thr Gly Val Asp Ser Leu Cys Asn Phe Ser Pro Leu
            20                  25                  30
```

<210> SEQ ID NO 16
<211> LENGTH: 32
<212> TYPE: PRT
<213> ORGANISM: Artificial Sequence
<220> FEATURE:
<223> OTHER INFORMATION: Synthetic

<400> SEQUENCE: 16

```
Val Thr Thr Arg Arg Arg Lys Lys Glu Gly Glu Tyr Asn Val Gln Gln
1               5                   10                  15

Gln Cys Pro Gly Tyr Tyr Gln Ser His Leu Asp Leu Glu Asp Leu Gln
            20                  25                  30
```

<210> SEQ ID NO 17
<211> LENGTH: 58
<212> TYPE: PRT
<213> ORGANISM: Artificial Sequence
<220> FEATURE:
<223> OTHER INFORMATION: Synthetic

<400> SEQUENCE: 17

```
Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro
    50                  55
```

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

```
Val Thr Thr Arg Arg Arg Lys Lys Glu Gly Glu Tyr Asn Val Gln Gln
1               5                   10                  15

Gln
```

<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

```
Cys Gln Val Ser Thr Phe Arg Ser Val Pro Asn Arg His His Thr Gly
```

1 5 10 15

Val Asp Ser Leu Cys
20

<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Leu Val Thr Thr Arg Arg Arg Lys Lys Glu Gly Glu Tyr Asn Val Gln
1 5 10 15

Gln Gln

<210> SEQ ID NO 21
<211> LENGTH: 18
<212> TYPE: PRT
<213> ORGANISM: Mus musculus

<400> SEQUENCE: 21

Thr Leu Asp Arg Lys Ser Val Phe Val Asp Gly Tyr Ser Gln Asn Arg
1 5 10 15

Asp Asp

<210> SEQ ID NO 22
<211> LENGTH: 33
<212> TYPE: PRT
<213> ORGANISM: Mus musculus

<400> SEQUENCE: 22

Lys Ser Tyr Phe Ser Asp Cys Gln Val Leu Ala Phe Arg Ser Val Ser
1 5 10 15

Asn Asn Asn Asn His Thr Gly Val Asp Ser Leu Cys Asn Phe Ser Pro
20 25 30

Leu

<210> SEQ ID NO 23
<211> LENGTH: 31
<212> TYPE: PRT
<213> ORGANISM: Mus musculus

<400> SEQUENCE: 23

Ser Leu Tyr Ser Asn Cys Arg Leu Ala Ser Leu Arg Pro Lys Lys Asn
1 5 10 15

Gly Thr Ala Thr Gly Val Asn Ala Ile Cys Ser Tyr His Gln Asn
20 25 30

<210> SEQ ID NO 24
<211> LENGTH: 402
<212> TYPE: PRT
<213> ORGANISM: Mus musculus

<400> SEQUENCE: 24

His Leu Ile Arg Pro Leu Val Gln Asn Glu Ser Leu Tyr Ser Asn Cys
1 5 10 15

Arg Leu Ala Ser Leu Arg Pro Lys Lys Asn Gly Thr Ala Thr Gly Val
20 25 30

Asn Ala Ile Cys Ser Tyr His Gln Asn Pro Asp His Pro Glu Leu Asp
35 40 45

```
Thr Gln Glu Leu Tyr Thr Lys Leu Thr Gln Leu Thr Gln Gly Val Thr
    50                  55                  60

Gln Leu Gly Ser Tyr Met Leu Asp Gln Asn Ser Ile Tyr Val Asn Gly
65                  70                  75                  80

Tyr Val Pro Leu Asn Ile Thr Ile Gln Gly Lys Tyr Gln Leu Asn Phe
                85                  90                  95

Cys Ile Ile Asn Trp Asn Leu Asn Asn Thr Asp Pro Thr Ser Ser Glu
            100                 105                 110

Tyr Ile Thr Leu Glu Arg Asp Ile Glu Asp Lys Val Thr Thr Leu Tyr
        115                 120                 125

Thr Gly Ser Gln Leu Lys Glu Val Phe Gln Ser Cys Leu Val Thr Asn
    130                 135                 140

Met Thr Ser Gly Ser Thr Val Val Thr Leu Glu Ala Leu Phe Ser Ser
145                 150                 155                 160

His Leu Asp Pro Asn Leu Val Lys Gln Val Phe Leu Asn Lys Thr Leu
                165                 170                 175

Asn Ala Ser Ser His Trp Leu Gly Ala Thr Tyr Gln Leu Lys Asp Leu
            180                 185                 190

His Val Ile Asp Met Lys Thr Ser Ile Leu Leu Pro Ala Glu Ile Pro
        195                 200                 205

Thr Thr Ser Ser Ser Ser Gln His Phe Asn Leu Asn Phe Thr Ile Thr
    210                 215                 220

Asn Leu Pro Tyr Ser Gln Asp Ile Ala Gln Pro Ser Thr Thr Lys Tyr
225                 230                 235                 240

Gln Gln Thr Lys Arg Ser Ile Glu Asn Ala Leu Asn Gln Leu Phe Arg
                245                 250                 255

Asn Ser Ser Ile Lys Ser Tyr Phe Ser Asp Cys Gln Val Leu Ala Phe
            260                 265                 270

Arg Ser Val Ser Asn Asn Asn Asn His Thr Gly Val Asp Ser Leu Cys
        275                 280                 285

Asn Phe Ser Pro Leu Ala Arg Arg Val Asp Arg Val Ala Ile Tyr Glu
    290                 295                 300

Glu Phe Leu Arg Met Thr His Asn Gly Thr Gln Leu Leu Asn Phe Thr
305                 310                 315                 320

Leu Asp Arg Lys Ser Val Phe Val Asp Gly Tyr Ser Gln Asn Arg Asp
                325                 330                 335

Asp Asp Val Met Lys Asn Ser Gly Leu Pro Phe Trp Ala Ile Ile Leu
            340                 345                 350

Ile Cys Leu Ala Val Leu Leu Val Leu Ile Thr Cys Leu Met Cys Cys
        355                 360                 365

Phe Leu Val Thr Val Cys Arg Arg Lys Lys Glu Gly Asp Tyr Gln Val
    370                 375                 380

Gln Arg His Arg Leu Ala Tyr Tyr Leu Ser His Leu Asp Leu Arg Lys
385                 390                 395                 400

Leu Gln


<210> SEQ ID NO 25
<211> LENGTH: 400
<212> TYPE: PRT
<213> ORGANISM: Homo sapiens

<400> SEQUENCE: 25

His Leu Leu Arg Pro Leu Phe Gln Lys Ser Ser Met Gly Pro Phe Tyr
1               5                   10                  15
```

-continued

```
Leu Gly Cys Gln Leu Ile Ser Leu Arg Pro Glu Lys Asp Gly Ala Ala
            20                  25                  30

Thr Gly Val Asp Thr Thr Cys Thr Tyr His Pro Asp Pro Val Gly Pro
        35                  40                  45

Gly Leu Asp Ile Gln Gln Leu Tyr Trp Glu Leu Ser Gln Leu Thr His
    50                  55                  60

Gly Val Thr Gln Leu Gly Phe Tyr Val Leu Asp Arg Asp Ser Leu Phe
65                  70                  75                  80

Ile Asn Gly Tyr Ala Pro Gln Asn Leu Ser Ile Arg Gly Glu Tyr Gln
                85                  90                  95

Ile Asn Phe His Ile Val Asn Trp Asn Leu Ser Asn Pro Asp Pro Thr
            100                 105                 110

Ser Ser Glu Tyr Ile Thr Leu Leu Arg Asp Ile Gln Asp Lys Val Thr
        115                 120                 125

Thr Leu Tyr Lys Gly Ser Gln Leu His Asp Thr Phe Arg Phe Cys Leu
    130                 135                 140

Val Thr Asn Leu Thr Met Asp Ser Val Leu Val Thr Val Lys Ala Leu
145                 150                 155                 160

Phe Ser Ser Asn Leu Asp Pro Ser Leu Val Glu Gln Val Phe Leu Asp
                165                 170                 175

Lys Thr Leu Asn Ala Ser Phe His Trp Leu Gly Ser Thr Tyr Gln Leu
            180                 185                 190

Val Asp Ile His Val Thr Glu Met Glu Ser Ser Val Tyr Gln Pro Thr
        195                 200                 205

Ser Ser Ser Ser Thr Gln His Phe Tyr Leu Asn Phe Thr Ile Thr Asn
    210                 215                 220

Leu Pro Tyr Ser Gln Asp Lys Ala Gln Pro Gly Thr Thr Asn Tyr Gln
225                 230                 235                 240

Arg Asn Lys Arg Asn Ile Glu Asp Ala Leu Asn Gln Leu Phe Arg Asn
                245                 250                 255

Ser Ser Ile Lys Ser Tyr Phe Ser Asp Cys Gln Val Ser Thr Phe Arg
            260                 265                 270

Ser Val Pro Asn Arg His His Thr Gly Val Asp Ser Leu Cys Asn Phe
        275                 280                 285

Ser Pro Leu Ala Arg Arg Val Asp Arg Val Ala Ile Tyr Glu Glu Phe
    290                 295                 300

Leu Arg Met Thr Arg Asn Gly Thr Gln Leu Gln Asn Phe Thr Leu Asp
305                 310                 315                 320

Arg Ser Ser Val Leu Val Asp Gly Tyr Ser Pro Asn Arg Asn Glu Pro
                325                 330                 335

Leu Thr Gly Asn Ser Asp Leu Pro Phe Trp Ala Val Ile Leu Ile Gly
            340                 345                 350

Leu Ala Gly Leu Leu Gly Val Ile Thr Cys Leu Ile Cys Gly Val Leu
        355                 360                 365

Val Thr Thr Arg Arg Arg Lys Lys Glu Gly Glu Tyr Asn Val Gln Gln
    370                 375                 380

Gln Cys Pro Gly Tyr Tyr Gln Ser His Leu Asp Leu Glu Asp Leu Gln
385                 390                 395                 400
```

<210> SEQ ID NO 26
<211> LENGTH: 360
<212> TYPE: DNA
<213> ORGANISM: Artificial Sequence
<220> FEATURE:

<223> OTHER INFORMATION: Synthetic

<400> SEQUENCE: 26
gaggtgaagc tggaggagtc aggtggagga ttggtgcagc ctaaaggatc attgaaactc 60
tcatgtgccg cctctggttt caccttcaat acctatgccg tgcactgggt ccgccaggct 120
ccaggaaagg gtatggaatg ggttgctcgc ataagaagta aaagtggaaa ttatgcaaca 180
tattatgccg attcagtgaa agacagattc accatctcca gaaatgattc acagagcatg 240
ctctatctgc aaatgaacaa cctgaaaact gaggacacag ccatatatta ctgtgtgaga 300
gcgggtaaca acggggcctt tccttactgg ggccaaggga ccacggtcac cgtctcctca 360

<210> SEQ ID NO 27
<211> LENGTH: 120
<212> TYPE: PRT
<213> ORGANISM: Artificial Sequence
<220> FEATURE:
<223> OTHER INFORMATION: Synthetic

<400> SEQUENCE: 27

```
Glu Val Lys Leu Glu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Val His Trp Val Arg Gln Ala Pro Gly Lys Gly Met Glu Trp Val
        35                  40                  45

Ala Arg Ile Arg Ser Lys Ser Gly Asn Tyr Ala Thr Tyr Tyr Ala Asp
    50                  55                  60

Ser Val Lys Asp Arg Phe Thr Ile Ser Arg Asn Asp Ser Gln Ser Met
65                  70                  75                  80

Leu Tyr Leu Gln Met Asn Asn Leu Lys Thr Glu Asp Thr Ala Ile Tyr
                85                  90                  95

Tyr Cys Val Arg Ala Gly Asn Asn Gly Ala Phe Pro Tyr Trp Gly Gln
            100                 105                 110

Gly Thr Thr Val Thr Val Ser Ser
        115                 120
```

<210> SEQ ID NO 28
<211> LENGTH: 330
<212> TYPE: DNA
<213> ORGANISM: Artificial Sequence
<220> FEATURE:
<223> OTHER INFORMATION: Synthetic

<400> SEQUENCE: 28
gacattgagc tcacccagtc tccatcctca ctgtctgcat ctctgggagg cagagtcacc 60
atcacttgca aggctagcca agatattaag aagtatatag cttggtacca acacaagcct 120
ggaaaaactc ctcgactact catacatttc acatctacat tacagacagg catcccatca 180
aggttcagtg gacgtgggtc tgggagagac tattccttca gcatcagcaa cctggagtct 240
gaagatattg caacttatta ttgtctacag tatgatagtc tgtacacgtt cggagggggg 300
accaagctgg agatcaaacg ggcggccgca 330

<210> SEQ ID NO 29
<211> LENGTH: 110
<212> TYPE: PRT
<213> ORGANISM: Artificial Sequence
<220> FEATURE:
<223> OTHER INFORMATION: Synthetic

<400> SEQUENCE: 29

Asp Ile Glu Leu Thr Gln Ser Pro Ser Ser Leu Ser Ala Ser Leu Gly
1 5 10 15

Gly Arg Val Thr Ile Thr Cys Lys Ala Ser Gln Asp Ile Lys Lys Tyr
20 25 30

Ile Ala Trp Tyr Gln His Lys Pro Gly Lys Thr Pro Arg Leu Leu Ile
35 40 45

His Phe Thr Ser Thr Leu Gln Thr Gly Ile Pro Ser Arg Phe Ser Gly
50 55 60

Arg Gly Ser Gly Arg Asp Tyr Ser Phe Ser Ile Ser Asn Leu Glu Ser
65 70 75 80

Glu Asp Ile Ala Thr Tyr Tyr Cys Leu Gln Tyr Asp Ser Leu Tyr Thr
85 90 95

Phe Gly Gly Gly Thr Lys Leu Glu Ile Lys Arg Ala Ala Ala
100 105 110

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Lys Ser Tyr Phe Ser Asp Cys Gln Val Asn Asn Phe Arg Ser
1 5 10

<210> SEQ ID NO 31
<211> LENGTH: 18
<212> TYPE: PRT
<213> ORGANISM: Artificial Sequence
<220> FEATURE:
<223> OTHER INFORMATION: Synthetic

<400> SEQUENCE: 31

Thr Leu Asp Arg Ser Ser Val Leu Val Asp Gly Tyr Ser Gln Asn Arg
1 5 10 15

Asp Asp

<210> SEQ ID NO 32
<211> LENGTH: 57
<212> TYPE: DNA
<213> ORGANISM: Artificial Sequence
<220> FEATURE:
<223> OTHER INFORMATION: CD8 leader sequence

<400> SEQUENCE: 32
atggctctcc cagtgactgc cctactgctt cccctagcgc ttctcctgca tgcagag 57

<210> SEQ ID NO 33
<211> LENGTH: 335
<212> TYPE: DNA
<213> ORGANISM: Artificial Sequence
<220> FEATURE:
<223> OTHER INFORMATION: CD3 zeta chain intracellular domain

<400> SEQUENCE: 33
agagtgaagt tcagcaggag cgcagagccc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcg 335

<210> SEQ ID NO 34
<211> LENGTH: 45
<212> TYPE: DNA
<213> ORGANISM: Artificial Sequence
<220> FEATURE:
<223> OTHER INFORMATION: (G4S)3 serine-glycine linker

<400> SEQUENCE: 34
ggtggaggtg gatcaggtgg aggtggatct ggtggaggtg gatct 45

<210> SEQ ID NO 35
<211> LENGTH: 225
<212> TYPE: DNA
<213> ORGANISM: Artificial Sequence
<220> FEATURE:
<223> OTHER INFORMATION: CD8 transmembrane domain

<400> SEQUENCE: 35
gcggccgcac ccaccacgac gccagcgccg cgaccaccaa ccccggcgcc cacgatcgcg 60
tcgcagcccc tgtccctgcg cccagaggcg tgccggccag cggcgggggg cgcagtgcac 120
acgagggggc tggacttcgc ctgtgatatc tacatctggg cgcccttggc cgggacttgt 180
ggggtccttc tcctgtcact ggttatcacc ctttactgca accac 225

<210> SEQ ID NO 36
<211> LENGTH: 223
<212> TYPE: DNA
<213> ORGANISM: Artificial Sequence
<220> FEATURE:
<223> OTHER INFORMATION: CD28 transmembrane + intracellular domains
(-STOP)

<400> SEQUENCE: 36
caattgaagt tatgtatcct cctccttacc tagacaatga gaagagcaat ggaaccatta 60
tccatgtgaa agggaaacac ctttgtccaa gtcccctatt tcccggacct tctaagccct 120
tttgggtgct ggtggtggtt ggtggagtcc tggcttgcta tagcttgcta gtaacagtgg 180
cctttattat tttctgggtg aggagtaaga ggagcaggct cct 223

<210> SEQ ID NO 37
<211> LENGTH: 7726
<212> TYPE: DNA
<213> ORGANISM: Artificial Sequence
<220> FEATURE:
<223> OTHER INFORMATION: SFG_4H11z forward sequence

<400> SEQUENCE: 37
ggatccggat tagtccaatt tgttaaagac aggatatcag tggtccaggc tctagttttg 60
actcaacaat atcaccagct gaagcctata gagtacgagc catagataaa ataaaagatt 120
ttatttagtc tccagaaaaa ggggggaatg aaagacccca cctgtaggtt tggcaagcta 180
gcttaagtaa cgccattttg caaggcatgg aaaaatacat aactgagaat agagaagttc 240
agatcaaggt caggaacaga tggaacagct gaatatgggc caaacaggat atctgtggta 300
agcagttcct gccccggctc agggccaaga acagatggaa cagctgaata tgggccaaac 360
aggatatctg tggtaagcag ttcctgcccc ggctcagggc caagaacaga tggtccccag 420

```
atgcggtcca gccctcagca gtttctagag aaccatcaga tgtttccagg gtgccccaag    480
gacctgaaat gaccctgtgc cttatttgaa ctaaccaatc agttcgcttc tcgcttctgt    540
tcgcgcgctt ctgctccccg agctcaataa aagagcccac aacccctcac tcggggcgcc    600
agtcctccga ttgactgagt cgcccgggta cccgtgtatc caataaaccc tcttgcagtt    660
gcatccgact tgtggtctcg ctgttccttg ggagggtctc ctctgagtga ttgactaccc    720
gtcagcgggg gtctttcaca catgcagcat gtatcaaaat taatttggtt ttttttctta    780
agtatttaca ttaaatggcc atagtactta aagttacatt ggcttccttg aaataaacat    840
ggagtattca gaatgtgtca taaatatttc taattttaag atagtatctc cattggcttt    900
ctactttttc ttttattttt ttttgtcctc tgtcttccat ttgttgttgt tgttgtttgt    960
ttgtttgttt gttggttggt tggttaattt ttttttaaag atcctacact atagttcaag   1020
ctagactatt agctactctg taacccaggg tgaccttgaa gtcatgggta gcctgctgtt   1080
ttagccttcc cacatctaag attacaggta tgagctatca tttttggtat attgattgat   1140
tgattgattg atgtgtgtgt gtgtgattgt gtttgtgtgt gtgactgtga aaatgtgtgt   1200
atgggtgtgt gtgaatgtgt gtatgtatgt gtgtgtgtga gtgtgtgtgt gtgtgtgtgc   1260
atgtgtgtgt gtgtgactgt gtctatgtgt atgactgtgt gtgtgtgtgt gtgtgtgtgt   1320
gtgtgtgtgt gtgtgtgtgt gttgtgaaaa aatattctat ggtagtgaga gccaacgctc   1380
cggctcaggt gtcaggttgg tttttgagac agagtctttc acttagcttg gaattcactg   1440
gccgtcgttt tacaacgtcg tgactgggaa aaccctggcg ttacccaact taatcgcctt   1500
gcagcacatc ccccctttcgc cagctggcgt aatagcgaag aggcccgcac cgatcgccct   1560
tcccaacagt tgcgcagcct gaatggcgaa tggcgcctga tgcggtattt tctccttacg   1620
catctgtgcg gtatttcaca ccgcatatgg tgcactctca gtacaatctg ctctgatgcc   1680
gcatagttaa gccagccccg acacccgcca acacccgctg acgcgccctg acgggcttgt   1740
ctgctcccgg catccgctta cagacaagct gtgaccgtct ccgggagctg catgtgtcag   1800
aggttttcac cgtcatcacc gaaacgcgcg atgacgaaag ggcctcgtga tacgcctatt   1860
tttataggtt aatgtcatga taataatggt ttcttagacg tcaggtggca cttttcgggg   1920
aaatgtgcgc ggaaccccta tttgtttatt tttctaaata cattcaaata tgtatccgct   1980
catgagacaa taaccctgat aaatgcttca ataatattga aaaaggaaga gtatgagtat   2040
tcaacatttc cgtgtcgccc ttattccctt ttttgcggca ttttgccttc ctgtttttgc   2100
tcacccagaa acgctggtga aagtaaaaga tgctgaagat cagttgggtg cacgagtggg   2160
ttacatcgaa ctggatctca acagcggtaa gatccttgag agttttcgcc ccgaagaacg   2220
ttttccaatg atgagcactt ttaaagttct gctatgtggc gcggtattat cccgtattga   2280
cgccgggcaa gagcaactcg gtcgccgcat acactattct cagaatgact tggttgagta   2340
ctcaccagtc acagaaaagc atcttacgga tggcatgaca gtaagagaat tatgcagtgc   2400
tgccataacc atgagtgata acactgcggc caacttactt ctgacaacga tcggaggacc   2460
gaaggagcta accgcttttt tgcacaacat gggggatcat gtaactcgcc ttgatcgttg   2520
ggaaccggag ctgaatgaag ccataccaaa cgacgagcgt gacaccacga tgcctgtagc   2580
aatggcaaca acgttgcgca aactattaac tggcgaacta cttactctag cttcccggca   2640
acaattaata gactggatgg aggcggataa agttgcagga ccacttctgc gctcggccct   2700
tccggctggc tggtttattg ctgataaatc tggagccggt gagcgtgggt ctcgcggtat   2760
```

cattgcagca ctggggccag atggtaagcc ctcccgtatc gtagttatct acacgacggg 2820
gagtcaggca actatggatg aacgaaatag acagatcgct gagataggtg cctcactgat 2880
taagcattgg taactgtcag accaagttta ctcatatata ctttagattg atttaaaact 2940
tcatttttaa tttaaaagga tctaggtgaa gatccttttt gataatctca tgaccaaaat 3000
cccttaacgt gagttttcgt tccactgagc gtcagacccc gtagaaaaga tcaaaggatc 3060
ttcttgagat cctttttttc tgcgcgtaat ctgctgcttg caaacaaaaa aaccaccgct 3120
accagcggtg gtttgtttgc cggatcaaga gctaccaact ctttttccga aggtaactgg 3180
cttcagcaga gcgcagatac caaatactgt ccttctagtg tagccgtagt taggccacca 3240
cttcaagaac tctgtagcac cgcctacata cctcgctctg ctaatcctgt taccagtggc 3300
tgctgccagt ggcgataagt cgtgtcttac cgggttggac tcaagacgat agttaccgga 3360
taaggcgcag cggtcgggct gaacgggggg ttcgtgcaca cagcccagct tggagcgaac 3420
gacctacacc gaactgagat acctacagcg tgagcattga gaaagcgcca cgcttcccga 3480
agggagaaag gcggacaggt atccggtaag cggcagggtc ggaacaggag agcgcacgag 3540
ggagcttcca gggggaaacg cctggtatct ttatagtcct gtcgggtttc gccacctctg 3600
acttgagcgt cgatttttgt gatgctcgtc aggggggcgg agcctatgga aaaacgccag 3660
caacgcggcc tttttacggt tcctggcctt ttgctggcct tttgctcaca tgttctttcc 3720
tgcgttatcc cctgattctg tggataaccg tattaccgcc tttgagtgag ctgataccgc 3780
tcgccgcagc cgaacgaccg agcgcagcga gtcagtgagc gaggaagcgg aagagcgccc 3840
aatacgcaaa ccgcctctcc ccgcgcgttg gccgattcat taatgcagct ggcacgacag 3900
gtttcccgac tggaaagcgg gcagtgagcg caacgcaatt aatgtgagtt agctcactca 3960
ttaggcaccc caggctttac actttatgct tccggctcgt atgttgtgtg gaattgtgag 4020
cggataacaa tttcacacag gaaacagcta tgaccatgat tacgccaagc tttgctctta 4080
ggagtttcct aatacatccc aaactcaaat atataaagca tttgacttgt tctatgccct 4140
agggggcggg gggaagctaa gccagctttt tttaacattt aaaatgttaa ttccatttta 4200
aatgcacaga tgtttttatt tcataagggt ttcaatgtgc atgaatgctg caatattcct 4260
gttaccaaag ctagtataaa taaaaataga taaacgtgga aattacttag agtttctgtc 4320
attaacgttt ccttcctcag ttgacaacat aaatgcgctg ctgagcaagc cagtttgcat 4380
ctgtcaggat caatttccca ttatgccagt catattaatt actagtcaat tagttgattt 4440
ttatttttga catatacatg tgaatgaaag accccacctg taggtttggc aagctagctt 4500
aagtaacgcc attttgcaag gcatggaaaa atacataact gagaatagaa aagttcagat 4560
caaggtcagg aacagatgga acagctgaat atgggccaaa caggatatct gtggtaagca 4620
gttcctgccc cggctcaggg ccaagaacag atggaacagc tgaatatggg ccaaacagga 4680
tatctgtggt aagcagttcc tgccccggct cagggccaag aacagatggt ccccagatgc 4740
ggtccagccc tcagcagttt ctagagaacc atcagatgtt tccagggtgc cccaaggacc 4800
tgaaatgacc ctgtgcctta tttgaactaa ccaatcagtt cgcttctcgc ttctgttcgc 4860
gcgcttatgc tccccgagct caataaaaga gcccacaacc cctcactcgg ggcgccagtc 4920
ctccgattga ctgagtcgcc cgggtacccg tgtatccaat aaaccctctt gcagttgcat 4980
ccgacttgtg gtctcgctgt tccttgggag ggtctcctct gagtgattga ctacccgtca 5040
gcgggggtct ttcatttggg ggctcgtccg ggatcgggag acccctgccc agggaccacc 5100
gacccaccac cgggaggtaa gctggccagc aacttatctg tgtctgtccg attgtctagt 5160
gtctatgact gattttatgc gcctgcgtcg gtactagtta gctaactagc tctgtatctg 5220
gcggacccgt ggtggaactg acgagttcgg aacacccggc cgcaaccctg ggagacgtcc 5280
cagggacttc gggggccgtt tttgtggccc gacctgagtc ctaaaatccc gatcgtttag 5340
gactctttgg tgcacccccc ttagaggagg gatatgtggt tctggtagga gacgagaacc 5400
taaaacagtt cccgcctccg tctgaatttt tgctttcggt ttgggaccga agccgcgccg 5460
cgcgtcttgt ctgctgcagc atcgttctgt gttgtctctg tctgactgtg tttctgtatt 5520
tgtctgaaaa tatgggcccg ggctagactg ttaccactcc cttaagtttg accttaggtc 5580
actggaaaga tgtcgagcgg atcgctcaca accagtcggt agatgtcaag aagagacgtt 5640
gggttacctt ctgctctgca gaatggccaa cctttaacgt cggatggccg cgagacggca 5700
cctttaaccg agacctcatc acccaggtta agatcaaggt cttttcacct ggcccgcatg 5760
gacacccaga ccaggtcccc tacatcgtga cctgggaagc cttggctttt gacccccctc 5820
cctgggtcaa gccctttgta caccctaagc ctccgcctcc tcttcctcca tccgccccgt 5880
ctctccccct tgaacctcct cgttcgaccc cgcctcgatc ctccctttat ccagccctca 5940
ctccttctct aggcgccccc atatggccat atgagatctt atatggggca cccccgcccc 6000
ttgtaaactt ccctgaccct gacatgacaa gagttactaa cagcccctct ctccaagctc 6060
acttacaggc tctctactta gtccagcacg aagtctggag acctctggcg gcagcctacc 6120
aagaacaact ggaccgaccg gtggtacctc acccttaccg agtcggcgac acagtgtggg 6180
tccgccgaca ccagactaag aacctagaac ctcgctggaa aggaccttac acagtcctgc 6240
tgaccacccc caccgccctc aaagtagacg gcatcgcagc ttggatacac gccgcccacg 6300
tgaaggctgc cgaccccggg ggtggaccat cctctagact gccatggctc tcccagtgac 6360
tgccctactg cttcccctag cgcttctcct gcatgcagag gtgaagctgc aggagtcagg 6420
gggaggcttc gtgaagcctg gagggtccct caaagtctcc tgtgcagcct ctggattcac 6480
tttcagtagc tatgccatgt cctgggttcg cctgagtccg gagatgaggc tggagtgggt 6540
cgcaaccatt agcagtgctg gtggttacat cttctattct gacagtgtgc agggacgatt 6600
caccatttcc agagacaatg ccaagaacac cctgcacctg caaatgggca gtctgaggtc 6660
tggggacacg gccatgtatt actgtgcaag gcagggattt ggtaactacg gtgattacta 6720
tgctatggac tactggggcc aagggaccac ggtcaccgtc tcctcaggtg gaggtggatc 6780
aggtggaggt ggatctggtg gaggtggatc tgacattgag ctcacccagt ctccatcctc 6840
cctggctgtg tcagcaggag agaaggtcac tatgagctgc aaatccagtc agagtctgct 6900
caacagtaga acccgaaaga accagttggc ttggtaccag caaaaaccag gacagtctcc 6960
tgaactgctg atctactggg catccactag gcaatctgga gtccctgatc gcttcacagg 7020
cagtggatct gggacagatt tcactctcac catcagcagt gtgcaggctg aagacctggc 7080
agtttattac tgccagcaat cttataatct actcacgttc ggtcctggga ccaagctgga 7140
gatcaaacgg gcggccgcac ccaccacgac gccagcgccg cgaccaccaa ccccggcgcc 7200
cacgatcgcg tcgcagcccc tgtccctgcg cccagaggcg tgccggccag cggcgggggg 7260
cgcagtgcac acgagggggc tggacttcgc ctgtgatatc tacatctggg cgcccttggc 7320
cgggacttgt ggggtccttc tcctgtcact ggttatcacc ctttactgca accacagagt 7380
gaagttcagc aggagcgcag agccccccgc gtaccagcag ggccagaacc agctctataa 7440
cgagctcaat ctaggacgaa gagaggagta cgatgttttg gacaagagac gtggccggga 7500
ccctgagatg gggggaaagc cgagaaggaa gaaccctcag gaaggcctgt acaatgaact 7560
gcagaaagat aagatggcgg aggcctacag tgagattggg atgaaaggcg agcgccggag 7620
gggcaagggg cacgatggcc tttaccaggg tctcagtaca gccaccaagg acacctacga 7680
cgcccttcac atgcaggccc tgccccctcg ctaacagcca ctcgag 7726

<210> SEQ ID NO 38
<211> LENGTH: 7726
<212> TYPE: DNA
<213> ORGANISM: Artificial Sequence
<220> FEATURE:
<223> OTHER INFORMATION: SFG_4H11z reverse sequence

<400> SEQUENCE: 38
cctaggccta atcaggttaa acaatttctg tcctatagtc accaggtccg agatcaaaac 60
tgagttgtta tagtggtcga cttcggatat ctcatgctcg gtatctattt tattttctaa 120
aataaatcag aggtcttttt ccccccttac tttctggggt ggacatccaa accgttcgat 180
cgaattcatt gcggtaaaac gttccgtacc tttttatgta ttgactctta tctcttcaag 240
tctagttcca gtccttgtct accttgtcga cttatacccg gtttgtccta tagacaccat 300
tcgtcaagga cggggccgag tcccggttct tgtctacctt gtcgacttat acccggtttg 360
tcctatagac accattcgtc aaggacgggg ccgagtcccg gttcttgtct accaggggtc 420
tacgccaggt cgggagtcgt caaagatctc ttggtagtct acaaaggtcc cacggggttc 480
ctggacttta ctgggacacg gaataaactt gattggttag tcaagcgaag agcgaagaca 540
agcgcgcgaa gacgaggggc tcgagttatt ttctcgggtg ttggggagtg agccccgcgg 600
tcaggaggct aactgactca gcgggcccat gggcacatag gttatttggg agaacgtcaa 660
cgtaggctga acaccagagc gacaaggaac cctcccagag gagactcact aactgatggg 720
cagtcgcccc cagaaagtgt gtacgtcgta catagtttta attaaaccaa aaaaaagaat 780
tcataaatgt aatttaccgg tatcatgaat ttcaatgtaa ccgaaggaac tttatttgta 840
cctcataagt cttacacagt atttataaag attaaaattc tatcatagag gtaaccgaaa 900
gatgaaaaag aaaataaaaa aaaacaggag acagaaggta aacaacaaca acaacaaaca 960
aacaaacaaa caaccaacca accaattaaa aaaaaatttc taggatgtga tatcaagttc 1020
gatctgataa tcgatgagac attgggtccc actggaactt cagtacccat cggacgacaa 1080
aatcggaagg gtgtagattc taatgtccat actcgatagt aaaaaccata taactaacta 1140
actaactaac tacacacaca cacactaaca caaacacaca cactgacact tttacacaca 1200
tacccacaca cacttacaca catacataca cacacacact cacacacaca cacacacacg 1260
tacacacaca cacactgaca cagatacaca tactgacaca cacacacaca cacacacaca 1320
cacacacaca cacacacaca caacactttt ttataagata ccatcactct cggttgcgag 1380
gccgagtcca cagtccaacc aaaaactctg tctcagaaag tgaatcgaac cttaagtgac 1440
cggcagcaaa atgttgcagc actgaccctt ttgggaccgc aatgggttga attagcggaa 1500
cgtcgtgtag gggaaagcg gtcgaccgca ttatcgcttc tccgggcgtg gctagcggga 1560
agggttgtca acgcgtcgga cttaccgctt accgcggact acgccataaa agaggaatgc 1620
gtagacacgc cataaagtgt ggcgtatacc acgtgagagt catgttagac gagactacgg 1680
cgtatcaatt cggtcggggc tgtgggcggt tgtgggcgac tgcgcgggac tgcccgaaca 1740
gacgagggcc gtaggcgaat gtctgttcga cactggcaga ggccctcgac gtacacagtc 1800
tccaaaagtg gcagtagtgg ctttgcgcgc tactgctttc ccggagcact atgcggataa 1860

```
aaatatccaa ttacagtact attattacca aagaatctgc agtccaccgt gaaaagcccc   1920
tttacacgcg ccttggggat aaacaaataa aaagatttat gtaagtttat acataggcga   1980
gtactctgtt attgggacta tttacgaagt tattataact ttttccttct catactcata   2040
agttgtaaag gcacagcggg aataagggaa aaaacgccgt aaaacggaag gacaaaaacg   2100
agtgggtctt tgcgaccact ttcattttct acgacttcta gtcaacccac gtgctcaccc   2160
aatgtagctt gacctagagt tgtcgccatt ctaggaactc tcaaaagcgg ggcttcttgc   2220
aaaaggttac tactcgtgaa aatttcaaga cgatacaccg cgccataata gggcataact   2280
gcggcccgtt ctcgttgagc cagcggcgta tgtgataaga gtcttactga accaactcat   2340
gagtggtcag tgtcttttcg tagaatgcct accgtactgt cattctctta atacgtcacg   2400
acggtattgg tactcactat tgtgacgccg gttgaatgaa gactgttgct agcctcctgg   2460
cttcctcgat tggcgaaaaa acgtgttgta cccccctagta cattgagcgg aactagcaac   2520
ccttggcctc gacttacttc ggtatggttt gctgctcgca ctgtggtgct acggacatcg   2580
ttaccgttgt tgcaacgcgt ttgataattg accgcttgat gaatgagatc gaagggccgt   2640
tgttaattat ctgacctacc tccgcctatt tcaacgtcct ggtgaagacg cgagccggga   2700
aggccgaccg accaaataac gactatttag acctcggcca ctcgcaccca gagcgccata   2760
gtaacgtcgt gaccccggtc taccattcgg gagggcatag catcaataga tgtgctgccc   2820
ctcagtccgt tgatacctac ttgctttatc tgtctagcga ctctatccac ggagtgacta   2880
attcgtaacc attgacagtc tggttcaaat gagtatatat gaaatctaac taaattttga   2940
agtaaaaatt aaattttcct agatccactt ctaggaaaaa ctattagagt actggtttta   3000
gggaattgca ctcaaaagca aggtgactcg cagtctgggg catcttttct agtttcctag   3060
aagaactcta ggaaaaaaag acgcgcatta gacgacgaac gtttgttttt ttggtggcga   3120
tggtcgccac caaacaaacg gcctagttct cgatggttga gaaaaaggct tccattgacc   3180
gaagtcgtct cgcgtctatg gtttatgaca ggaagatcac atcggcatca atccggtggt   3240
gaagttcttg agacatcgtg gcggatgtat ggagcgagac gattaggaca atggtcaccg   3300
acgacggtca ccgctattca gcacagaatg gcccaacctg agttctgcta tcaatggcct   3360
attccgcgtc gccagcccga cttgcccccc aagcacgtgt gtcgggtcga acctcgcttg   3420
ctggatgtgg cttgactcta tggatgtcgc actcgtaact ctttcgcggt gcgaagggct   3480
tccctctttc cgcctgtcca taggccattc gccgtcccag ccttgtcctc tcgcgtgctc   3540
cctcgaaggt cccccttttgc ggaccataga aatatcagga cagcccaaag cggtggagac   3600
tgaactcgca gctaaaaaca ctacgagcag tccccccgcc tcggatacct ttttgcggtc   3660
gttgcgccgg aaaaatgcca aggaccggaa aacgaccgga aaacgagtgt acaagaaagg   3720
acgcaatagg ggactaagac acctattggc ataatggcgg aaactcactc gactatggcg   3780
agcggcgtcg gcttgctggc tcgcgtcgct cagtcactcg ctccttcgcc ttctcgcggg   3840
ttatgcgttt ggcggagagg ggcgcgcaac cggctaagta attacgtcga ccgtgctgtc   3900
caaagggctg acctttcgcc cgtcactcgc gttgcgttaa ttacactcaa tcgagtgagt   3960
aatccgtggg gtccgaaatg tgaaatacga aggccgagca tacaacacac cttaacactc   4020
gcctattgtt aaagtgtgtc ctttgtcgat actggtacta atgcggttcg aaacgagaat   4080
cctcaaagga ttatgtaggg tttgagttta tatatttcgt aaactgaaca agatacggga   4140
tcccccgccc cccttcgatt cggtcgaaaa aaattgtaaa ttttacaatt aaggtaaaat   4200
```

-continued

```
ttacgtgtct acaaaaataa agtattccca aagttacacg tacttacgac gttataagga   4260
caatggtttc gatcatattt atttttatct atttgcacct ttaatgaatc tcaaagacag   4320
taattgcaaa ggaaggagtc aactgttgta tttacgcgac gactcgttcg gtcaaacgta   4380
gacagtccta gttaaagggt aatacggtca gtataattaa tgatcagtta atcaactaaa   4440
aataaaaact gtatatgtac acttactttc tggggtggac atccaaaccg ttcgatcgaa   4500
ttcattgcgg taaaacgttc cgtacctttt tatgtattga ctcttatctt ttcaagtcta   4560
gttccagtcc ttgtctacct tgtcgactta tacccggttt gtcctataga caccattcgt   4620
caaggacggg gccgagtccc ggttcttgtc taccttgtcg acttataccc ggtttgtcct   4680
atagacacca ttcgtcaagg acggggccga gtcccggttc ttgtctacca ggggtctacg   4740
ccaggtcggg agtcgtcaaa gatctcttgg tagtctacaa aggtcccacg ggttcctgg   4800
actttactgg gacacggaat aaacttgatt ggttagtcaa gcgaagagcg aagacaagcg   4860
cgcgaatacg aggggctcga gttattttct cgggtgttgg ggagtgagcc ccgcggtcag   4920
gaggctaact gactcagcgg gcccatgggc acataggtta tttgggagaa cgtcaacgta   4980
ggctgaacac cagagcgaca aggaaccctc ccagaggaga ctcactaact gatgggcagt   5040
cgcccccaga aagtaaaccc ccgagcaggc cctagccctc tggggacggg tccctggtgg   5100
ctgggtggtg gccctccatt cgaccggtcg ttgaatagac acagacaggc taacagatca   5160
cagatactga ctaaaatacg cggacgcagc catgatcaat cgattgatcg agacatagac   5220
cgcctgggca ccaccttgac tgctcaagcc ttgtgggccg gcgttgggac cctctgcagg   5280
gtccctgaag cccccggcaa aaacaccggg ctggactcag gattttaggg ctagcaaatc   5340
ctgagaaacc acgtgggggg aatctcctcc ctatacacca agaccatcct ctgctcttgg   5400
attttgtcaa gggcggaggc agacttaaaa acgaaagcca aaccctggct tcggcgcggc   5460
gcgcagaaca gacgacgtcg tagcaagaca caacagagac agactgacac aaagacataa   5520
acagactttt atacccgggc ccgatctgac aatggtgagg gaattcaaac tggaatccag   5580
tgacctttct acagctcgcc tagcgagtgt tggtcagcca tctacagttc ttctctgcaa   5640
cccaatggaa gacgagacgt cttaccggtt ggaaattgca gcctaccggc gctctgccgt   5700
ggaaattggc tctggagtag tgggtccaat tctagttcca gaaaagtgga ccgggcgtac   5760
ctgtgggtct ggtccagggg atgtagcact ggacccttcg gaaccgaaaa ctggggggag   5820
ggacccagtt cgggaaacat gtgggattcg gaggcggagg agaaggaggt aggcggggca   5880
gagaggggga acttggagga gcaagctggg gcggagctag gagggaaata ggtcgggagt   5940
gaggaagaga tccgcggggg tataccggta tactctagaa tataccccgt gggggcgggg   6000
aacatttgaa gggactggga ctgtactgtt ctcaatgatt gtcggggaga gaggttcgag   6060
tgaatgtccg agagatgaat caggtcgtgc ttcagacctc tggagaccgc cgtcggatgg   6120
ttcttgttga cctggctggc caccatggag tgggaatggc tcagccgctg tgtcacaccc   6180
aggcggctgt ggtctgattc ttggatcttg gagcgacctt tcctggaatg tgtcaggacg   6240
actggtgggg gtggcgggag tttcatctgc cgtagcgtcg aacctatgtg cggcgggtgc   6300
acttccgacg gctggggccc ccacctggta ggagatctga cggtaccgag agggtcactg   6360
acgggatgac gaaggggatc gcgaagagga cgtacgtctc cacttcgacg tcctcagtcc   6420
ccctccgaag cacttcggac ctcccaggga gtttcagagg acacgtcgga gacctaagtg   6480
aaagtcatcg atacggtaca ggacccaagc ggactcaggc ctctactccg acctcaccca   6540
gcgttggtaa tcgtcacgac caccaatgta gaagataaga ctgtcacacg tccctgctaa   6600
```

gtggtaaagg tctctgttac ggttcttgtg ggacgtggac gtttacccgt cagactccag 6660
acccctgtgc cggtacataa tgacacgttc cgtccctaaa ccattgatgc cactaatgat 6720
acgatacctg atgaccccgg ttccctggtg ccagtggcag aggagtccac ctccacctag 6780
tccacctcca cctagaccac ctccacctag actgtaactc gagtgggtca gaggtaggag 6840
ggaccgacac agtcgtcctc tcttccagtg atactcgacg tttaggtcag tctcagacga 6900
gttgtcatct tgggctttct tggtcaaccg aaccatggtc gtttttggtc ctgtcagagg 6960
acttgacgac tagatgaccc gtaggtgatc cgttagacct cagggactag cgaagtgtcc 7020
gtcacctaga ccctgtctaa agtgagagtg gtagtcgtca cacgtccgac ttctggaccg 7080
tcaaataatg acggtcgtta gaatattaga tgagtgcaag ccaggaccct ggttcgacct 7140
ctagtttgcc cgccggcgtg ggtggtgctg cggtcgcggc gctggtggtt ggggccgcgg 7200
gtgctagcgc agcgtcgggg acagggacgc gggtctccgc acggccggtc gccgcccccc 7260
gcgtcacgtg tgctcccccg acctgaagcg gacactatag atgtagaccc gcgggaaccg 7320
gccctgaaca ccccaggaag aggacagtga ccaatagtgg gaaatgacgt tggtgtctca 7380
cttcaagtcg tcctcgcgtc tcggggggcg catggtcgtc ccggtcttgg tcgagatatt 7440
gctcgagtta gatcctgctt ctctcctcat gctacaaaac ctgttctctg caccggccct 7500
gggactctac ccccctttcg gctcttcctt cttgggagtc cttccggaca tgttacttga 7560
cgtctttcta ttctaccgcc tccggatgtc actctaaccc tactttccgc tcgcggcctc 7620
cccgttcccc gtgctaccgg aaatggtccc agagtcatgt cggtggttcc tgtggatgct 7680
gcgggaagtg tacgtccggg acgggggagc gattgtcggt gagctc 7726

<210> SEQ ID NO 39
<211> LENGTH: 7831
<212> TYPE: DNA
<213> ORGANISM: Artificial Sequence
<220> FEATURE:
<223> OTHER INFORMATION: SFG_4H11-28z forward sequence

<400> SEQUENCE: 39
ggatccggat tagtccaatt tgttaaagac aggatatcag tggtccaggc tctagttttg 60
actcaacaat atcaccagct gaagcctata gagtacgagc catagataaa ataaaagatt 120
ttatttagtc tccagaaaaa ggggggaatg aaagacccca cctgtaggtt tggcaagcta 180
gcttaagtaa cgccattttg caaggcatgg aaaaatacat aactgagaat agagaagttc 240
agatcaaggt caggaacaga tggaacagct gaatatgggc caaacaggat atctgtggta 300
agcagttcct gccccggctc agggccaaga acagatggaa cagctgaata tgggccaaac 360
aggatatctg tggtaagcag ttcctgcccc ggctcagggc caagaacaga tggtccccag 420
atgcggtcca gccctcagca gtttctagag aaccatcaga tgtttccagg gtgccccaag 480
gacctgaaat gaccctgtgc cttatttgaa ctaaccaatc agttcgcttc tcgcttctgt 540
tcgcgcgctt ctgctccccg agctcaataa aagagcccac aacccctcac tcggggcgcc 600
agtcctccga ttgactgagt cgcccgggta cccgtgtatc caataaaccc tcttgcagtt 660
gcatccgact tgtggtctcg ctgttccttg ggagggtctc ctctgagtga ttgactaccc 720
gtcagcgggg gtctttcaca catgcagcat gtatcaaaat taatttggtt ttttttctta 780
agtatttaca ttaaatggcc atagtactta aagttacatt ggcttccttg aaataaacat 840
ggagtattca gaatgtgtca taaatatttc taattttaag atagtatctc cattggcttt 900

-continued

```
ctactttttc ttttattttt ttttgtcctc tgtcttccat ttgttgttgt tgttgtttgt    960
ttgtttgttt gttggttggt tggttaattt ttttttaaag atcctacact atagttcaag   1020
ctagactatt agctactctg taacccaggg tgaccttgaa gtcatgggta gcctgctgtt   1080
ttagccttcc cacatctaag attacaggta tgagctatca tttttggtat attgattgat   1140
tgattgattg atgtgtgtgt gtgtgattgt gtttgtgtgt gtgactgtga aaatgtgtgt   1200
atgggtgtgt gtgaatgtgt gtatgtatgt gtgtgtgtga gtgtgtgtgt gtgtgtgtgc   1260
atgtgtgtgt gtgtgactgt gtctatgtgt atgactgtgt gtgtgtgtgt gtgtgtgtgt   1320
gtgtgtgtgt gtgtgtgtgt gttgtgaaaa aatattctat ggtagtgaga gccaacgctc   1380
cggctcaggt gtcaggttgg tttttgagac agagtctttc acttagcttg gaattcactg   1440
gccgtcgttt tacaacgtcg tgactgggaa aaccctggcg ttacccaact taatcgcctt   1500
gcagcacatc ccccttttcgc cagctggcgt aatagcgaag aggcccgcac cgatcgccct   1560
tcccaacagt tgcgcagcct gaatggcgaa tggcgcctga tgcggtattt tctccttacg   1620
catctgtgcg gtatttcaca ccgcatatgg tgcactctca gtacaatctg ctctgatgcc   1680
gcatagttaa gccagccccg acacccgcca acacccgctg acgcgccctg acgggcttgt   1740
ctgctcccgg catccgctta cagacaagct gtgaccgtct ccgggagctg catgtgtcag   1800
aggttttcac cgtcatcacc gaaacgcgcg atgacgaaag ggcctcgtga tacgcctatt   1860
tttataggtt aatgtcatga taataatggt ttcttagacg tcaggtggca cttttcgggg   1920
aaatgtgcgc ggaaccccta tttgtttatt tttctaaata cattcaaata tgtatccgct   1980
catgagacaa taaccctgat aaatgcttca ataatattga aaaaggaaga gtatgagtat   2040
tcaacatttc cgtgtcgccc ttattccctt ttttgcggca ttttgccttc ctgtttttgc   2100
tcacccagaa acgctggtga aagtaaaaga tgctgaagat cagttgggtg cacgagtggg   2160
ttacatcgaa ctggatctca acagcggtaa gatccttgag agttttcgcc ccgaagaacg   2220
ttttccaatg atgagcactt ttaaagttct gctatgtggc gcggtattat cccgtattga   2280
cgccgggcaa gagcaactcg gtcgccgcat acactattct cagaatgact tggttgagta   2340
ctcaccagtc acagaaaagc atcttacgga tggcatgaca gtaagagaat tatgcagtgc   2400
tgccataacc atgagtgata acactgcggc caacttactt ctgacaacga tcggaggacc   2460
gaaggagcta accgcttttt tgcacaacat gggggatcat gtaactcgcc ttgatcgttg   2520
ggaaccggag ctgaatgaag ccataccaaa cgacgagcgt gacaccacga tgcctgtagc   2580
aatggcaaca acgttgcgca aactattaac tggcgaacta cttactctag cttcccggca   2640
acaattaata gactggatgg aggcggataa agttgcagga ccacttctgc gctcggccct   2700
tccggctggc tggtttattg ctgataaatc tggagccggt gagcgtgggt ctcgcggtat   2760
cattgcagca ctggggccag atggtaagcc ctcccgtatc gtagttatct acacgacggg   2820
gagtcaggca actatggatg aacgaaatag acagatcgct gagataggtg cctcactgat   2880
taagcattgg taactgtcag accaagttta ctcatatata ctttagattg atttaaaact   2940
tcatttttaa tttaaaagga tctaggtgaa gatccttttt gataatctca tgaccaaaat   3000
cccttaacgt gagttttcgt tccactgagc gtcagacccc gtagaaaaga tcaaaggatc   3060
ttcttgagat cctttttttc tgcgcgtaat ctgctgcttg caaacaaaaa aaccaccgct   3120
accagcggtg gtttgtttgc cggatcaaga gctaccaact ctttttccga aggtaactgg   3180
cttcagcaga gcgcagatac caaatactgt ccttctagtg tagccgtagt taggccacca   3240
cttcaagaac tctgtagcac cgcctacata cctcgctctg ctaatcctgt taccagtggc   3300
```

-continued tgctgccagt ggcgataagt cgtgtcttac cgggttggac tcaagacgat agttaccgga 3360
taaggcgcag cggtcgggct gaacgggggg ttcgtgcaca cagcccagct tggagcgaac 3420
gacctacacc gaactgagat acctacagcg tgagcattga gaaagcgcca cgcttcccga 3480
agggagaaag gcggacaggt atccggtaag cggcagggtc ggaacaggag agcgcacgag 3540
ggagcttcca gggggaaacg cctggtatct ttatagtcct gtcgggtttc gccacctctg 3600
acttgagcgt cgatttttgt gatgctcgtc aggggggcgg agcctatgga aaaacgccag 3660
caacgcggcc tttttacggt tcctggcctt ttgctggcct tttgctcaca tgttctttcc 3720
tgcgttatcc cctgattctg tggataaccg tattaccgcc tttgagtgag ctgataccgc 3780
tcgccgcagc cgaacgaccg agcgcagcga gtcagtgagc gaggaagcgg aagagcgccc 3840
aatacgcaaa ccgcctctcc ccgcgcgttg gccgattcat taatgcagct ggcacgacag 3900
gtttcccgac tggaaagcgg gcagtgagcg caacgcaatt aatgtgagtt agctcactca 3960
ttaggcaccc caggctttac actttatgct tccggctcgt atgttgtgtg gaattgtgag 4020
cggataacaa tttcacacag gaaacagcta tgaccatgat tacgccaagc tttgctctta 4080
ggagtttcct aatacatccc aaactcaaat atataaagca tttgacttgt tctatgccct 4140
agggggcggg gggaagctaa gccagctttt tttaacattt aaaatgttaa ttccatttta 4200
aatgcacaga tgtttttatt tcataagggt ttcaatgtgc atgaatgctg caatattcct 4260
gttaccaaag ctagtataaa taaaaataga taaacgtgga aattacttag agtttctgtc 4320
attaacgttt ccttcctcag ttgacaacat aaatgcgctg ctgagcaagc cagtttgcat 4380
ctgtcaggat caatttccca ttatgccagt catattaatt actagtcaat tagttgattt 4440
ttatttttga catatacatg tgaatgaaag accccacctg taggtttggc aagctagctt 4500
aagtaacgcc attttgcaag gcatggaaaa atacataact gagaatagaa aagttcagat 4560
caaggtcagg aacagatgga acagctgaat atgggccaaa caggatatct gtggtaagca 4620
gttcctgccc cggctcaggg ccaagaacag atggaacagc tgaatatggg ccaaacagga 4680
tatctgtggt aagcagttcc tgccccggct cagggccaag aacagatggt ccccagatgc 4740
ggtccagccc tcagcagttt ctagagaacc atcagatgtt tccagggtgc cccaaggacc 4800
tgaaatgacc ctgtgcctta tttgaactaa ccaatcagtt cgcttctcgc ttctgttcgc 4860
gcgcttatgc tccccgagct caataaaaga gcccacaacc cctcactcgg ggcgccagtc 4920
ctccgattga ctgagtcgcc cgggtacccg tgtatccaat aaaccctctt gcagttgcat 4980
ccgacttgtg gtctcgctgt tccttgggag ggtctcctct gagtgattga ctacccgtca 5040
gcgggggtct ttcatttggg ggctcgtccg ggatcgggag acccctgccc agggaccacc 5100
gacccaccac cgggaggtaa gctggccagc aacttatctg tgtctgtccg attgtctagt 5160
gtctatgact gattttatgc gcctgcgtcg gtactagtta gctaactagc tctgtatctg 5220
gcggacccgt ggtggaactg acgagttcgg aacacccggc cgcaaccctg ggagacgtcc 5280
cagggacttc gggggccgtt tttgtggccc gacctgagtc ctaaaatccc gatcgtttag 5340
gactctttgg tgcacccccc ttagaggagg gatatgtggt tctggtagga gacgagaacc 5400
taaaacagtt cccgcctccg tctgaatttt tgctttcggt ttgggaccga agccgcgccg 5460
cgcgtcttgt ctgctgcagc atcgttctgt gttgtctctg tctgactgtg tttctgtatt 5520
tgtctgaaaa tatgggcccg ggctagactg ttaccactcc cttaagtttg accttaggtc 5580
actggaaaga tgtcgagcgg atcgctcaca accagtcggt agatgtcaag aagagacgtt 5640

-continued

```
gggttacctt ctgctctgca gaatggccaa cctttaacgt cggatggccg cgagacggca   5700
cctttaaccg agacctcatc acccaggtta agatcaaggt cttttcacct ggcccgcatg   5760
gacacccaga ccaggtcccc tacatcgtga cctgggaagc cttggctttt gacccccctc   5820
cctgggtcaa gccctttgta caccctaagc ctccgcctcc tcttcctcca tccgccccgt   5880
ctctcccccct tgaacctcct cgttcgaccc cgcctcgatc ctccctttat ccagccctca   5940
ctccttctct aggcgccccc atatggccat atgagatctt atatggggca cccccgcccc   6000
ttgtaaactt ccctgaccct gacatgacaa gagttactaa cagcccctct ctccaagctc   6060
acttacaggc tctctactta gtccagcacg aagtctggag acctctggcg gcagcctacc   6120
aagaacaact ggaccgaccg gtggtacctc acccttaccg agtcggcgac acagtgtggg   6180
tccgccgaca ccagactaag aacctagaac ctcgctggaa aggaccttac acagtcctgc   6240
tgaccacccc caccgccctc aaagtagacg gcatcgcagc ttggatacac gccgcccacg   6300
tgaaggctgc cgaccccggg ggtggaccat cctctagact gccatggctc tcccagtgac   6360
tgccctactg cttcccctag cgcttctcct gcatgcagag gtgaagctgc aggagtcagg   6420
gggaggcttc gtgaagcctg gagggtccct caaagtctcc tgtgcagcct ctggattcac   6480
tttcagtagc tatgccatgt cctgggttcg cctgagtccg gagatgaggc tggagtgggt   6540
cgcaaccatt agcagtgctg gtggttacat cttctattct gacagtgtgc agggacgatt   6600
caccatttcc agagacaatg ccaagaacac cctgcacctg caaatgggca gtctgaggtc   6660
tggggacacg gccatgtatt actgtgcaag gcagggattt ggtaactacg gtgattacta   6720
tgctatggac tactggggcc aagggaccac ggtcaccgtc tcctcaggtg gaggtggatc   6780
aggtggaggt ggatctggtg gaggtggatc tgacattgag ctcacccagt ctccatcctc   6840
cctggctgtg tcagcaggag agaaggtcac tatgagctgc aaatccagtc agagtctgct   6900
caacagtaga acccgaaaga accagttggc ttggtaccag caaaaaccag gacagtctcc   6960
tgaactgctg atctactggg catccactag gcaatctgga gtccctgatc gcttcacagg   7020
cagtggatct gggacagatt tcactctcac catcagcagt gtgcaggctg aagacctggc   7080
agtttattac tgccagcaat cttataatct actcacgttc ggtcctggga ccaagctgga   7140
gatcaaacgg gcggccgcaa ttgaagttat gtatcctcct ccttacctag acaatgagaa   7200
gagcaatgga accattatcc atgtgaaagg gaaacacctt tgtccaagtc ccctatttcc   7260
cggaccttct aagccctttt gggtgctggt ggtggttggt ggagtcctgg cttgctatag   7320
cttgctagta acagtggcct ttattatttt ctgggtgagg agtaagagga gcaggctcct   7380
gcacagtgac tacatgaaca tgactccccg ccgccccggg cccacccgca agcattacca   7440
gccctatgcc ccaccacgcg acttcgcagc ctatcgctcc agagtgaagt tcagcaggag   7500
cgcagagccc cccgcgtacc agcagggcca gaaccagctc tataacgagc tcaatctagg   7560
acgaagagag gagtacgatg ttttggacaa gagacgtggc cgggaccctg agatgggggg   7620
aaagccgaga aggaagaacc ctcaggaagg cctgtacaat gaactgcaga aagataagat   7680
ggcggaggcc tacagtgaga ttgggatgaa aggcgagcgc cggaggggca aggggcacga   7740
tggcctttac cagggtctca gtacagccac caaggacacc tacgacgccc ttcacatgca   7800
ggccctgccc cctcgctaac agccactcga g                                   7831
```

<210> SEQ ID NO 40
<211> LENGTH: 7831
<212> TYPE: DNA
<213> ORGANISM: Artificial Sequence
<220> FEATURE:
<223> OTHER INFORMATION: SFG_4H11-28z reverse sequence

<400> SEQUENCE: 40
cctaggccta atcaggttaa acaatttctg tcctatagtc accaggtccg agatcaaaac 60
tgagttgtta tagtggtcga cttcggatat ctcatgctcg gtatctattt tattttctaa 120
aataaatcag aggtcttttt ccccccttac tttctggggt ggacatccaa accgttcgat 180
cgaattcatt gcggtaaaac gttccgtacc tttttatgta ttgactctta tctcttcaag 240
tctagttcca gtccttgtct accttgtcga cttatacccg gtttgtccta tagacaccat 300
tcgtcaagga cggggccgag tcccggttct tgtctacctt gtcgacttat acccggtttg 360
tcctatagac accattcgtc aaggacgggg ccgagtcccg gttcttgtct accaggggtc 420
tacgccaggt cgggagtcgt caaagatctc ttggtagtct acaaaggtcc cacggggttc 480
ctggacttta ctgggacacg gaataaactt gattggttag tcaagcgaag agcgaagaca 540
agcgcgcgaa gacgaggggc tcgagttatt ttctcgggtg ttggggagtg agccccgcgg 600
tcaggaggct aactgactca gcgggcccat gggcacatag gttatttggg agaacgtcaa 660
cgtaggctga acaccagagc gacaaggaac cctcccagag gagactcact aactgatggg 720
cagtcgcccc cagaaagtgt gtacgtcgta catagtttta attaaaccaa aaaaaagaat 780
tcataaatgt aatttaccgg tatcatgaat ttcaatgtaa ccgaaggaac tttatttgta 840
cctcataagt cttacacagt atttataaag attaaaattc tatcatagag gtaaccgaaa 900
gatgaaaaag aaaataaaaa aaaacaggag acagaaggta aacaacaaca acaacaaaca 960
aacaaacaaa caaccaacca accaattaaa aaaaaatttc taggatgtga tatcaagttc 1020
gatctgataa tcgatgagac attgggtccc actggaactt cagtacccat cggacgacaa 1080
aatcggaagg gtgtagattc taatgtccat actcgatagt aaaaaccata taactaacta 1140
actaactaac tacacacaca cacactaaca caaacacaca cactgacact tttacacaca 1200
tacccacaca cacttacaca catacataca cacacacact cacacacaca cacacacacg 1260
tacacacaca cacactgaca cagatacaca tactgacaca cacacacaca cacacacaca 1320
cacacacaca cacacacaca caacactttt ttataagata ccatcactct cggttgcgag 1380
gccgagtcca cagtccaacc aaaaaactctg tctcagaaag tgaatcgaac cttaagtgac 1440
cggcagcaaa atgttgcagc actgaccctt ttgggaccgc aatgggttga attagcggaa 1500
cgtcgtgtag ggggaaagcg gtcgaccgca ttatcgcttc tccgggcgtg gctagcggga 1560
agggttgtca acgcgtcgga cttaccgctt accgcggact acgccataaa agaggaatgc 1620
gtagacacgc cataaagtgt ggcgtatacc acgtgagagt catgttagac gagactacgg 1680
cgtatcaatt cggtcggggc tgtgggcggt tgtgggcgac tgcgcgggac tgcccgaaca 1740
gacgagggcc gtaggcgaat gtctgttcga cactggcaga ggccctcgac gtacacagtc 1800
tccaaaagtg gcagtagtgg ctttgcgcgc tactgctttc ccggagcact atgcggataa 1860
aaatatccaa ttacagtact attattacca aagaatctgc agtccaccgt gaaaagcccc 1920
tttacacgcg ccttggggat aaacaaataa aaagatttat gtaagtttat acataggcga 1980
gtactctgtt attgggacta tttacgaagt tattataact ttttccttct catactcata 2040
agttgtaaag gcacagcggg aataagggaa aaaacgccgt aaaacggaag gacaaaaacg 2100
agtgggtctt tgcgaccact ttcattttct acgacttcta gtcaacccac gtgctcaccc 2160
aatgtagctt gacctagagt tgtcgccatt ctaggaactc tcaaaagcgg ggcttcttgc 2220

-continued

```
aaaaggttac tactcgtgaa aatttcaaga cgatacaccg cgccataata gggcataact   2280
gcggcccgtt ctcgttgagc cagcggcgta tgtgataaga gtcttactga accaactcat   2340
gagtggtcag tgtcttttcg tagaatgcct accgtactgt cattctctta atacgtcacg   2400
acggtattgg tactcactat tgtgacgccg gttgaatgaa gactgttgct agcctcctgg   2460
cttcctcgat tggcgaaaaa acgtgttgta ccccctagta cattgagcgg aactagcaac   2520
ccttggcctc gacttacttc ggtatggttt gctgctcgca ctgtggtgct acggacatcg   2580
ttaccgttgt tgcaacgcgt ttgataattg accgcttgat gaatgagatc gaagggccgt   2640
tgttaattat ctgacctacc tccgcctatt tcaacgtcct ggtgaagacg cgagccggga   2700
aggccgaccg accaaataac gactatttag acctcggcca ctcgcaccca gagcgccata   2760
gtaacgtcgt gaccccggtc taccattcgg gagggcatag catcaataga tgtgctgccc   2820
ctcagtccgt tgatacctac ttgctttatc tgtctagcga ctctatccac ggagtgacta   2880
attcgtaacc attgacagtc tggttcaaat gagtatatat gaaatctaac taaattttga   2940
agtaaaaatt aaattttcct agatccactt ctaggaaaaa ctattagagt actggtttta   3000
gggaattgca ctcaaaagca aggtgactcg cagtctgggg catcttttct agtttcctag   3060
aagaactcta ggaaaaaaag acgcgcatta gacgacgaac gtttgttttt ttggtggcga   3120
tggtcgccac caaacaaacg gcctagttct cgatggttga gaaaaaggct tccattgacc   3180
gaagtcgtct cgcgtctatg gtttatgaca ggaagatcac atcggcatca atccggtggt   3240
gaagttcttg agacatcgtg gcggatgtat ggagcgagac gattaggaca atggtcaccg   3300
acgacggtca ccgctattca gcacagaatg gcccaacctg agttctgcta tcaatggcct   3360
attccgcgtc gccagcccga cttgcccccc aagcacgtgt gtcgggtcga acctcgcttg   3420
ctggatgtgg cttgactcta tggatgtcgc actcgtaact ctttcgcggt gcgaagggct   3480
tccctctttc cgcctgtcca taggccattc gccgtcccag ccttgtcctc tcgcgtgctc   3540
cctcgaaggt ccccctttgc ggaccataga aatatcagga cagcccaaag cggtggagac   3600
tgaactcgca gctaaaaaca ctacgagcag tccccccgcc tcggatacct tttgcggtc   3660
gttgcgccgg aaaaatgcca aggaccggaa aacgaccgga aaacgagtgt acaagaaagg   3720
acgcaatagg ggactaagac acctattggc ataatggcgg aaactcactc gactatggcg   3780
agcggcgtcg gcttgctggc tcgcgtcgct cagtcactcg ctccttcgcc ttctcgcggg   3840
ttatgcgttt ggcggagagg ggcgcgcaac cggctaagta attacgtcga ccgtgctgtc   3900
caaagggctg acctttcgcc cgtcactcgc gttgcgttaa ttacactcaa tcgagtgagt   3960
aatccgtggg gtccgaaatg tgaaatacga aggccgagca tacaacacac cttaacactc   4020
gcctattgtt aaagtgtgtc ctttgtcgat actggtacta atgcggttcg aaacgagaat   4080
cctcaaagga ttatgtaggg tttgagttta tatatttcgt aaactgaaca agatacggga   4140
tcccccgccc cccttcgatt cggtcgaaaa aaattgtaaa ttttacaatt aaggtaaaat   4200
ttacgtgtct acaaaaataa agtattccca aagttacacg tacttacgac gttataagga   4260
caatggtttc gatcatattt atttttatct atttgcacct ttaatgaatc tcaaagacag   4320
taattgcaaa ggaaggagtc aactgttgta tttacgcgac gactcgttcg gtcaaacgta   4380
gacagtccta gttaaagggt aatacggtca gtataattaa tgatcagtta atcaactaaa   4440
aataaaaact gtatatgtac acttactttc tggggtggac atccaaaccg ttcgatcgaa   4500
ttcattgcgg taaaacgttc cgtacctttt tatgtattga ctcttatctt ttcaagtcta   4560
gttccagtcc ttgtctacct tgtcgactta tacccggttt gtcctataga caccattcgt   4620
```

```
caaggacggg gccgagtccc ggttcttgtc taccttgtcg acttataccc ggtttgtcct   4680
atagacacca ttcgtcaagg acggggccga gtcccggttc ttgtctacca ggggtctacg   4740
ccaggtcggg agtcgtcaaa gatctcttgg tagtctacaa aggtcccacg gggttcctgg   4800
actttactgg gacacggaat aaacttgatt ggttagtcaa gcgaagagcg aagacaagcg   4860
cgcgaatacg aggggctcga gttattttct cgggtgttgg ggagtgagcc ccgcggtcag   4920
gaggctaact gactcagcgg gcccatgggc acataggtta tttgggagaa cgtcaacgta   4980
ggctgaacac cagagcgaca aggaaccctc ccagaggaga ctcactaact gatgggcagt   5040
cgcccccaga aagtaaaccc ccgagcaggc cctagccctc tggggacggg tccctggtgg   5100
ctgggtggtg gccctccatt cgaccggtcg ttgaatagac acagacaggc taacagatca   5160
cagatactga ctaaaatacg cggacgcagc catgatcaat cgattgatcg agacatagac   5220
cgcctgggca ccaccttgac tgctcaagcc ttgtgggccg gcgttgggac cctctgcagg   5280
gtccctgaag cccccggcaa aaacaccggg ctggactcag gattttaggg ctagcaaatc   5340
ctgagaaacc acgtgggggg aatctcctcc ctatacacca agaccatcct ctgctcttgg   5400
attttgtcaa gggcggaggc agacttaaaa acgaaagcca aaccctggct tcggcgcggc   5460
gcgcagaaca gacgacgtcg tagcaagaca caacagagac agactgacac aaagacataa   5520
acagactttt atacccgggc ccgatctgac aatggtgagg gaattcaaac tggaatccag   5580
tgacctttct acagctcgcc tagcgagtgt tggtcagcca tctacagttc ttctctgcaa   5640
cccaatggaa gacgagacgt cttaccggtt ggaaattgca gcctaccggc gctctgccgt   5700
ggaaattggc tctggagtag tgggtccaat tctagttcca gaaaagtgga ccgggcgtac   5760
ctgtgggtct ggtccagggg atgtagcact ggacccttcg gaaccgaaaa ctggggggag   5820
ggacccagtt cgggaaacat gtgggattcg gaggcggagg agaaggaggt aggcggggca   5880
gagaggggga acttggagga gcaagctggg gcggagctag gagggaaata ggtcgggagt   5940
gaggaagaga tccgcggggg tataccggta tactctagaa tataccccgt gggggcgggg   6000
aacatttgaa gggactggga ctgtactgtt ctcaatgatt gtcggggaga gaggttcgag   6060
tgaatgtccg agagatgaat caggtcgtgc ttcagacctc tggagaccgc cgtcggatgg   6120
ttcttgttga cctggctggc caccatggag tgggaatggc tcagccgctg tgtcacaccc   6180
aggcggctgt ggtctgattc ttggatcttg gagcgacctt tcctggaatg tgtcaggacg   6240
actggtgggg gtggcgggag tttcatctgc cgtagcgtcg aacctatgtg cggcgggtgc   6300
acttccgacg gctggggccc ccacctggta ggagatctga cggtaccgag agggtcactg   6360
acgggatgac gaaggggatc gcgaagagga cgtacgtctc cacttcgacg tcctcagtcc   6420
ccctccgaag cacttcggac ctcccaggga gtttcagagg acacgtcgga gacctaagtg   6480
aaagtcatcg atacggtaca ggacccaagc ggactcaggc ctctactccg acctcaccca   6540
gcgttggtaa tcgtcacgac caccaatgta gaagataaga ctgtcacacg tccctgctaa   6600
gtggtaaagg tctctgttac ggttcttgtg ggacgtggac gtttacccgt cagactccag   6660
acccctgtgc cggtacataa tgacacgttc cgtccctaaa ccattgatgc cactaatgat   6720
acgatacctg atgaccccgg ttccctggtg ccagtggcag aggagtccac ctccacctag   6780
tccacctcca cctagaccac ctccacctag actgtaactc gagtgggtca gaggtaggag   6840
ggaccgacac agtcgtcctc tcttccagtg atactcgacg tttaggtcag tctcagacga   6900
gttgtcatct tgggctttct tggtcaaccg aaccatggtc gtttttggtc ctgtcagagg   6960
```

-continued

```
acttgacgac tagatgaccc gtaggtgatc cgttagacct cagggactag cgaagtgtcc   7020
gtcacctaga ccctgtctaa agtgagagtg gtagtcgtca cacgtccgac ttctggaccg   7080
tcaaataatg acggtcgtta gaatattaga tgagtgcaag ccaggaccct ggttcgacct   7140
ctagtttgcc cgccggcgtt aacttcaata cataggagga ggaatggatc tgttactctt   7200
ctcgttacct tggtaatagg tacactttcc ctttgtggaa acaggttcag gggataaagg   7260
gcctggaaga ttcgggaaaa cccacgacca ccaccaacca cctcaggacc gaacgatatc   7320
gaacgatcat tgtcaccgga aataataaaa gacccactcc tcattctcct cgtccgagga   7380
cgtgtcactg atgtacttgt actgaggggc ggcggggccc gggtgggcgt tcgtaatggt   7440
cgggatacgg ggtggtgcgc tgaagcgtcg gatagcgagg tctcacttca agtcgtcctc   7500
gcgtctcggg gggcgcatgg tcgtcccggt cttggtcgag atattgctcg agttagatcc   7560
tgcttctctc ctcatgctac aaaacctgtt ctctgcaccg gccctgggac tctacccccc   7620
tttcggctct tccttcttgg gagtccttcc ggacatgtta cttgacgtct ttctattcta   7680
ccgcctccgg atgtcactct aaccctactt tccgctcgcg gcctccccgt tccccgtgct   7740
accggaaatg gtcccagagt catgtcggtg gttcctgtgg atgctgcggg aagtgtacgt   7800
ccgggacggg ggagcgattg tcggtgagct c                                  7831
```

ANTIBODIES TO MUC16 AND METHODS OF USE THEREOF

This application is a divisional of U.S. patent application Ser. No. 14/850,675, filed Sep. 10, 2015, issued as U.S. Pat. No. 9,790,283, which is a divisional of U.S. patent application Ser. No. 13/635,090, issued as U.S. Pat. No. 9,169,328, national stage of International Application No. PCT/US2011/030025, filed Mar. 25, 2011, which claims benefit of U.S. Provisional Application No. 61/317,964, filed Mar. 26, 2010, each of which is hereby incorporated herein by reference in its entirety for all purposes.

This invention was made with government support under grant number CA052477 awarded by the National Institutes of Health. The government has certain rights in the invention.

FIELD OF THE INVENTION

The invention relates to antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

BACKGROUND OF THE INVENTION

Cell surface markers and shed antigens are used in the diagnosis of several cancers. For example, the CA125 antigen, recognized by the OC125 antibody, is a tissue-specific, circulating antigen expressed in ovarian cancer. The CA125 antigen is encoded by the MUC16 gene, cloned by Lloyd and Yin. The full-length gene describes a complex tethered mucin protein present primarily in a variety of gynecologic tissues, especially neoplasms. OC125 and other related antibodies react with glycosylation-dependent antigens present exclusively in the cleaved portion of the molecule.

A serum assay can detect elevated levels of the circulating CA125 antigen in many epithelial ovarian cancer patients, and this antigen, derived using the ovarian cell line OVCA433, is recognized by the OC125 antibody (1-2). The detection of circulating CA125 in serum has proven to be a useful tool for the management of ovarian cancer patients and clinical trials (3-4). However, CA125 is neither sufficiently sensitive nor specific for general cancer screening (5-6). A variety of CA125 linked antibodies including VK8 and M11 have subsequently been defined as present on ovarian cancer cells (7-9). Although these antibodies have been used to develop serum assays and various other studies in ovarian cancer, they have significant shortcomings for clinical use in screening or tissue delivery. These antibodies are not useful as screening tools, nor can they detect the proximal residual MUC16 protein fragment after cleavage. This has limited their diagnostic and therapeutic applications.

For example, OC125, M11, and most other antibodies prepared against ovarian cancer cell extracts are directed at complex, glycosylation-dependent antigens. These antigens are exclusively present in the shed portion of MUC16 and cannot be employed to follow the biology of the proximal portion of MUC16 and may not accurately reflect tissue distribution since the glycosylation patterns can vary substantially among tissues. Because the vast majority of MUC16-reactive antibodies, including OC125, react with the glycosylation-dependent antigen present exclusively in the cleaved portion of the molecule, the true distribution of MUC16 expression is not known (21). There is currently no antibody available to track the fate of the remaining MUC16 protein fragment after cleavage and CA125 release.

Thus, there remains a need for the identification of antibodies that are directed against sequences in the peptide backbone of MUC16, and that are useful for diagnosis and treatment of cancers in which MUC16 is expressed and/or overexpressed.

SUMMARY OF THE INVENTION

The invention provides an antibody, or an antigen-binding fragment thereof, that specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO: 19). In one embodiment, the antibody internalizes into a cell. While not intending to limit the invention to a particular sequence of MUC16 ectodomain, in one embodiment, the MUC16 ectodomain polypeptide comprises a polypeptide selected from the group of Polypeptide 1 NFSPLARRVDRVAIYEE (SEQ ID NO:01) and Polypeptide 2 TLDRSSVLVDGYSPNRNE (SEQ ID NO:02). In another embodiment, the antibody lacks specific binding to a glycosylated MUC16 extracellular domain. In yet a further embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:06, and a variable light ($V_L$) chain encoded by SEQ ID NO:07. In yet another alternative embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:04, and a variable light ($V_L$) chain encoded by SEQ ID NO:05. In a further embodiment, the antibody specifically binds to the Polypeptide 1 (SEQ ID NO:01) of the MUC16 ectodomain polypeptide, and wherein the antibody comprises a variable heavy ($V_H$) chain encoded by SEQ ID NO:08, and a variable light ($V_L$) chain encoded by at least one of SEQ ID NO:09 and SEQ ID NO: 10. In one embodiment, the MUC16 cytoplasmic domain polypeptide comprises VTTRR RKKEGEYNVQ QQ (SEQ ID NO:18). More preferably, but without limitation, the MUC16 cytoplasmic domain polypeptide comprises Polypeptide 3 CGVLVTTRRRKKEGEYNVQQQ (SEQ ID NO:03). In an alternative embodiment, the MUC16 extracellular domain polypeptide that contains a cysteine loop polypeptide comprises CQVSTFRSVPNRHHTGVDSLC (SEQ ID NO: 19). More preferably, but without limitation, the MUC16 extracellular domain polypeptide comprises Polypeptide 4 KSYF SDCQVSTFRS VPNRHHTGVD SLCNFSPL (SEQ ID NO:15). In yet another alternative embodiment, the antibody specifically binds to the Polypeptide 4 (SEQ ID NO: 15) of the MUC16 extracellular domain polypeptide, and wherein the antibody comprises a variable heavy ($V_H$) chain encoded by SEQ ID NO: 11, and a variable light ($V_L$) chain encoded by SEQ ID NO: 12. In a further alternative embodiment, the antibody is selected from the group of a chimeric antibody, a monoclonal antibody, a recombinant antibody, an antigen-binding fragment of a recombinant antibody, a humanized antibody, and an antibody displayed upon the surface of a phage. In another embodiment, the antigen-binding fragment is selected from the group of a Fab fragment, a F(ab')2 fragment, and a Fv fragment. In an alternative embodiment, the antibody, or antigen-binding fragment thereof, is covalently linked to a cytotoxic agent or a prodrug of a cytotoxic agent. In a preferred embodiment, the antibody is a monoclonal antibody produced by a hybridoma cell line.

The invention also provides an isolated monoclonal antibody, or an antigen-binding fragment thereof, produced by a hybridoma cell line, wherein the antibody specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the MUC16 ectodomain polypeptide comprises Polypeptide 1 (SEQ ID NO:01) and the antibody is selected from the group of 9B11.20.16, 10A2, 2F4, 23D3, 30B1, and 31B2. In an alternative embodiment, the MUC16 ectodomain polypeptide comprises Polypeptide 2 (SEQ ID NO:02), and wherein the antibody is selected from the group of 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10. In yet a further embodiment, the MUC16 cytoplasmic domain polypeptide comprises Polypeptide 3 CGVLVTTRRRKKEGEYNVQQQ (SEQ ID NO:03), and wherein the antibody is selected from the group of 31A3.5.1, 19D1, 10F6, 22E10, 22F1, 3H8, 22F11, 4D7, 24G12, 19G4, 9A5, 4C2, 31C8, 27G4, and 6H2. In another alternative embodiment, the MUC16 extracellular domain polypeptide comprises Polypeptide 4 KSYF SDCQVSTFRS VPNRHHTGVD SLCNFSPL (SEQ ID NO:15), and wherein the antibody is selected from the group of 24B3 and 9C7.

The invention additionally provides a composition comprising (a) any one or more of the antibodies, or antigen-binding fragments thereof, that are described herein, and (b) a pharmaceutically acceptable carrier.

Also provided by the invention is a hybridoma cell line that produces a monoclonal antibody that specifically binds to a polypeptide, or antigenic portion thereof, selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19).

The invention additionally provides a method for detecting a disease that comprises overexpression of MUC16 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of MUC16, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

The invention also provides an isolated antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31). In one embodiment, the antibody is selected from the group of a monoclonal antibody, a chimeric antibody, a recombinant antibody, an antigen-binding fragment of a recombinant antibody, a humanized antibody, and an antibody displayed upon the surface of a phage. In a preferred embodiment, the antibody is a monoclonal antibody produced by hybridoma cells selected from the group of 12B10-3G10, 10C4-3H5, 10C4-1F2, 10C4-2H8, 10C4-1G7, 17F2-3G5, 17F2-3F6, 17F2-2F9, 17F2-1E11, 12B10-3F7, 12B10-2F6, 12B10-2F10, 25E9-3, 25E9-5, 25E9-1, 25E9-16, 21B8-1H11, 21B8-3G6, 21B8-3H9, 21B8-1G8, 21E1-1E3, 21E1-1G9, 21E1-2G7, 21E1-3G12, 4H1-2E1, 4H1-2E3, 4H1-3E1, 4H1-3H3, 15A8-2E2, 15A8-2E10, 15A8-2E11, 15A8-3D2, 22B5-1F6, 22B5-3G9, 22B5-2G8, and 22B5-3F11. In a particular embodiment, the MUC16 polypeptide is TLDRKSVFVDGYSQNRDD (SEQ ID NO:21), and the antibody comprises a variable heavy ($V_H$) chain sequence SEQ ID NO:27, and a variable light ($V_L$) chain sequence SEQ ID NO:29, such as the monoclonal antibody produced by hybridoma cell 12B10-3G10. In an alternative embodiment, the antigen-binding fragment is selected from the group of a Fab fragment, a F(ab')2 fragment, and a Fv fragment. In a more preferred embodiment, the antibody, or antigen-binding fragment thereof, is covalently linked to a cytotoxic agent and/or to a prodrug of a cytotoxic agent. In a further embodiment, the antibody specifically binds to human MUC16 (SEQ ID NO:25). In another embodiment, the antibody internalizes into a cell. In an alternative embodiment, the antibody lacks specific binding to a glycosylated MUC16 extracellular domain.

The invention also provides a composition comprising (a) any one or more of the invention's antibodies and/or antigen-binding fragments thereof, and (b) a pharmaceutically acceptable carrier.

The invention further provides a hybridoma cell that produces an antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31).

The invention also provides an isolated nucleotide sequence comprising a polynucleotide that encodes at least one of a variable heavy ($V_H$) chain sequence and the variable light ($V_L$) chain sequence of an antibody that specifically binds to a MUC16 polypeptide, wherein the MUC16 polypeptide is selected from the group of a) TLDRKSVFVDGYSQNRDD (SEQ ID NO:21), b) KSYFSDCQV- LAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31). In one embodiment, the MUC16 polypeptide is TLDRKSVFVDGYSQNRDD (SEQ ID NO:21) and the polynucleotide encoding the variable heavy ($V_H$) chain sequence comprises SEQ ID NO:26, and wherein the polynucleotide encoding the variable light ($V_L$) chain sequence comprises SEQ ID NO:28.

The invention also provides a method for producing an antibody that specifically binds to a MUC16 polypeptide or to an antigenic portion thereof, comprising administering to a subject an immunologically effective amount of a MUC16 polypeptide selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS (SEQ ID NO: 30), and e) TLDRSSVLVDGYSQNRDD (SEQ ID NO: 31).

The invention additionally provides a method for identifying a subject as having disease, comprising determining the level, in a sample from the subject, of specific binding of any one or more of the invention's antibodies and/or antigen-binding fragments thereof, with the MUC16 polypeptide or with the antigenic portion thereof, wherein detecting an altered level of the specific binding relative to a control sample identifies the subject as having disease. In one embodiment, the disease is cancer exemplified by ovarian cancer and breast cancer. In another embodiment, the method further comprises detecting an altered level of binding of the antibody to the sample compared to a control sample. Optionally, the detecting is selected from the group of immunohistochemistry, enzyme-linked immunosorbent assay (ELISA), fluorescence-activated cell sorting (FACS), Western blot, immunoprecipitation, and radiographic imaging.

The invention also provides a method for reducing one or more symptoms of disease comprising administering to a subject in need thereof a therapeutically effective amount of any one or more of the invention's antibodies and/or antigen-binding fragment thereof. In one embodiment, the disease is cancer, exemplified by ovarian cancer and breast cancer. Optionally, the method further comprises detecting a reduction in one or more symptoms of the disease after the administration step.

BRIEF DESCRIPTION OF THE DRAWINGS

FIG. 1: Three MUC16 carboxy terminus peptides were synthesized at the MSKCC Microchemistry Core Facility. Polypeptide 1 is near the putative cleavage site, Polypeptide 2 is before the transmembrane, and Polypeptide 3 is the internal peptide, which is inside the transmembrane.

FIG. 2: Comparison staining of high-grade serous ovarian carcinomas using OC125 (left panel) and 4H11 (right panel)

FIG. 3A: OC125 (Score 0); FIG. 3B: OC125 (Score 1); FIG. 3C: OC125 (Score 2); FIG. 3D: OC125 (Score 3); FIG. 3E: OC125 (Score 4); FIG. 3F: OC125 (Score 5); FIG. 3G: 4H11 (Score 0); FIG. 3H: 4H11 (Score 1); FIG. 3I: 4H11 (Score 2); FIG. 3J: 4H11 (Score 3); FIG. 3K: 4H11 (Score 4); FIG. 3L: 4H11 (Score 5).

FIG. 4A: Western blot analysis of GST-$\Delta$MUC16$^{c114}$ fusion protein with monoclonal antibodies 9C9.21.5.13 and 4H11.2.5. FIG. 4B: Western blot analysis of SKOV3-phrGFP-$\Delta$MUC16$^{c114}$ and SKOV3-phrGFP-$\Delta$MUC16$^{c334}$ protein extract and probed with monoclonal antibodies 9C9.21.5.13 and 4H11.2.5.

FIGS. 8A-8I: Nucleotide sequence encoding antibody variable heavy ($V_H$) chain and antibody variable light ($V_L$) chain. FIG. 8A: 4A5 $V_H$ (SEQ ID NO:04), FIG. 8B: 4A5 $V_L$ (SEQ ID NO:05), FIG. 8C: 4H11 $V_H$ (SEQ ID NO:06), FIG. 8D: 4H11 $V_L$ (SEQ ID NO:07), FIG. 8E: 9B11 $V_H$ (SEQ ID NO:08), FIG. 8F: 9B11 $V_{L.A}$ (SEQ ID NO:09), FIG. 8G: 9B11 $V_{L.B}$ (SEQ ID NO: 10), FIG. 8H: 24B3 $V_H$ (SEQ ID NO: 11), FIG. 8I: 24B3 $V_L$ (SEQ ID NO: 12).

FIGS. 9A-9F: *Homo sapiens* MUC16 (GenBank NP_078966) (SEQ ID NO: 13), FIG. 9G: Polypeptide 1 (SEQ ID NO:01), FIG. 9H: Polypeptide 2 (SEQ ID NO:02), FIG. 9I: Polypeptide 3 (SEQ ID NO:03), FIG. 9J: Transmembrane domain (SEQ ID NO:14), FIG. 9K: Polypeptide 4 (SEQ ID NO:15) containing a cysteine loop polypeptide (SEQ ID NO: 19).

FIG. 15A: Kaplan-Meier survival curve of SCID-Beige mice treated ip or iv with 4H11-28z$^+$ T cells. SCID-Beige mice were injected intraperitoneally with $3\times10^6$ OV-CAR3(MUC-CD/GFP-FF-Luc) tumor cells followed by either iv or ip infusion of $3\times10^7$ 4H11-28z$^+$ T cells. Tumor eradication is enhanced after either ip or iv infusion of 4H11-28z$^+$ T cells when compared to control treated mice. Both ip and iv 4H11-28z$^+$ T cell treated mice exhibited statistically enhanced survival (*p<0.0001 and p=0.0038, respectively) when compared to 19-28z$^+$ T cell treated control cohorts. Conversely, difference in survival between the ip and iv 4H11-28z$^+$ T cell cohorts was not statistically significant (p=0.22). FIG. 15B: BLI of tumor progression of representative ip and iv 4H11-28z$^+$ T cell treated mice with ultimately progressive disease following treatment compared to BLI of tumor progression in a representative control 19-28z$^+$ T cell treated mouse. FIG. 15C: Systemically injected CFSE stained 4H11-28z$^+$ T cells traffic to advanced ip OV-CAR(MUC-CD) tumors. Presence of iv injected CFSE labeled 19-28z$^+$ control T cells (left panel) and 4H11-28z$^+$ T cells (right panel) 1 day following infusion into SCID-Beige mice with advanced OV-CAR(MUC-CD) tumors (injected 7 days earlier), as assessed by FACS analysis of single cell OV-CAR3(MUC-CD) tumor suspensions, reveals a marked population of 4H11-28z$^+$ but not control 19-28z$^+$ T cells within peritoneal OV-CAR3(MUC-CD) tumors.

FIG. 16A: BLI of 4H11-28z$^+$ T cell treated mice with either relapsed disease (middle row) or eradicated disease (bottom row) compared to a representative 19-28z$^+$ T cell treated control mouse. FIG. 16B: Kaplan-Meier survival curve of SCID-Beige mice with advanced OV-CAR3(MUC-CD/GFP-FFLuc) tumors treated ip with 4H11-28z$^+$ T cells. All 4H11-28z$^+$ T cell treated mice demonstrated enhanced survival when compared to control 19-28z$^+$ T cell treated mice (**p=0.0011), with an overall long-term survival of 25% at day 120.

FIG. 17: CD8 leader sequence (SEQ ID NO:32), CD3 zeta chain intracellular domain sequence (SEQ ID NO:33), (G4S)3 serine-glycine linker sequence (SEQ ID NO:34), CD8 transmembrane domain sequence (SEQ ID NO:35), and CD28 transmembrane+intracellular domains (-STOP) sequence (SEQ ID NO:36).

FIGS. 18A-18E: SFG_4H11z sequence.

FIGS. 19A-19F: SFG-4H11-28z sequence.

FIG. 24A: Nucleotide sequence encoding 12B10-3G10-$V_H$ (SEQ ID NO:26), FIG. 24B: 12B10-3G10-$V_H$ Amino Acid sequence (SEQ ID NO:27), FIG. 24C: Nucleotide sequence encoding 12B10-3G10-$V_L$ (SEQ ID NO:28) (Note the $V_L$ has an optional NotI site added by the primer for cloning, and FIG. 24D: 12B10-3G10-$V_L$ Amino Acid sequence (SEQ ID NO:29).

DEFINITIONS

Figure 3A:
FIGS. 3A-FIG. 3L: Immunohistochemical scoring of OC125 and 4H11 on tissue microarrays of high-grade ovarian serous carcinoma. Only membranous and/or cytoplasmic staining was considered positive. Score 0: No staining; Score 1: <5% strong or weak; Score 2: 5-50% strong or weak; Score 3: 51-75% strong or 51-100% weak; Score 4: 76-99% strong; Score 5: 100% strong.
Figure 3B:
Figure 3C:
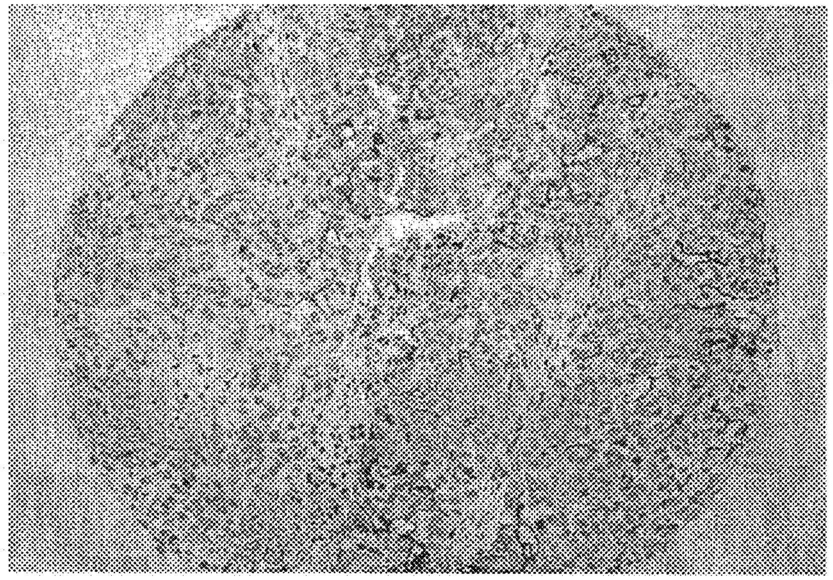
Figure 3D:
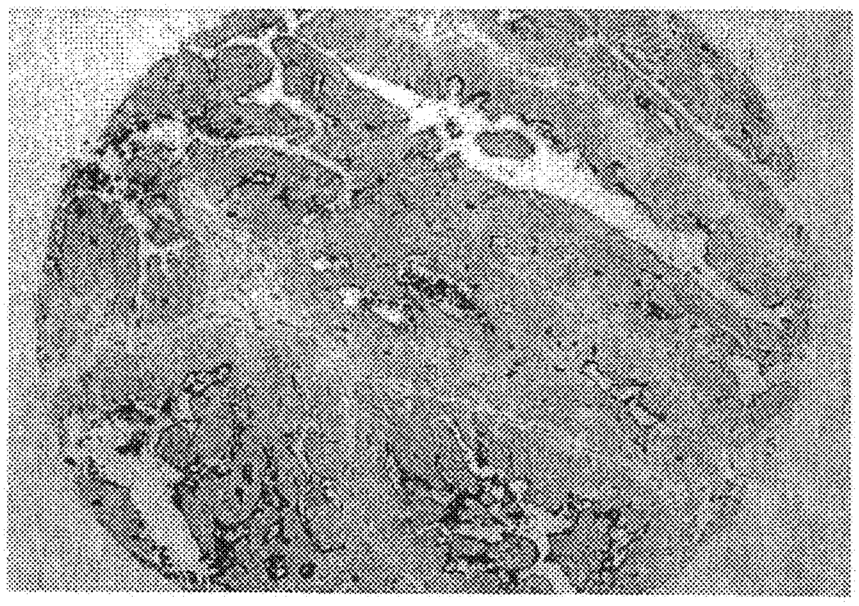
Figure 3E:
Figure 3F:
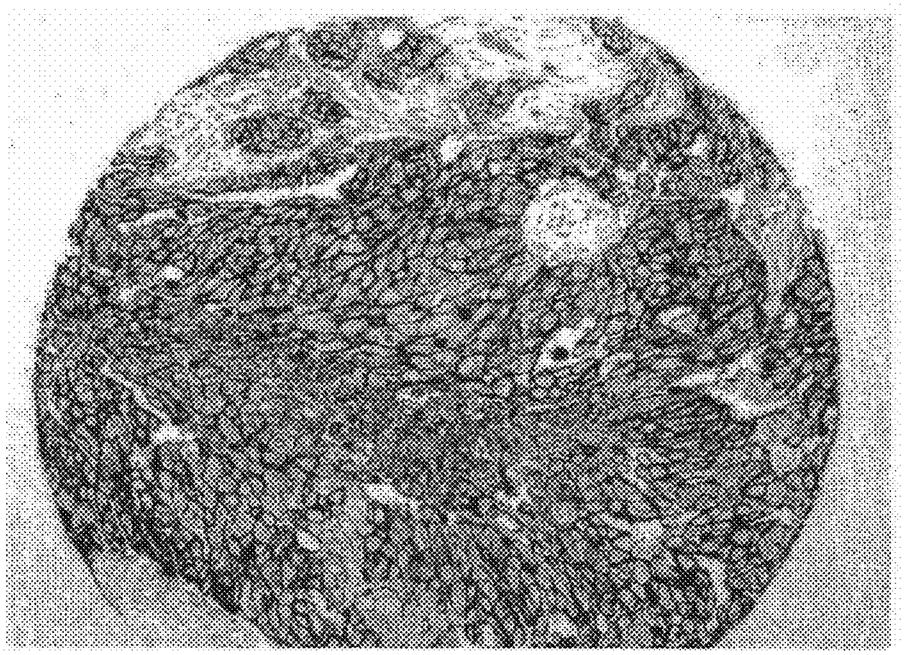
Figure 3G:
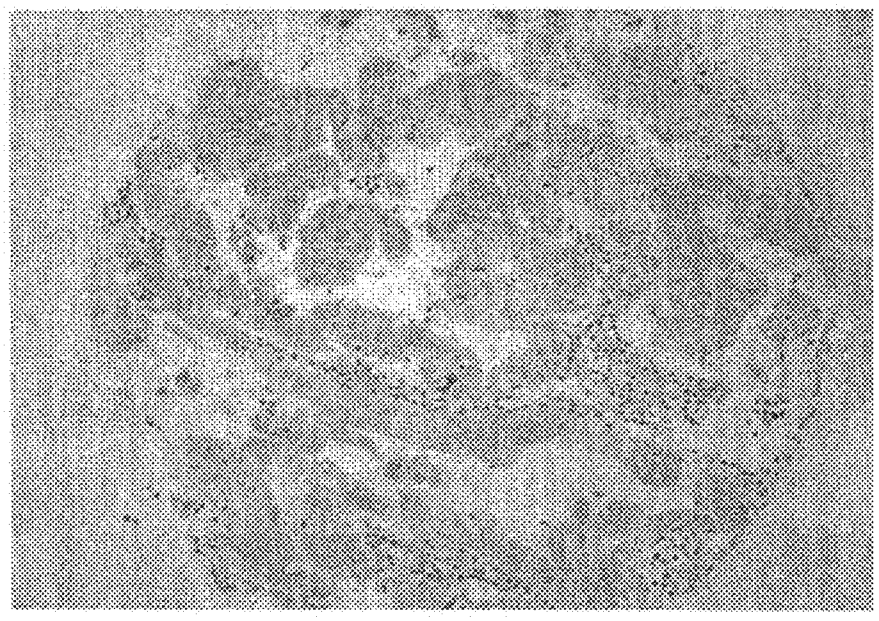
Figure 3H:
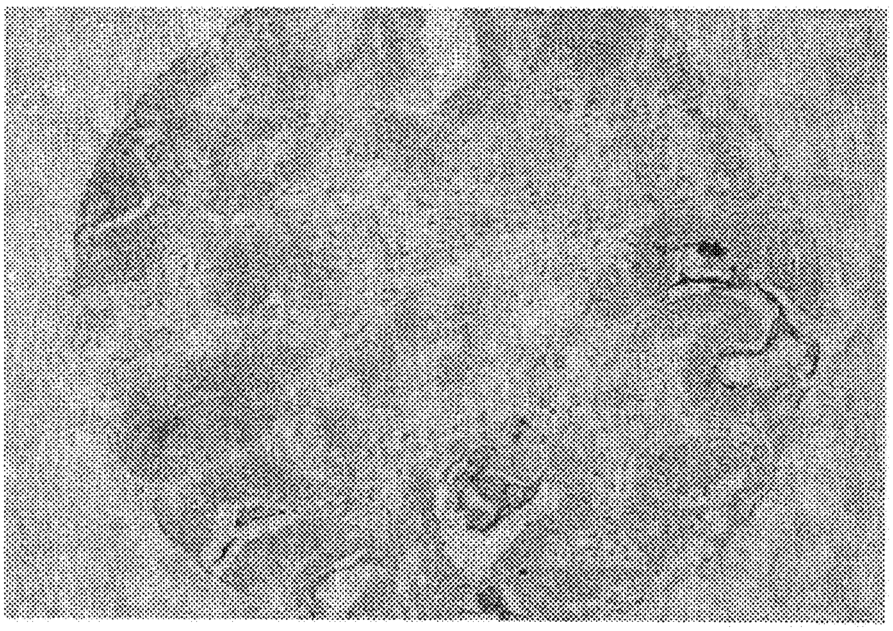
Figure 3I:
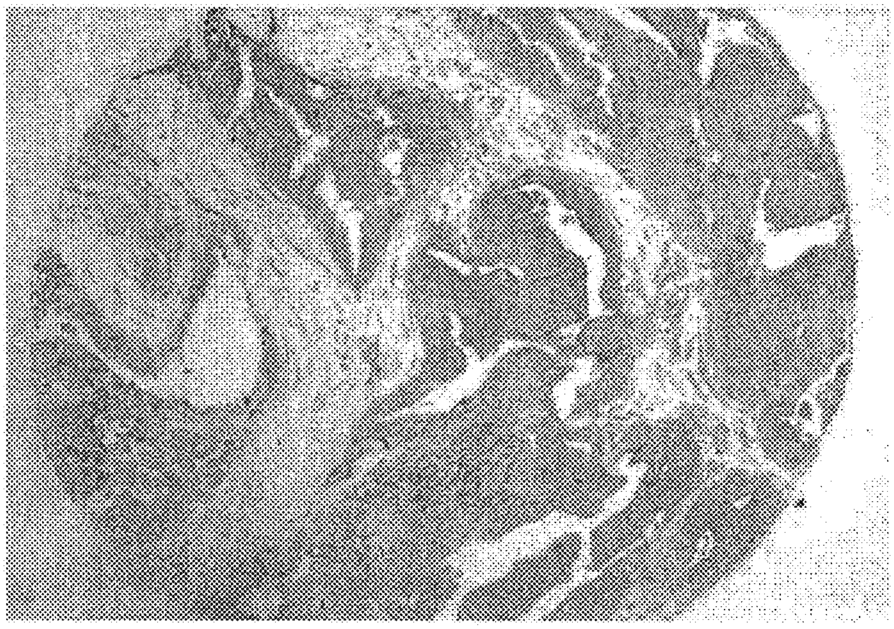
Figure 3J:
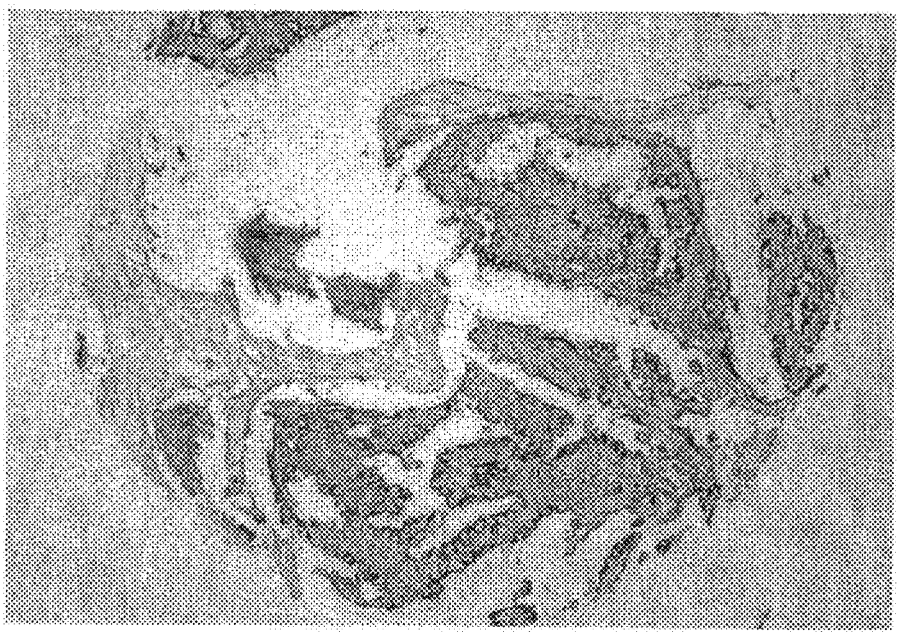
Figure 3K:
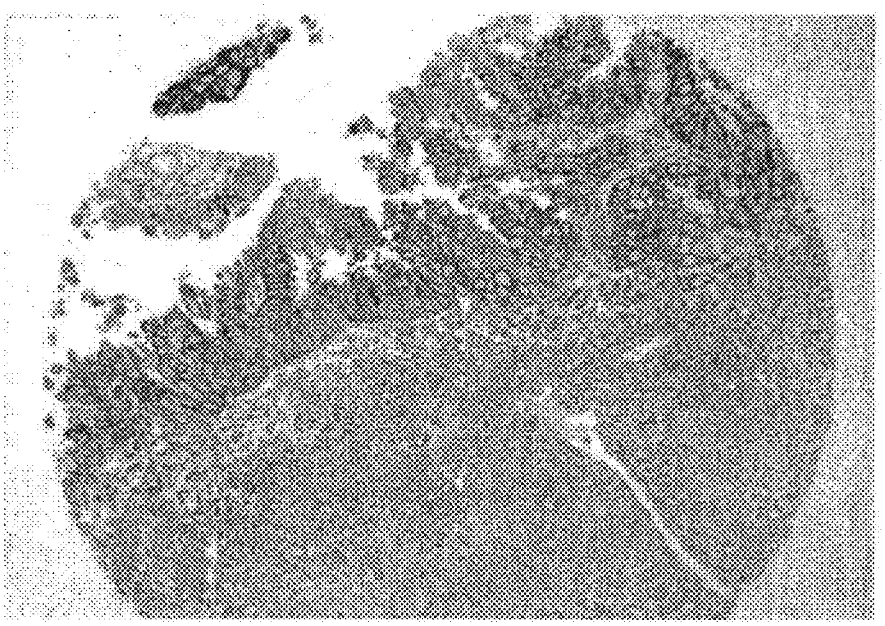
Figure 3L:
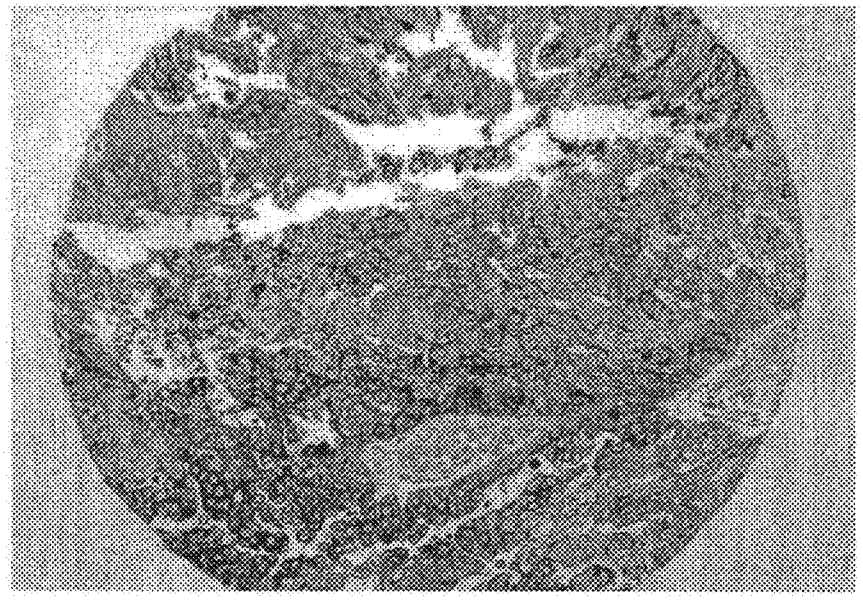

To facilitate understanding of the invention, a number of terms are defined below.

The terms "purified," "isolated," and grammatical equivalents thereof as used herein, refer to the reduction in the amount of at least one undesirable component (such as cell, protein, nucleic acid sequence, carbohydrate, etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable component cell, protein, nucleic acid sequence, carbohydrate, etc.).

The term "antibody" refers to an immunoglobulin (e.g., IgG, IgM, IgA, IgE, IgD, etc.). The basic functional unit of each antibody is an immunoglobulin (Ig) mononer (containing only one immunoglobulin ("Ig") unit). Included within this definition are polyclonal antibody, monoclonal antibody, and chimeric antibody.

The variable part of an antibody is its "V domain" (also referred to as "variable region"), and the constant part is its "C domain" (also referred to as "constant region") such as the kappa, lambda, alpha, gamma, delta, epsilon and mu constant regions. The "variable domain" is also referred to as the "Fv region" and is the most important region for binding to antigens. More specifically, variable loops, three each on the light ($V_L$) and heavy ($V_H$) chains are responsible for binding to the antigen. These loops are referred to as the "complementarity determining regions" ("CDRs" and "idiotypes."

The immunoglobulin (Ig) monomer of an antibody is a "Y"-shaped molecule that contains four polypeptide chains: two light chains and two heavy chains, joined by disulfide bridges.

Light chains are classified as either (λ) or kappa (κ). A light chain has two successive domains: one constant domain ("$C_L$") and one variable domain ("$V_L$"). The variable domain, $V_L$, is different in each type of antibody and is the active portion of the molecule that binds with the specific antigen. The approximate length of a light chain is 211 to 217 amino acids.

Each heavy chain has two regions, the constant region and the variable region. The There are five types of mammalian Ig heavy denoted a α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region ("$C_H$") and the variable ("$V_H$") region. The constant region ($C_H$) is identical in all antibodies of the same isotype, but differs in antibodies of different isotypes. Heavy chains γ, α and δ have a constant region composed of three tandem (in a line) Ig domains, and a hinge region for added flexibility. Heavy chains μ and ε have a constant region composed of four immunoglobulin domains. The variable region ($V_H$) of the heavy chain differs in antibodies produced by different B cells, but is the same for all antibodies produced by a single B cell or B cell clone. The variable region of each heavy chain is approximately 110 amino acids long.

The term "specifically binds" and "specific binding" when made in reference to the binding of two molecules (e.g. antibody to an antigen, etc.) refer to an interaction of the two molecules that is dependent upon the presence of a particular structure on one or both of the molecules. For example, if an antibody is specific for epitope "A" on the molecule, then the presence of a protein containing epitope A (or free, unlabelled A) in a reaction containing labeled "A" and the antibody will reduce the amount of labeled A bound to the antibody.

The term "capable of binding" when made in reference to the interaction between a first molecule (such as antibody, polypeptide, glycoprotein, nucleic acid sequence, etc.) and a second molecule (such as antigen, polypeptide, glycoprotein, nucleic acid sequence, etc.) means that the first molecule binds to the second molecule in the presence of suitable concentration of salts, and suitable temperature, and pH. The conditions for binding molecules may be determined using routine and/or commercially available methods The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response). Antigenic peptides preferably contain at least 5, at least 6, at least 7, at least 8, at least 9, and more preferably at least 10 amino acids. To elicit antibody production, in one embodiment, antigens may be conjugated to keyhole limpet hemocyanin (KLH) or fused to glutathione-S-transferase (GST).

A "cognate antigen" when in reference to an antigen that binds to an antibody, refers to an antigen that is capable of specifically binding to the antibody.

In one embodiment, the antigen comprises an epitope. The terms "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody.

As used herein the terms "portion" and "fragment" when made in reference to a nucleic acid sequence or protein sequence refer to a piece of that sequence that may range in size from 2 contiguous nucleotides and amino acids, respectively, to the entire sequence minus one nucleotide and amino acid, respectively.

A "subject" that may benefit from the invention's methods includes any multicellular animal, preferably a mammal. Mammalian subjects include humans, non-human primates, murines, ovines, bovines, ruminants, lagomorphs, porcines, caprines, equines, canines, felines, aves, etc.). Thus, mammalian subjects are exemplified by mouse, rat, guinea pig, hamster, ferret and chinchilla. The invention's compositions and methods are also useful for a subject "in need of reducing one or more symptoms of" a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease (such as cancer) refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

"Sample" and "specimen" as used herein are used in their broadest sense to include any composition that is obtained and/or derived from a biological source, as well as sampling devices (e.g., swabs), which are brought into contact with biological or environmental samples. "Biological samples" include those obtained from a subject, including body fluids (such as urine, blood, plasma, fecal matter, cerebrospinal fluid (CSF), semen, sputum, and saliva), as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. These examples are illustrative, and are not to be construed as limiting the sample types applicable to the present invention.

"Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

"Internalize" when in reference to a cell refers to entry from the extracellular medium into the cell membrane and/or cytoplasm.

"Glycosylated" when in reference to a sequence (e.g., an amino acid sequence or nucleotide sequence) refers to a sequence that is covalently linked to one or more saccharides.

"Pharmaceutical" and "physiologically tolerable" composition refers to a composition that contains pharmaceutical molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutical molecule does not substantially reduce the activity of the invention's compositions. Pharmaceutical molecules include "diluent" (i.e., "carrier") molecules and excipients.

"Immunogenically effective" and "antigenically effective" amount of a molecule interchangeably refer to an amount of the molecule that is capable of inducing a specific humoral immune response (including eliciting a soluble antibody response) and/or cell-mediated immune response (including eliciting a cytotoxic T-lymphocyte (CTL) response).

"Treating" a disease refers to reducing one or more symptoms (such as objective, subjective, pathological, clinical, sub-clinical, etc.) of the disease.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "alter" and "modify" when in reference to the level of any molecule and/or phenomenon refer to an increase or decrease.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

Using synthetic peptides, the inventors raised novel-specific antibodies to the carboxy-terminal portion of MUC16, retained by the cell, proximal to the putative cleavage site. These antibodies were characterized using fluorescence-activated cell-sorting analysis, enzyme-linked immunoassay, Western blot analysis, and immunohistochemistry. Each of the selected monoclonal antibodies was reactive against recombinant GST-$\Delta$MUC16$^{c114}$ protein and the MUC16 transfected SKOV3 cell line. Three antibodies, 4H11, 9C9, and 4A5 antibodies demonstrated high affinities by Western blot analysis and saturation-binding studies of transfected SKOV3 cells, and displayed antibody internalization. Immunohistochemical positivity with novel antibody 4H11 was similar to OC125, but with important differences, including diffuse positivity in lobular breast cancer and a small percentage of OC125-negative ovarian carcinomas which showed intense and diffuse 4H11 antibody binding.

The invention's compositions and methods are useful for diagnostic and therapeutic applications, as well as biologic studies such as membrane receptor trafficking and intracellular events. Diagnostic applications include, for example, detection of cancer using immunohistochemical, radiographic imaging, enzyme-linked immunosorbent assay (ELISA), fluorescence-activated cell sorting (FACS), Western blot, and/or immunoprecipitation detection.

The invention is further described under (A) MUC16, (B) Prior Art Antibodies, (C) Invention's Antibodies, (D) Hybridoma Cell Lines, (E) Conjugates Of The Invention's Antibodies Linked To Cytotoxic Agents And/Or Prodrugs, (F) Detecting Muc16 Portions And Diagnostic Applications, and (G) Therapeutic Applications.

A. MUC16

Figure 10:
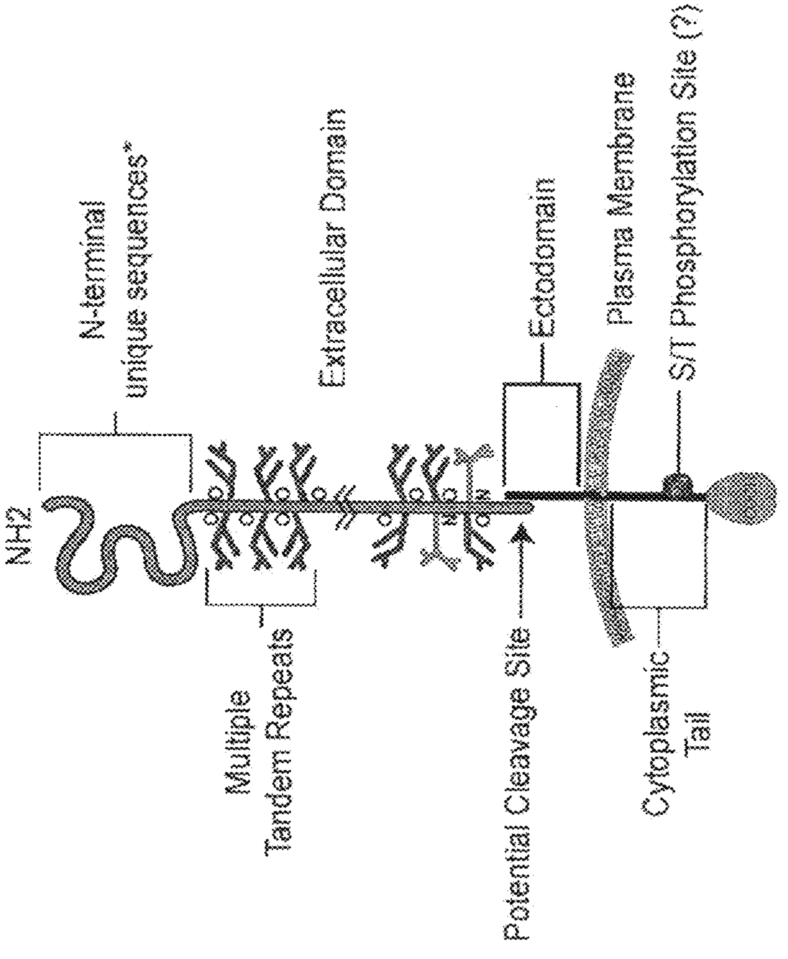
FIG. 10: Schematic of MUC16 structure.
Figure 20B:
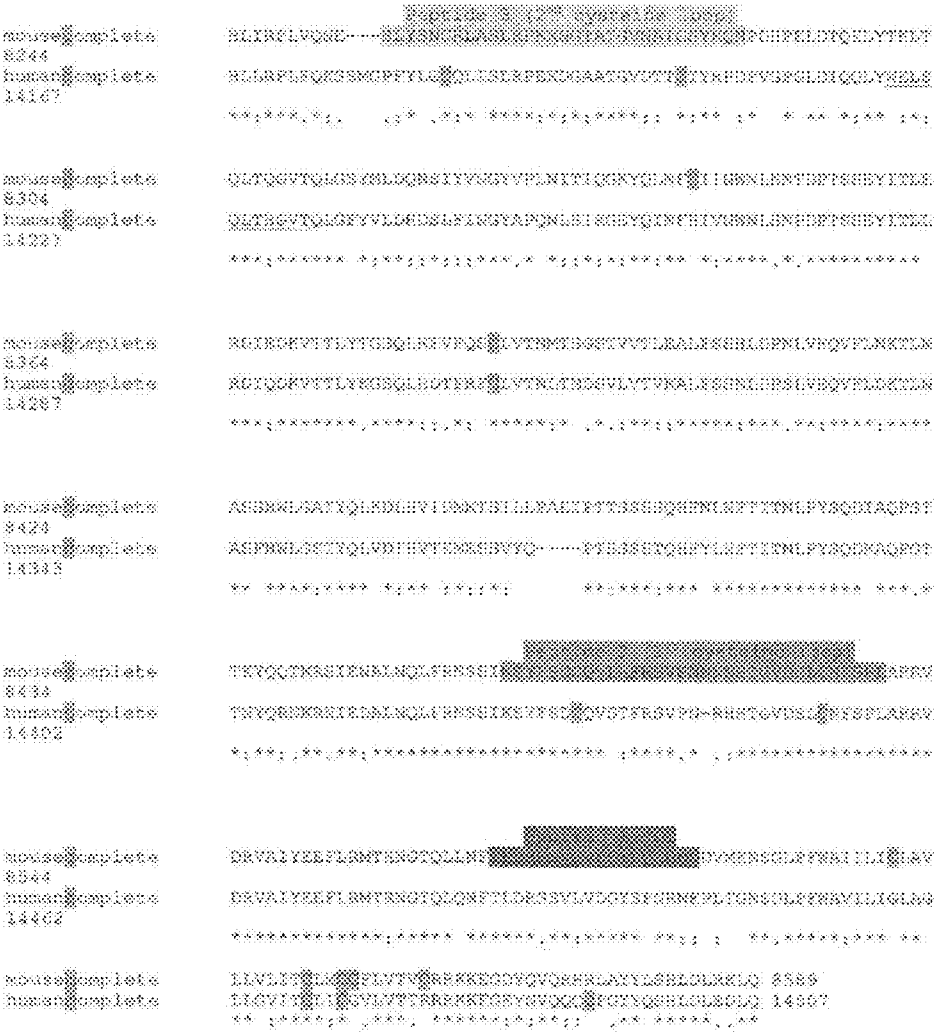
FIG. 20: (A) Mouse MUC16-CD Peptide 1 (SEQ ID NO:21), Mouse first Cysteine Loop Peptide 2 (SEQ ID NO:22), and Mouse second Cysteine Loop Peptide 3 (SEQ ID NO:23). (B) Alignment of mouse MUC16 (SEQ ID NO:24) and human MUC16 (SEQ ID NO:25) amino acid sequences. A cysteine was added to the peptide sequence at the N terminus of Peptide 1 and Peptide 3 for better conjugation with KLH.

"MUC16," "MUC-16" and "Mucin 16" interchangeably refer to a type I membrane protein that is part of a family of tethered mucins. A schematic of Muc16 is in FIG. 10, and an exemplary human Muc16 amino acid sequence (SEQ ID NO: 13) is shown in FIGS. 9A-9F. An alignment of mouse MUC16 (SEQ ID NO:24) and human MUC16 (SEQ ID NO:25) amino acid sequences is shown in FIG. 20B. The term "type 1 protein" refers to a "membrane protein" that is at least partially embedded in the lipid bilayer of a cell, virus and the like, and that contains a transmembrane domain (TM) sequence embedded in the lipid bilayer of the cell, virus and the like. The portion of the protein on the $NH_2$-terminal side of the TM domain is exposed on the exterior side of the membrane, and the COOH-terminal portion is exposed on the cytoplasmic side.

Recently, the sequence of the cDNA-encoding MUC16/CA125 was described by Yin and Lloyd in 2001 and completed by O'Brien in 2002 (10-12). The complete MUC16 protein has various components consisting of a cytoplasmic tail with potential phosphorylation sites, a transmembrane domain, and an external domain proximal to an apparent cleavage site. Distal to the cleavage site, the released external domain contains 16-20 tandem repeats of 156 amino acids, each with many potential glycosylation sites (11). The overall repeat structure (FIG. 10) is well conserved across mammals, but the repeats are not completely identical in exact amino acid composition.

The MUC16 protein is part of a family of tethered mucins that includes both MUC1 and MUC4 (13). MUC1 is present in a variety of tissues and appears to signal through a beta catenin pathway, interact with EGF receptor, mediates drug resistance and can act as an oncogene (14-17). The MUC4 protein is also expressed in a variety of tissues but is common on neoplasms of the gastrointestinal track (18-20). In contrast, the CA125 antigen has been more restricted in its distribution and is present primarily in gynecologic tissues and overexpressed in Millerian neoplasms (21). However, the CA125 antigen, recognized by the OC125 antibody, is a heavily glycosylated antigen expressed in the tandem repeat region of the larger MUC16 protein. This glycoprotein is typically shed from a putative cleavage site in the extracellular domain of the MUC16 peptide backbone.

Thus, "MUC16" protein contains (a) a "cytoplasmic domain," (b) a "transmembrane domain," and (c) a "extracellular domain." The MUC16 extracellular domain contains a cleavage site between a non-glycosylated ectodomain and a large glycosylated ectodomain of tandem repeats.

The terms "cytoplasmic domain," "cytoplasmic tail," and "CT" are used interchangeably to refer to a protein sequence, and portions thereof, that is on the cytoplasmic side of the lipid bilayer of a cell, virus and the like. Methods for determining the CT of a protein are known in the art Elofsson et al. (2007) Annu. Rev. Biochem. 76:125-140; Bernsel et al. (2005) Protein Science 14:1723-1728).

The terms "transmembrane domain" and "TM" are used interchangeably to refer to a protein sequence, and portions thereof, that spans the lipid bilayer of a cell, virus and the like. Methods for determining the TM of a protein are known in the art (Elofsson et al. (2007) Annu. Rev. Biochem. 76:125-140; Bernsel et al. (2005) Protein Science 14:1723-1728).

The terms "ectodomain" and "extracellular domain" are interchangeably used when in reference to a membrane protein to refer to the portion of the protein that is exposed on the extracellular side of a lipid bilayer of a cell, virus and the like. Methods for determining the ectodomain of a protein are known in the art (Singer (1990) Annu. Rev. Cell Biol. 6:247-296 and High et al. (1993) J. Cell Biol. 121: 743-750, and McVector software, Oxford Molecular).

The exemplary Muc16 of FIGS. 9A-9F contains (a) a "MUC16 cytoplasmic domain" from amino acid 14476 to 14507, vttrr rkkegeynvq qqcpgyyqsh ldledlq (SEQ ID NO:16), that interacts with the intracellular signal transduction machinery; (b) a "MUC16 transmembrane domain" from amino acid 14452 to 14475, fwaviligl agllgvitcl icgvl (SEQ ID NO: 14) that spans the plasma membrane; and (c) a "MUC16 extracellular domain" amino acid 1 to 14392 (SEQ ID NO: 13) that contains a cleavage site between an non-glycosylated ectodomain and a large glycosylated ectodomain of tandem repeats. The "MUC16 ectodomain" is exemplified by nfsplar rvdrvaiyee flrmtrngtq lqnftldrss vlvdgyspnr nepltgnsdl p (SEQ ID NO: 17) from amino acid 14394 to 14451 of SEQ ID NO:13 of FIGS. 9A-9F.

The exemplary MUC16 ectodomain contains both Polypeptide 1 (nfsplar rvdrvaiyee (SEQ ID NO:01), which is from amino acid 14394 to 14410 of SEQ ID NO: 13), and Polypeptide 2 (tldrss vlvdgyspnr ne (SEQ ID NO:02), which is from amino acid 14425 to 14442 of SEQ ID NO: 13), against which the invention's exemplary antibodies were produced. Polypeptide 3, cgvlvttrr rkkegeynvq qq (SEQ ID NO:03) is from amino acid 14472 to 14492 of SEQ ID NO: 13, and contains both a transmembrane domain portion (cgvl) and a cytoplasmic domain portion (vttrr rkkegeynvq qq (SEQ ID NO:18)). Thus, the CGVL is optional in SEQ ID NO:03, as it is part of the transmembrane domain.

Polypeptide 4 (ksyf sdcqvstfrs vpnrhhtgvd slcnfspl (SEQ ID NO: 15), is located in a non-glycosylated portion of the Muc16 extracellular domain, is from amino acid 14367 to 14398 of SEQ ID NO: 13, and contains a cysteine loop polypeptide cqvstfrsvpnrhhtgvdslc (SEQ ID NO:13).

B. Prior Art Antibodies

The expression of the MUC16/CA125 antigen has long been associated with gynecologic tissues. "CA125," "CA-125," "Cleaved CA125," and "cleaved CA-125," interchangeably refer to the glycosylated external domain of the tethered mucin MUC16, that is distal to the cleavage site (Payne et al., U.S. Pat. No. 7,202,346). This released external domain contains 16-20 tandem repeats of 156 amino acids, each with potential glycosylation sites. An apparent cysteine-based disulfide loop of 19 amino acids is present in all repeats and the N-terminal end contains a hairbrush structure that is heavily O-glycosylated (11). The deduced size would be 2.5 MD for the protein part, and with added carbohydrates, this could increase to 5 MD (10, 26).

CA125, though it is not sensitive or specific enough to be used as a general screening tool, is routinely used to monitor patients with ovarian carcinoma. The tests used to measure CA125 are antibody based detection methods, as are the immunohistochemical stains routinely performed for diagnostic purposes. The epitope specificity of 26 antibodies to MUC16 was studied in the first report from the International Society of Oncodevelopmental Biology and Medicine (ISOBM) TD-1 Workshop and the application of 22 antibodies to immunohistochemistry was reported in the second report from the TD-1 workshop (7, 21). The existing antibodies were grouped as OC125-like, M11-like, or OV197-like and all of the known antibodies recognized CA125 epitopes in the repeating, glycosylated elements in the external domain of the tethered mucin MUC16, distal to the putative cleavage site.

The vast majority of MUC16-reactive antibodies, including OC125, react with the glycosylation-dependent antigen present exclusively in the cleaved portion of the molecule so the true distribution of MUC16 expression is not known (21). There is currently no antibody available to track the fate of the remaining MUC16 protein fragment after cleavage and CA125 release.

C. Invention's Antibodies

In order to better explore the biology of human MUC16, the inventors have derived monoclonal antibodies against the extracellular portion of the MUC16-carboxy terminus, proximal to the putative cleavage site, as well as one monoclonal antibody against the internal cytoplasmic domain. In contrast to prior antibodies, these are derived against the peptide backbone of MUC16 and are not directed at complex glycoprotein epitopes. Since these epitopes are proximal to the cleavage site, they are unlikely to be found in the circulation and provide novel targets for diagnostic methods and therapeutic interventions. Data herein demonstrate the identification and characterization of exemplary antibodies developed against the MUC16 peptide backbone.

The inventors have developed novel antibodies that are directed at the non-cleaved, non-glycosylated peptide backbone of MUC16. These are exemplified by both 4H11 and 9C9 antibodies, which react with peptide sequences in the non-cleaved ectodomain of MUC16 and are detectable on the surface of ovarian cancer cell lines and in paraffin-fixed tissues from human ovarian cancer surgical specimens. The antibodies show high affinity and are readily internalized by ovarian cancer cells when bound to the ectodomain of MUC16. This suggests that the proximal portion of MUC16 has an independent biology from the more distal, cleaved portion of the mucin. It also suggests that the proximal portions of MUC16 could provide convenient targets for diagnostic and therapeutic interventions. Targeting the peptide backbone of MUC16 provides highly specific tissue delivery for genetically engineered cells, liposomes, or antibody conjugates, including conjugates with the invention's antibodies.

The invention's antibodies, exemplified by antibody 4H11, are useful as tools in immunohistochemistry. Date herein show that 4H11 is relatively specific to high-grade ovarian serous carcinoma. Invasive lobular breast carcinoma is the major exception and shows extensive MUC16 protein as detected by 4H11. Lobular carcinoma of the breast has unique biology which is characterized by a propensity to metastasize to serosal surfaces (27). Since MUC16 is the cognate binding partner of mesothelin, this may have important implications for lobular cancer (28). The discordance rates for OC125 and 4H11 also suggest that 4H11 might provide additional, independent information from OC125 in a subset of ovarian carcinomas. Some tumors that are negative with OC125 retain cytoplasmic and extracellular portions of the MUC16 glycoprotein, portions of the molecule that are likely involved in transduction of signals potentially important in the malignant phenotype.

Thus, in one embodiment, the invention provides an isolated antibody, or an antigen-binding fragment thereof, that specifically binds to a polypeptide, or antigenic portion thereof, wherein the polypeptide is exemplified by a) MUC16 ectodomain polypeptide (exemplified by NFSPLAR RVDRVAIYEE FLRMTRNGTQ LQNFTLDRSS VLVDGYSPNR NEPLTGNSDL P (SEQ ID NO: 17)), b) MUC16 cytoplasmic domain polypeptide (exemplified by VTTRR RKKEGEYNVQ QQ (SEQ ID NO:18), which is contained within each of CGVLVTTRR RKKEGEYNVQ QQ (SEQ ID NO:03) and LVTTRR RKKEGEYNVQ QQ (SEQ ID NO:20)), and c) MUC16 extracellular domain polypeptide that contains a cysteine loop polypeptide CQVSTFRSVPNRHHTGVDSLC (SEQ ID NO: 19).

Figure 5A:
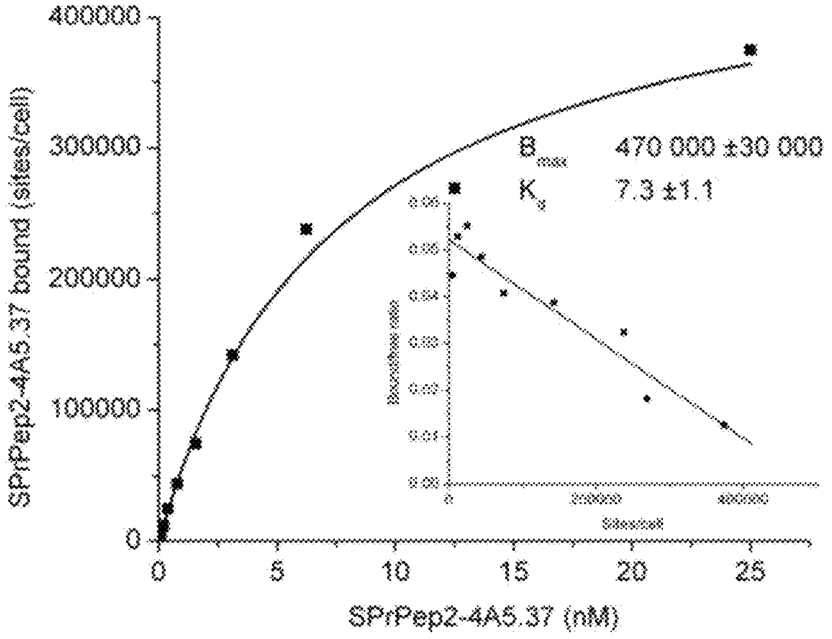
FIGS. 5A-5D: MUC16 carboxy terminus monoclonal antibodies binding affinity on OVCAR3 cells.
Figure 5B:
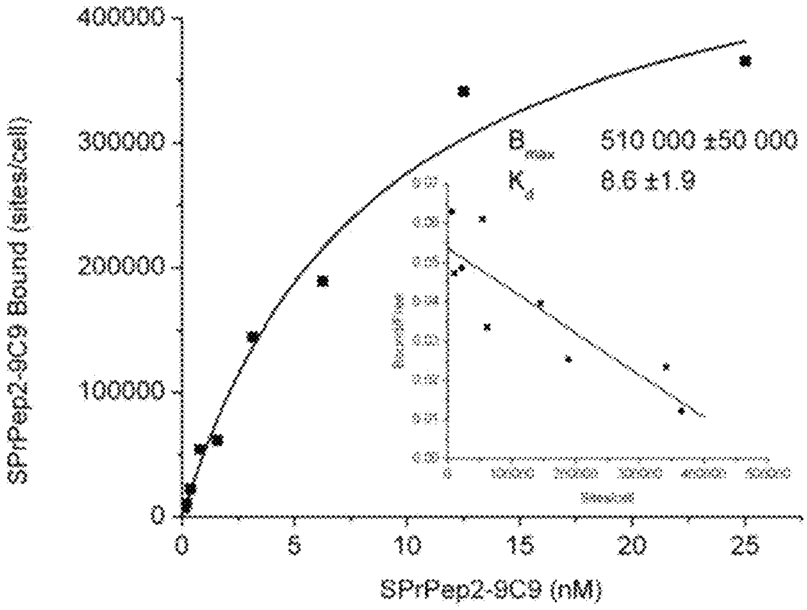
Figure 5C:
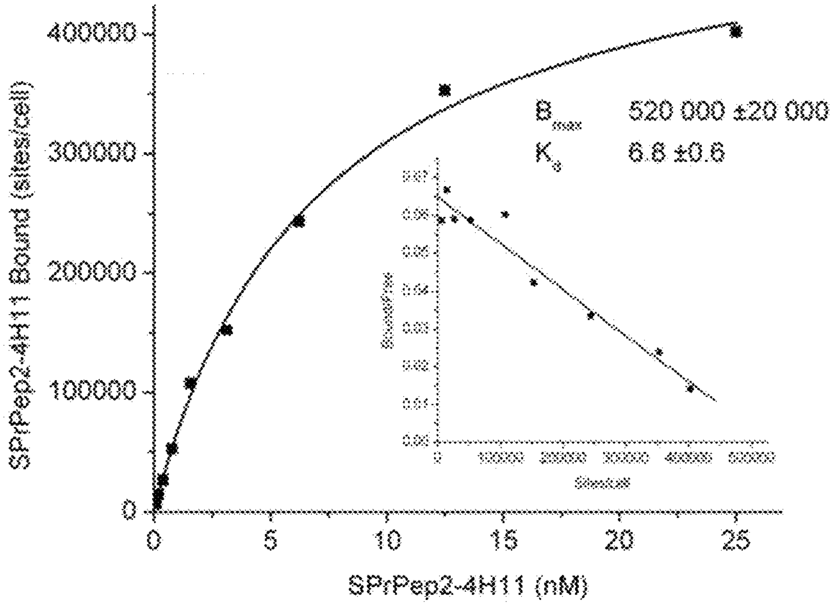
Figure 5D:
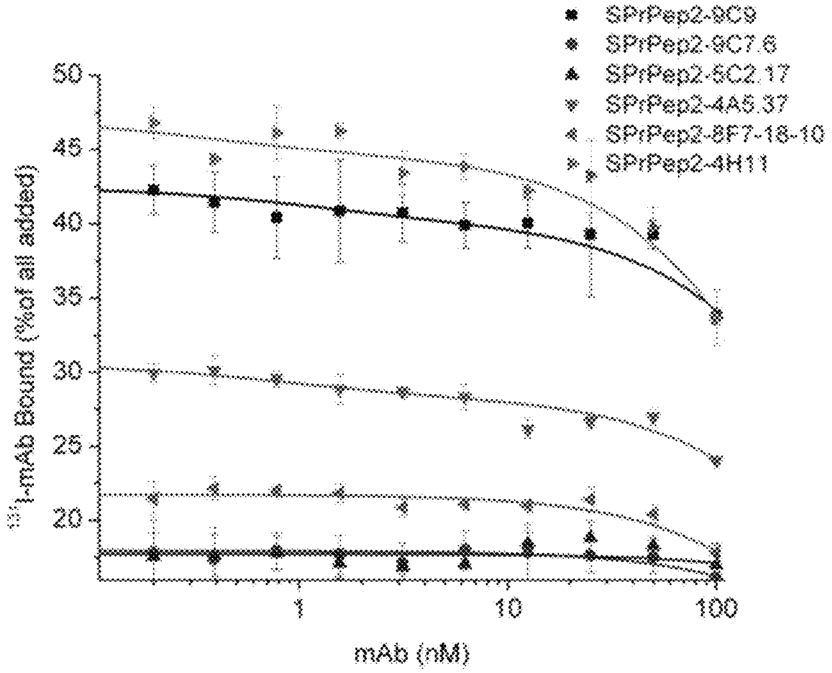
Figure 5E:
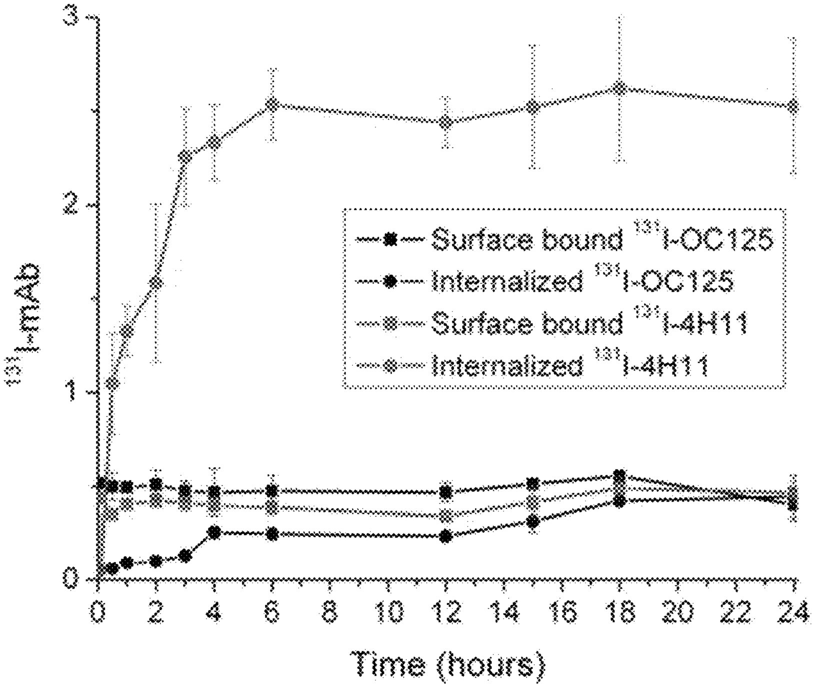
FIG. 5E: Internalization of radio-labeled 4H11 and OC125 monoclonal antibodies on SKOV3-phrGFP-$\Delta$MUC16$^{c334}$ stable transfected cells.
Figure 6A:
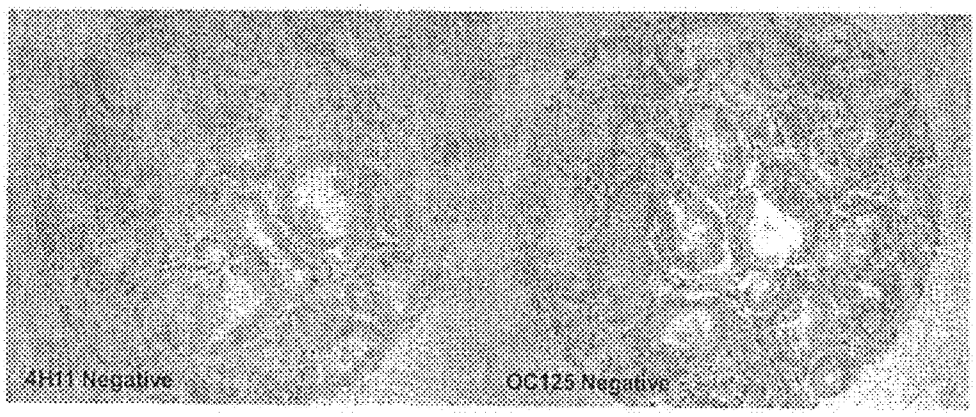
FIG. 6A-D: Comparison staining intensities of OC125 and 4H11 monoclonal antibodies on tissue microarrays containing cancers of the prostate (2A, concordant), lung (2B, discordant), breast (2C, discordant), and pancreas (2D, discordant).
Figure 6B:
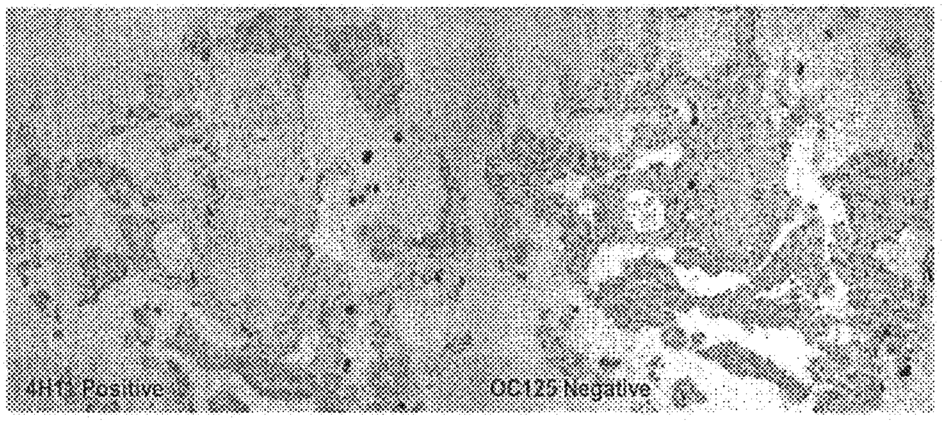
Figure 6C:
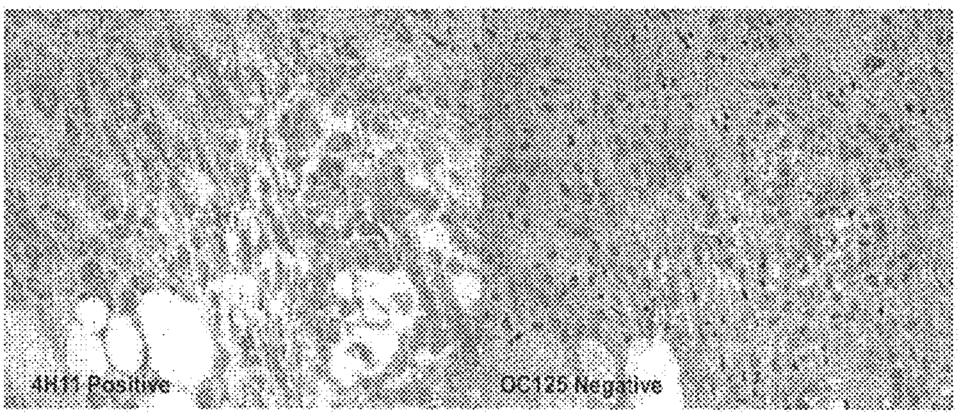
Figure 6D:
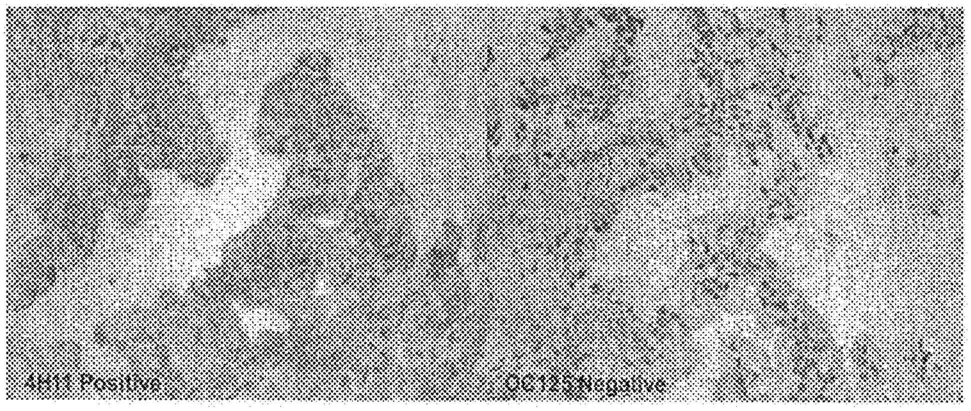
Figure 7A:
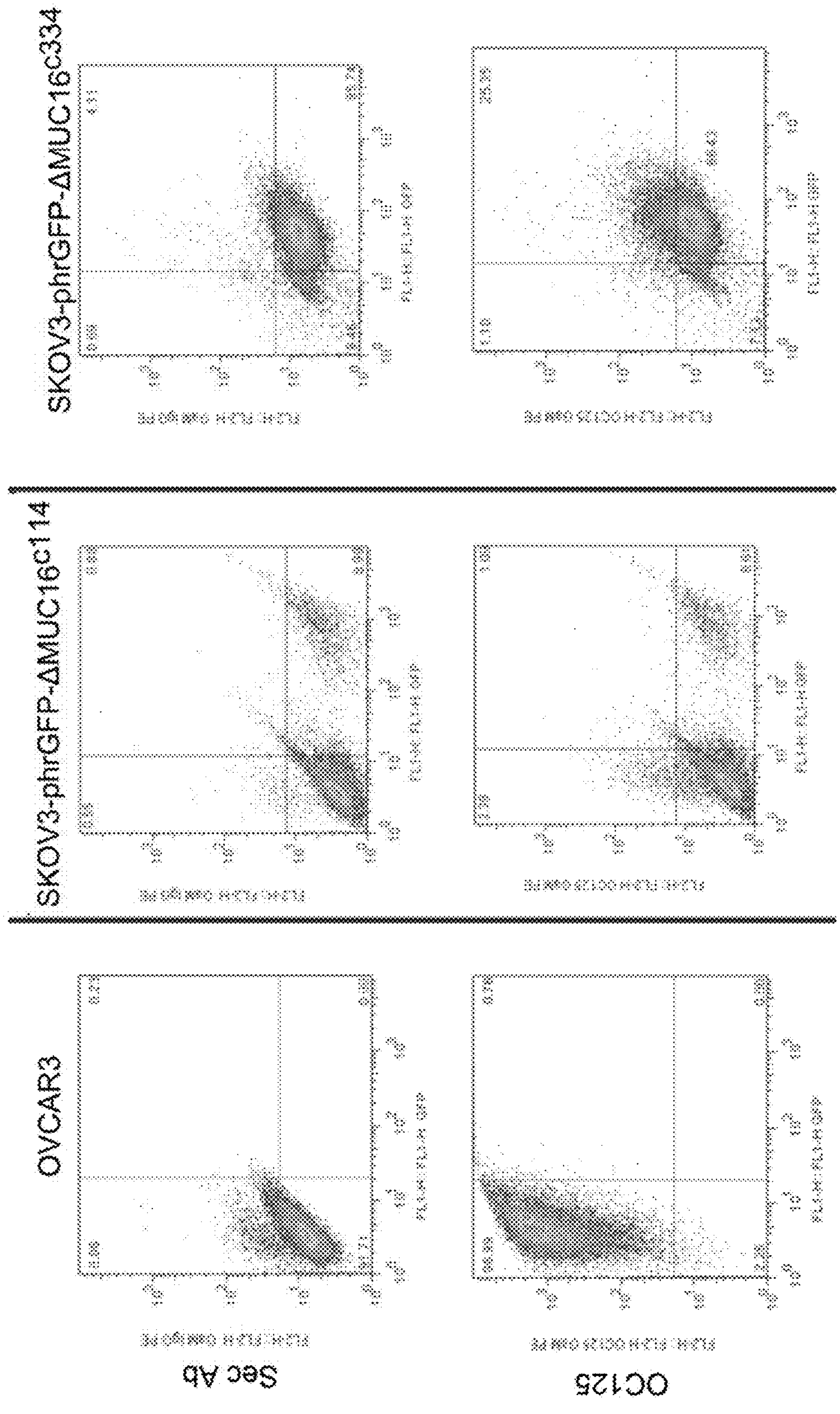
FIGS. 7A-7F: FACS analysis as described in the Material and Methods section was performed with commercial antibodies and MUC16 carboxy terminus monoclonal antibodies on OVCAR3 wt, SKOV3-phrGFP-$\Delta$MUC16$^{c114}$ and SKOV3-phrGFP-$\Delta$MUC16$^{c334}$ stable transfected cell lines.
Figure 7B:
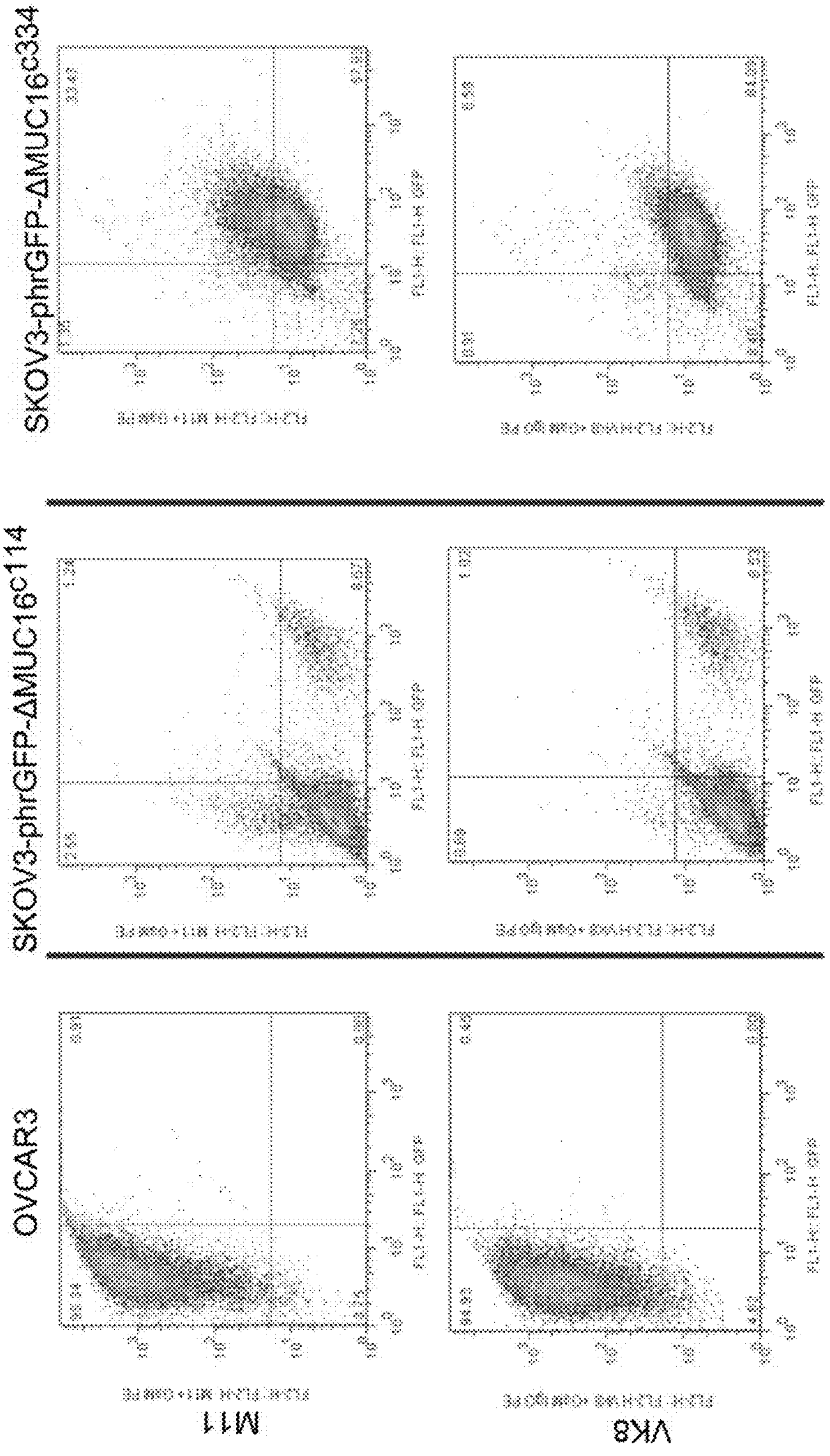
Figure 7C:
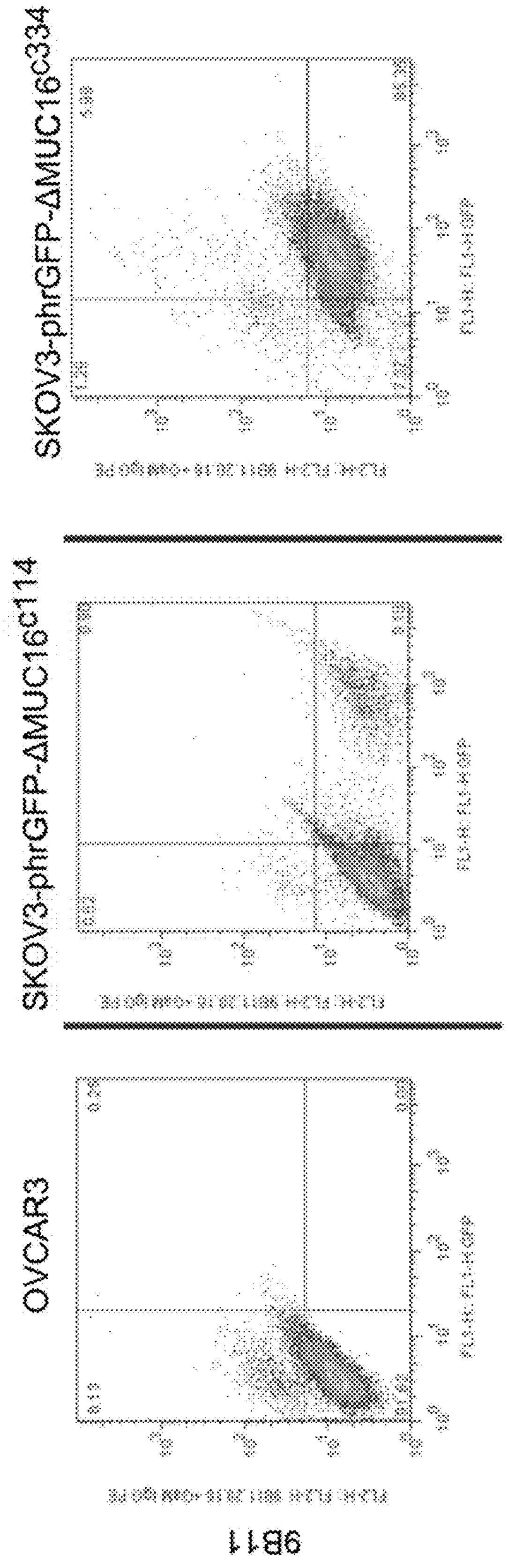
Figure 7D:
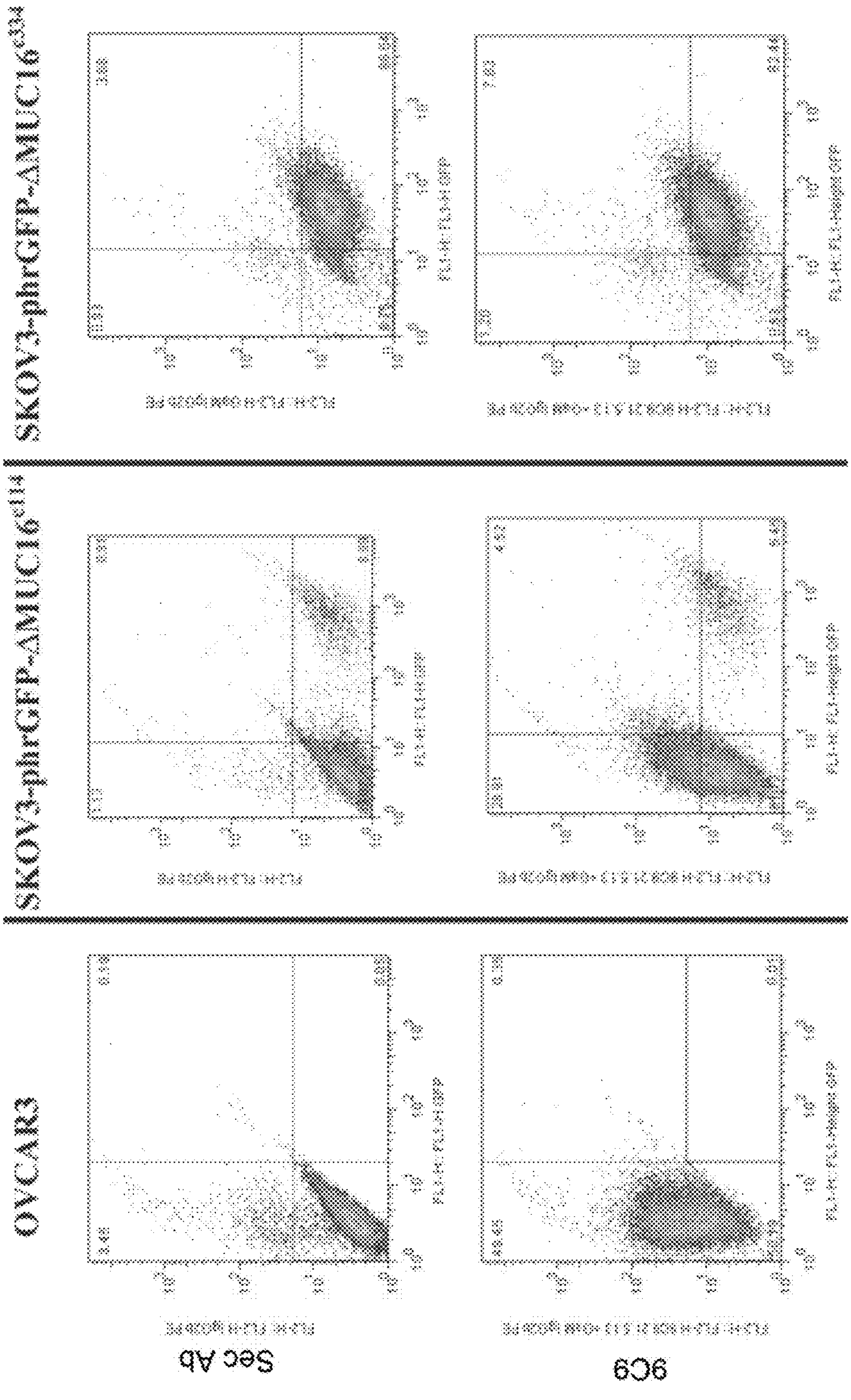
Figure 7E:
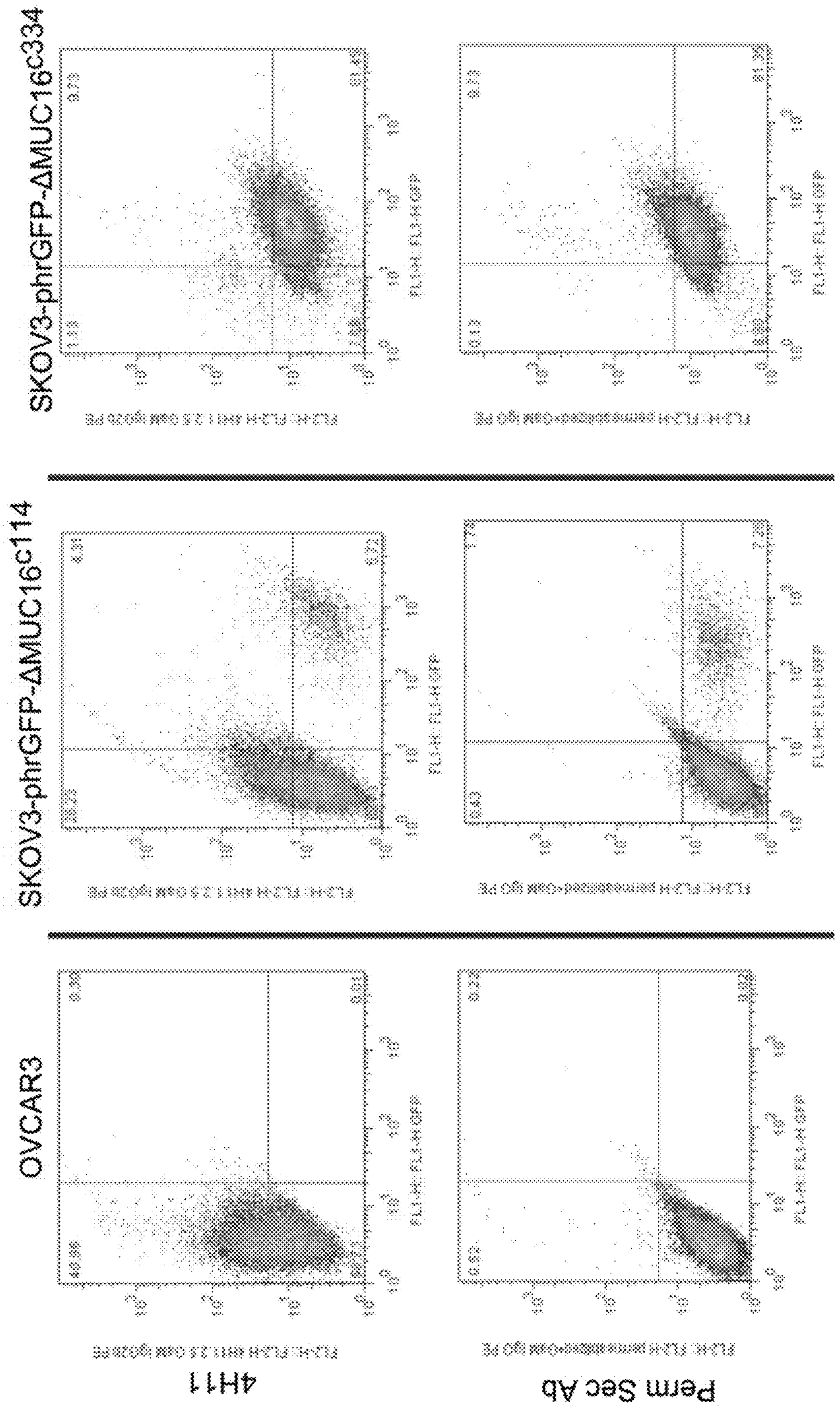
Figure 7F:
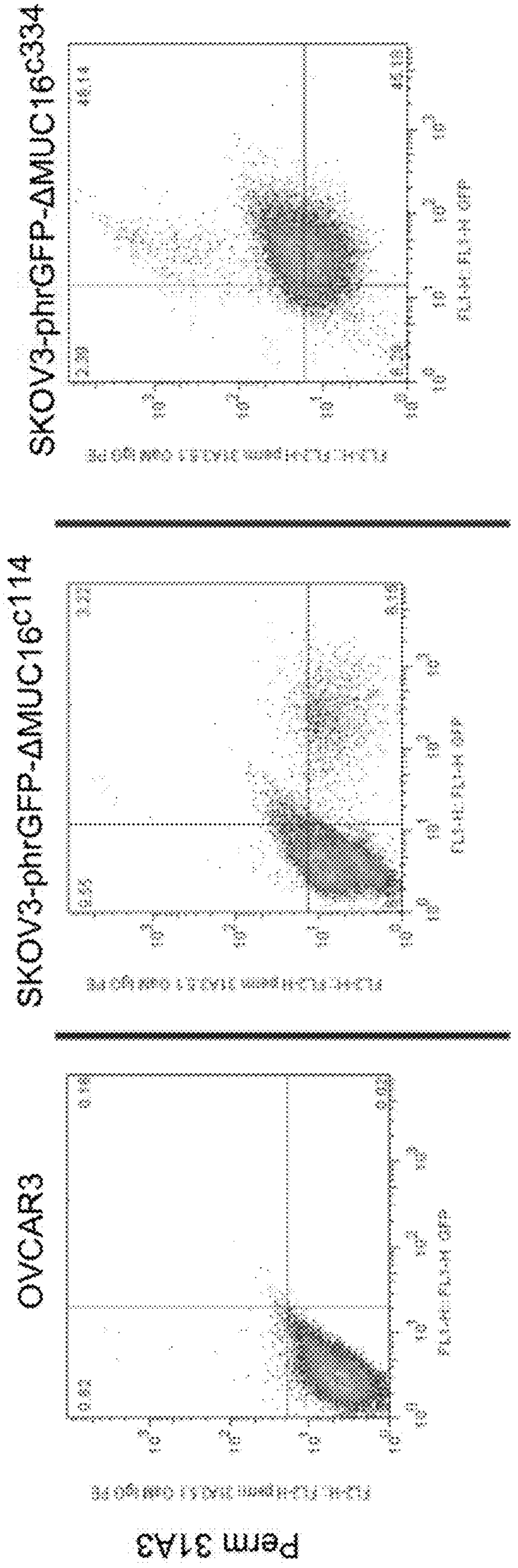

One advantage of the invention's antibodies is that the antibody internalizes into a cell, thereby being useful in applications for delivery inside a cell, such as disease therapy. "Internalized" when in reference to a molecule that is internalized by a cell refers to passage of the molecule that is in contact with the extracellular surface of a cell membrane across the cell membrane to the intracellular surface of the cell membrane and/or into the cell cytoplasm. Methods for determining internalization are disclosed herein, including the detection of radiolabeled molecule inside the cell (FIG. 5E).

In one embodiment, the invention's antibodies specifically bind to MUC16 ectodomain polypeptide that comprises a polypeptide selected from the group consisting of Polypeptide 1 NFSPLARRVDRVAIYEE (SEQ ID NO:01) and Polypeptide 2 TLDRSSVLVDGYSPNRNE (SEQ ID NO:02). Data herein show that the invention's antibodies specifically bind to GST-ΔMUC16$^{c114}$ (Example 2, Table 1A). The specificity of the invention's antibodies is in contrast to prior art antibodies (e.g., VK8, M11 and OC125 antibodies) that did not bind to GST-$\Delta$MUC16$^{c114}$ purified protein or cell lysates of the SKOV3-phrGFP-$\Delta$MUC16$^{c114}$ cell line (Example 2, FIG. 2).

In a further embodiment, the invention's antibodies lack specific binding to a glycosylated MUC16 extracellular domain, exemplified by the cleaved CA-125 described in Payne et al., U.S. Pat. No. 7,202,346.

While not intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:06 (i.e., the antibody 4H11 variable heavy ($V_H$) chain amino acid sequence of FIG. 8C), and a variable light ($V_L$) chain encoded by SEQ ID NO:07 (i.e., the antibody 4H11 variable light ($V_L$) chain amino acid sequence of FIG. 8D). In a particular embodiment, the antibody is chimeric, wherein at least one of the $V_L$ and $V_H$ chains is fused to a human immunoglobulin constant region.

Also without intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:04 (i.e., the antibody 4A5 variable heavy ($V_H$) chain nucleotide sequence of FIG. 8A), and a variable light ($V_L$) chain encoded by SEQ ID NO:05 (i.e., the antibody 4A5 variable light ($V_L$) chain nucleotide sequence of FIG. 8B). In a particular embodiment, the antibody is chimeric wherein at least one of the $V_L$ and $V_H$ chains is covalently linked to a human immunoglobulin constant region.

Still without intending to limit the sequence of the $V_L$ and $V_H$ regions of the invention's antibodies, in one embodiment, the antibody specifically binds to the Polypeptide 1 (SEQ ID NO:01) of the MUC16 ectodomain polypeptide, wherein the antibody comprises a variable heavy ($V_H$) chain encoded by SEQ ID NO:08 (i.e., the antibody 9B11 variable heavy ($V_H$) chain nucleotide sequence of FIG. 8E), and a variable light ($V_L$) chain encoded by at least one of SEQ ID NO:09 (i.e., antibody 9B11 variable light ($V_{L.A}$) chain nucleotide sequence of FIG. 8F), and SEQ ID NO: 10 (i.e., the antibody 9B11 variable light ($V_{L.B}$) chain nucleotide sequence of FIG. 8G). In a particular embodiment, the antibody is chimeric wherein at least one of the $V_L$ and $V_H$ chains is covalently linked to a human immunoglobulin constant region.

While not intending to restrict the source of antigen to which the invention's antibodies bind, in one embodiment, the MUC16 ectodomain polypeptide is expressed by a cell. Data herein show that the invention's exemplary antibodies bind to SKOV3 cells transduced with phrGFP-$\Delta$MUC16$^{c114}$ (Example 2).

While not limiting the sequence of antigen to which the invention's antibodies bind, in a further embodiment, the invention's antibodies specifically bind to a MUC16 cytoplasmic domain polypeptide that comprises VTTRR RKKEGEYNVQ QQ (SEQ ID NO: 18). In a particular embodiment, the MUC16 cytoplasmic domain polypeptide comprises Polypeptide 3 CGVLVTTRRRKKEGEYN-VQQQ (SEQ ID NO:03). In some embodiment, the MUC16 cytoplasmic domain polypeptide is expressed by a cell. For example, data herein show that the invention's exemplary antibody binds to SKOV3 cells transduced with phrGFP-$\Delta$MUC16$^{c114}$ (Example 2). In a particular embodiment, the cell is permeabilized to facilitate internalization of the antibody into the cell so that it comes into contact with its cytoplasmic antigen.

Still without limiting the sequence of antigen to which the invention's antibodies bind, in a further embodiment, the invention's antibodies bind to a MUC16 extracellular domain polypeptide that contains a cysteine loop polypeptide CQVSTFRSVPNRHHTGVDSLC (SEQ ID NO:19). In a more preferred embodiment, the MUC16 extracellular domain polypeptide comprises Polypeptide 4 KSYF SDC-QVSTFRS VPNRHHTGVD SLCNFSPL (SEQ ID NO:15).

Still without intending to limit the sequence of the $V_L$ and $V_H$ regions of the invention's antibodies, in one embodiment, the antibody specifically binds to Polypeptide 4 (SEQ ID NO:15) of the MUC16 extracellular domain polypeptide, wherein the antibody comprises a variable heavy ($V_H$) chain encoded by SEQ ID NO: 11 (i.e., the antibody 24B3 variable heavy ($V_H$) chain amino acid sequence of FIG. 8H), and a variable light ($V_L$) chain encoded by SEQ ID NO: 12 (i.e., the antibody 24B3 variable light ($V_L$) chain amino acid sequence of FIG. 8I).

The invention contemplates chimeric antibodies (see U.S. Pat. No. 7,662,387), monoclonal antibodies, recombinant antibodies, an antigen-binding fragment of a recombinant antibody, a humanized antibody, and an antibody displayed upon the surface of a phage (U.S. Pat. No. 7,202,346). In particular, the invention contemplates antibody fragments that contain the idiotype ("antigen-binding region" or "antigen-binding fragment") of the antibody molecule. For example, such antigen-binding fragments include, but are not limited to, the Fab region, F(ab')2 fragment, pFc' fragment, and Fab' fragments.

The "Fab region" and "fragment, antigen binding region," interchangeably refer to portion of the antibody arms of the immnoglobulin "Y" that function in binding antigen. The Fab region is composed of one constant and one variable domain from each heavy and light chain of the antibody. Methods are known in the art for the construction of Fab expression libraries (Huse et al., Science, 246:1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The invention also contemplates a "single-chain antibody" fragment, i.e., an amino acid sequence having at least one of the variable or complementarity determining regions (CDRs) of the whole antibody, and lacking some or all of the constant domains of the antibody. These constant domains are not necessary for antigen binding, but constitute a major portion of the structure of whole antibodies. Single-chain antibody fragments are smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. Techniques for the production of single-chain antibodies are known (U.S. Pat. No. 4,946,778). The variable regions of the heavy and light chains can be fused together to form a "single-chain variable fragment" ("scFv fragment"), which is only half the size of the Fab fragment, yet retains the original specificity of the parent immunoglobulin.

The "Fc region" and "Fragment, crystallizable region" interchangeably refer to portion of the base of the immnoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

The invention contemplates polyclonal antibodies and monoclonal antibodies. "Polyclonal antibody" refers to an immunoglobulin produced from more than a single clone of plasma cells; in contrast "monoclonal antibody" refers to an immunoglobulin produced from a single clone of plasma cells. Generic methods are available for making polyclonal and monoclonal antibodies that are specific to a desirable polypeptide. For the production of monoclonal and polyclonal antibodies, various host animals can be immunized by injection with the peptide corresponding to any molecule of interest in the present invention, including but not limited to hamsters, rabbits, mice, rats, sheep, goats, etc. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Kohler and Milstein, Nature, 256:495-497 (1975)), techniques using germ-free animals and utilizing technology such as that described in PCT/US90/02545, as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)). In some particularly preferred embodiments of the present invention, the present invention provides monoclonal antibodies.

Also contemplated are chimeric antibodies. As used herein, the term "chimeric antibody" contains portions of two different antibodies, typically of two different species. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Chimeric antibodies include monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a He region that aggregates (e.g., IgM H chain).

The invention also contemplates "humanized antibodies," i.e., chimeric antibodies that have constant regions derived substantially or exclusively from human antibody constant regions, and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human. Thus, in one embodiment, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Humanized antibodies may be generated using methods known in the art, e.g., U.S. Pat. No. 5,225,539 to Winter et al., including using human hybridomas (Cote et al., Proc. Natl. Acad. Sci. U.S.A. 80:2026-2030 (1983)) or by transforming human B cells with EBV virus in vitro (Cole et al., in *Monoclonal Antibodies and Cancer Therapy*, Alan R. Liss, pp. 77-96 (1985)). Additional methods include, for example, generation of transgenic non-human animals which contain human immunoglobulin chain genes and which are capable of expressing these genes to produce a repertoire of antibodies of various isotypes encoded by the human immunoglobulin genes (U.S. Pat. Nos. 5,545,806; 5,569,825 and 5,625,126). Humanized antibodies may also be made by substituting the complementarity determining regions of, for example, a mouse antibody, into a human framework domain (PCT Pub. No. WO92/22653).

Importantly, early methods for humanizing antibodies often resulted in antibodies with lower affinity than the non-human antibody starting material. More recent approaches to humanizing antibodies address this problem by making changes to the CDRs. See U.S. Patent Application Publication No. 20040162413, hereby incorporated by reference. In some embodiments, the invention's humanized antibodies contain an optimized heteromeric variable region (e.g. that may or may not be part of a full antibody other molecule) having equal or higher antigen binding affinity than a donor heteromeric variable region, wherein the donor heteromeric variable region comprises three light chain donor CDRs, and wherein the optimized heteromeric variable region comprises: a) a light chain altered variable region comprising; i) four unvaried human germline light chain framework regions, and ii) three light chain altered variable region CDRs, wherein at least one of the three light chain altered variable region CDRs is a light chain donor CDR variant, and wherein the light chain donor CDR variant comprises a different amino acid at only one, two, three or four positions compared to one of the three light chain donor CDRs (e.g. the at least one light chain donor CDR variant is identical to one of the light chain donor CDRs except for one, two, three or four amino acid differences).

Chimeric antibodies containing amino acid sequences that are fused to constant regions from human antibodies, or to toxins or to molecules with cytotoxic effect, are known in the art (e.g., U.S. Pat. Nos. 7,585,952; 7,227,002; 7,632,925; 7,501,123; 7,202,346; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 6,429,295; 7,666,425; and 5,057,313).

Antibodies that are specific for a particular antigen may be screened using methods known in the art (e.g., U.S. Pat. No. 7,202,346) and disclosed herein. For example, In the production of antibodies, screening for the desired antibody can be accomplished by radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In one embodiment, the invention's antibodies are monoclonal antibodies produced by a hybridoma cell line. In a particular embodiment, the monoclonal antibody specifically binds to a MUC16 ectodomain polypeptide that comprises Polypeptide 1 (SEQ ID NO:01), as exemplified by the antibody selected from the group consisting of 9B11.20.16, 10A2, 2F4, 23D3, 30B1, and 31B2 (Tables 1 and 2). In a preferred embodiment, the antibody is 9B11.

In another embodiment, the monoclonal antibody specifically binds to a MUC16 ectodomain polypeptide that comprises Polypeptide 2 (SEQ ID NO:02), wherein the antibody is exemplified by 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10 (Tables 1 and 2). In a preferred embodiment, the antibody is exemplified by 4H11.2.5, 4A5.37, 9C9.21.5.13, 28F7.18.10, 9C7.6, and 5C2.17.

In a further embodiment, the monoclonal antibody specifically binds to a MUC16 cytoplasmic domain polypeptide that comprises Polypeptide 3 CGVLVTTRRRKKEGEYNVQQQ (SEQ ID NO:03), wherein the antibody is exemplified by 31A3.5.1, 19D1, 10F6, 22E10, 22F1, 3H8, 22F11, 4D7, 24G12, 19G4, 9A5, 4C2, 31C8, 27G4, and 6H2 (Tables 1 and 2). In a preferred embodiment, the antibody is 31A3.5.1.

In another embodiment, the monoclonal antibody specifically binds to a MUC16 extracellular domain polypeptide that comprises Polypeptide 4 KSYF SDCQVSTFRS VPNRHHTGVD SLCNFSPL (SEQ ID NO: 15), wherein the antibody is exemplified by 24B3 and 9C7 (Table 2).

The invention's antibodies and methods for their use (both diagnostic and therapeutic) are disease specific. "Specificity" of a method and/or molecule for disease, such as "specificity for cancer" which is interchangeably used with "cancer specificity", refers to the proportion (e.g., percentage, fraction, etc.) of negatives (i.e., healthy individuals not having disease) that are correctly identified, i.e., the percentage of healthy subjects who are correctly identified as not having disease. Specificity may be calculated according to the following equation:

$$\text{Specificity} = \text{number of true negatives}/(\text{number of true negatives} + \text{number of false positives}).$$

Thus, in some embodiments, the invention's compositions and/or methods have a "cancer specificity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% specificity is most desirable, i.e., not predicting anyone from the healthy group as having cancer, it is not necessary. Data herein demonstrate the invention's cancer specificity (Table 3).

In alternative embodiments, specificity is expressed (together with sensitivity) as a statistical measure of the performance of a binary classification test, such as using a Receiver Operator Characteristic (ROC) curve". For any test, there is usually a trade-off between specificity and sensitivity. For example: in cancer screening tests of human subjects, it is undesirable to risk falsely identifying healthy people as having cancer (low specificity), due to the high costs. These costs are both physical (unnecessary risky procedures) and financial. This trade-off can be represented graphically using a ROC curve. "Receiver Operator Characteristic curve" and "ROC curve" refer to a plot of the true positive rate (AKA sensitivity) versus true negative rate (AKA 1-specificity). The measured result of the test is represented on the x axis while the y axis represents the number of control (e.g., healthy) or case (e.g., cancer) subjects. For any given cut point (each point along the x axis) a sensitivity and specificity of the assay can be measured. The range of sensitivity and specificity for any given assay can range from 0% to 100%, depending on the selected cut point. For this reason, in some preferred embodiments, the AUC is used as the standard measure of an assay's specificity and/or sensitivity. The "area under the curve" ("AUC") for the ROC curve plot is equal to the probability that a classifier will rank a randomly chosen positive instance higher than a randomly chosen negative one. Thus, AUC is a general measure of a tests ability to successfully discriminate between case (e.g., cancer) and control (e.g., healthy) subjects. Random chance would generate an AUC of 0.5. Therefore, in one embodiment, useful tests preferably have AUC's greater than 0.50, including any value from 0.51 to 1.00, such as from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, from 0.95 to 1.00, and most preferably 1.00. AUC values greater than 0.50 include 0.51, 0.52, 0.52, 0.54, 0.55, 0.56, 0.57, 0.58, 0.59, 0.60, 0.61, 0.62, 0.63, 0.64, 0. 65, 0.66, 0.67, 0. 68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, and 0. 99.

The invention's antibodies and methods for their use (both diagnostic and therapeutic) are disease sensitive. "Sensitivity" of a method and/or molecule for disease, such as "sensitivity for cancer" which is interchangeably used with "cancer sensitivity," refers to the proportion (e.g., percentage, fraction, etc.) of positives (i.e., individuals having cancer) that are correctly identified as such (e.g. the percentage of people with cancer who are identified as having the condition). Sensitivity may be calculated according to the following equation; Sensitivity=number of true positives/(number of true positives+number of false negatives).

Thus, in some embodiments, the invention's compositions and/or methods have a "disease sensitivity," such as "cancer sensitivity," greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% sensitivity is most desirable (i.e., predicting all subjects from the cancer group as having cancer), it is not necessary.

In alternative embodiments, the invention's compositions and/or methods have a "disease sensitivity," such as "cancer sensitivity," equal to or lower than 50%, including any numerical value from 0% to 50%, such as 1%, 2%, 3%, 4%, 6%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, and 49%.

In some embodiments, sensitivity is expressed (together with specificity) as a statistical measure of the performance of a binary classification test, such as using AUC of a ROC curve, as discussed above with respect to specificity.

D. Hybridoma Cell Lines

In addition to the invention's novel antibodies, the invention also provides hybridoma cell lines that produce these antibodies. "Hybridoma cell" refers to a cell line produced by fusing a specific antibody-producing B cell with a myeloma (B cell cancer) cell that is selected for its ability to grow in tissue culture and for an absence of antibody chain synthesis. The antibodies produced by the hybridoma cell are all of a single specificity and are therefore monoclonal antibodies (in contrast to polyclonal antibodies).

In a particular embodiment, the invention provides hybridoma cell lines that produce a monoclonal antibody that specifically binds to a polypeptide, or antigenic portion thereof, selected from the group consisting of a) MUC16 ectodomain polypeptide (e.g., NFSPLAR RVDRVAIYEE FLRMTRNGTQ LQNFTLDRSS VLVDGYSPNR NEPLTGNSDL P (SEQ ID NO: 17)), b) MUC16 cytoplasmic domain polypeptide (e.g., VTTRR RKKEGEYNVQ QQ (SEQ ID NO:18)), and c) MUC16 extracellular domain polypeptide that contains a cysteine loop polypeptide CQVSTFRSVPNRHHTGVDSLC (SEQ ID NO:19). The MUC16 polypeptide SEQ ID NO: 18 is contained within LVTTRR RKKEGEYNVQ QQ (SEQ ID NO:20). Thus, SEQ ID NO:20 contains both a transmembrane domain amino acid (L) and a cytoplasmic domain portion VTTRR RKKEGEYNVQ QQ (SEQ ID NO:18), i.e., the L is optional, as it is part of the transmembrane domain. The MUC16 polypeptide SEQ ID NO:18 is also contained within CGVLVTTRR RKKEGEYNVQ QQ (SEQ ID NO:03). Thus, SEQ ID NO:03 contains both a transmembrane domain portion (CGVL) and a cytoplasmic domain portion VTTRR RKKEGEYNVQ QQ (SEQ ID NO:18), i.e., the CGVL is optional, as it is part of the transmembrane domain.

E. Conjugates of the Invention's Antibodies Linked to Cytotoxic Agents and/or Prodrugs The invention contemplates conjugate antibodies. A "conjugate" antibody refers to an antibody of the present invention covalently linked to a cytotoxic agent and/or a prodrug of a cytotoxic agent.

"Cytotoxic agent" refers any agent that is capable of reducing the growth of, and/or killing, a target cell. A "prodrug" represents an analog of a cytotoxic agent that substantially lacks cytotoxic activity until subjected to an activation step. Activation steps may include enzymatic cleavage, a chemical activation step such as exposure to a reductant, or a physical activation step such as photolysis.

The covalent linkage between the invention's antibodies and the cytotoxic agent or prodrug can include cleavable linkages such as disulfide bonds, which may advantageously result in cleavage of the covalent linkage within the reducing environment of the target cell. Such conjugates are useful as tumor-cell specific therapeutic agents.

In one embodiment, the cytotoxic agent is a small drug molecule (Payne et al., U.S. Pat. No. 7,202,346). In another embodiment, the cytotoxic agent a maytansinoid, an analog of a maytansinoid, a prodrug of a maytansinoid, or a prodrug of an analog of a maytansinoid (U.S. Pat. Nos. 6,333,410; 5,475,092; 5,585,499; 5,846,545; 7,202,346). In another embodiment, the cytotoxic agent may be a taxane (see U.S. Pat. Nos. 6,340,701 & 6,372,738 & 7,202,346) or CC-1065 analog (see U.S. Pat. Nos. 5,846,545; 5,585,499; 5,475,092 & 7,202,346).

In another embodiment, the cytotoxic agent is exemplified by an auristatin, a DNA minor groove binding agent, a DNA minor groove alkylating agent, an enediyne, a duocarmycin, a maytansinoid, and a vinca alkaloid (U.S. Pat. No. 7,662,387).

In a further embodiment, the cytotoxic agent is an anti-tubulin agent (U.S. Pat. No. 7,662,387). In yet another embodiment, the cytotoxic agent is exemplified by dimethylvaline-valine-dolaisoleuine-dolaproine-phenylalanine-p-phenylenediamine (AFP), dovaline-valine-dolaisoleunine-dolaproine-phenylalanine (MMAF), and monomethyl auristatin E (MAE) (U.S. Pat. No. 7,662,387).

In an additional embodiment the toxic agent is exemplified by radioisotope emitting radiation, immunomodulator, lectin, and toxin (U.S. Pat. No. 6,429,295). In particular, the radioisotope emitting radiation is an alpha-emitter selected from the group consisting of $^{212}$Bi, $^{213}$Bi, and $^{211}$At, or a beta-emitter selected from the group consisting of $^{186}$Re and $^{90}$Y, or a gamma-emitter $^{131}$I (U.S. Pat. No. 7,666,425).

In an alternative embodiment, the toxin is exemplified by ricin, the A-chain of ricin, and pokeweed antiviral protein (U.S. Pat. No. 5,057,313).

In yet another embodiment, the cytotoxic agent is an anti-cancer drug selected from the group consisting of methotrexate, 5-fluorouracil, cycloheximide, daunomycin, doxorubicin, chlorambucil, trenimon, phenylenediamine mustard, adriamycin, bleomycin, cytosine arabinoside or Cyclophosphamide (U.S. Pat. No. 5,057,13).

F. Detecting Muc16 Portions and Diagnostic Applications

The invention provides a method for detecting a disease that comprises overexpression of MUC16 in a subject, wherein the method comprises a) providing i) a sample from a subject, and ii) any one or more of the invention's antibodies, b) contacting the sample with the antibody under conditions for specific binding of the antibody with its cognate antigen, and c) detecting an increased level of binding of the antibody to the sample compared to a control sample lacking the disease, thereby detecting the disease in the subject. Generic methods for detecting disease using antibodies are known in the art (Payne et al., U.S. Pat. No. 7,202,346). The invention's methods are particularly useful in detecting cancer, such as ovarian cancer and breast cancer.

The invention's methods are not limited to a particular approach to detecting binding of the invention's antibodies to their antigens. In one embodiment, detecting binding to the invention's antibodies typically involves using antibodies that are labeled with a detectable moiety, such as radioisotope (e.g., $^{3}H$, $^{14}C$, $^{32}P$, $^{35}S$, and/or $^{125}I$), fluorescent or chemiluminescent compound (e.g., fluorescein isothiocyanate, rhodamine, and/or luciferin) and/or an enzyme (e.g., alkaline phosphatase, beta-galactosidase and/or horseradish peroxidase).

Methods for conjugating antibodies to a detectable moiety are known in the art (e.g., Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

Thus, the invention's antibodies may be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

For example, with respect to immunohistochemical detection, data herein demonstrate that antibody 4H11 is useful in detecting high-grade ovarian serous carcinoma, lobular cancer (28), and a subset of ovarian carcinomas that are negative with OC125 and that retain cytoplasmic and extracellular portions of the MUC16 glycoprotein.

The antibodies of the invention also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The invention's antibodies are additionally useful as affinity purification agents. In this process, the antibodies are immobilized on a suitable support, such a Sephadex resin or filter paper, using methods well known in the art, to capture and purify molecules that contain antigens that specifically bind to the invention's antibodies.

G. Therapeutic Applications

The invention provides methods for treating a disease that comprises overexpression of MUC16, comprising administering to a subject having the disease a therapeutically effective amount of any one or more of the invention's antibodies. Generic methods for treating disease with antibodies are known in the art (Payne et al., U.S. Pat. No. 7,202,346). The invention's methods are particularly useful in treating cancer, such as ovarian cancer and breast cancer. These methods are also applicable to primary cancer, metastatic cancer, and recurrent cancer.

The term "administering" to a subject means providing a molecule to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrastemal injection, and infusion routes.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

Antibody treatment of human beings with cancer is known in the art, for example in U.S. Pat. Nos. 5,736,137; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 7,662,387; 6,429,295; 7,666,425; 5,057,313.

The invention's antibodies may be administered with pharmaceutically acceptable carriers, diluents, and/or excipients. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The invention's antibodies are typically administered in a therapeutic amount. The terms "therapeutic amount," "pharmaceutically effective amount," "therapeutically effective amount," and "biologically effective amount," are used interchangeably herein to refer to an amount that is sufficient to achieve a desired result, whether quantitative or qualitative. In particular, a pharmaceutically effective amount is that amount that results in the reduction, delay, and/or elimination of undesirable effects (such as pathological, clinical, biochemical and the like) that are associated with disease. For example, a "therapeutic amount that reduces cancer" is an amount that reduces, delays, and/or eliminates one or more symptoms of cancer.

For example, specific "dosages" of a "therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize. The dosage amount and frequency are selected to create an effective level of the compound without substantially harmful effects.

When present in an aqueous dosage form, rather than being lyophilized, the antibody typically will be formulated at a concentration of about 0.1 mg/ml to 100 mg/ml.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs.

The methods of the present invention can be practiced in vitro, in vivo, or ex vivo.

EXPERIMENTAL

The following examples serve to illustrate certain preferred embodiments and aspects of the present invention and are not to be construed as limiting the scope thereof.

Example 1

Materials And Methods

The following is a brief description of the exemplary materials and methods used in the subsequent Examples.

Cell Cultures:

OVCAR3, SKOV3, and A2780 cell lines were obtained through the American Type Culture Collection (ATCC, Manassas, Va.) and sustained in culture according to the ATCC literature. For the creation of MUC16+ transfected cell lines, the carboxyterminus portion of the MUC16 cDNA was introduced as green fluorescent protein fusion proteins using the Vitality phrGFP vector expression system (Stratagene, La Jolla, Calif.). Stable cell lines were selected using geneticin (G418, Invitrogen, Grand Island, N.Y.) in their respective culture media and isolated by expression of Green Fluorescence Protein. Stable transfectants were routinely maintained in G418 in their culture media respectively. The $\Delta MUC16^{114}$ transfectants have cell surface expression of MUC16 protein from the putative cleavage site to the carboxyterminus (AA 1776 to 1890) (12).

Monoclonal Preparation:

Using the MUC16 sequence, peptide sequences encoding elements of the $\Delta MUC16^{c114}$ amino acid sequence were synthesized at the Memorial Sloan-Kettering Cancer Center (MSKCC) Microchemistry Core Facility. The inventors synthesized 3 polypeptides (FIG. 1) and modified Polypeptide 1 and Polypeptide 2 with a cysteine at the N-terminus for better conjugation to KLH. Equal concentrations of the KLH-conjugated peptides were mixed and then used as the immunogen for 5 BALB/c mice. The inventors selected 1 of the 5 mice whose serum showed the highest reactivity to individual peptides by ELISA, and the MSKCC Monoclonal Antibody Core Facility performed the fusion and selected the antibodies using standard protocols. After 10 days of fusion, supernatants were selected and screened for reactivity by ELISA against the individual synthetic peptides.

ELISA:

Sandwich ELISA was performed to see the positivity of the antibodies to individual peptides and GST-$\Delta MUC16^{c114}$ fusion protein following routine core facility protocol for ELISA assay.

FACS Analyses:

Adherent target cells were removed by 0.05% Trypsin and 0.1% EDTA, washed, and counted by a hemocytometer. Cells were distributed into multiple Eppendorf tubes with at least $0.5\text{-}1\times10^{6}$ cells per tube. Cells were washed with phosphate buffered saline (PBS) containing 1% FCS and 0.025% Sodium Azide (FACS buffer). For internal FACS staining, cells in the Eppendorf tubes were permeabilized with 1:10 diluted FACS Permeabilizing Solution 2 (BD BioSciences, San Jose, Calif.) for 10 minutes at room temperature and then washed twice with ice cold FACS buffer. Then they were incubated either without (for second antibody control) or with 1 μg/tube of bioreactive supernatants of mouse MUC16 monoclonals for 30 minutes on ice. For surface FACS staining, cells were incubated either without (for second antibody control) or with 1 μg/tube of bioreactive supernatants of MUC16 monoclonals (9B11.20.16, 9C9.21.5.13 and 4H11.2.5), Mouse anti-human OC125 (M3519), Mouse anti-human M11 (M3520) (DakoCytomation, Dako North America Inc., Carpinteria, Calif.) or VK8 (kindly provided by Dr. Beatrice Yin and Dr. Ken Lloyd, MSKCC, New York, N.Y.) for 30 minutes on ice. Cells in Eppendorf tubes were also surface stained with 1 μg/tube of non-specific isotype matched control mouse antibodies (13C4 for IgG1 and 4E11 for IgG2b monoclonals obtained from MSKCC Monoclonal Core Facility) and incubated on ice for 30 minutes. All cells were washed three times with FACS buffer. Cells were incubated with 1 μg/tube of second antibody Goat anti-mouse IgG1-PE or IgG2b-PE for 30 minutes on ice and then washed three times with FACS buffer. The cells were analyzed by a FACS Calibur machine at the MSKCC Flow Cytometry Core Facility.

Western Blot Analysis:

Stable cell lines were cultured in 10 cm dishes in their respective culture media and incubated with 5% $CO_2$ at 37° C. for 3 days. They were washed twice with ice cold PBS to remove the serum-containing media. Adherent cells were scraped with 1-2 ml of ice cold PBS, and the cells were spun down in an Eppendorf tube at 4° C. in an Eppendorf centrifuge. Supernatant was discarded, and the cells were lysed with 0.2 ml of modified Ripa lysis buffer (20 mM Tris-HCL; pH 7.4; 150 mM NaCl; 1% NP-40; 1 mM Na3VO4; 1 mM PMSF; 1 mM DTT; 10 μg/ml leupeptin; and 10 μg/ml aprotinin) for 30 minutes on ice and spun at 4° C. for 10 minutes. The soluble solution was separated into a tube and the debris pellet was discarded. Protein concentration was measured using the Bio-Rad Protein Assay (Bio-RaD Laboratories, Hercules, Calif.). Equal amounts of proteins (GST-MUC16-CD-fusion protein or stable cell line extracts) were separated by sodium dodecyl sulfate polyacrylamide gel electrophoresis (SDS-PAGE) and transferred to nitrocellulose membrane using a BioRad transfer apparatus in a cold room at 4° C. The membranes were blocked with 3% bovine serum albumin (BSA) in PBS with 0.1% Tween-20 (PBST) at 4° C. overnight. Membranes were probed with primary antibody (1:1000 dilution) for 1 hr at room temperature and then washed three times with PBST. Then the membranes were stained with corresponding second antibody, anti-Mouse IgG Horse Radish Peroxidase (HRP) linked whole antibody from sheep (GE Healthcare, UK) (1:5000 dilution), for 1 hr at room temperature. Membranes were washed three times with PBST and developed with a Western Lightning® chemiluminescence reagent (ECL, Perkin Elmer, Waltham, Mass.) for 1-5 minutes at room temperature, and the signals were developed on Kodak BioMax Film.

Binding and internalization studies with monoclonal antibodies and OVCAR3 and SKOV3 stable transfectants:

Purified monoclonal antibodies were labeled with $^{131}I$ using the iodogen method and purified by size exclusion chromatography (22). Saturation binding studies were performed with radiolabeled antibodies using substrates of intact OVCAR-3 cells. Briefly, 10 test solutions were prepared (in triplicate) and they contained increasing amounts of the radioiodinated antibodies, 3-500 000 cells in a total volume of 500 μL of PBS (0.2% BSA; pH 7.4). The cells were isolated by rapid filtration through a glass fiber membrane and washed with ice cold tris buffered saline. Cells were counted in a gamma counter with standards of total activity added. For each concentration of radiolabeled antibody, non-specific binding was determined in the presence of 100 nM of the unmodified antibody. The data were analyzed with a least squares regression method (Origin, Microcal, Software Inc., Northampton, Mass.) to determine the $K_d$ and $B_{max}$ values, and a Scatchard transformation was performed.

Antibody cell internalization studies were performed with $^{131}$I-4H11 and $^{131}$I-OC125 monoclonal antibodies and SKOV3-phrGFP-ΔMUC16$^{c334}$ stable transfected cells. Briefly, radiolabeled antibody (370 MBq/mg, 100 kcpm) in 2 mL of medium was added to SKOV3 cells plated in a 6-well plate. The plates were incubated at 37° C. for up to 24 hours. At various time points, the medium was removed from three wells and the cells washed with 2×2 mL PBS. Cell surface bound activity was then stripped and collected with 2×2 mL of an ice cold acid wash (100 mM acetic acid 100 mM glycine; pH 3.0). The cells were then dissolved with 2×1 ml 1 M NaOH and collected. At the end of the study all samples were counted with a gamma counter together with standards, representing the initial amount of radioactivity added. All the media samples were analyzed by ITLC-SG with mobile phases of 5% TCA to determine unbound $^{131}$I.

Tissue Microarray (TMA):

Tissue microarrays were either constructed within our institution or bought from a commercial laboratory if not available internally. Briefly, core-needle biopsies of pre-existing paraffin-embedded tissue were obtained from the so-called donor blocks and then relocated into a recipient paraffin-arrayed "master" block by using the techniques by Kononen et al. and subsequently modified by Hedvat et al (23-24). A manually operated Tissue Arrayer MTA-1 from Beecher Instruments Inc. (Sun Prairie, Wis.) was used to produce sample circular spots (cores) that measured 0.6 to 1.0 mm in diameter. The cores were arrayed 0.3 to 0.4 mm apart from each other. A layer of control tissues was strategically laid around the actual tissue microarrays in order to avoid edging effects. The specific composition of each tissue microarray is delineated below. Slides of tissue microarrays for ovarian cancer, prostate cancer, adenocarcinoma of the lung, mucinous neoplasms of the pancreas, and invasive ductal and invasive lobular breast carcinoma were prepared by cutting 4 um sections from formalin-fixed paraffin-embedded tissue. Normal adult and fetal tissue microarrays were obtained from a commercial source (Biomax, US). OVCAR3 cells were used as positive controls.

Immunohistochemistry:

Immunohistochemistry was performed on the tissue microarrays with both standard OC125 (Ventana, Tucson, Ariz.) and the novel monoclonal antibodies. Sections of the tissue microarrays were cut at 4 microns, placed on Superfrost/Plus microscope slides (Fisher brand) and baked in a 60° oven for at least 60 minutes. The slides were then deparaffinized and hydrated to distilled water, soaked in citrate buffer at pH 6.00 for 30 minutes at 97° C., washed in running water for 2-5 minutes, incubated for 5 minutes in 3% hydrogen peroxide diluted in distilled water. Slides were washed in distilled water for 1 minute, transferred to a bath of phosphate buffered saline (PBS), pH 7.2, for two changes of 5 minutes each and placed in 0.05% BSA diluted in PBS for a minimum of 1 minute. After drying around tissue sections, normal serum was applied at a 1:20 dilution in 2% BSA/PBS and incubated for a minimum of 10 minutes at room temperature in a humidity chamber. The serum was then suctioned off without allowing the sections to dry, and approximately 150 lambda of novel antibody at a dilution of 1:1000 was placed on the tissue. The slide was incubated overnight (approximately 15-18 hours) at 4° C. in a humidity chamber. Primary antibody was washed off using three changes of PBS for 10 minutes each. Secondary antibody, biotinylated α-mouse from Vector laboratories (Burlingame, Ca), was applied at 1:500 dilution in 1% BSA/PBS and incubated for 45-60 minutes at room temperature in humidity chamber. The antibody was washed off again using three changes of PBS as above. Slides were then transferred to a bath of diaminobenzidine (DAB), diluted in PBS for 5-15 minutes. The slides were then washed in tap water for 1 minute, counterstained using Harris modified hematoxylin (Fisher), decolorized with 1% acid alcohol and blue in ammonia water, dehydrated with 3 changes each of 95% ethanol, 100% ethanol and xylene for 2 minutes each and coverslipped with permanent mounting medium.

Immunohistochemistry Scoring:

Commercially available antibodies, such as OC125 and M11, target complex glycosylation-dependent epitopes. Our hypothesis is that glycosylation may be tissue specific; therefore, it was important to examine the utility of the peptide-directed antibodies in paraffin-fixed tissues and survey the prevalence of MUC16 expression. The three candidate antibodies, 4H11, 9C9 and 4A5, were characterized using OVCAR3 cell line pellets. Of the three, the 4H11 antibody showed the strongest, most diffuse and consistent staining pattern at multiple dilutions, with the least amount of background staining and, therefore, was optimized for use in human tissues in the pathology core facility.

Using 4H11, the inventors stained and scored positivity using tissue microarrays from high-stage, high-grade ovarian serous carcinomas (FIG. 2), these tumors being the most common type of ovarian cancer, representing approximately 80-85% of all ovarian carcinomas in Western industrialized nations (25). To test the specificity of the novel antibody, the inventors also stained tissue microarrays of cancers of the prostate, lung, breast, and pancreas and compared their staining intensities with that of OC125 monoclonal antibody (FIG. 6A-D). To determine whether there would be any cross-reactivity with normal human tissues, the antibodies were also tested on normal human adult and fetal TMAs.

All of the stained sections were reviewed by a reference pathologist (KJP). A subset of cores for which there was equivocal staining was also independently scored by a second pathologist (RAS) to ensure consistency in scoring methods. Only cytoplasmic and/or membranous staining was considered positive. If a portion of the cell showed membranous staining, that was considered partial staining. A scoring system was devised to provide a semiquantitative assessment of staining distribution and intensity in individual cores. At the same time, it was designed to be useful for comparing the staining distribution and intensity between OC125 and the novel antibodies. The score incorporated the percentage of cells, the intensity and pattern of the staining according to the following standards: score 0: no staining; score 1: <5% strong or weak; score 2: 5-50% strong or weak; score 3: 51-75% strong or 51-100% weak; score 4: 76-99% strong; and score 5: 100% strong staining (FIG. 3A-FIG. 3L). The pathologist first reviewed all tissue microarrays stained with OC125 and scored each core. Then the same cores stained with the novel antibodies were scored 1 to several days after OC125 without reference to the previous results. Direct comparison of the scoring between the stains for each core was made only after all of the scoring was completed. The same process was used for all non-ovarian tissue microarrays. After comparison, core staining was determined to be concordant, equivocal, or discordant based on the point differentials. Concordant cores differed by 0 to 1 point, equivocal cores differed by 2 points, and discordant cores differed by 3 to 5 points. The one exception to this rule was when the difference of 1 point was between a score of 0 and 1, in which case, the differences were considered equivocal. This was in order to truly separate negative cases from even focally positive ones.

Example 2

Generation and Characterization of Anti-MUC16 Monoclonal Antibodies

MUC16-directed monoclonal antibodies were isolated by ELISA-based screening using both the individual peptides and recombinant GST-$\Delta$MUC16$^{114}$ protein followed by sequential subcloning for single cell clones.

Tables 1A and 1B: MUC16-carboxyterminus monoclonal antibodies showing their reactivity to GST-$\Delta$MUC16$^{c114}$ western, FACS analysis on OVCAR3 wild type cells

TABLE 1A

| Peptide 1 | | | | Peptide 2 | | | | Peptide 3 | | | |
|---|---|---|---|---|---|---|---|---|---|---|---|
| ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype | ELISA Hybridoma Sups (1:1) | (1:10) GST MucCD Western +/− | (1:1) OVCAR3 FACS +/− | Isotype |
| 10A2 | + | − | IgG1, IgM | 13H1 | Weak | − | IgG1 | 22E10 | + | − | IgG2b |
| 23D4 | − | − | missing | 28F8 | + | + | IgG1, IgM | 22F11 | Weak | − | IgM |
| 2F4 | Weak | − | IgG1, IgM | 11B6 | − | − | IgM | 19G4 | Weak | − | IgG1, IgM |
| 9B11 | Weak | +/− | IgG1 | 4C7 | + | − | IgG1 | 31A3 | Weak | − | IgG1 |
| 23D3 | Weak | + | IgG1, IgG2 | 28F7 | + | + | IgG1 | 4C2 | + | − | IgG1, IgM |
| 30B1 | − | − | IgG1 | 9C7 | + | + | IgG1 | 27G4 | + | − | IgM |
| 31B2 | + | − | IgM | 9C9 | + | + | IgG1, IgG2b | 19D1 | + | − | IgG2b |
| | | | | 4H11 | + | + | IgG2b, IgM | 22F1 | + | − | IgG2b, IgM |
| | | | | 4A2 | − | − | IgG1 | 4D7 | + | − | IgG3 |
| | | | | 4A5 | + | + | IgG1 | 9A5 | − | − | IgM |
| | | | | 29G9 | + | − | IgG1 | 31C8 | − | − | IgG2b |
| | | | | 5C2 | + | + | IgG1 | 6H2 | Weak | − | IgG1, IgM |
| | | | | 23G12 | − | − | IgG1, IgG2a | 10F6 | − | − | IgG1 |
| | | | | 25G4 | − | − | IgG1, IgM | 3H8 | + | − | IgG1, IgM |
| | | | | 26B2 | + | + | IgG1, IgG2b, IgM | 24G12 | − | − | IgG1, IgM |
| | | | | 25H3 | − | − | IgG1, IgM | | | | |

TABLE 1B

| Peptide 1 | | | Peptide 2 | | | Peptide 3 | | |
|---|---|---|---|---|---|---|---|---|
| | OVCAR3 FACS +/− | Isotype | | OVCAR3 FACS +/− | Isotype | | OVCAR3 FACS +/− | Isotype |
| 9B11.20.16 | +/− | IgG1 | 9C9.21.5.13 | + | IgG2b | 31A3.5.1 | − | IgG1 |
| | | | 4H11.2.5 | + | IgG2b | | | |
| | | | 9C7.6 | + | IgG1 | | | |
| | | | 5C2.17 | + | IgG1 | | | |
| | | | 4A5.37 | + | IgG1 | | | |
| | | | 28F7.18.10 | + | IgG1 | | | |

TABLE 2

| Antibodies specific for exemplary portions of MUC16 | | |
|---|---|---|
| 1. Muc16 Polypeptide 1: | | |
| 14394 | 14410 | (MUC16 sequence) |
| NFSPLARRVDRVAIYEE (SEQ ID NO: 01) | | 17 aa |
| Mouse monoclonals which are specific to this peptide are: | | |
| 9B11.20.16 (IgG1) | | |

TABLE 2-continued

| Antibodies specific for exemplary portions of MUC16 | | |
|---|---|---|
| 10A2 (IgG1, IgM) | | |
| 2F4 (IgG1, IgM) | | |
| 23D3 (IgG1, IgG2b) | | |
| 30B1 (IgG1) | | |
| 31B2 (IgM) | | |
| 2. Muc16 Polypeptide 2: | | |
| 14425 | 14442 | (MUC16 sequence) |
| TLDRSSVLVDGYSPNRNE (SEQ ID NO: 02) | | 18 aa |
| Mouse monoclonals which are specific to this peptide are: | | |
| 4H11.2.5 (IgG2b) | 13H1 (IgG1) | 29G9 (IgG1) |
| 9C9.21.5.13 (IgG2b) | 28F8 (IgG1, IgM) | 23G12 (IgG1, IgG2a) |
| 9C7.6 (IgG1) | 11B6 (IgM) | 25G4 (IgG1, IgM) |
| 5C2.17 (IgG1) | 4C7 (IgG1) | 26B2 (IgG1, IgG2b, IgM) |
| 4A5.37 (IgG1) | 4A2 (IgG1) | 25H3 (IgG1, IgM) |
| 28F7.18.10 (IgG1) | | |
| 3. Muc16 Polypeptide 3 (SEQ ID NO: 03) | | |
| 14472 | 14492 | (MUC16 sequence) |
| <u>CGVL</u>VTTRRRKKEGEYNVQQQ | | 21 aa |
| Mouse monoclonals which are specific to this peptide are: | | |
| 31A3.5.1 (IgG1) | 19D1 (IgG2b) | 10F6 (IgG1) |
| 22E10 (IgG2b) | 22F1 (IgG2b, IgM) | 3H8 (IgG1, IgM) |
| 22F11 (IgM) | 4D7 (IgG3) | 24G12 (IgG1, IgM) |
| 19G4 (IgG1, IgM) | 9A5 (IgM) | |
| 4C2 (IgG1, IgM) | 31C8 (IgG2b) | |
| 27G4 (IgM) | 6H2 (IgG1, IgM) | |
| 14452 | 14475 | |
| <u>FWAVILIGLAGLLGLITCLICGVL</u> (SEQ ID NO:14) is Transmembrane region | | 24 aa |
| 4. Muc16 Polypeptide 4 (SEQ ID NO: 15) containing a cysteine loop polypeptide (SEQ ID NO: 19): | | |
| 14367 | 14398 | (MUC16 sequence) |
| KSYFSD<u>CQVSTFRSVPNRHHTGVDSLC</u>NFSPL (SEQ ID NO: 15)<br>S-S | | 32 aa |
| Mouse monoclonals which are specific to this peptide are: | | |
| 24B3 (IgM) | | |
| 9C7 (IgM) | | |
| 4F12 | | IgM kappa |
| 6H6 | | IgM kappa |
| 25C2 | | IgM kappa |
| 6E8 | | IgM kappa |
| 2A3 | | IgM, IgG1, IgG2b, kappa |
| 2G4 | | IgM, IgG1, kappa |
| 4C8 | | IgM, kappa |
| 2A6 | | IgG1 kappa |
| 24G12 | | IgG1 kappa |
| 15D5 | | IgG1 kappa |
| 6E2 | | IgM, IgG1, IgG3, IgG2a, kappa |
| 7E6 | | IgM, kappa, lambda |
| 7G11 | | IgM kappa |

TABLE 2-continued

| Antibodies specific for exemplary portions of MUC16 | |
|---|---|
| 20C3 | IgG1, IgG2b |
| 9A3 | IgM kappa |
| 15B6 | IgM kappa |
| 19D3 | IgM kappa |
| 5H8 | IgM, IgG1, IgG2b, kappa |
| 24A12 | IgM kappa |
| 2D10 | IgG3, IgM kappa |
| 5B2 | IgM, IgG3, IgG2b, IgG2a, IgG1, kappa |
| 8B6 | IgG2a, IgG3, kappa |
| 5A11 | IgM, kappa |
| 7D11 | light kappa only |
| 9F10 | IgM, kappa |
| 15D10 | IgM, kappa |
| 18D2 | IgM, kappa |
| 13A11 | IgM, kappa |
| 1A9 | IgM, kappa |
| 3B2 | IgM, kappa |
| 24F6 | IgM, kappa |
| 24E4 | IgM, kappa |
| 5A1 | IgG2a, IgM, kappa |
| 7B9 | IgM, kappa |
| 22F4 | IgM, kappa |

The identified monoclonal antibodies are listed in Table 1A and Table 2. Each of the selected monoclonal antibodies was reactive against GST-ΔMUC16$^{c114}$. The commercial MUC16-directed antibodies (OC125, M11, or VK8) did not bind to GST-ΔMUC16$^{c114}$ in ELISA or Western blotting. The clones were tested in FACS against OVCAR3 ovarian cancer cells and in Western blot analysis against GST-ΔMUC16$^{c114}$ (Table 1B), and selected purified monoclonal antibodies were isolated.

The inventors used the OVCAR3 wild type and the SKOV3 cells transduced with phrGFP-ΔMUC16$^{c114}$ to characterize the selected antibodies by FACS analysis. All of the selected monoclonal antibodies bound to both cell lines while commercial VK8, M11 and OC125 antibodies bound to the OVCAR3 cells but not to the SKOV3-phrGFP-ΔMUC16$^{c114}$ cell line. The antibodies against Polypeptide 3 required permeabilization since it is an internal epitope (FIGS. 7A-7F).

Figure 4A:
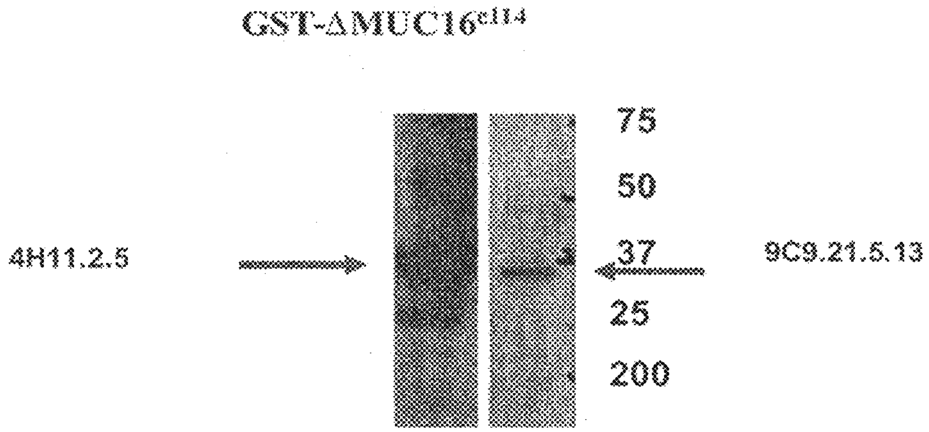
FIG. 4A and FIG. 4B: Western blot analysis.
Figure 4B:
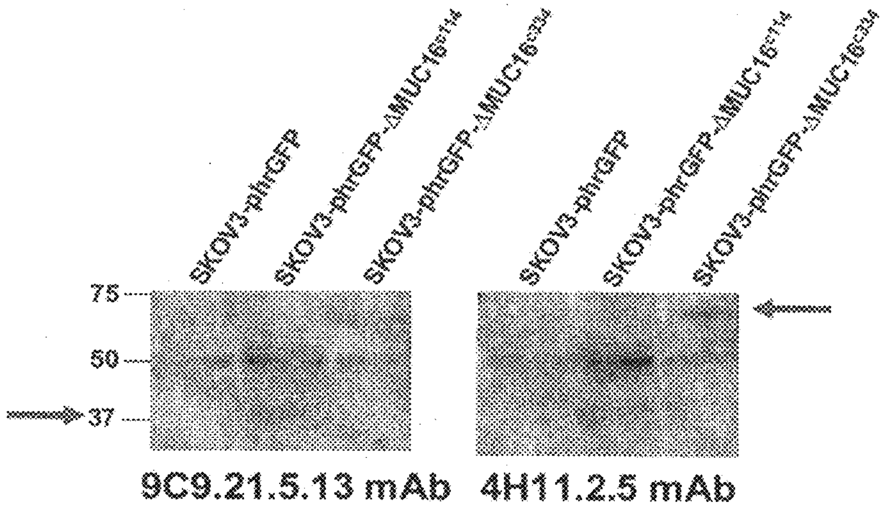

Western blot analysis using the GST-ΔMUC16$^{c114}$ purified protein showed strong binding with 4H11 and 9C9 antibodies (FIG. 4A), while the other selected antibodies showed less binding. The SKOV3-phrGFP-ΔMUC16$^{c114}$ transfectant was also positive by Western blot analysis using 4H11 and 9C9 antibodies (FIG. 4B). As before, the commercial antibodies did not interact with the GST- $\Delta MUC16^{c114}$ purified protein or cell lysates of the SKOV3-phrGFP-$\Delta MUC16^{114}$ cell line.

The binding of six monoclonal antibodies against OVCAR3 MUC16 were examined in affinity binding studies. Three antibodies—9C7, 5C2 and 28F7—showed only modest levels of binding compared to the nonspecific binding of these antibodies to the OVCAR3 cells, which carry large numbers of MUC16 binding sites. In contrast, 4H11, 9C9, and 4A5 monoclonal antibodies showed highly specific binding affinity, as shown in FIGS. 5A-5D, with binding affinities of 6.8-8.6 nM against the cell surface epitopes of OVCAR3 cells. The inventors also examined the internalization of antibody bound to cell surface MUC16 protein. The inventors examined internalization in the transfected SKOV3-phrGFP-$\Delta MUC16^{c334}$ cell line which bears the carboxy terminus of MUC16, including the 4H11 epitope and a single degenerate tandem repeat sequence to interact with the OC125 antibody. The commercial antibodies OC125, M11, and VK8 all bind to the cell surface of this transduced cell line. The $^{131}I$-labeled 4H11 showed rapid internalization at a high level, whereas $^{131}I$-labeled OC125 antibody was internalized at a much lower rate (FIG. 5E).

Example 3

Immunohistochemistry Results:

Given their highly specific binding affinities, the antibodies 9C9, 4A5, and 4H11 were characterized for utility in immunohistochemistry using OVCAR3 cell lines. Of the three, the 4H11 antibody was selected to be optimized for use in human tissues based on its robust, sensitive and specific staining pattern as compared to the other two antibodies.

A. Ovary

Two high-stage, high-grade ovarian serous carcinoma tissue microarray slides composed of 419 cores, representing primary, metastatic and recurrent tumors from 40 patients were stained with both OC125 and 4H11 monoclonal antibodies (FIG. 2). The OC125 tissue microarrays showed 279 (66%) cores with 3-5 staining, 99 (24%) with 1-2 staining, and 41 (10%) with no staining. The 4H11 tissue microarrays showed 236 (56%) with 3-5 staining, 91 (22%) with 1-2 staining, and 92 (22%) with no staining. The two antibodies were concordant in 233 (56%) cores, equivocal in 161 (38%), and discordant in 25 (6%). Of the 25 discordant cores, 12 (48% of discordant cases, 3% of all cases) showed greater 4H11 positivity than OC125. Nine were discordant by a difference of 4 points, and 3 were discordant by a difference of 5 points. There was a total of 186 discordant and equivocal cores together, 48 (26%) of which showed greater staining with 4H11 than OC125. The staining pattern of both 4H11 and OC125 was cytoplasmic and membranous, although the membranous pattern of OC125 was stronger and better defined than 4H11 in the majority of cases. Discordant cases demonstrated higher levels of 4H11 than other cases.

B. Breast Cancer

A variety of other tissues were also examined for 4H11 staining to test the antibody's specificity. Of the 50 cores of invasive ductal carcinomas of the breast (number of patients unavailable), only 2 (4%) showed a score of 4 or greater 4H11 staining and none had scores of 3-5 for OC125 staining. The staining pattern with OC125 was mostly apical/luminal with some granular cytoplasmic staining. Some tumors with intracytoplasmic lumina also picked up the OC125 stain. 4H11 showed a more diffuse cytoplasmic blush without membranous accentuation.

In contrast, the invasive lobular breast carcinoma tissue microarray (composed of 179 cores with viable tumor, number of patients unavailable) had frequent MUC16 staining with 4H11. In this tissue microarray, 168 cores (94%) showed no staining for OC125, 5 (3%) showed 1-2 staining, and only 6 (3%) showed a staining intensity of 3. 4H11 staining was different in its distribution pattern, with 49 (27%) showing no staining, 81 (45%) showing 1-2 staining, and 49 (27%) showing 3-4 staining. Neither OC125 nor 4H11 had cores with a staining intensity of 5. The staining pattern was of cytoplasmic, luminal/membranous, or intraluminal for both OC125 and 4H11. The intraluminal pattern was strong and intense for both stains and highlighted the intracytoplasmic lumen that is commonly present in lobular carcinomas. The concordance rates were 34% concordant, 43% equivocal, and 23% discordant. Of the equivocal and discordant cases, there was none in which the OC125 was greater than the 4H11. All 42 discordant cases and 76 of 77 equivocal cases had 4H11 greater than OC125. There was also focal luminal staining with 4H11 in benign breast ducts and lobular carcinoma in situ.

C. Lung, Pancreatic and Prostatic Adenocarcinomas

Tumors from other organs were not reactive with either antibody. The lung adenocarcinoma TMA had 237 cores from 86 patients containing viable tumor. In the pancreatic TMA there were 92 cores from 21 patients containing pancreatic mucinous tumors, including intraductal papillary mucinous neoplasms (IPMN) and invasive ductal carcinomas. In the prostate cancer TMA there were 169 cores (number of patients not available). None of these cancer tissue microarrays had significant binding to either OC125 or 4H11. This information is summarized in Table 3.

TABLE 3

Staining intensity of OC125 as compared to 4H11 in tissue microarrays

| | OC125 vs. 4H11 staining intensity score (%) Site | | | | | |
|---|---|---|---|---|---|---|
| | 0 | | 1-2 | | 3-5 | |
| | OC125 | 4H11 | OC125 | 4H11 | OC125 | 4H11 |
| Ovary high grade serous | 10 | 28 | 24 | 22 | 66 | 56 |
| Breast invasive ductal | 68 | 78 | 32 | 18 | 0 | 4 |
| Breast invasive lobular | 94 | 27 | 3 | 45 | 3 | 27 |
| Lung adenocarcinoma | 63 | 77 | 24 | 18 | 13 | 5 |
| Pancreas mucinous neoplasms | 98 | 88 | 2 | 10 | 0 | 2 |
| Prostate adenocarcinoma | 0 | 0 | 0 | 0 | 0 | 0 |

Score 0: 0% staining; 1: <5% strong or weak; 2: 5-50% strong or weak; 3: 51-75% strong or 51-100% weak; 4: 76-99% strong; 5: 100% strong D. Normal Tissues There was no staining with OC125 or 4H11 in normal adult colon, rectum, ectocervix, small intestine, ovary, liver, pancreatic ducts, spleen, kidney, and skin. OC125 and 4H11 both stained endocervical glands (OC125 luminal, 4H11 weak cytoplasmic), esophageal glands (luminal), bronchial epithelium (OC125 luminal, 4H11 intracytoplasmic granules), and thymic corpuscles (cytoplasmic). 4H11 demonstrated weak to moderate staining of the gastric glands, particularly at the crypts, with an intracytoplasmic granular pattern. Other organs that showed punctuate intracytoplasmic staining with 4H11 only were prostate, seminiferous tubules of the testes, and the islet cells of the pancreas. The staining in the pancreatic islets cells was particularly strong and consistent. There was also nonspecific staining of liver, kidney and brain with 4H11. There were no cases that stained with OC125 and not 4H11.

Similarly, there was no staining with either OC125 or 4H11 in fetal heart, gallbladder, colon, small intestine, liver, rectum, adrenal, thyroid, spleen, skin, bone, epididymis, brain, lung, muscle, smooth muscle, kidney, eye, umbilical cord, and placenta. OC125 only stained thymic corpuscles in a pattern similar to that in adult tissue. 4H11 stained both fetal pancreatic endocrine cells and endocervical glands in a similar pattern to that of their adult counterparts. Islet cells showed a granular cytoplasmic pattern, and endocervical glands showed a linear luminal pattern, which was more similar to the OC125 pattern in the adult tissue.

Example 4

Successful Eradication of Established Peritoneal Ovarian Tumors in SCID-Beige Mice Following Adoptive Transfer of T Cells Genetically Targeted to the MUC16 Antigen.

Purpose:

Most patients diagnosed with ovarian cancer will ultimately die from their disease. For this reason, novel approaches to the treatment of this malignancy are needed. Adoptive transfer of a patients own T cells, genetically modified ex vivo through the introduction of a gene encoding an chimeric antigen receptor (CAR), an artificial T cell receptor, targeted to a tumor associated antigen, is a novel and promising approach to cancer therapy applicable to the treatment of ovarian cancer.

Experimental Design:

We have generated several CARs targeted to the retained extracellular domain of MUC16, termed MUC-CD, an antigen highly expressed on a majority of ovarian carcinomas. We investigate the in vitro biology of human T cells retrovirally transduced to express these CARs by co-culture assays on artificial antigen presenting cells (AAPCs) generated from NIH3T3 fibroblasts genetically modified to express the target MUC-CD antigen, as well as by cytotoxicity assays utilizing the human OV-CAR3(MUC-CD) ovarian tumor cell line and primary patient tumor cells. Finally, we assess the in vivo anti-tumor efficacy of MUC-CD targeted T cells in a SCID-Beige orthotopic, xenogeneic OV-CAR3(MUC-CD) murine tumor model.

Exemplary sequences used in this work are in FIG. 17-19.

Results:

CAR modified MUC-CD targeted T cells derived from both healthy donors and ovarian cancer patients exhibited efficient in vitro cytolytic activity against both human ovarian cell lines as well as primary ovarian carcinoma cells. MUC-CD targeted T cells may be further expanded ex vivo through multiple cycles of co-culture on 3T3(MUC-CD/B7.1) AAPCs. Expanded MUC-CD targeted T cells infused into SCID-Beige mice bearing intraperitoneal human OV-CAR3(MUC-CD) tumors either delayed progression or fully eradicated tumor even in the setting of advanced disease.

Conclusion:

These promising pre-clinical studies justify further investigation of MUC-CD targeted T cells as a potential therapeutic approach in the clinical setting treating patients with high risk MUC-16$^+$ ovarian carcinomas.

Introduction

Ovarian cancer is the sixth most common cancer worldwide and the seventh leading cause of cancer-related deaths in women (1, 2). Despite multimodality therapy with surgery and chemotherapy, most patients with ovarian carcinomas have a poor prognosis. For this reason, alternative approaches to treating this disease are urgently needed.

Infusion of a patient's own T cells genetically targeted ex vivo to antigens expressed on the surface of tumor cells is a promising novel approach to the adoptive immunotherapy of cancer, and one which has only recently been explored in earnest in the clinical setting. T cells may be genetically modified to target tumor associated antigens through the retroviral introduction of genes encoding artificial T cell receptors termed chimeric antigen receptors (CARs). Genetic engineering of T cells to express artificial T cell receptors that direct cytotoxicity toward a tumor cell presents a means to enhance immune recognition and elimination of cancer cells. CARs are most commonly composed of a single chain fragment length antibody (scFv), derived from a murine monoclonal antibody targeting a given tumor associated antigen, fused to a transmembrane domain (typically CD8, CD28, OX-40, and 4-1BB), fused to the TCR ζ chain cytoplasmic signaling domain (3-13). When used to reprogram T-cell specificity, these fusion receptors permit recognition of native antigen. When expressed by the T cells, the resulting construct, upon engagement with the targeted antigen, induces T cell activation, proliferation, and lysis of targeted cells. These fusion receptors transduce a functional antigen-dependent co-stimulatory signal in primary T cells, permitting sustained T-cell proliferation when both endogenous TCR and a chimeric receptor for stimulatory signaling are engaged. To date, preclinical studies utilizing CAR-modified T cells have demonstrated promising results in a wide variety of malignancies (3, 4, 11, 14-18). More recently this approach been investigated clinically in the form of phase I trials (6, 19-21). These genetic approaches offer a means to enhance immune recognition and elimination of cancer cells.

Ovarian carcinomas appear to be relatively immunogenic tumors capable of inducing an endogenous immune response based on the fact that long-term prognosis of patients is markedly influenced by the degree and quality of the endogenous immune response to the tumor. Specifically, it has been well documented that the presence of endogenous effector T cells within the ovarian cancer tumor microenvironment directly correlates to prolonged patient survival (22-25). In contrast, increasing numbers of immune suppressive CD4$^+$ CD25$^{hi}$ regulatory T cells (Tregs) within the tumor, which in turn presumably abrogate the anti-tumor activity of infiltrating effector T cells, correlates with shorter patient survival (26-29). In fact, it appears that it is the ratio of Tregs to effector T cells within the tumor microenvironment which ultimately dictates whether the endogenous immune response to the cancer is of benefit or detriment to the patient (24, 28). In this setting, the ability to generate and subsequently expand a population of tumor targeted effector T cells ex vivo which are subsequently infused back into the patient, may in turn skew the Treg to effector T cell ratio to one more favorable to eradicating the disease.

Mucins are important biomolecules for cellular homeostasis and protection of epithelial surfaces. Changes to expression of mucins in ovarian cancer might be exploited in diagnosis, prognosis and treatment (1). MUC16 is one such mucin which is over expressed on most ovarian carcinomas and is an established surrogate serum marker (CA-125) for the detection and progression of ovarian cancers (30-33). MUC16 is a high-glycosylated mucin composed of a large cleaved and released domain, termed CA-125, consisting of multiple repeat sequences, and a retained domain (MUC-CD) which includes a residual non-repeating extracellular fragment, a transmembrane domain, and a cytoplasmic tail (34). Since the antigen is otherwise only expressed at low levels in the uterus, endometrium, fallopian tubes, ovaries, and serosa of the abdominal and thoracic cavities, MUC16 is a potentially attractive target for immune-based therapies.

However, the fact that most of the extracellular domain of MUC16 is cleaved and secreted limits the utility of MUC16 as a target antigen on ovarian carcinomas. In fact, to date, all reported MAbs to MUC16 bind to epitopes present on the large secreted CA-125 fraction of the glycoprotein, with none known to bind to the retained extra-cellular fraction (MUC-CD) of the antigen (35-37). Since the MUC-CD fraction of the antigen is retained on cell surface, generating T cells specific to this portion of MUC16 may largely overcome the limitation of MUC16 as a target for adoptive cellular immunotherapy. To this end, we have previously generated a series of murine MAbs specific to the retained MUC-CD extracellular domain (38). Utilizing a hybridoma which expresses one such MAb, 4H11, we have successfully constructed several CARs specific to the MUC-CD antigen. This invention provides a nucleic acid encoding a chimeric T cell receptor, composed of, at least a zeta chain, a signaling region and a binding element that specifically interacts with a selected target as well as the chimeric T cell receptor comprising a zeta chain portion, a signaling region and a binding element.

In this report, we demonstrate highly efficient retroviral transduction of these MUC-CD targeted CARs into human T cells with resulting T cells able to specifically target and lyse MUC-CD$^+$ tumor cells in vitro. Furthermore, we demonstrate efficient MUC-CD targeted T cell expansion in vitro through repeated co-culture on NIH (3T3) fibroblasts genetically modified to express MUC-CD and the co-stimulatory ligand B7.1 (CD80). Successful expansion of modified T cells allowed us to subsequently generate sufficient T cell numbers to conduct in vivo studies in immune compromised SCID-Beige mice bearing established intraperitoneal MUC-CD$^+$ human ovarian tumors. Significantly, in these studies we demonstrate marked anti-tumor efficacy of MUC-CD targeted T cells, both following direct intraperitoneal as well as intravenous injection when compared to either untreated mice, or mice treated with T cells bearing a CAR targeted to an irrelevant antigen. In addition, we demonstrate significant cytotoxicity of 4H11-28z$^+$ patient's T cells and healthy donor's T cells targeting primary ascites-derived ovarian carcinoma cells from cancer patients.

To our knowledge this is the first report wherein T cells genetically targeted to the MUC16 antigen demonstrate marked anti-tumor efficacy against MUC16$^+$ tumors either in vitro or in vivo. These data serve as a rationale for proposing future clinical trials utilizing this approach in patients with high risk ovarian carcinomas.

Materials and Methods

Cell Lines and T Cells

The OV-CAR3 tumor cell line was cultured in RPMI 1640 (Invitrogen, Grand Island, N.Y.) supplemented with 10% heat-inactivated FBS, nonessential amino acids, HEPES buffer, pyruvate, and BME (Invitrogen). The PG13 and gpg29 retroviral producer cell lines were cultured in DMEM (Invitrogen) supplemented with 10% FCS, and NIH-3T3 artificial antigen-presenting cells (AAPC), described previously (3), were cultured in DMEM supplemented with 10% heat-inactivated donor calf serum. T cells were obtained from peripheral blood of healthy donors under IRB approved protocol #95-054, in BD Vacutainer CPT tubes (Becton Dickinson, Franklin Lakes, N.J.) as per the manufacturers instructions. All media were supplemented with 2 mmol/L L-glutamine (Invitrogen), 100 units/mL penicillin, and 100 μg/mL streptomycin (Invitrogen). T cells were cultured RPMI 1640 media as above supplemented with 20 IU/ml IL-2 (Novartis Pharmaceuticals, East Hanover, N.J.) and where indicated, medium was supplemented with 10 ng/mL interleukin 15 (R&D Systems, Minneapolis, Minn.).

Isolation of Patients Ascites-Derived Cancer Cells

Primary human ascites-derived cancer cells were obtained from ovarian cancer patients undergoing surgery for newly diagnosed advanced serous ovarian carcinoma under IRB approved protocol #97-134. The tumor cells were isolated from ascitic fluid of patients by centrifugation at 600 g for 10 min at room temperature. Cells were washed once with 1×PBS and cultured in RPMI 1640 media supplemented with 10% FBS for future analysis.

Generation of the MUC-CD Targeted 4H11z and 4H11-28z CARs

The heavy and light chain variable regions of the 4H11 monoclonal antibody were derived from the hybridoma cell line 4H11. Utilizing cDNA generated from 4H11 RNA we isolated the $V_H$ coding region by RACE PCR utilizing modified primers as described elsewhere (39, 40). The $V_L$ chain variable region was cloned by standard PCR utilizing modified primers as described by Orlandi et al (41, 42). The resulting $V_H$ and $V_L$ fragments were subcloned into the TopoTA PCR 2.1 cloning vector (Invitrogen) and sequenced. The $V_H$ and $V_L$ fragments were subsequently ligated to a $(Gly_4Ser)_3$ spacer domain, generating the 4H11 scFv and fused to the human CD8 leader peptide (CD8L) by overlapping PCR (9, 41). In order to construct the MUC-CD targeted 4H11 CARs, the coding region of the CD8L-4H11 scFv was fused to the human CD8 hinge and transmembrane domains (to generate the 4H11z CAR), or alternatively to the CD28 transmembrane and cytoplasmic signaling domains (to generate the 4H11-28z CAR), fused to the T cell receptor CD3ζ-signaling domain (3, 9, 43). The resulting CAR constructs were subsequently sub-cloned into the modified MMLV retroviral vector SFG (44). VSV-G preudotyped retroviral supernatants derived from transduced gpg29 fibroblasts were used to construct stable PG13 gibbon ape leukemia virus (GaLV) envelope-pseudotyped retroviral producing cell lines (41).

Retroviral Gene Transfer

Isolated healthy donor peripheral blood mononuclear cells (PBMCs) were activated with phytohemagglutinin (PHA) at 2 μg/ml (Sigma. St. Louis, Mo.) and retrovirally transduced on retronectin coated non-tissue culture plates (45). Briefly, six-well non-tissue culture plates (BD Biosciences, San Jose, Calif.) were coated with RetroNectin (RN) (Takara Biomedicals, Otsu, Japan) as per manufacturer's instructions. Forty-eight hours after PHA activation, aliquots of $1\times10^6$ T cells in 1 ml of supplemented RPMI medium were placed in each well of the RN-coated plates, along with 1 ml of SFG retroviral supernatant. T cells were centrifuged daily for 3 consecutive days with fresh retroviral supernatant added daily at 2000 g at 30° C. for 1 hr (45). Gene transfer was assessed on day 7 by FACS.

In order to generate the relevant NIH-3T3 murine fibroblast artificial antigen presenting cells, a MUC-CD construct encoding the retained extracellular, transmembrane and cytoplasmic domains of the MUC-16 antigen was initially subcloned into SFG retroviral vector, SFG(MUC-CD). 3T3 (MUC-CD) AAPCs were generated by retroviral transduction of SFG(MUC-CD) into wild-type NIH-3T3 fibroblasts, while 3T3(MUC-CD/B7.1) AAPCs were generated by retroviral transduction of previously established 3T3(B7.1) fibroblasts (41, 46). Highly enriched cell lines were isolated by FACS.

To generate the OV-CAR3(MUC-CD) and OV-CAR3 (MUC-CD/GFP-FFLuc) cell lines, we retrovirally transduced the WT OV-CAR3 human ovarian cancer cell line with SFG(GFP-FFLuc) as described previously (47) and/or SFG(MUC-CD) VSV-G pseudotyped retroviral supernatants derived from gpg29 fibroblasts as described elsewhere (44). Resulting tumor cells were sorted by FACS for either MUC-CD expression alone for the OVCAR3(MUC-CD) cell line, or dual MUC-CD and GFP expression for the OVCAR3(MUC-CD/GFP-FFLuc) cell line. MUC-CD expression by FACS was assessed using the 4H11 MAb.

In Vitro Analyses of $CAR^+$ Human T Cells

To assess in vitro expansion and cytokine release upon stimulation, transduced T cells were co-cultured for 7 days after retroviral transduction in 6-well tissue culture plates (BD Biosciences) on confluent NIH 3T3 AAPCs in RPMI medium supplemented with 10% FBS in the absence of supplemented cytokines. In order to generate sufficient numbers of CAR-modified T cells for in vivo studies, transduced T cells were co-cultured on $B7.1^+$ AAPCs (3T3(MUC-CD/B7.1)) in RPMI medium supplemented with 20 IU IL-2/mL and 10 ng/mL IL-15 as described previously (3, 43). Patients T cells were activated and expanded with human CD3/CD28 beads (DYNAL®, Invitrogen, Carlsbad, Calif.) following manufacturer's recommendations.

Western Blot Analysis of CAR Expression

Western blot analysis of T-cell lysates under reducing conditions with 0.1 mol/L DTT (Sigma) was performed as previously described (46). Briefly, transduced T cells were washed in PBS and resuspended in radioimmunoprecipitation assay (RIPA) buffer (Boston BioProducts, Worcester, Mass.) with mini complete protease inhibitor as per the manufacturer's instructions (Roche Diagnostics, Indianapolis, Ind.). Resulting proteins were separated on 12% SDS-PAGE mini gels (Bio-Rad, Hercules, Calif.) after the addition of 6× reducing loading buffer (Boston BioProducts, Worcester, Mass.) and heating at 100° C. for 10 min. Separated proteins were subsequently transferred to Immobilon membranes and probed using an anti-human CD3C chain monoclonal antibody (BD Biosciences). Antibody binding was detected by probing the blot with goat anti-mouse horse radish peroxidase-conjugated antibody followed by luminescent detection using Western Lighting Chemiluminescence Reagent Plus (Perkin-Elmer Life Sciences, Boston, Mass.) as per the manufacturer's instructions.

Cytotoxicity Assays

In vitro modified T cell cytotoxicity was assessed using the DELFIA® EuTDA assay (PerkinElmer LAS, Inc, Boston, Mass.) following manufacturer's recommendations. Cytotoxocity was assessed at 2 hours at effector T cell to target OV-CAR3(MUC-CD) or primary tumor cells (E:T) at indicated ratios. Effector T cells in these assays represent the number of $CD8^+$ $CAR^+$ T cells.

Cytokine Detection Assays

Cytokine assays were performed as per manufacturer's specifications using a multiplex Human Cytokine Detection assay to detect IL-2 and IFNγ (Millipore Corporation, Billerica, Mass.) utilizing the Luminex IS 100 system. Cytokine concentrations were assessed using IS 2.3 software (Luminex Corp., Austin, Tex.).

In Vivo SCID-Beige Mouse Tumor Models

In all in vivo studies, 8-12 week-old FOX CHASE C.B.-17 (SCID-Beige mice) (Taconic, Hudson, N.Y.) were initially injected ip with either $3\times10^6$ OV-CAR3(MUC-CD), or for bioluminescent imaging (BLI) studies $3\times10^6$ OV-CAR3(MUC-CD/GFP-FFLuc) tumor cells. Subsequently, $3\times10^7$ $CAR^+$ T cells were injected ip or iv on day 1 or 7 following tumor injection as indicated. Mice were monitored for distress as assessed by increasing abdominal girth, ruffled fur, and decreased response to stimuli. Distressed mice were euthanized. All murine studies were done in context of an Institutional Animal Care and Use Committee-approved protocol (#00-05-065).

Bioluminescent Imaging (BLI) of OVCAR3(MUC-CD/GFP-FFLuc) Tumor Cells in SCID-Beige Mice BLI was performed using Xenogen IVIS imaging system with Living Image software (Xenogen; Alameda, Calif.). Briefly, OVCAR3(MUC-CD/GFP-FFLuc) tumor bearing mice were injected by ip with D-luciferin (150 mg/kg; Xenogen) suspended in 200 μl PBS and imaged under 2% isoflurane anesthesia after 10 min. Image acquisition was done on a 25-cm field of view at medium binning level for 0.5-min exposure time (3, 43).

Flow Cytometry

All flow cytometric analyses of T cells and tumor cells was performed using a FACScan cytometer with Cellquest software (BD Biosciences). T cells were analyzed using CAR-specific polyclonal goat Alexa Fluor 647 antibody (Molecular probes, Eugene, Oreg.) phycoerythrin-labeled anti-human CD4, CD8, B7.1 (Caltag Laboratories, Burlingame, Calif.), B7.2 (Invitrogen, Camarillo, Calif.), 4-1BBL, and OX40 antibodies (Ancell Corporation, Bayport, Minn.). 3T3(MUC-CD) and OV-CAR3(MUC-CD) cells were stained with Alexa Fluor 647 labeled 4H11 antibody (generated and labeled in the MSKCC monoclonal antibody core facility).

CFSE Labeling of $CAR^+$ T Cells $CAR^+$ T cells were stained with CFSE using the CellTrace™ CFSE cell proliferation kit following manufacturer's recommendations (Molecular Probes, Eugene, Oreg.). Proliferation of CFSE labeled T cells was analyzed by FACS. For detection of CFSE labeling T cells in vivo, ovarian tumors were macerated through 40 μm cell strainer (BD Falcon, Franklin Lakes, N.J.) and washed twice with 2% FBS/PBS before antibody staining and FACS analysis.

Statistics

Survival data assessed by log-rank analysis using GraphPad Prism software (GraphPad Prism software, San Diego, Calif.). Cytokine data were analyzed by Student's one-tailed t-test.

Results

Figure 11:
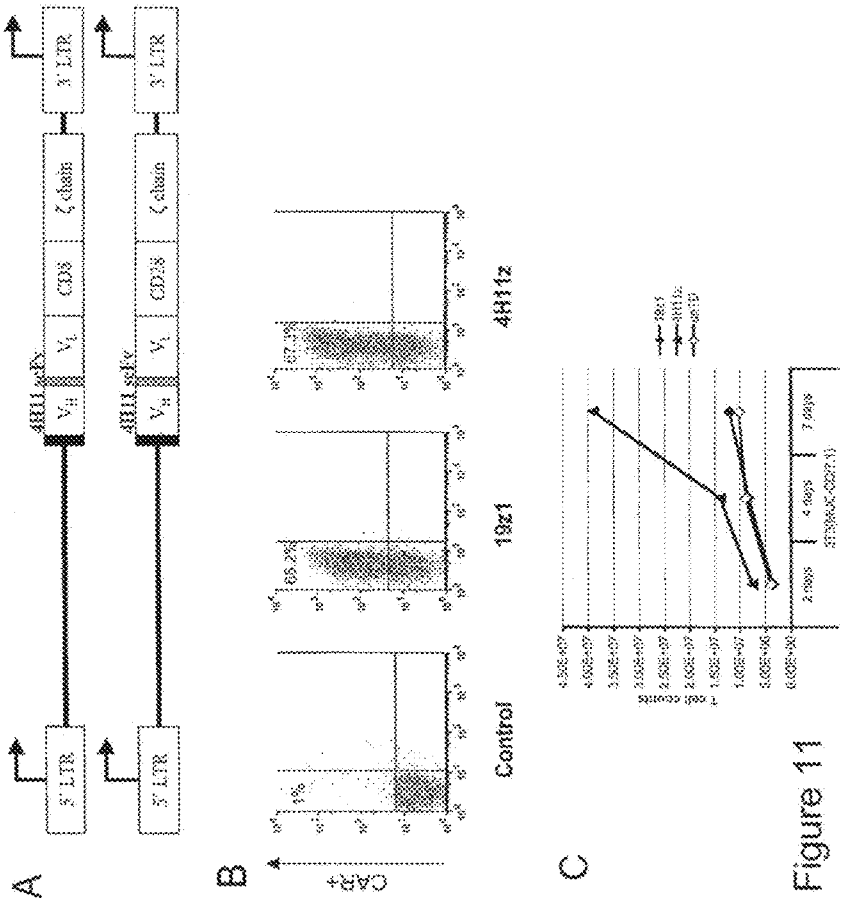
FIG. 11. Design and in vitro analysis of MUC-CD targeted CARs. (A) Schematic diagram of the first generation 4H11z and second generation 4H11-28z retroviral vectors. 4H11scFv: MUC16 specific scFv derived from the heavy ($V_H$) and light ($V_L$) chain variable regions of the monoclonal antibody 4H11; CD8: CD8 hinge and transmembrane domains; CD28: CD28 transmembrane and cytoplasmic signaling domains; ζ chain: T cell receptor ζ chain cytoplasmic signaling domain; LTR: long terminal repeat; black box: CD8 leader sequence; grey box: $(Gly_4Ser)_3$ linker; arrows indicate start of transcription. (B) FACS analysis of human T cells retrovirally transduced to express either the 4H11z or 19z1 CAR. (C) 4H11z$^+$ but not 19z1$^+$ T cells expand on 3T3(MUC-CD/B7.1) AAPC. CAR$^+$ were co-cultured on 3T3(MUC-CD/B7.1) AAPC monolayers at $3\times10^6$ CAR$^+$ T cells/well of a 6 well plate. Proliferation of CAR$^+$ T cells, normalized to the CAR$^+$ T cell fraction as assessed by FACS for the CAR$^+$ fraction in combination with viable T cell counts obtained on days 2, 4 and 7, as assessed by trypan blue exclusion assays.

We have constructed SFG retroviral vectors encoding first (4H11z) and second generation (4H11-28z) CARs targeted to the MUC-CD antigen using the 4H11 hybridoma which generates a MAb specific to the MUC-CD antigen (FIG. 11A). We confirmed expression of appropriately sized CAR proteins by Western blot analysis of resulting PG-13 retroviral producer cells (SFG-4H11z and SFG-4H11-28z) probed with a ζ-chain specific antibody (data not shown).

In order to assess the function of the first generation 4H11z CAR, healthy donor T cells isolated from peripheral blood were retrovirally transduced to express the 4H11z and control 19z11 CARs (FIG. 11B). Function of the 4H11z CAR was assessed by proliferation of 4H11z transduced T cells following co-culture on 3T3(MUC-CD/B7.1) AAPCs. Results demonstrate specific proliferation of 4H11z transduced T cells, when compared to 19z11 modified T cells (FIG. 11C). These data are consistent 4H11z CAR mediated specific binding to the MUC-CD antigen and subsequent T cell activation.

Figure 12:
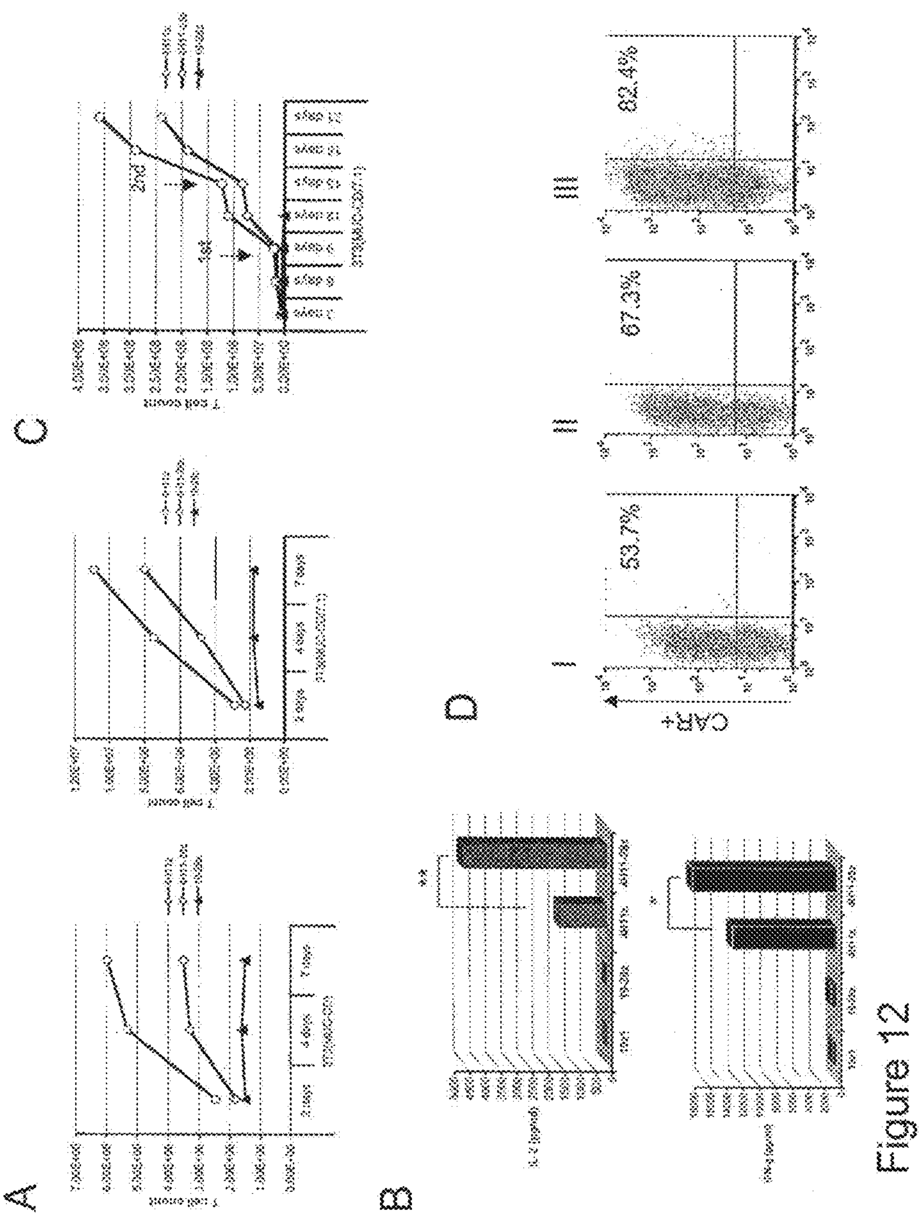
FIG. 12. In vitro comparison of T cells modified to express the first generation 4H11z CAR to T cells modified to express the second generation co-stimulatory 4H11-28z CAR. (A) CAR$^+$ T cells were co-cultured on MUC-CD monolayers with (right panel) or without B7.1 (left panel). $3\times10^6$ CAR$^+$ T cells were co-cultured on AAPC monolayers in 6 well tissue culture plates in cytokine-free medium. Total viable T cells counts were assessed on days 2, 4 and 7, by trypan blue exclusion assays. 4H11-28z$^+$ T cells markedly expanded when compared to 4H11z$^+$ T cells upon co-culture with 3T3(MUC-CD) AAPCs, p=0.0023 (4H11z compared to 4H11-28z). In contrast, both 4H11z$^+$ and 4H11-28z$^+$ T cells expanded similarly on 3T3(MUC-CD/B7.1) AAPCs, p=0.09, (4H111z compared to 4H11-28z). Control 19-28z$^+$ T cells did not proliferate on 3T3(MUC-CD), p=0.0056 (19-28z compared to 4H11z), p=0.0011 (19-28z compared to 4H11-28z), or on 3T3(MUC-CD/B7.1), p=0.0026 (19-28z compared to 4H11z), p=0.0087 (19-28z compared to 4H11-28z). (B) 4H11-28z$^+$ but not 4H11z$^+$ T cells secrete IL-2 upon co-culture with 3T3(MUC-CD) AAPCs. Tissue culture supernatants at day 2 following activation on 3T3(MUC-CD) AAPCs were analyzed for cytokine secretion. 4H11-28z$^+$ T cells, in contrast to 4H11z$^+$ T cells, demonstrated enhanced secretion of IL-2 consistent with T cell co-stimulation mediated through the 4H11-28z CAR. *p=0.0008 (19z11 or 19-28z compared to 4H11z), p=0.0026 (19z11 or 19-28z compared to 4H11-28z), p=0.0046 (4H11z compared to 4H11-28z). Furthermore, both 4H11-28z$^+$ and 4H11z$^+$ T cells secreted IFNγ. *p=0.011 (4H11z compared to 4H11-28z). Control 19z11 and 1928z transduced T cells failed to secrete either IL-2 or IFNγ. p=0.0034 (19z11 compared to 4H11z), p=0.036 (19-28z compared to 4H11z), ***p=0.0008 (19-28z compared to 4H11-28z). (C) Expansion of CAR$^+$ T cells following 3 cycles of stimulation on 3T3(MUC-CD/B7.1). Human T cells transduced to express either 4H11z or 4H11-28z CARs demonstrated a >2 log expansion over 2 cycles of stimulation on 3T3(MUC-CD/B7.1) AAPCs. Arrows indicate 1st and 2nd cycles of restimulation on AAPCs. (D) FACS analysis of the CAR$^+$ T cell fraction of 4H11-28z$^+$ T cells increased following each weekly cycle of stimulation. (I) FACS following initial transduction, (II) FACS at 7 days following first stimulation on AAPCs, (III) FACS at 7 days following second stimulation on AAPCs. These data are representative of one of three different experiments using three different healthy donor T cell populations, all of which demonstrated similar proliferation and cytokine secretion patterns.

Since most malignancies fail to express co-stimulatory ligands, we further modified the 4H11z CAR to express the CD28 transmembrane and cytoplasmic co-stimulatory signaling domains, constructing the second generation 4H11-28z CAR (FIG. 11A). To assess whether the 4H11-28z CAR, when expressed by human T cells, was capable of generating both a primary activating signal (termed "signal 1") through the ζ chain, as well as a co-stimulatory signal (termed "signal 2") through the CD28 cytoplasmic domain, which in turn allows for efficient T cell proliferation in the absence of exogenous co-stimulatory ligands, we compared T cell proliferation following co-culture on either 3T3(MUC-CD) or 3T3(MUC-CD/B7.1) AAPCs in the absence of exogenous cytokines. As expected, the second generation 4H11-28z$^+$ T cells markedly expanded when compared to 4H11z$^+$ T cells upon co-culture with 3T3(MUC-CD) AAPCs. In contrast, both 4H11z$^+$ and 4H11-28z$^+$ T cells expanded similarly on 3T3(MUC-CD/B7.1) AAPCs (FIG. 12A). Co-stimulation mediated by the 4H11-28z CAR was further verified by analysis of day 2 tissue culture supernatants from co-culture experiments on 3T3(MUC-CD) AAPCs demonstrating enhanced IL-2 secretion, a cytokine typically secreted in the context of T cell co-stimulation, when compared to control 19z1+ and 19-28z$^+$ T cells and first generation 4H11z$^+$ T cells (FIG. 12B). Secretion of IFNγ was comparable between 4H11z$^+$ and 4H11-28z$^+$ activated T cells.

We next assessed the ability of MUC-CD targeted T cells to expand following weekly re-stimulations through co-culture on 3T3(MUC-CD/B7.1) AAPCs in the context of exogenous IL-2 and IL-15 (3). Both 4H11z$^+$ and 4H11-28z$^+$ T cells expanded greater than 2 logs over 3 weeks (FIG. 12C). T cells transduced with the 4H11-28z were further analyzed by FACS for CAR expression 7 days after initial activation on AAPCs and following two subsequent co-stimulations on AAPCs demonstrating an expected enrichment of the CAR$^+$ T cell fraction (FIG. 12D). Similar data was generated with expanded 4H11z$^+$ T cells (data not shown).

In Vitro Cytotoxicity and Proliferation of MUC-CD Targeted T Cells Following Co-Culture with OV-CAR3(MUC-CD) and Freshly Isolated Ascites Derived Ovarian Tumor Cells.

Figure 13:
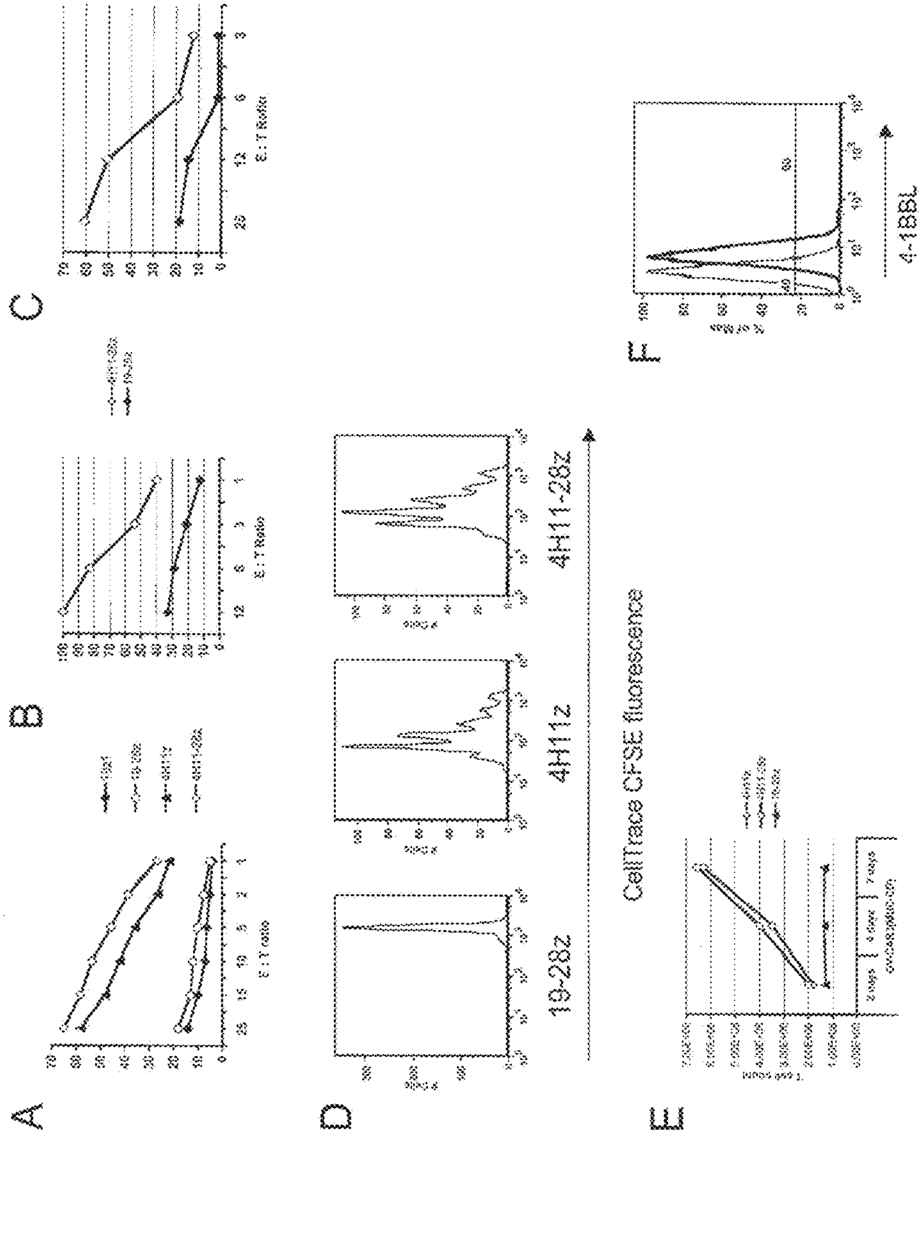
FIG. 13. MUC-CD targeted T cells specifically expand and lyse MUC-CD$^+$ tumor cells. (A) Cytotoxicity assay of 4H11z$^+$ and 4H11-28z$^+$ T cells targeting OV-CAR(MUC-CD) tumor cells demonstrates efficient cytotoxicity mediated by T cells from healthy donors modified to express the first and second generation MUC-CD targeted CARs. Control T cells modified to express the first and second generation CD19-targeted 19z11 and 19-28z CARs failed to demonstrate significant lysis of target tumor cells. (B) Healthy donor T cells modified to express the 4H11-28z CAR equally lyse primary patient ascites-derived MUC-CD$^+$ tumor cells when compared to T cells modified to express the control 19-28z CAR. This data represents 1 or 3 experiments targeting primary tumor cells from 3 ovarian carcinoma patients with similar results. (C) Autologous T cells isolated from peripheral blood, when modified with the 4H11-28z CAR, exhibit significant lysis of autologous MUC-CD$^+$ ascites-derived tumor cells when compared to control 19-28z$^+$ autologous T cells. These data represent 1 of 3 experiments utilizing T cells and autologous tumor cells from 3 different ovarian carcinoma patients with similar results. (D) Antigen specific proliferation of MUC-CD targeted CFSE labeled T cells after co-culture with OV-CAR3 (MUC-CD) tumor cells. CFSE labeled CAR$^+$ T cells were co-cultured with MUC-CD expressing OV-CAR3 tumor cells at 1:1 ratio for 5 days. Proliferation of CFSE labeled T cells was assessed by FACS demonstrating efficient proliferation of both 4H11z$^+$ and 4H11-28z$^+$ T cells but not control 19-28z$^+$ T cells. (E) CFSE results were further confirmed by absolute T cell numbers assessed on days 2, 4 and 7 following co-culture with OV-CAR3(MUC-CD) tumor cells. (F) FACS analysis of the expression of 4-1BBL on OVCAR3(MUC-CD) cells. OV-CAR3(MUC-CD) cells were stained with anti-human 4-1BBL antibody (thick line) or with isotype control (thin line). FACS analysis demonstrated expression of 4-1BBL on OV-CAR3(MUC-CD) tumor cells. Further FACS analyses failed to reveal expression of the co-stimulatory ligands B7.1, B7.2, or OX-40L.

In order to assess the ability of 4H11z$^+$ and 4H11-28z$^+$ T cells to target and lyse human ovarian carcinoma tumors, we utilized the human OV-CAR3 cell line which was genetically modified to express the MUC-CD antigen thereby better reflecting the majority of clinical ovarian tumor samples which express the 4H11-targeted MUC-CD antigen (48). We initially verified specific lysis by MUC-CD targeted T cells demonstrating similar significant cytotoxic activity of 4H11z and 4H11-28z CAR modified T cells targeting OV-CAR3(MUC-CD) tumor cells when compared control T cells expressing the irrelevant first and second generation CD19-targeted 19z1 and 1928z CARs (FIG. 13A). Healthy donor T cells modified to express the 4H11-28z CAR similarly exhibited lysis of freshly isolated ascites derived MUC-CD$^+$ ovarian carcinoma cells when compared to 19-28z transduced T cells (FIG. 13B). Moreover, patient's peripheral blood T cells modified to express the 4H11-28z CAR similarly lysed autologous primary MUC-CD$^+$ tumor cells derived from the same ascites sample when compared to T cells modified to express the control 19-28z CAR (FIG. 13C).

We further assessed the ability of 4H11z$^+$ and 4H11-28z$^+$ T cells from healthy donors to proliferate following co-culture on OV-CAR3(MUC-CD) as assessed by FACS of CFSE labeled T cells, as well as absolute T cells numbers over 7 days following co-culture with tumor (FIGS. 13D and E). Surprisingly, we found that both 4H11z$^+$ and 4H11-28z$^+$ T cells expanded equally well following co-culture with OV-CAR3(MUC-CD) tumor cells suggesting the ability of this tumor cell line to co-stimulate T cells through expression of a co-stimulatory ligand. To address this possibility, we conducted further FACS analyses of OV-CAR3(MUC-CD) tumor cells demonstrating expression of the co-stimulatory 4-1BBL ligand (FIG. 13F), but not the B7. 1, B7.2, or OX-40L co-stimulatory ligands (data not shown).

In Vivo Anti-Tumor Activity of MUC-CD Targeted T Cells in SCID-Beige Mice.

Figure 14:
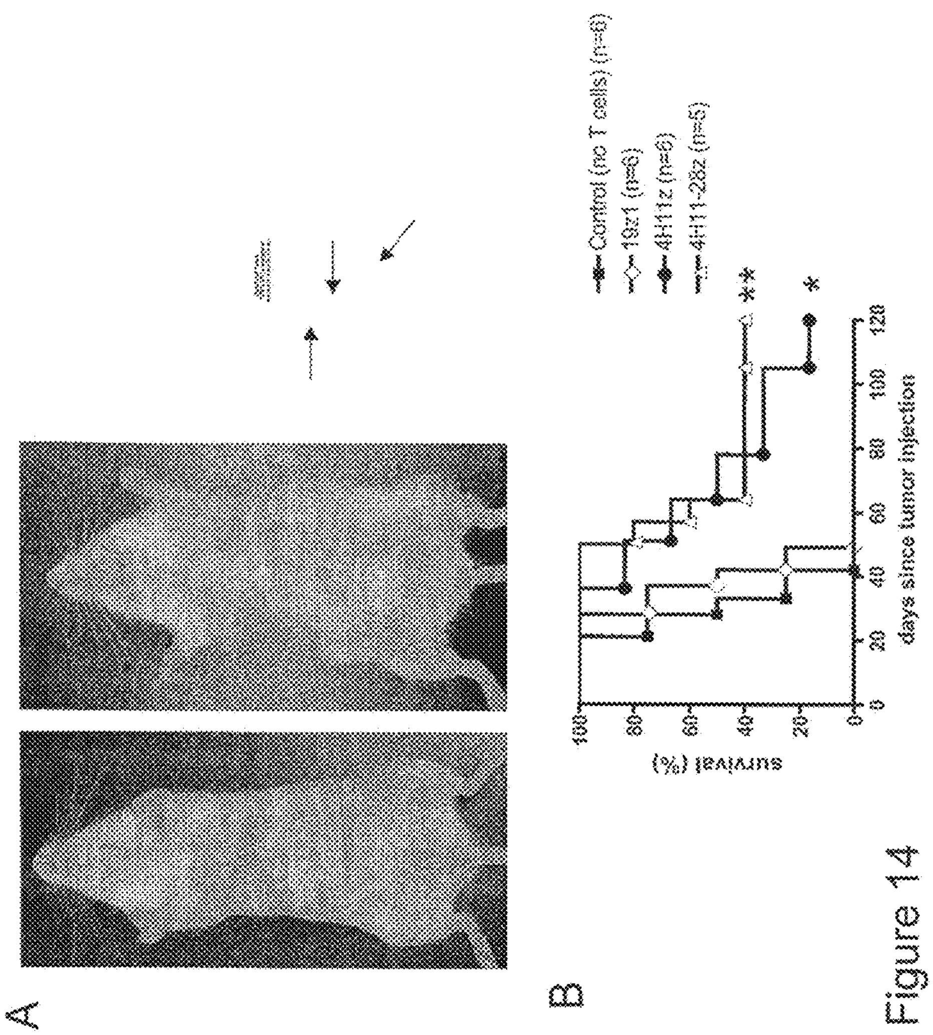
FIG. 14. Eradication of OV-CAR3(MUC-CD) tumors after intra-peritoneal treatment with first and second generation of MUC-CD targeted T cells. (A) Intraperitoneal injection of OV-CAR3(MUC-CD) tumors in untreated SCID-Beige mice results in abdominal distension and nodular peritoneal tumors. SCID-Beige mice were injected intraperitoneally with $3\times10^6$ OV-CAR3(MUC-CD) cells. At 5 weeks post intraperitoneal injection of OV-CAR3(MUC-CD) tumor cells mice developed ascities as evidenced by a distended abdomen (center panel) when compared to a tumor free mouse (left panel). Post mortem visualization of the peritoneum demonstrates nodular tumor masses (arrows) within the abdominal cavity (right panel). (B) Intraperitoneal injection of 4H11z$^+$ and 4H11-28z$^+$ T cells either delay tumor progression or fully eradicate disease. Kaplan-Meier survival curve of SCID-Beige mice treated with first or second generation of MUC-CD targeted T cells. SCID-Beige mice were infused ip with $3\times10^6$ OV-CAR3(MUC-CD) tumor cells on day 1 followed by $3\times10^7$ 4H11z$^+$ or 4H11-28z$^+$ T cells on day 2. All untreated mice or mice treated with control 19z1$^+$ T cells developed established tumors and were sacrificed by day 50. In contrast, 27% of mice treated with either 4H11 z$^+$ or 4H11-28z$^+$ T cells remained without clinical evidence of disease by day 120. *p=0.01 (4H11z compared to 19z11), **p=0.0023 (4H11-28z compared to 19z11), p=0.63 (4H11z compared to 4H11-28z).

To assess the in vivo anti-tumor activity of 4H11z$^+$ and 4H11-28z$^+$ T cells, we next generated an orthotopic xenotransplant ovarian cancer tumor model by ip injection of OV-CAR3(MUC-CD) tumor cells into SCID-Beige mice. If left untreated, these mice developed marked ascites and multiple nodular peritoneal tumors by 3 weeks following tumor cell injection (FIG. 14A). All untreated tumor bearing mice had to be euthanized by 7 weeks following tumor cell injection due to evidence of distress.

To assess the in vivo anti-tumor efficacy of MUC-CD-targeted T cells, SCID-Beige mice were injected ip with OV-CAR3(MUC-CD/GFP-FFLuc) tumor cells on day 1 followed by ip injection of 4H11z$^+$ or 4H11-28z$^+$ T cells on day 2. For negative controls, tumor bearing mice were either untreated or treated with T cells modified to express the irrelevant CD19-targeted CAR. Collectively, we found that 27% of all mice treated with MUC-CD targeted T cells (3/11 mice) remained alive without clinical evidence of disease 120 days out from tumor injection with no statistically significant difference in survival when comparing the 4H11z$^+$ and 4H11-28z$^+$ T cell treated cohorts (FIG. 14B). In contrast, both MUC-CD-targeted T cell treated cohorts demonstrated statistically significant enhanced survival when compared to untreated and 19z1$^+$ T cell treated control cohorts.

Figure 15A:
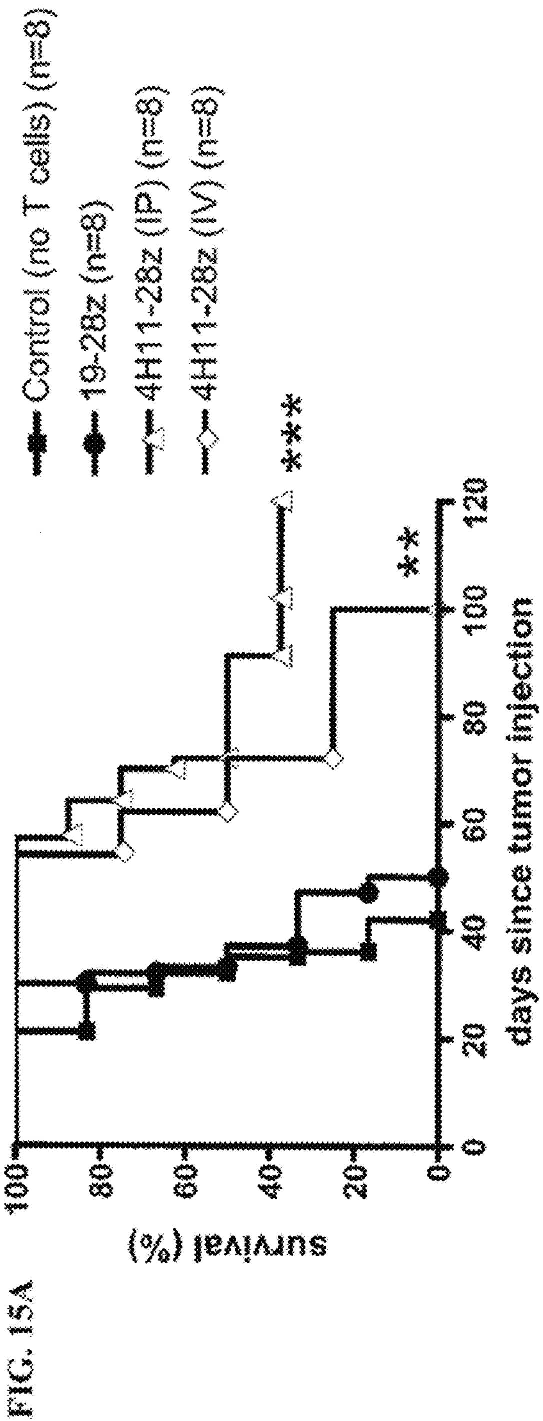
FIGS. 15A-15C: MUC-CD targeted 4H11-28z$^+$ T cells successfully traffic to ip OV-CAR3(MUC-CD/GFP-FFLuc) tumors following systemic intravenous infusion resulting in equally efficient anti-tumor efficacy when compared to ip 4H11-28z$^+$ treated tumor bearing mice.
Figure 15B:
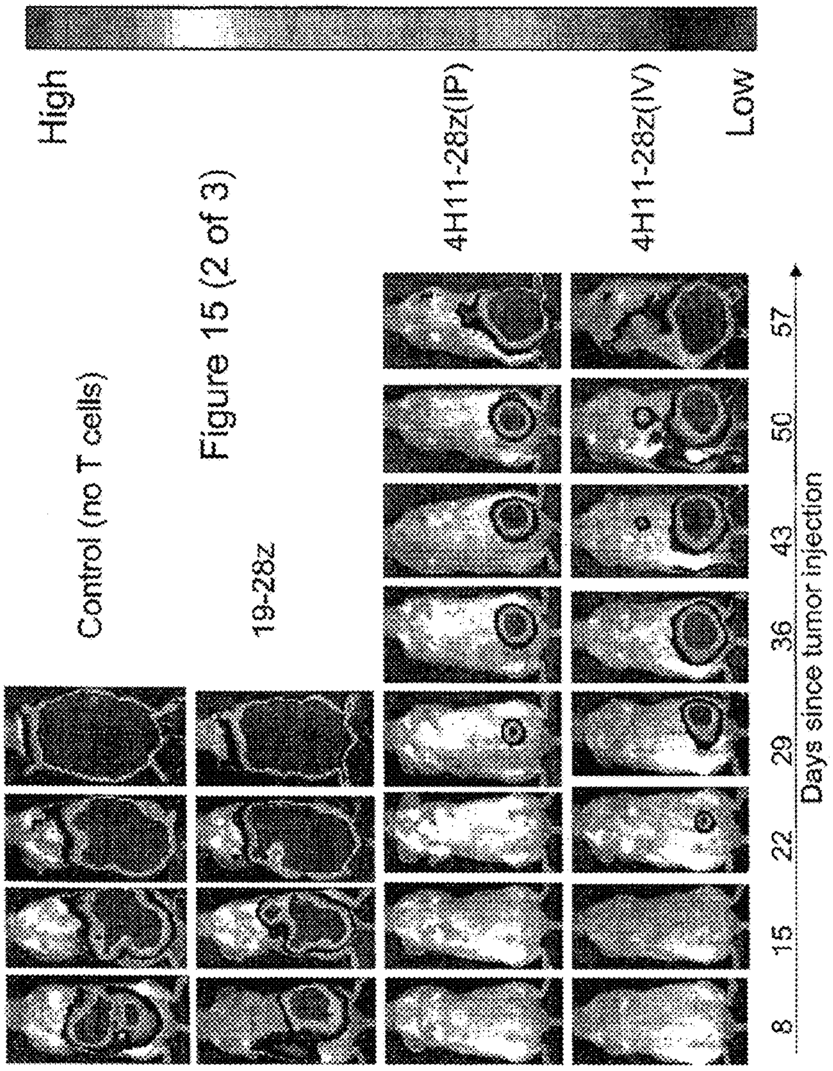
Figure 15C:
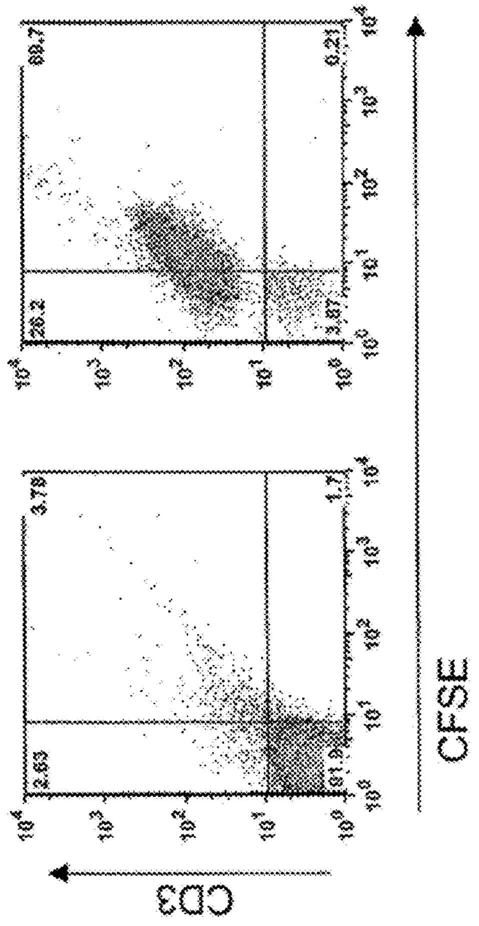

To assess whether systemically infused MUC-CD-targeted T cells successfully traffic to ip tumors, we next compared ip to iv infusion of 4H11-28z$^+$ T cells in SCID-Beige mice bearing ip OV-CAR3(MUC-CD/GFP-FFLuc) tumors. Both ip and iv 4H11-28z$^+$ T cell treated mice exhibited statistically enhanced survival when compared to untreated or 19-28z$^+$ T cell treated control cohorts as assessed by overall survival (FIG. 15A) as well as by BLI of tumor progression (FIG. 15B). Furthermore, we found overall survival between the ip and iv treated groups to be statistically equivalent by log rank analysis. These data imply successful trafficking of iv infused 4H11-28z$^+$ T cells to peritoneal tumors. We further confirmed trafficking of iv infused CFSE labeled 4H11-28z$^+$ T cells to the peritoneum by FACS analysis of single cell suspensions of macerated OV-CAR3(MUC-CD) tumors (FIG. 15C).

In Vivo Anti-Tumor Activity of MUC-CD Targeted T Cells in SCID-Beige Mice Bearing Well Established OV-CAR3(MUC-CD/GFP-FFLuc) Tumors.

Figure 16A:
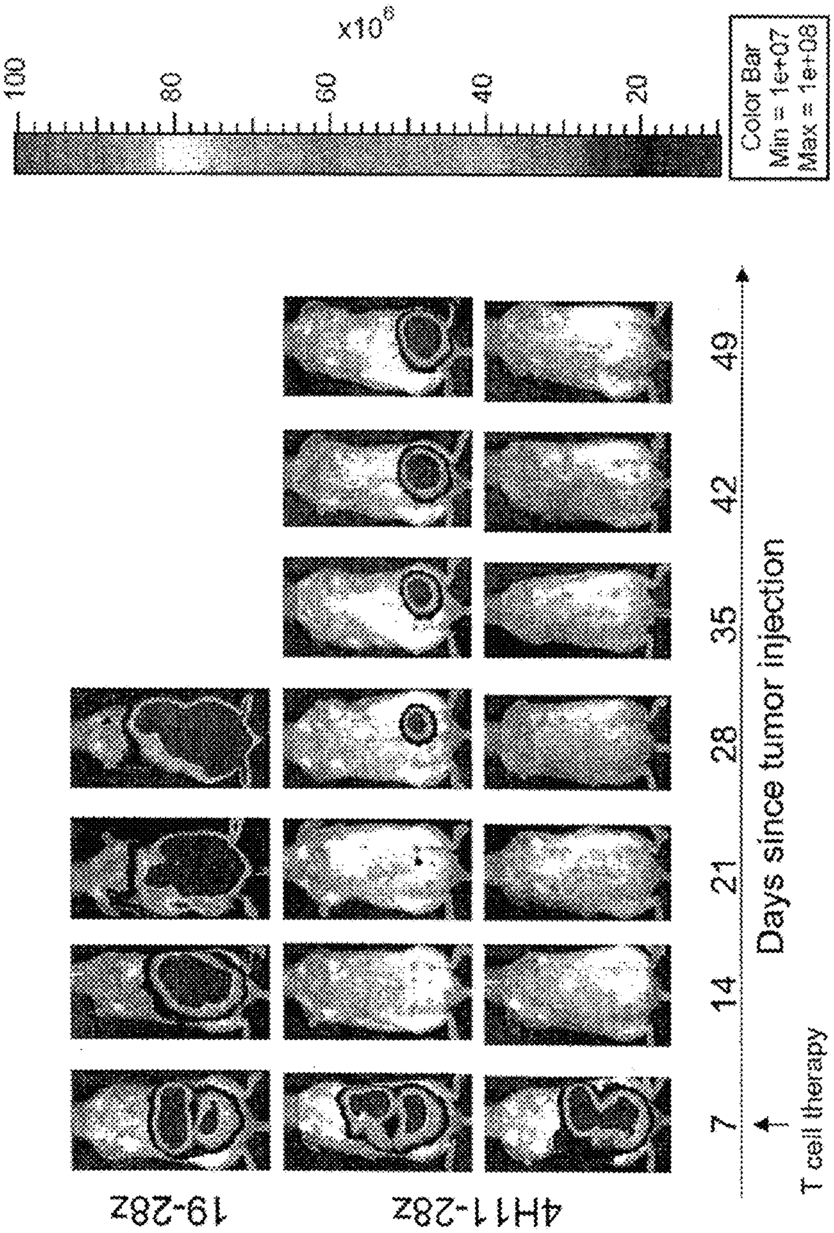
FIGS. 16A-16B. Eradication of advanced OV-CAR3 (MUC-CD) tumors in SCID-Beige mice by ip infusion of 4H11-28z$^+$ T cells. SCID-Beige mice were injected ip with 3x10$^6$ OV-CAR3(MUC-CD/GFP-FFLuc) tumor cells 7 days prior to ip treatment with 3x10$^7$ 4H11-28z$^+$ T cells.
Figure 16B:
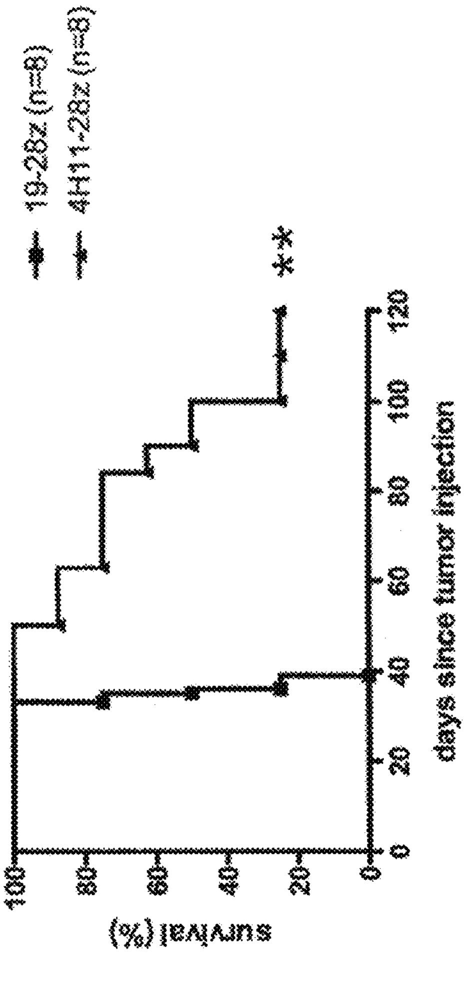

To further assess whether 4H11-28z$^+$ T cells were able to eradicate more clinically relevant tumor burdens, we next treated SCID-Beige mice bearing well established ip OV-CAR3(MUC-CD/GFP-FFLuc) tumor injected 7 days prior to adoptive T cell therapy. Once more, we found that therapy with MUC-CD targeted T cells markedly eradicated BLI evident disease in all treated mice (FIG. 16A) with 5 of 8 treated mice eventually developing relapsed progressive disease, and 3 mice remaining disease free as assessed by BLI imaging (not shown) out to 120 days post-tumor cell infusion (FIG. 16B). These data demonstrate potent in vivo anti-tumor activity mediated by MUC-CD targeted T cells even in the setting of advanced disease.

Discussion

Based on extensive analyses of patient tumor samples, ovarian carcinomas appear to be relatively immunogenic tumors. Specifically, researchers have found there to be a direct correlation between prognosis following surgery and chemotherapy and the quantity of tumor infiltrating effector T cells (TILs) in pretreatment tumor samples (25, 49, 50). Furthermore, others have described an inverse correlation between prognosis following therapy and pre-treatment levels of Tregs within the tumor, which in turn presumably inhibit the anti-tumor function of tumor specific effector TILs (26, 28, 51). Both of these findings imply a role for an endogenous effector T cell response to tumor in controlling disease progression both prior to and following initial therapy and strongly support the contention that ovarian carcinomas may be susceptible to killing by adoptive infusion of autologous T cells targeted to ovarian tumor cell antigens.

While endogenous effector TILs are one source for presumably tumor specific T cells, an alternative approach to adoptive T cell therapy is to isolate autologous peripheral blood T cells which in turn may be genetically modified ex vivo to target tumor cell antigens. One such genetic approach is to retrovirally transduce patient T cells with CARs targeted to surface exposed antigens either unique to or over-expressed by the tumor. To this end, promising preclinical studies utilizing this approach in other malignancies have recently been translated into the clinical setting (6, 16, 19, 52). Similarly, we have previously generated CARs targeted to the CD19 antigen expressed on normal B cells as well as most B cell malignancies and are currently conducting clinical trials treating patients with relapsed B cell chronic lymphocytic leukemia and acute lymphoblastic leukemias with autologous T cell modified to express a CD19 specific CAR (53).

Application of this approach to ovarian carcinomas requires the identification to suitable target antigens expressed on the tumor cell surface. Significantly, other investigators have studied this approach in both the preclinical and clinical setting (4, 11, 54-57). Specifically, several groups have demonstrated significant anti-tumor responses to subcutaneous human ovarian carcinoma cell line tumors in immune compromised mice following intratumoral and/or intravenous infusion of T cells expressing CARs specific to the mesothelin and Lewis-Y antigens overexpressed on these tumor cell lines (56, 58, 59). Furthermore, Kershaw et al recently published the results of a phase I clinical trial treating patients with relapsed ovarian carcinomas with autologous T cells modified to express a CAR specific to the alpha-folate receptor (6). The authors of this study found that therapy with targeted T cells was well tolerated, but noted a lack of anti-tumor response in these studies related to poor persistence of modified T cells over time as well as a yet undefined T cell inhibitory factor in the serum of several treated patients.

In our studies, we have chosen to target the MUC-16 glycoprotein which is over-expressed on a majority of ovarian carcinomas (1, 30, 32, 33). The utility of MUC-16 as a target antigen for adoptive T cell therapy is compromised by the fact that most of the extracellular portion of this molecule is cleaved by the tumor cell, secreted, and may be detected in the serum as the CA-125 tumor marker. However, following cleavage of this secreted fraction of MUC-16, there remains a residual extracellular fraction of the glycoprotein, termed MUC-CD, which is retained on the tumor surface and is therefore an attractive target for immune-based therapies. To this end, we utilized a series of murine hybridomas generated to the MUC-CD antigen to construct CARs specific to MUC-CD. Of these CARs, we identified a CAR generated from the 4H11 murine hybridoma termed 4H11z, which, when expressed in human T cells, following co-culture on 3T3(MUC-CD/B7.1) AAPCs, resulted in rapid destruction of AAPC monolayers as well as marked modified T cell expansion. Significantly, the antigen to the 4H11 antibody is highly expressed on a majority of pre-treatment ovarian carcinoma surgical tumor samples obtained from patients treated at our institution as assessed by immuno-histochemistry (48).

Optimal T cell activation requires both a primary T cell receptor mediated signal, "signal 1," along with a co-stimulatory "signal 2." Classically, this co-stimulatory signal may be provided by ligation of either B7.1 (CD80) or B7.2 (CD86) on the target cell with the T cell co-stimulatory receptor CD28. Alternatively, co-stimulation may be generated by ligation of 4-1BBL or OX-40L on the target cell with the respective 4-1BB or OX40 co-stimulatory receptors on the T cell (12, 60, 61). Since most tumor cells fail to express co-stimulatory ligands, we and others have previously demonstrated that second generation CARs further incorporating the cytoplasmic signaling domains the co-stimulatory receptors CD28, 4-1BB, and/or OX40 resulted in CARs capable of providing both signal 1 and signal 2 to the T cell upon binding to cognate antigen in the absence of exogenous co-stimulatory ligands (7-10, 12, 13, 15, 16, 62-65). To this end, we constructed a second generation CAR from the 4H11z CAR incorporating the transmembrane and cytoplasmic signaling domain of CD28 as described elsewhere (3, 9, 43). Consistent with previous studies, we found that T cells transduced to express the resulting 4H11-28z CAR, but not the first generation 4H11z CAR, efficiently expanded upon co-culture with 3T3(MUC-CD) fibroblasts in the absence of exogenous co-stimulation consistent with the ability of the 4H11-28z CAR to deliver both signal 1 and signal 2 to the T cell. This conclusion is further supported by the finding that 4H11-28z$^+$ T cells secreted significantly higher levels of IL-2, a cytokine indicative of T cell co-stimulation, upon co-culture on 3T3(MUC-CD) fibroblasts when compared to T cells transduced to express the first generation 4H11z CAR.

We next assessed the ability of 4H11z$^+$ and 4H11-28z$^+$ T cells to target and lyse human ovarian carcinoma tumor cells. To this end, we initially utilized the OV-CAR3 human ovarian cancer cell line. Since the OV-CAR3 tumor cell line binds the 4H11 antibody weakly, we further genetically modified the cell line to express MUC-CD (OV-CAR3 (MUC-CD)) to better mimic the clinical setting wherein a majority of clinical ovarian carcinoma tumor specimens highly express the 4H11 MUC-CD antigen (48). We demonstrated that human T cells modified to express either 4H11z$^+$ or 4H11-28z$^+$ eradicated OV-CAR3(MUC-CD) tumor cells in vitro, and surprisingly observed that both 4H11z$^+$ and 4H11-28z$^+$ T cells expanded following co-culture with tumor in vitro. To define the etiology of this unanticipated 4H11z$^+$ T cell expansion, we further assessed whether OV-CAR3(MUC-CD) tumor cells expressed co-stimulatory ligands, and found that this tumor cell line expressed 4-1BBL, consistent with our experimental findings as well as with previously published reports demonstrating 4-1BBL expression by a variety of carcinoma cell lines (66-68). In order to further validate the clinical relevance of these findings, we subsequently demonstrated specific in vitro lysis of primary ascites-derived tumor cells isolated from untreated ovarian carcinoma patients by both healthy donor allogeneic 4H11-28z$^+$ T cells as well as more significantly autologous 4H11-28z$^+$ patient peripheral blood T cells. These data strongly support the contention that treatment with autologous 4H11-based CAR$^+$ T cells have promise in future clinical applications.

In order to assess the in vivo relevance of our in vitro findings, we next generated a murine orthotopic OV-CAR3 (MUC-CD) tumor model in SCID-Beige mice. We injected mice i.p. with OV-CAR3(MUC-CD) tumor cells and the following day infused 4H11z$^+$, 4H11-28z$^+$, and control 19z1$^+$ T cells i.p. This treatment approach resulted in a significant but similar delay to tumor progression and long-term survival in both the 4H11z$^+$ and 4H11-28z$^+$ T cell treated cohorts when compared to untreated mice or mice treated with control T cells targeted to the irrelevant CD19 antigen. We next compared ip to iv treatment with 4H11-28z$^+$ T cells of orthotopic OV-CAR3(MUC-CD/GFP-FF-Luc) bearing mice, and found similar statistically significant survivals of mice over time with either direct ip infusion of T cells or systemic iv infusion of targeted T cells. Significantly, iv treated mice by day 1 following treatment, exhibited successful trafficking of targeted T cells to the peritoneum. These data suggests that adoptive therapy with targeted T cells may be equally efficacious following either a direct infusion into the peritoneum or through systemic iv infusion. These findings further support the future clinical potential of this approach in treating patients both with local relapse of disease as well as metastatic relapse to sites outside of the peritoneum.

Finally, we assessed the ability of 4H11-28z$^+$ T cells to eradicate more established disease by delaying modified T cell ip infusion by 7 days, when mice had greater established tumor burdens as assessed by bioluminescent imaging. This experimental setting better reflects the initial clinical setting wherein this adoptive T cell approach would be utilized. Significantly, despite the setting of markedly established disease, 4H11-28z$^+$ T cells retained the ability to lyse larger tumor burdens, delay relapse of tumor, and in a significant percentage of mice, fully eradicate disease.

In the studies presented here, we have consistently utilized mixed populations of CD4$^+$ and CD8$^+$ CAR$^+$ T cells to assess both in vitro and in vivo anti-tumor activity. To this end, ongoing studies will address the role of isolated CD4$^+$ and CD8$^+$ CAR$^+$ T cell subsets in the successful eradication of disease in this SCID-Beige OV-CAR3(MUC-CD) tumor model. The results of these studies may have implications to translating this therapeutic approach to the clinical setting. Furthermore, we acknowledge the limitations associated with the presented SCID-Beige tumor model. Namely, this is a xenotransplant model in an immune compromised mouse. To this end, ongoing studies in or laboratory are focused on generating a more clinically relevant syngeneic immune competent tumor model to better define the biology and anti-tumor efficacy of MUC-CD targeted CAR-modified T cells in the context of an intact immune system.

In conclusion, herein we present the first published data demonstrating the feasibility of targeting MUC-16, an antigen over-expressed on a majority of ovarian carcinomas, through adoptive therapy with genetically modified T cells targeted to the retained MUC-CD portion of the MUC-16 antigen. Further, this report is the first to demonstrate efficient targeting of T cells in an orthotopic, clinically relevant, murine model of ovarian cancer, demonstrating efficacy both by ip and iv infusion of modified T cells. Finally, these data support the further translation of this approach to the clinical setting in the form of a phase I clinical trial in patients with persistent or relapsed ovarian carcinomas following initial therapy with surgery and chemotherapy.

Example 5

Raising Mouse MUC16 Monoclonal Antibodies in Mice and Hamsters.

We selected 3 different regions of mouse MUC16 genome for which monoclonal antibodies were generated in mouse and hamster. The selected regions of the mouse MUC16 are Peptide 1 (SEQ ID NO:21, ecto region of cytoplasmic domain), Peptide 2 (SEQ ID NO:22, first cysteine loop) and Peptide 3 (SEQ ID NO:23, second cysteine loop) (FIG. 20A) and its comparison with human MUC16 is shown in FIG. 20B. A cysteine was added to the peptide sequence at the N terminus of Peptide 1 (SEQ ID NO:21) and Peptide 3 (SEQ ID NO:23) for better conjugation with KLH. Individual peptides were conjugated to KLH using Promega kit. These 3 conjugated peptides were pooled and immunized into 5 mice and 4 hamsters. 5 immunizations with a 3 week interval for each immunization were administered. Sera from these animals were tested by ELISA for their specific reactivity with individual peptides (SEQ ID NO:21, 22 and 23). Positive selected animals were allowed to rest for a month and then i.v. boosted with pooled peptides immunogen (SEQ ID NO:21, 22 and 23) and harvested the spleens after 4 days. Splenocytes were mixed with hybridoma partners and plated into microtiter plates at various clonal densities. Plates were cultured at 37° C. 5% $CO_2$ for 10 days and then selected the clones. Supernatants from these selected clones were tested by ELISA for their specific reactivity with individual peptides (SEQ ID NO:21, 22 and 23). Positive clonal sups were tested by FACS, western blot and imaging using 2 mouse cell lines (ID8 and BR5-FVB1) and a human cell line (OVCAR-3).

Table 4 shows the summary of mouse and hamster monoclonal antibodies against mouse MUC16 peptide antigens Peptide 1 (SEQ ID NO:21), Peptide 2 (SEQ ID NO:22), and Peptide 3 (SEQ ID NO:23). A very strong antigenic response was seen with Peptide 1 (SEQ ID NO:21).

TABLE 4

| Mouse MUC16 | Mouse mAbs | Frozen Mouse mAb |
|---|---|---|
| Peptide 1 | 46 | 16 (3-IgG1; 8-IgG2b; 1-IgM; 4-Unkown isotype) |
| Peptide 2 | 0 | 0 |
| Peptide 3 | 6 | 6 (4-IgG1; 2-IgM) |
| Peptide 1, 2, 3 | 0 | 0 |
| Peptide 1, 2 | 0 | 0 |
| Peptide 2, 3 | 0 | 0 |
| No Peptide | 0 | 0 |
| **Mouse MUC16** | **Hamster mAbs** | **Frozen Hamster mAb** |
| Peptide 1 | 69 | 21 |
| Peptide 2 | 6 | 6 |
| Peptide 3 | 7 | 7 |
| Peptide 1, 2, 3 | 2 | 1 |
| Peptide 1, 2 | 1 | 1 |
| Peptide 2, 3 | 1 | 0 |
| No Peptide | 10 | 2 |

Animals not iv boosted with peptide 2

Details of mouse and hamster mAbs against Peptide 1 (SEQ ID NO:21), Peptide 2 (SEQ ID NO:22), and Peptide 3 (SEQ ID NO:23 are listed in Table 5 and Table 6 respectively.

TABLE 5

| isotype | PEPTIDE | Fusion Well | Cloned | Clones | | | |
|---|---|---|---|---|---|---|---|
| — | 1 | 01D01 | | | | | |
| — | 1 | 09F07 | | | | | |
| IgG 1 | 1 | 16A09 | no success | | | | |
| — | 1 | 21A07 | | | | | |
| — | 1 | 24G10 | | | | | |
| IgG 1 | 1 | 10C04 | yes | 10C4-3H5 | 10C4-1F2 | 10C4-2H8 | 10C4-1G7 |
| IgG 1 | 1 | 17F02 | yes | 17F2-3G5 | 17F2-3F6 | 17F2-2F9 | 17F2-1E11 |
| IgG 2b | 1 | 01A08 | | | | | |
| IgG 2b | 1 | 01F08 | | | | | |
| IgG 2b | 1 | 12B10 | yes | 12B10-3F7 | 12B10-3G10 | 12B10-2F6 | 12B10-2F10 |
| IgG 2b | 1 | 17H10 | | | | | |
| IgG 2b | 1 | 18D05 | | | | | |
| IgG 2b | 1 | 23B12 | | | | | |
| IgG 2b | 1 | 25E09 | | 25E9-3 | 25E9-5 | 25E9-13 | 25E9-16 |
| IgM | 1 | 16F12 | | | | | |
| IgG 1 | 3 | 04A06 | no success | | | | |
| IgG 1 | 3 | 05D01 | no success | | | | |
| IgG 1 | 3 | 21B08 | yes | 21B8-1H11 | 21B8-3G6 | 21B8-3H9 | 21B8-1G8 |
| IgG 1 | 3 | 21E01 | yes | 21E1-1E3 | 21E1-1G9 | 21E1-2G7 | 21E1-3G12 |
| IgM | 3 | 08A02 | | | | | |
| IgM | 3 | 13E05 | | | | | |

TABLE 6

| Hamster mAb | Peptide | Cloned | | | |
|---|---|---|---|---|---|
| 01H03 | | | | | |
| 02F02 | 1 | | | | |
| 04E 4 | | | | | |
| 04G07 | 1 | | | | |
| 04H01 | 3 | 4H1-2E1 | 4H1-2E3 | 4H1-3E1 | 4H1-3H3 |
| 06A08 | 1 | | | | |
| 06F02 | 1 | | | | |
| 07F08 | 3 | | | | |
| 07H05 | 2 | | | | |
| 09A05 | | | | | |
| 09E 1 | 3 | | | | |
| 09F08 | 1 | | | | |
| 09H10 | | | | | |
| 10G06 | 1 | | | | |
| 10H11 | 1 | | | | |
| 11B10 | 1 | | | | |
| 12F09 | 2 | | | | |
| 15A08 | 1 | 15A8-2E2 | 15A8-2E10 | 15A8-2E11 | 15A8-3D2 |
| 15H08 | 3 | | | | |
| 19B05 | 1 | | | | |
| 21H04 | 3 | | | | |
| 22B05 | 2 | 22B5-1F6 | 22B5-3G9 | 22B5-2G8 | 22B5-3F11 |
| 22D11 | 3 | | | | |
| 23G12 | 1 | | | | |
| 25E 8 | 1 | | | | |
| 27H09 | 3 | | | | |
| 28B12 | 1&2&3 | | | | |
| 28C12 | 2 | | | | |
| 30H02 | 1 | | | | |
| 31A11 | 2 | | | | |
| 31C01 | 2 | | | | |
| 33H06 | 1&2 | | | | |
| 34F10 | 1 | | | | |
| 34H05 | 1 | | | | |
| 36C01 | 1 | | | | |
| 36C11 | | | | | |
| 36E 4 | 1 | | | | |
| 37E 10 | 1 | | | | |
| 10H11 | 1 | | | | |

Hamster antibody 22B05 recognizes mouse (SEQ ID NO:22) and also the corresponding human sequence (SEQ ID NO:15).

Figure 21:
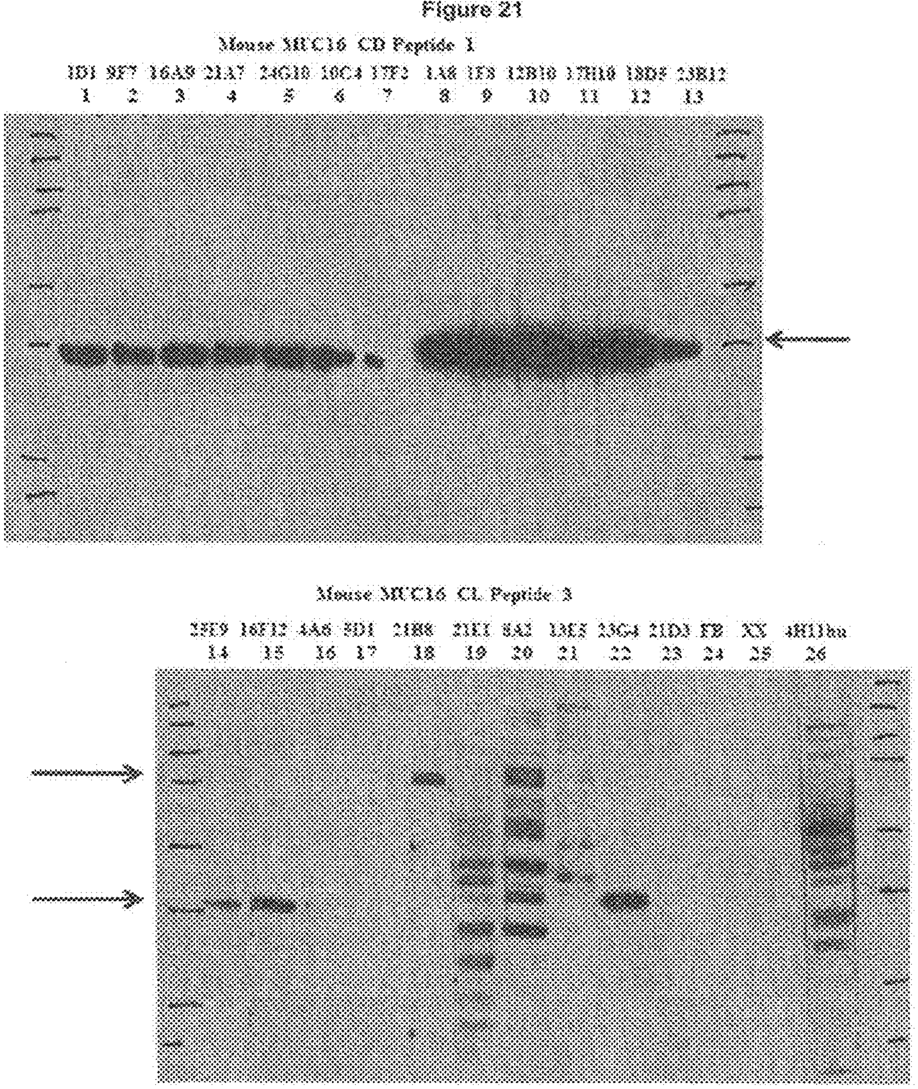
FIG. 21: ID8 extract with 1:10 dilution of Mouse MUC16 monoclonal Primary Supernatants.
Figure 22:
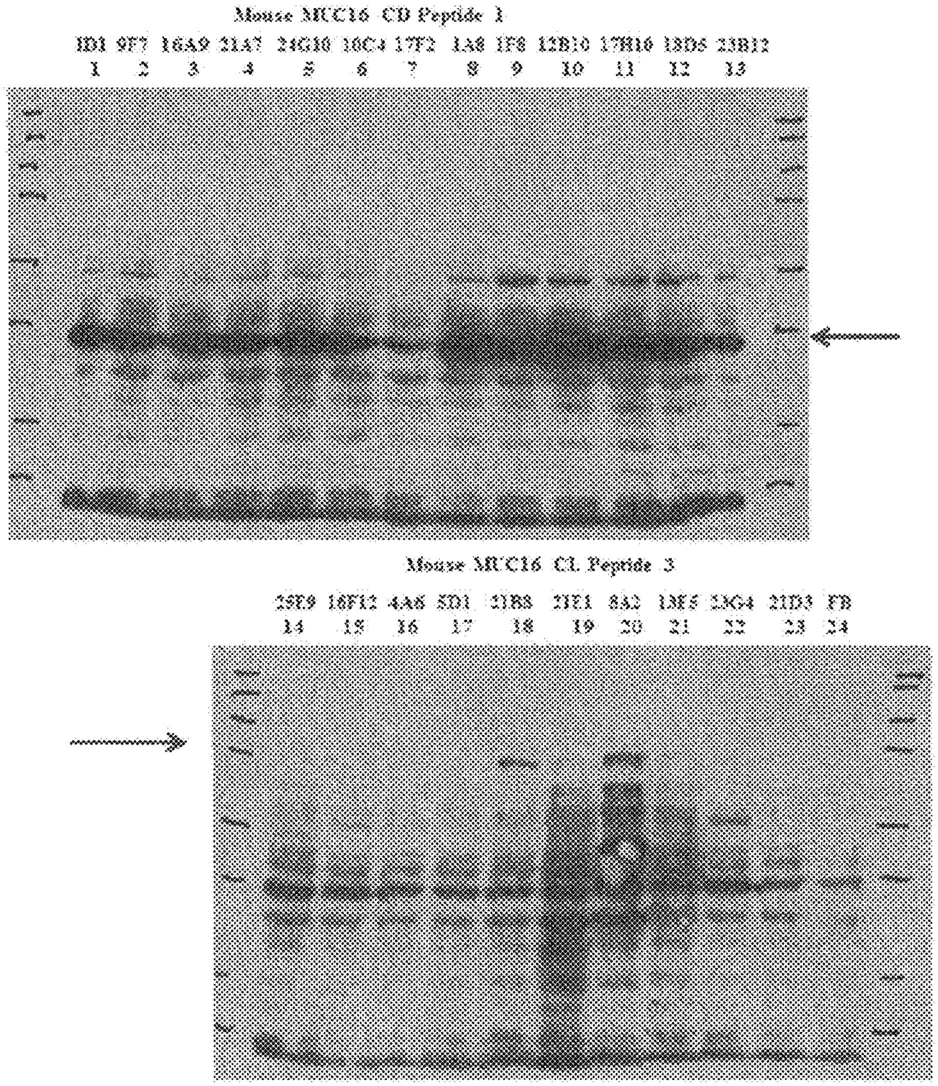
FIG. 22: BR5-FVB1 extract with 1:10 dilution of Mouse MUC16 monoclonal Primary Supernatants

Western blot analysis using mouse ID8 and BR5-FVB1 cell extracts were also performed for all the selected monoclonal antibodies as shown in FIG. 21 and FIG. 22 respectively.

Among the mouse MUC16 monoclonal antibodies, we selected 12B10-3G10 subclone mouse mAb for further screening. Similarly, hamster monoclonal antibodies, 15A8-2E10, 22B5-2G8 and 4H1-2E1 subclones were selected for further screening.

Figure 23A:
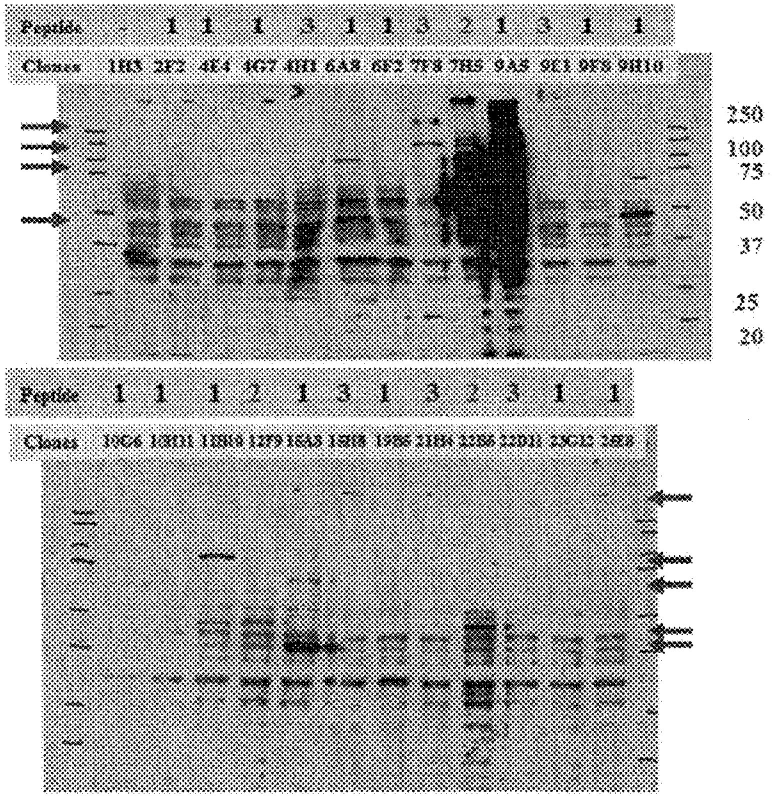
FIG. 23A and FIG. 23B: Western Blot showing 38 hamster's monoclonal antibody Supernatants on ID8 cell extracts.
Figure 23B:
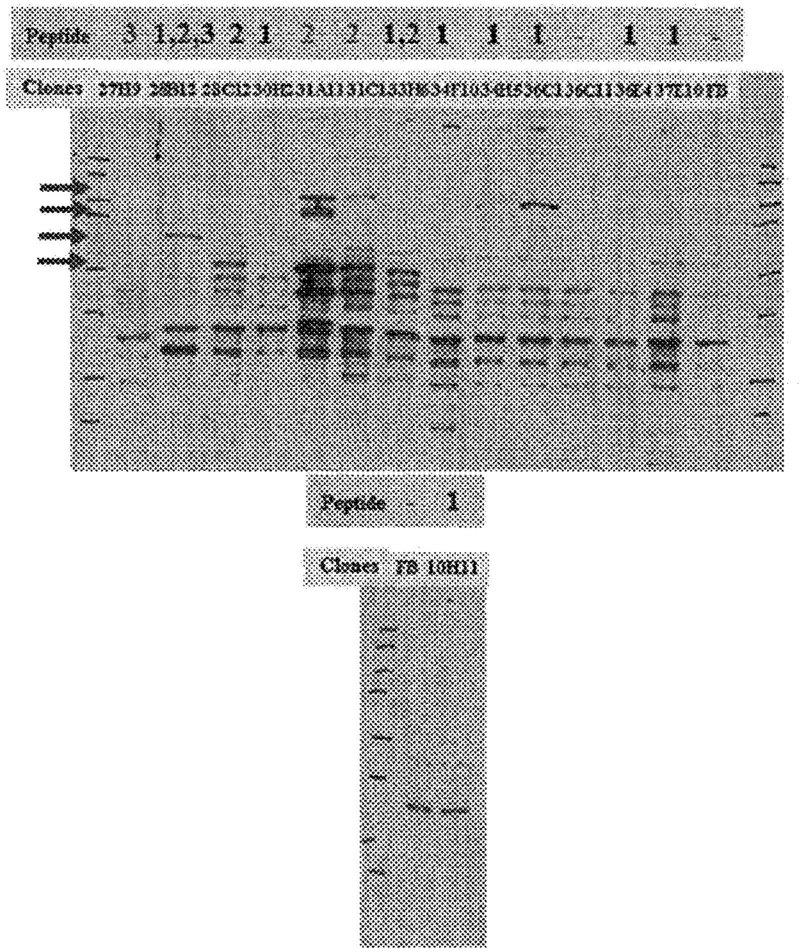

Immunohistochemical analysis was performed with paraffin and cryosections of ID8 (mouse), OVCAR-3 (human), BR5-FVB1 (mouse) cell lines and 13.5 days of Embryo. Paraffin or cryosections were probed with mouse 12B10 mAb, hamster 15A8, hamster 22B5 and hamster 4E1 mAbs to see the early development of mouse MUC16 (FIGS. 23A-23B)

Figure 25:
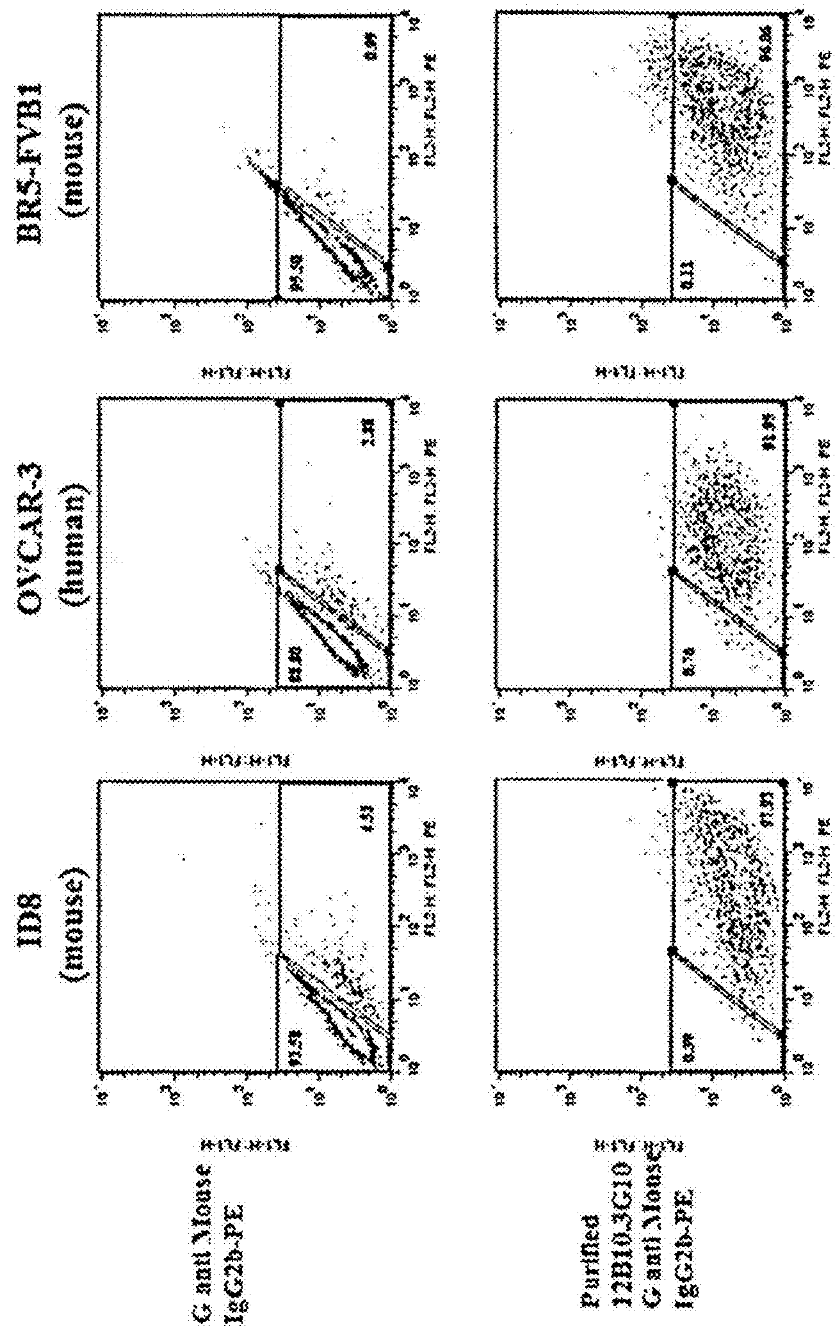
FIG. 25: FACS Analysis with Purified 12B10-3G10 mAb on ID8 (mouse), OVCAR-3 (human) and BR5-FVB1 (mouse) cell lines.

12B10-3G10 sub clone were further analyzed for single chain Fv fragments. FIG. 24 show 12B10-3G10 $V_H$ and $V_L$ DNA and Amino Acids sequences. Bioreactive supernatants and purified 12B10-3G10 were generated for animal studies and other characterization studies. FACS analysis was performed with purified 12B10-3G10 on ID8, OVCAR3 and BR5-FVB1 cells showing over 90% positivity to both mouse and human MUC16 ecto-domain fragment (FIG. 25).

REFERENCES CITED IN THE SPECIFICATION AND EXAMPLES 1-3

1. Bast R C, Jr., Feeney M, Lazarus H, Nadler L M, Colvin R B, Knapp R C. Reactivity of a monoclonal antibody with human ovarian carcinoma. J Clin Invest 1981; 68(5): 1331-7.
2. Bast R C, Jr., Klug T L, St John E, Jenison E, Niloff J M, Lazarus H, et al. A radioimmunoassay using a monoclonal antibody to monitor the course of epithelial ovarian cancer. N Engl J Med 1983; 309(15):883-7.

3. Rustin G J, Bast R C, Jr., Kelloff G J, Barrett J C, Carter S K, Nisen P D, et al. Use of CA-125 in clinical trial evaluation of new therapeutic drugs for ovarian cancer. Clin Cancer Res 2004; 10(11):3919-26.

4. Rosen D G, Wang L, Atkinson J N, Yu Y, Lu K H, Diamandis E P, et al. Potential markers that complement expression of CA125 in epithelial ovarian cancer. Gynecol Oncol 2005; 99(2):267-77.

5. Bast R C, Jr., Badgwell D, Lu Z, Marquez R, Rosen D, Liu J, et al. New tumor markers: CA125 and beyond. Int J Gynecol Cancer 2005; 15 Suppl 3:274-81.

6. Moore R G, Maclaughlan S, Bast R C, Jr. Current state of biomarker development for clinical application in epithelial ovarian cancer. Gynecol Oncol 2009.

7. Nustad K, Lebedin Y, Lloyd K O, Shigemasa K, de Bruijn H W, Jansson B, et al. Epitopes on CA125 from cervical mucus and ascites fluid and characterization of six new antibodies. Third report from the ISOBM TD-1 workshop. Tumour Biol 2002; 23(5):303-14.

8. Fendrick J L, Konishi I, Geary S M, Parmley T H, Quirk J G, Jr., O'Brien T J. CA125 phosphorylation is associated with its secretion from the WISH human amnion cell line. Tumour Biol 1997; 18(5):278-89.

9. Fendrick J L, Staley K A, Gee M K, McDougald S R, Quirk J G, Jr., O'Brien T J.

Characterization of CA125 synthesized by the human epithelial amnion WISH cell line. Tumour Biol 1993; 14(5): 310-8.

10. O'Brien T J, Beard J B, Underwood L J, Shigemasa K. The CA125 gene: a newly discovered extension of the glycosylated N-terminal domain doubles the size of this extracellular superstructure. Tumour Biol 2002; 23(3): 154-69.

11. Yin B W, Dnistrian A, Lloyd K O. Ovarian cancer antigen CA125 is encoded by the MUC16 mucin gene. Int J Cancer 2002; 98(5):737-40.

12. Yin B W, Lloyd K O. Molecular cloning of the CA125 ovarian cancer antigen: identification as a new mucin, MUC16. J Biol Chem 2001; 276(29):27371-5.

13. Hollingsworth M, Swanson B. Mucins in Cancer: protection and control of the cell surface. Nature Rviews: Cancer 2004; 4(1):45-60.

14. Huang L, Ren J, Chen D, Li Y, Kharbanda S, Kufe D. MUC1 cytoplasmic domain coactivates Wnt target gene transcription and confers transformation. Cancer Biol Ther 2003; 2(6):702-6.

15. Li Q, Ren J, Kufe D. Interaction of human MUC1 and beta-catenin is regulated by Lck and ZAP-70 in activated Jurkat T cells. Biochem Biophys Res Commun 2004; 315(2):471-6.

16. Ren J, Agata N, Chen D, Li Y, Yu W H, Huang L, et al. Human MUC1 carcinoma-associated protein confers resistance to genotoxic anticancer agents. Cancer Cell 2004; 5(2):163-75.

17. Ren J, Bharti A, Raina D, Chen W, Ahmad R, Kufe D. MUC1 oncoprotein is targeted to mitochondria by heregulin-induced activation of c-Src and the molecular chaperone HSP90. Oncogene 2006; 25(1):20-31.

18. Ramsauer V P, Pino V, Farooq A, Carothers Carraway C A, Salas P J, Carraway K L. Muc4-ErbB2 Complex Formation and Signaling in Polarized CACO-2 Epithelial Cells Indicate That Muc4 Acts as an Unorthodox Ligand for ErbB2. Mol Biol Cell 2006.

19. Bafna S, Singh A P, Moniaux N, Eudy J D, Meza J L, Batra S K. MUC4, a multifunctional transmembrane glycoprotein, induces oncogenic transformation of NIH3T3 mouse fibroblast cells. Cancer Res 2008; 68(22): 9231-8.

20. Ponnusamy M P, Singh A P, Jain M, Chakraborty S, Moniaux N, Batra S K. MUC4 activates HER2 signalling and enhances the motility of human ovarian cancer cells. Br J Cancer 2008; 99(3):520-6.

21. Nap M, Vitali A, Nustad K, Bast R C, Jr., O'Brien T J, Nilsson O, et al. Immunohistochemical characterization of 22 monoclonal antibodies against the CA125 antigen: 2nd report from the ISOBM TD-1 Workshop. Tumour Biol 1996; 17(6):325-31.

22. Markwell M A, Fox C F. Surface—specific iodination of membrane proteins of viruses and eucarytic cells using 1,3,4,6-tetrachloro-3alpha,6alpha-diphenylglycouril. Biochemistry 1978; 17:4807-4817.

23. Kononen J, Bubendorf L, Kallioniemi A, Barlund M, Schraml P, Leighton S, et al. Tissue microarrays for high-throughput molecular profiling of tumor specimens. Nat Med 1998; 4(7):844-7.

24. Hedvat C V, Hegde A, Chaganti R S, Chen B, Qin J, Filippa D A, et al. Application of tissue microarray technology to the study of non-Hodgkin's and Hodgkin's lymphoma. Hum Pathol 2002; 33(10):968-74.

25. Soslow R A. Histologic subtypes of ovarian carcinoma: an overview. Int J Gynecol Pathol 2008; 27(2):161-74.

26. O'Brien T J, Beard J B, Underwood L J, Dennis R A, Santin A D, York L. The CA125 gene: an extracellular superstructure dominated by repeat sequences. Tumour Biol 2001; 22(6):348-66.

27. Harris M, Howell A, Chrissohou M, Swindell R I, Hudson M, Sellwood R A. A comparison of the metastatic pattern of infiltrating lobular carcinoma and infiltrating duct carcinoma of the breast. Br J Cancer 1984; 50(1): 23-30.

28. Kaneko O, Gong L, Zhang J, Hansen J K, Hassan R, Lee B, et al. A binding domain on mesothelin for CA125/MUC16. J Biol Chem 2009; 284(6):3739-49.

REFERENCES CITED IN EXAMPLE 4

1. Singh A P, Senapati S, Ponnusamy M P, et al. Clinical potential of mucins in diagnosis, prognosis, and therapy of ovarian cancer. Lancet Oncol 2008; 9(11): 1076-85.

2. Sun C C, Ramirez P T, Bodurka D C. Quality of life for patients with epithelial ovarian cancer. Nat Clin Pract Oncol 2007; 4(1):18-29.

3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-86.

4. Hwu P, Yang J C, Cowherd R, et al. In vivo antitumor activity of T cells redirected with chimeric antibody/T-cell receptor genes. Cancer Res 1995; 55(15):3369-73.

5. Imai C, Mihara K, Andreansky M, et al. Chimeric receptors with 4-1BB signaling capacity provoke potent cytotoxicity against acute lymphoblastic leukemia. Leukemia 2004; 18(4):676-84.

6. Kershaw M H, Westwood J A, Parker L L, et al. A phase I study on adoptive immunotherapy using gene-modified T cells for ovarian cancer. Clin Cancer Res 2006; 12(20 Pt 1):6106-15.

7. Kochenderfer J N, Feldman S A, Zhao Y, et al. Construction and preclinical evaluation of an anti-CD19 chimeric antigen receptor. J Immunother 2009; 32(7):689-702.

8. Loskog A, Giandomenico V, Rossig C, Pule M, Dotti G, Brenner M K. Addition of the CD28 signaling domain to chimeric T-cell receptors enhances chimeric T-cell resistance to T regulatory cells. Leukemia 2006; 20(10):1819-28.

9. Maher J, Brentjens R J, Gunset G, Riviere I, Sadelain M. Human T-lymphocyte cytotoxicity and proliferation directed by a single chimeric TCRzeta/CD28 receptor. Nat Biotechnol 2002; 20(1):70-5.

10. Moeller M, Haynes N M, Trapani J A, et al. A functional role for CD28 costimulation in tumor recognition by single-chain receptor-modified T cells. Cancer Gene Ther 2004; 11(5):371-9.

11. Parker L L, Do M T, Westwood J A, et al. Expansion and characterization of T cells transduced with a chimeric receptor against ovarian cancer. Hum Gene Ther 2000; 11(17):2377-87.

12. Sadelain M, Brentjens R, Riviere I. The promise and potential pitfalls of chimeric antigen receptors. Curr Opin Immunol 2009; 21(2):215-23.

13. Stephan M T, Ponomarev V, Brentjens R J, et al. T cell-encoded CD80 and 4-1BBL induce auto- and transcostimulation, resulting in potent tumor rejection. Nat Med 2007; 13(12):1440-9.

14. Daly T, Royal R E, Kershaw M H, et al. Recognition of human colon cancer by T cells transduced with a chimeric receptor gene. Cancer Gene Ther 2000; 7(2):284-91.

15. Jensen M C, Cooper L J, Wu A M, Forman S J, Raubitschek A. Engineered CD20-specific primary human cytotoxic T lymphocytes for targeting B-cell malignancy. Cytotherapy 2003; 5(2):131-8.

16. Pule M A, Savoldo B, Myers G D, et al. Virus-specific T cells engineered to coexpress tumor-specific receptors: persistence and antitumor activity in individuals with neuroblastoma. Nat Med 2008; 14(11): 1264-70.

17. Savoldo B, Rooney C M, Di Stasi A, et al. Epstein Barr virus specific cytotoxic T lymphocytes expressing the anti-CD30zeta artificial chimeric T-cell receptor for immunotherapy of Hodgkin disease. Blood 2007; 110(7): 2620-30.

18. Wang G, Chopra R K, Royal R E, Yang J C, Rosenberg S A, Hwu P. A T cell-independent antitumor response in mice with bone marrow cells retrovirally transduced with an antibody/Fc-gamma chain chimeric receptor gene recognizing a human ovarian cancer antigen. Nat Med 1998; 4(2):168-72.

19. Hollyman D, Stefanski J, Przybylowski M, et al. Manufacturing validation of biologically functional T cells targeted to CD19 antigen for autologous adoptive cell therapy. J Immunother 2009; 32(2):169-80.

20. Lamers C H, Sleijfer S, Vulto A G, et al. Treatment of metastatic renal cell carcinoma with autologous T-lymphocytes genetically retargeted against carbonic anhydrase IX: first clinical experience. J Clin Oncol 2006; 24(13):e20-2.

21. Till B G, Jensen M C, Wang J, et al. Adoptive immunotherapy for indolent non-Hodgkin lymphoma and mantle cell lymphoma using genetically modified autologous CD20-specific T cells. Blood 2008; 112(6):2261-71.

22. Hamanishi J, Mandai M, Iwasaki M, et al. Programmed cell death 1 ligand 1 and tumor-infiltrating CD8+ T lymphocytes are prognostic factors of human ovarian cancer. Proc Natl Acad Sci USA 2007; 104(9):3360-5.

23. Leffers N, Gooden M J, de Jong R A, et al. Prognostic significance of tumor-infiltrating T-lymphocytes in primary and metastatic lesions of advanced stage ovarian cancer. Cancer Immunol Immunother 2009; 58(3):449-59.

24. Sato E, Olson S H, Ahn J, et al. Intraepithelial CD8+ tumor-infiltrating lymphocytes and a high CD8+/regulatory T cell ratio are associated with favorable prognosis in ovarian cancer. Proc Natl Acad Sci USA 2005; 102(51): 18538-43.

25. Zhang L, Conejo-Garcia J R, Katsaros D, et al. Intratumoral T cells, recurrence, and survival in epithelial ovarian cancer. N Engl J Med 2003; 348(3):203-13.

26. Curiel T J, Coukos G, Zou L, et al. Specific recruitment of regulatory T cells in ovarian carcinoma fosters immune privilege and predicts reduced survival. Nat Med 2004; 10(9):942-9.

27. Leffers N, Lambeck A J, de Graeff P, et al. Survival of ovarian cancer patients overexpressing the tumour antigen p53 is diminished in case of MHC class I down-regulation. Gynecol Oncol 2008; 110(3):365-73.

28. Nelson B H. The impact of T-cell immunity on ovarian cancer outcomes. Immunol Rev 2008; 222:101-16.

29. Wolf D, Wolf A M, Rumpold H, et al. The expression of the regulatory T cell-specific forkhead box transcription factor FoxP3 is associated with poor prognosis in ovarian cancer. Clin Cancer Res 2005; 11(23):8326-31.

30. Badgwell D, Bast R C, Jr. Early detection of ovarian cancer. Dis Markers 2007; 23(5-6):397-410.

31. Bast R C, Jr., Badgwell D, Lu Z, et al. New tumor markers: CA125 and beyond. Int J Gynecol Cancer 2005; 15 Suppl 3:274-81.

32. Fritsche H A, Bast R C. CA125 in ovarian cancer: advances and controversy. Clin Chem 1998; 44(7):1379-80.

33. Krivak T C, Tian C, Rose G S, Armstrong D K, Maxwell G L. A Gynecologic Oncology Group Study of serum CA-125 levels in patients with stage III optimally debulked ovarian cancer treated with intraperitoneal compared to intravenous chemotherapy: an analysis of patients enrolled in GOG 172. Gynecol Oncol 2009; 115(1):81-5.

34. O'Brien T J, Beard J B, Underwood L J, Dennis R A, Santin A D, York L. The CA125 gene: an extracellular superstructure dominated by repeat sequences. Tumour Biol 2001; 22(6):348-66.

35. Bellone S, Anfossi S, O'Brien T J, et al. Generation of CA125-specific cytotoxic T lymphocytes in human leukocyte antigen-A2.1-positive healthy donors and patients with advanced ovarian cancer. Am J Obstet Gynecol 2009; 200(1):75 e1-10.

36. Berek J S. Immunotherapy of ovarian cancer with antibodies: a focus on oregovomab. Expert Opin Biol Ther 2004; 4(7): 1159-65.

37. O'Brien T J, Tanimoto H, Konishi I, Gee M. More than 15 years of CA125: what is known about the antigen, its structure and its function. Int J Biol Markers 1998; 13(4):188-95.

38. Rao T D, Park K J, Smith-Jones P, et al. Novel monoclonal antibodies against proximal (carboxy-terminal) portions of MUC16 (submitted to Applied Immunohistochemistry and Molecular Morphometry).

39. Wang Z, Raifu M, Howard M, et al. Universal PCR amplification of mouse immunoglobulin gene variable regions: the design of degenerate primers and an assessment of the effect of DNA polymerase 3' to 5' exonuclease activity. J Immunol Methods 2000; 233(1-2): 167-77.

40. Doenecke A, Winnacker E L, Hallek M. Rapid amplification of cDNA ends (RACE) improves the PCR-based isolation of immunoglobulin variable region genes from murine and human lymphoma cells and cell lines. Leukemia 1997; 11(10):1787-92.

41. Gong M C, Latouche J B, Krause A, Heston W D, Bander N H, Sadelain M. Cancer patient T cells genetically targeted to prostate-specific membrane antigen specifically lyse prostate cancer cells and release cytokines in response to prostate-specific membrane antigen. Neoplasia 1999; 1(2):123-7.
42. Orlandi R, Gussow D H, Jones P T, Winter G. Cloning immunoglobulin variable domains for expression by the polymerase chain reaction. Proc Natl Acad Sci USA 1989; 86(10):3833-7.
43. Brentjens R J, Santos E, Nikhamin Y, et al. Genetically targeted T cells eradicate systemic acute lymphoblastic leukemia xenografts. Clin Cancer Res 2007; 13(18 Pt 1):5426-35.
44. Riviere I, Brose K, Mulligan R C. Effects of retroviral vector design on expression of human adenosine deaminase in murine bone marrow transplant recipients engrafted with genetically modified cells. Proc Natl Acad Sci USA 1995; 92(15):6733-7.
45. Quintas-Cardama A, Yeh R K, Hollyman D, et al. Multifactorial optimization of gammaretroviral gene transfer into human T lymphocytes for clinical application. Hum Gene Ther 2007; 18(12):1253-60.
46. Latouche J B, Sadelain M. Induction of human cytotoxic T lymphocytes by artificial antigen-presenting cells. Nat Biotechnol 2000; 18(4):405-9.
47. Santos E B, Yeh R, Lee J, et al. Sensitive in vivo imaging of T cells using a membrane-bound *Gaussia princeps* luciferase. Nat Med 2009; 15(3):338-44.
48. Park K J, Soslow R, Linkov I, Rao T D, D S. The extracellular portion of the MUC16 cytoplasmic domain is detectable in ovarian carcinomas using novel monoclonal antibody, 4H11. Mod Pathol, 2008; 21(1s):217A-218A.
49. Raspollini M R, Castiglione F, Rossi Degl'innocenti D, et al. Tumour-infiltrating gamma/delta T-lymphocytes are correlated with a brief disease-free interval in advanced ovarian serous carcinoma. Ann Oncol 2005; 16(4):590-6.
50. Tomsova M, Melichar B, Sedlakova I, Steiner I. Prognostic significance of CD3+ tumor-infiltrating lymphocytes in ovarian carcinoma. Gynecol Oncol 2008; 108(2): 415-20.
51. Woo E Y, Chu C S, Goletz T J, et al. Regulatory CD4(+)CD25(+) T cells in tumors from patients with early-stage non-small cell lung cancer and late-stage ovarian cancer. Cancer Res 2001; 61(12):4766-72.
52. Lamers C H, Langeveld S C, Groot-van Ruijven C M, Debets R, Sleijfer S, Gratama J W. Gene-modified T cells for adoptive immunotherapy of renal cell cancer maintain transgene-specific immune functions in vivo. Cancer Immunol Immunother 2007; 56(12):1875-83.
53. Brentjens R, Hollyman D, Weiss M, et al. A Phase I trial for the treatment of chemo-refractory chronic lymphocytic leukemia with CD19-targeted autologous T cells. Molecular Therapy 2008; 16:S15.
54. Barber A, Zhang T, DeMars L R, Conejo-Garcia J, Roby K F, Sentman C L. Chimeric NKG2D receptor-bearing T cells as immunotherapy for ovarian cancer. Cancer Res 2007; 67(10):5003-8.
55. Barber A, Zhang T, Sentman C L. Immunotherapy with chimeric NKG2D receptors leads to long-term tumor-free survival and development of host antitumor immunity in murine ovarian cancer. J Immunol 2008; 180(1):72-8.
56. Carpenito C, Milone M C, Hassan R, et al. Control of large, established tumor xenografts with genetically retargeted human T cells containing CD28 and CD137 domains. Proc Natl Acad Sci USA 2009; 106(9):3360-5.
57. Kershaw M H, Westwood J A, Hwu P. Dual-specific T cells combine proliferation and antitumor activity. Nat Biotechnol 2002; 20(12):1221-7.
58. Hung C F, Wu T C, Monie A, Roden R. Antigen-specific immunotherapy of cervical and ovarian cancer. Immunol Rev 2008; 222:43-69.
59. Westwood J A, Smyth M J, Teng M W, et al. Adoptive transfer of T cells modified with a humanized chimeric receptor gene inhibits growth of Lewis-Y-expressing tumors in mice. Proc Natl Acad Sci USA 2005; 102(52): 19051-6.
60. Habib-Agahi M, Jaberipour M, Searle P F. 4-1BBL costimulation retrieves CD28 expression in activated T cells. Cell Immunol 2009; 256(1-2):39-46.
61. Habib-Agahi M, Phan T T, Searle P F. Co-stimulation with 4-1BB ligand allows extended T-cell proliferation, synergizes with CD80/CD86 and can reactivate anergic T cells. Int Immunol 2007; 19(12):1383-94.
62. Brentjens R J, Sadelain M. Somatic cell engineering and the immunotherapy of leukemias and lymphomas. Adv Pharmacol 2004; 51:347-70.
63. Finney H M, Akbar A N, Lawson A D. Activation of resting human primary T cells with chimeric receptors: costimulation from CD28, inducible costimulator, CD134, and CD137 in series with signals from the TCR zeta chain. J Immunol 2004; 172(1):104-13.
64. Sadelain M, Riviere I, Brentjens R. Targeting tumours with genetically enhanced T lymphocytes. Nat Rev Cancer 2003; 3(1):35-45.
65. Wilkie S, Picco G, Foster J, et al. Retargeting of human T cells to tumor-associated MUC1: the evolution of a chimeric antigen receptor. J Immunol 2008; 180(7):4901-9.
66. Li Q, Ai J, Song Z, Liu J, Shan B. 4-1BB (CD137) ligand enhanced anti-tumor immune response against mouse forestomach carcinoma in vivo. Cell Mol Immunol 2008; 5(5):379-84.
67. Salih H R, Kosowski S G, Haluska V F, et al. Constitutive expression of functional 4-1BB (CD137) ligand on carcinoma cells. J Immunol 2000; 165(5):2903-10.
68. Wan Y L, Zheng S S, Zhao Z C, Li M W, Jia C K, Zhang H. Expression of co-stimulator 4-1BB molecule in hepatocellular carcinoma and adjacent non-tumor liver tissue, and its possible role in tumor immunity. World J Gastroenterol 2004; 10(2):195-9.

MICROORGANISM DEPOSIT

A hybridoma designated huMUC16Pep3-31A3.5, which produces the antibody designated 31A3 (also designated 31A3.5.1) in this specification, was deposited with the American Type Culture Collection (ATCC), located at 10801 University Boulevard, Manassas, Va. 20110-2209, on Mar. 25, 2011, in compliance with the Budapest Treaty on the International Recognition of the Deposit of Microorganisms for the Purposes of Patent Procedure, and was assigned ATCC Accession No. PTA-11773.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. An antibody or antigen-binding fragment thereof that specifically binds to a MUC16 polypeptide or to an antigenic portion thereof, wherein the MUC16 polypeptide is (SEQ ID NO: 02)
TLDRSSVLVDGYSPNRNE, and wherein the antibody comprises a variable heavy ("$V_H$") chain encoded by SEQ ID NO:04 and a variable light ("$V_L$") chain encoded by SEQ ID NO:05.

2. The antibody or antigen-binding fragment of claim 1, wherein the antibody is a monoclonal antibody.

3. The antibody or antigen-binding fragment of claim 1, wherein the antibody is a chimeric antibody.

4. A humanized antibody or antigen-binding fragment thereof made by substituting the complementarity determining regions of a first antibody into a human framework domain, wherein the humanized antibody or antigen-binding fragment thereof specifically binds to a MUC16 polypeptide or to an antigenic portion thereof, wherein the first antibody specifically binds to the MUC16 polypeptide or the antigenic portion thereof, wherein the MUC16 polypeptide is TLDRSSVLVDGYSPNRNE (SEQ ID NO:02), and wherein the first antibody comprises a $V_H$ chain encoded by SEQ ID NO:04 and a $V_L$ chain encoded by SEQ ID NO:05.

5. The antibody or antigen-binding fragment of claim 4, wherein substantially all of the framework domain residues of the humanized antibody are those of a human immunoglobulin sequence, and wherein one or more of the framework domain residues are replaced by corresponding non-human residues.

6. The antibody or antigen-binding fragment of claim 1, wherein the antigen-binding fragment is selected from the group consisting of a Fab fragment, a F(ab')$_2$ fragment, and a Fv fragment.

7. The antibody or antigen-binding fragment of claim 1, wherein the antibody or antigen-binding fragment is covalently linked to a cytotoxic agent or a prodrug of a cytotoxic agent.

8. A composition comprising (a) the antibody or antigen-binding fragment of claim 1 and (b) a pharmaceutically acceptable carrier.

9. A composition comprising (a) the antibody or antigen-binding fragment of claim 4 and (b) a pharmaceutically acceptable carrier.

10. A hybridoma cell that produces a monoclonal antibody or an antigen-binding fragment thereof that specifically binds to the MUC16 polypeptide or to an antigen portion thereof, wherein the MUC16 polypeptide is (SEQ ID NO: 2)
TLDRSSVLVDGYSPNRNE, and wherein the antibody comprises a variable heavy ("VH") chain encoded by SEQ ID NO:04 and a variable light ("VL") chain encoded by SEQ ID NO:05.

11. A method for identifying a subject as having a cancer in which MUC16 is expressed, wherein said method comprises administering the antibody of claim 1 the subject, and determining the presence and location of the antibody in the subject, wherein said antibody is labeled.

12. A method for identifying a subject as having a cancer in which MUC16 is expressed, wherein said method comprises administering the antibody of claim 4 to the subject, and determining the presence and location of the antibody in the subject, wherein said antibody is labeled.

13. The method of claim 11, wherein the cancer is selected from the group consisting of ovarian cancer and breast cancer.

14. The method of claim 12, wherein the cancer is selected from the group consisting of ovarian cancer and breast cancer.

15. An ex vivo method for identifying a subject as having a cancer in which MUC16 is expressed, wherein said method comprises (a) obtaining a first sample from a first subject;

(b) contacting the first sample with the antibody of claim 1; and (c) determining whether the antibody has an increased level of binding to the first sample as compared to a control sample lacking the cancer.

16. The ex vivo method of claim 15, wherein the cancer is selected from the group consisting of ovarian cancer and breast cancer.

17. An ex vivo method for identifying a subject as having a cancer in which MUC16 is expressed, wherein said method comprises (a) obtaining a first sample from a first subject;

(b) contacting the first sample with the antibody of claim 4; and (c) determining whether the antibody has an increased level of binding to the first sample as compared to a control sample lacking the cancer.

18. The ex vivo method of claim 17, wherein the cancer is selected from the group consisting of ovarian cancer and breast cancer.

19. A single chain variable fragment (scFv) comprising a VH chain sequence encoded by SEQ ID NO:04 and a VL chain sequence encoded by SEQ ID NO:05.

20. A single chain variable fragment (scFv) comprising a VH chain sequence and a VL chain sequence of the humanized antibody or antigen-binding fragment of claim 4.

21. A chimeric antigen receptor (CAR) comprising the scFv of claim 19.

22. A chimeric antigen receptor (CAR) comprising the scFv of claim 20.

23. A CAR comprising the scFv of claim 19 fused to a transmembrane domain.

24. A CAR comprising the scFv of claim 20 to a transmembrane domain.

25. The CAR of claim 23, wherein the transmembrane domain is fused to a T cell receptor ζ chain cytoplasmic signaling domain.

26. The CAR of claim 24, wherein the transmembrane domain is fused to a T cell receptor ζ chain cytoplasmic signaling domain.

27. The CAR of claim 25, further comprising a cytoplasmic signaling domain of a co-stimulatory receptor, wherein the co-stimulatory receptor comprises CD28, 4-1BB, or OX40.

28. The CAR of claim 26, further comprising a cytoplasmic signaling domain of a co-stimulatory receptor, wherein the co-stimulatory receptor comprises CD28, 4-1BB, or OX40.

29. The CAR of claim 23, comprising in amino- to carboxy-terminal order: a human CD8 leader peptide, the scFv, a human CD28 transmembrane domain and cytoplasmic signaling domain, and a CD3-zeta signaling domain.

30. The CAR of claim 24, comprising in amino- to carboxy-terminal order: a human CD8 leader peptide, the scFv, a human CD28 transmembrane domain and cytoplasmic signaling domain, and a CD3-zeta signaling domain.

31. A T cell expressing the CAR of claim 21.

32. A T cell expressing the CAR of claim 22.

33. A method for treating a cancer in which MUC16 is expressed, comprising administering to a subject the antibody or antigen binding fragment of claim 1.

34. A method for treating a cancer in which MUC16 is expressed, comprising administering to a subject the antibody or antigen binding fragment of claim 2.

35. A method for treating a cancer in which MUC16 is expressed, comprising administering to a subject the antibody or antigen binding fragment of claim 3.

36. A method for treating a cancer in which MUC16 is expressed, comprising administering to a subject the antibody or antigen binding fragment of claim 4.

37. A method for treating a cancer in which MUC16 is expressed, comprising administering to a subject the antibody or antigen binding fragment of claim 5.

38. A method for treating a cancer in which MUC16 is expressed, comprising administering to a subject the antibody or antigen binding fragment of claim 6.

39. A method for treating a cancer in which MUC16 is expressed, comprising administering to a subject the antibody or antigen binding fragment of claim 7.

40. A method for treating a cancer in which MUC16 is expressed, comprising administering to a subject the T cell of claim 31.

41. A method for treating a cancer in which MUC16 is expressed, comprising administering to a subject the T cell of claim 32.

42. The method of claim 40, wherein the administering is intraperitoneally or intravenously.

43. The method of claim 41, wherein the administering is intraperitoneally or intravenously.

44. The method of claim 33, wherein the cancer is selected from the group consisting of ovarian cancer and breast cancer.

45. The method of claim 34, wherein the cancer is selected from the group consisting of ovarian cancer and breast cancer.

46. The method of claim 35, wherein the cancer is selected from the group consisting of ovarian cancer and breast cancer.

47. The method of claim 36, wherein the cancer is selected from the group consisting of ovarian cancer and breast cancer.

48. The method of claim 37, wherein the cancer is selected from the group consisting of ovarian cancer and breast cancer.

49. The method of claim 38, wherein the cancer is selected from the group consisting of ovarian cancer and breast cancer.

50. The method of claim 39, wherein the cancer is selected from the group consisting of ovarian cancer and breast cancer.

51. The method of claim 40, wherein the cancer is selected from the group consisting of ovarian cancer and breast cancer.

52. The method of claim 41, wherein the cancer is selected from the group consisting of ovarian cancer and breast cancer.

53. The method of claim 23, which further comprises detecting a reduction in one or more symptoms of the cancer after the administering step.

54. A chimeric antibody that is the antibody of claim 3.

55. A humanized antibody that is the antibody of claim 4.

56. A method for treating a cancer in which MUC16 is expressed, comprising administering to a subject the antibody of claim 54.

57. A method for treating a cancer in which MUC16 is expressed, comprising administering to a subject the antibody of claim 55.

* * * * *